(12) United States Patent
Nakai et al.

(10) Patent No.: US 11,564,971 B2
(45) Date of Patent: Jan. 31, 2023

(54) HYALURONIC ACID DERIVATIVE HAVING AMINO ACID AND STERYL GROUP INTRODUCED THEREINTO

(71) Applicant: CHUGAI SEIYAKU KABUSHIKI KAISHA, Tokyo (JP)

(72) Inventors: Takashi Nakai, Shizuoka (JP); Tomoko Yasugi, Shizuoka (JP); Yoshihiro Tampo, Shizuoka (JP); Kenji Yasugi, Shizuoka (JP); Tsuyoshi Shimoboji, Shizuoka (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/426,485

(22) PCT Filed: Sep. 5, 2013

(86) PCT No.: PCT/JP2013/073995
§ 371 (c)(1),
(2) Date: Mar. 6, 2015

(87) PCT Pub. No.: WO2014/038641
PCT Pub. Date: Mar. 13, 2014

(65) Prior Publication Data
US 2015/0231268 A1 Aug. 20, 2015

(30) Foreign Application Priority Data
Sep. 5, 2012 (JP) .............................. JP2012-195528

(51) Int. Cl.
| | | |
|---|---|---|
| C08B 37/08 | (2006.01) | |
| A61K 47/61 | (2017.01) | |
| A61K 38/13 | (2006.01) | |
| A61K 47/36 | (2006.01) | |
| C08L 5/08 | (2006.01) | |
| A61K 31/337 | (2006.01) | |

(52) U.S. Cl.
CPC ............ *A61K 38/13* (2013.01); *A61K 31/337* (2013.01); *A61K 47/36* (2013.01); *A61K 47/61* (2017.08); *C08B 37/0072* (2013.01); *C08L 5/08* (2013.01)

(58) Field of Classification Search
CPC .................. A61K 47/4823; C08B 37/0072
See application file for complete search history.

(56) References Cited

U.S. PATENT DOCUMENTS

| | | |
|---|---|---|
| 2009/0148534 A1 | 6/2009 | Yasugi et al. |
| 2010/0167991 A1 | 7/2010 | Soula |
| 2010/0204102 A1 | 8/2010 | Akiyoshi et al. |
| 2010/0305035 A1 | 12/2010 | Soula |
| 2011/0212901 A1 | 9/2011 | Akiyoshi |
| 2012/0035128 A1 | 2/2012 | Kaneko |
| 2013/0338352 A1 | 12/2013 | Yasugi |

FOREIGN PATENT DOCUMENTS

| | | |
|---|---|---|
| EP | 416250 A2 | 3/1991 |
| EP | 0506976 A1 | 10/1992 |
| EP | 2143446 A1 | 1/2010 |
| EP | 2360188 A1 | 8/2011 |
| JP | H02273176 | 11/1990 |
| JP | H0388802 A | 4/1991 |
| JP | H05085942 | 4/1993 |
| JP | 2001081103 A | 3/2001 |
| JP | 2002519481 A | 7/2002 |
| JP | 2007535607 A | 12/2007 |
| JP | 2012504697 A | 2/2012 |
| WO | 9206714 A1 | 4/1992 |
| WO | 9220349 A1 | 11/1992 |
| WO | 9635721 A1 | 11/1996 |
| WO | 2000001733 A1 | 1/2000 |
| WO | 0105434 A2 | 1/2001 |
| WO | 0160412 A2 | 8/2001 |
| WO | 2002022154 A2 | 3/2002 |
| WO | 2004035629 A2 | 4/2004 |
| WO | 2005110505 A2 | 11/2005 |
| WO | 2006028110 A1 | 3/2006 |
| WO | 2008136536 A1 | 11/2008 |
| WO | 2009074678 A2 | 6/2009 |
| WO | 2010053140 A1 | 5/2010 |
| WO | 2010119994 A1 | 10/2010 |
| WO | 2011148116 A2 | 12/2011 |
| WO | 2012118189 A1 | 9/2012 |

OTHER PUBLICATIONS

Bergman et al "Hyaluronic Acid Derivatives Prepared in Aqueous Media by Triazine-Activated Amidation" Biomacromolecules, 8;2190-2195 (Apr. 2007).

Schante et al "Synthesis of N-alanyl-hyaluronamide with high degree of substitution for enhanced resistance to hyaluronidase-mediated digestion" Carbohydrate Polymers, 86 : 747-752 (Feb. 2011).

Schante et al "Improvement of hyaluronic acid enzymatic stability by the grafting of amino-acids" Carbohydrate Polymers, 87 : 2211-2216 (Aug. 2012).

Akiyoshi et al "Self-Aggregates of Hydrophobized Polysaccharides in Water. Formation and Characteristics of Nanoparticles" Macromolecules, 26 : 3062-3068 (Mar. 1993).

Akiyoshi et al "Self-assembly of polymer amphiphiles: thermodynamics of complexation between bovine serum albumin and self-aggregate of cholesterol-bearing pullulan" Colloids and Surfaces, 112 : 91-95 (1996).

(Continued)

*Primary Examiner* — Leigh C Maier
(74) *Attorney, Agent, or Firm* — Browdy and Neimark, PLLC

(57) ABSTRACT

The present invention provides a hyaluronic acid derivative containing a disaccharide unit represented by formula (I) or formula (I) and (II), and a complex containing the hyaluronic acid derivative and a drug.

12 Claims, 119 Drawing Sheets

(56) References Cited

OTHER PUBLICATIONS

Liu et al "Self-assembled based on linoleic-acid modified chitosan: Stability and adsorption of trypsin" Carbohydrate Polymers, 62 : 293-298, (Sep. 2005).

Platt et al "Anticancer Therapeutics: Targeting Macromolecules and Nanocarriers to Hyaluronan or CD44. a Hyaluronan Receptor" Molecular Pharmaceutics 5 : 474-486 (Apr. 2008).

Yadav et al "An insight on hyaluronic acid in drug targeting and drug deliver" Journal of Drug Targeting, 16 (2) 91-107 (Feb. 2008).

Luo et al "Synthesis and Selective Cytotoxicity of a Hyaluronic Acid-Antitumor Bioconjugate" Bioconjugate Chem., 10 : 755-763 (May 1999).

Banzato et al "A Paclitaxel-Hyaluronan Bioconjugate Targeting Ovarian Cancer Affords a Potent In vivo Therapeutic Activity" Clinical Cancer Research, 14 : 3598-3606, (2008).

Lee et al "Hyaluronic Acid-Paclitaxel Conjugate Micelles: Synthesis, Characterization, and Antitumor Activity" Bioconjugate Chem., 19 : 1319-1325, (2008).

Luo "Targeted Delivery of Doxorubicin by HPMA Copolymer-Hyaluronan Bioconjugates" Pharmaceutical Research, 19 : 396-402, (Apr. 2002).

Corahini et al "Inhibition of Hepatocellular Carcinomas in vitro and Hepatic Metastases in vivo in Mice by the Histone Deacetylase Inhibitor HA-But" Clinical Cancer Research, 10 : 4822-4830 (Jul. 2004).

Yadav et al "Development and characterization of hyaluronic acid-anchored PLGA nanoparticulate carriers of doxorubicin" Nanomedicine: Nanotechnology, Biology, and Medicine, 3 : 246-257, (Sep. 2007).

Lee et al "Target-specific intracellular delivery of siRNA using degradable hyaluronic acid nanogels" Journal of Controlled Release, 119 : 245-252, (Feb. 2007).

Peer et al "Tumor-Targeted Hyaluronan Nanoliposomes Increase the Antitumor Activity of Liposomal Doxorubicin in syngeneic and Human Xenograft Mouse Tumor Models" Neoplasia, 6 (4) 343-353, (Jul./Aug. 2004).

Choi et al "Self-assembled hyaluronic acid nanoparticles as a potential drug carrier for cancer therapy: synthesis, characterization, and in vivo biodistribution" Journal of Materials Chemistry 19, 4102-4107, (May 2009).

Fraser et al "Uptake of circulating hyaluronic acid by the rat liver" Cell and Tissue Research, 242 : 505-510, (1985).

Zhou et al "Identification of the Hyaluronan Receptor for Endocytosis (HARE)*" The Journal of Biological Chemistry, 275 (48) 37733-37741, (Aug. 2000).

Fraser et al "Plasma clearance, tissue distribution and metabolism of hyaluronic acid injection intravenously in the rabbit" The Biochemical Journal, 200 : 415-424, (1981).

European Search Report, dated Apr. 26, 2016. In corresponding application No. EP 13836138.

Search Report of PCT/JP2013/073995, dated Oct. 15, 2013.

Esposito et al., Hyaluronan-based microspheres as tools for drug delivery: a comparative study, International Journal of Pharmaceutics, 288:35-49 (2005).

99k HA-Gly-OEt

99k HA-Gly

99k HA—Ser—OEt/Chol/FL

99k HA—Ser/Chol—6%/FL

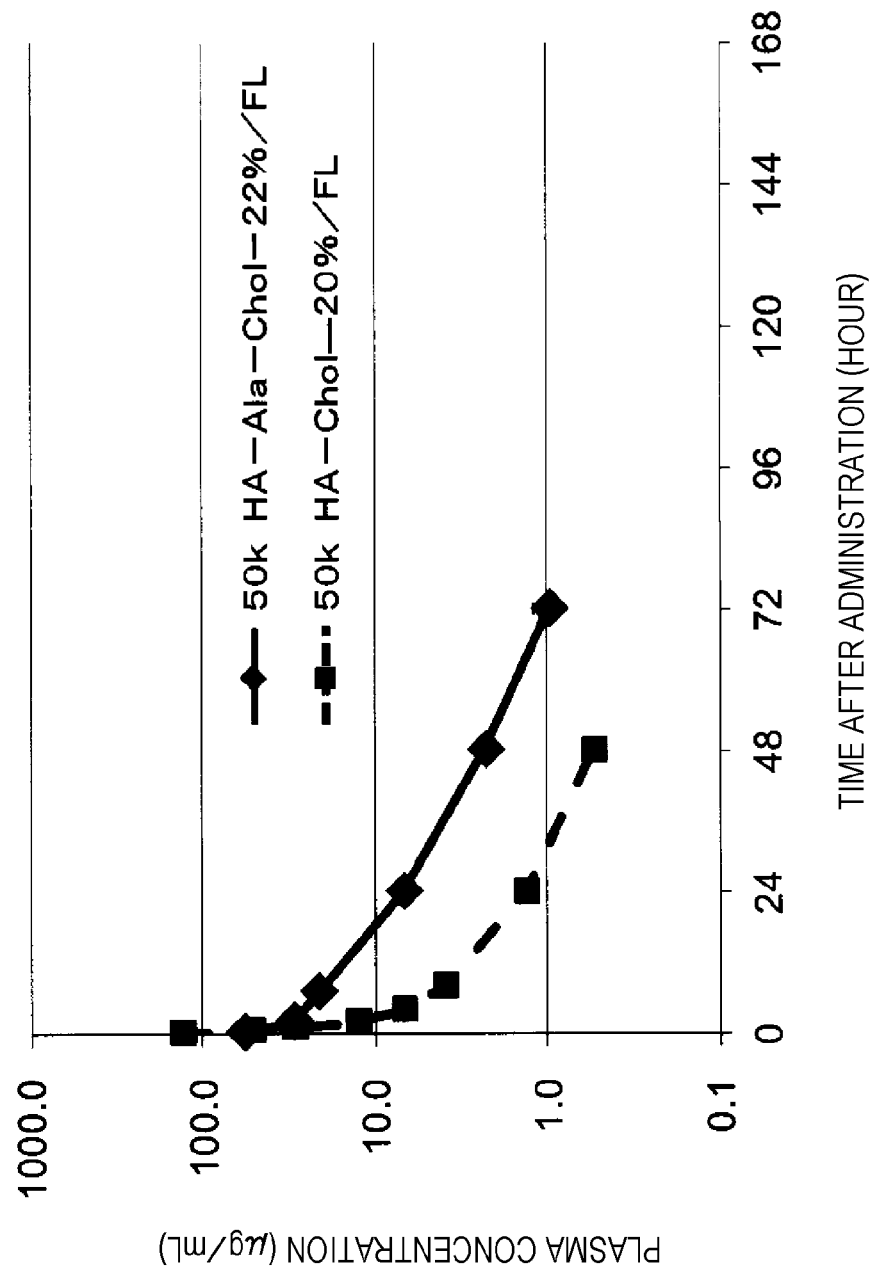

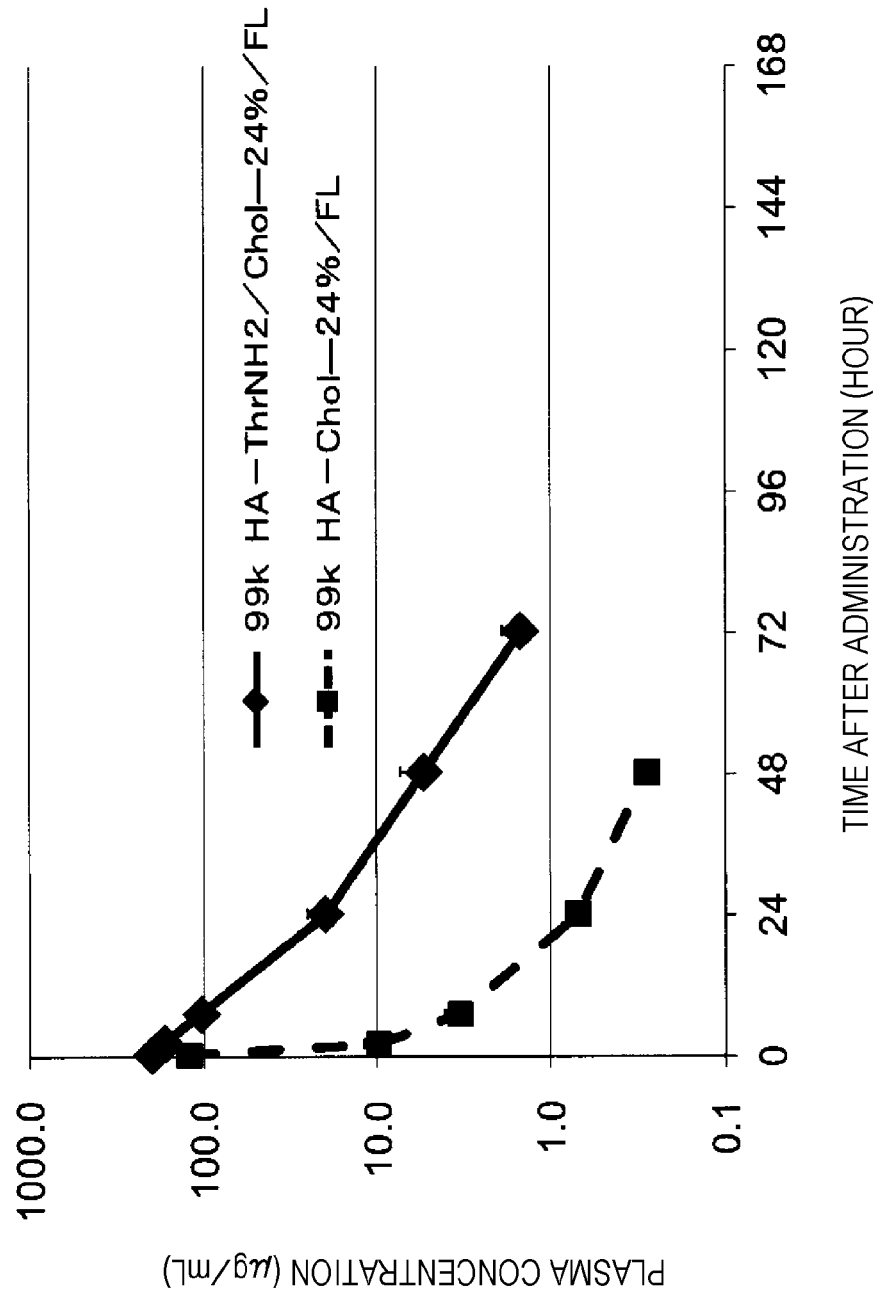

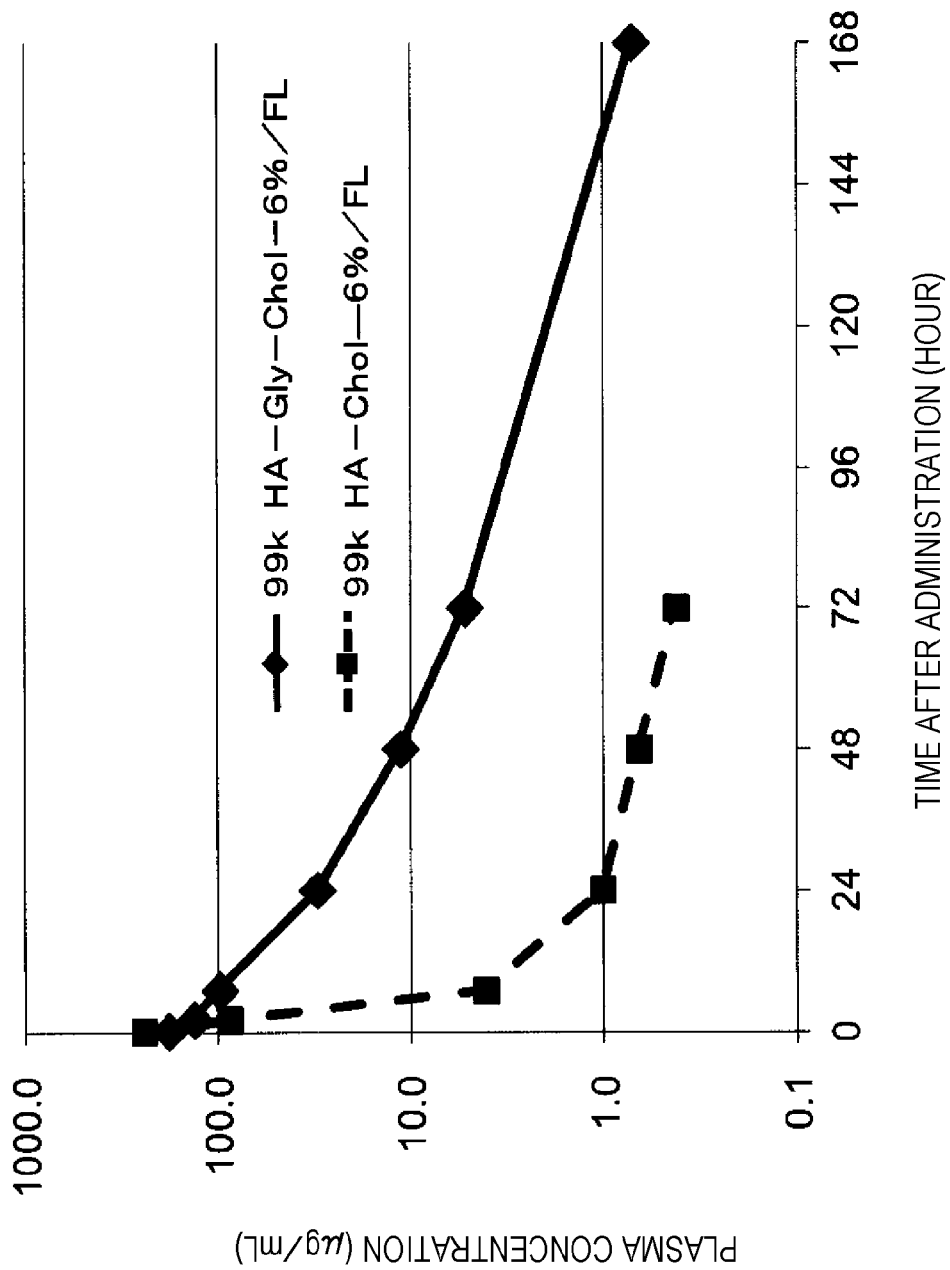

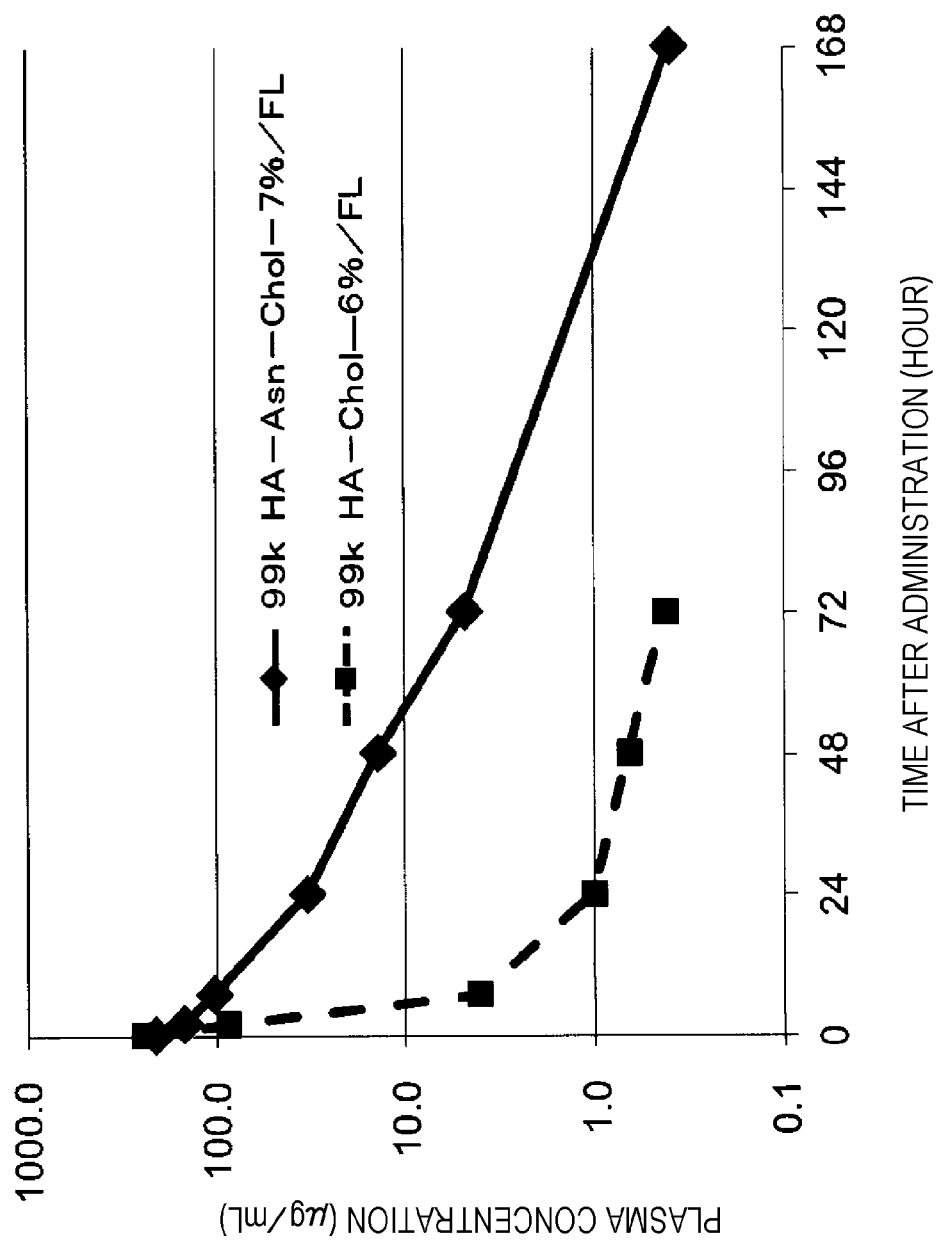

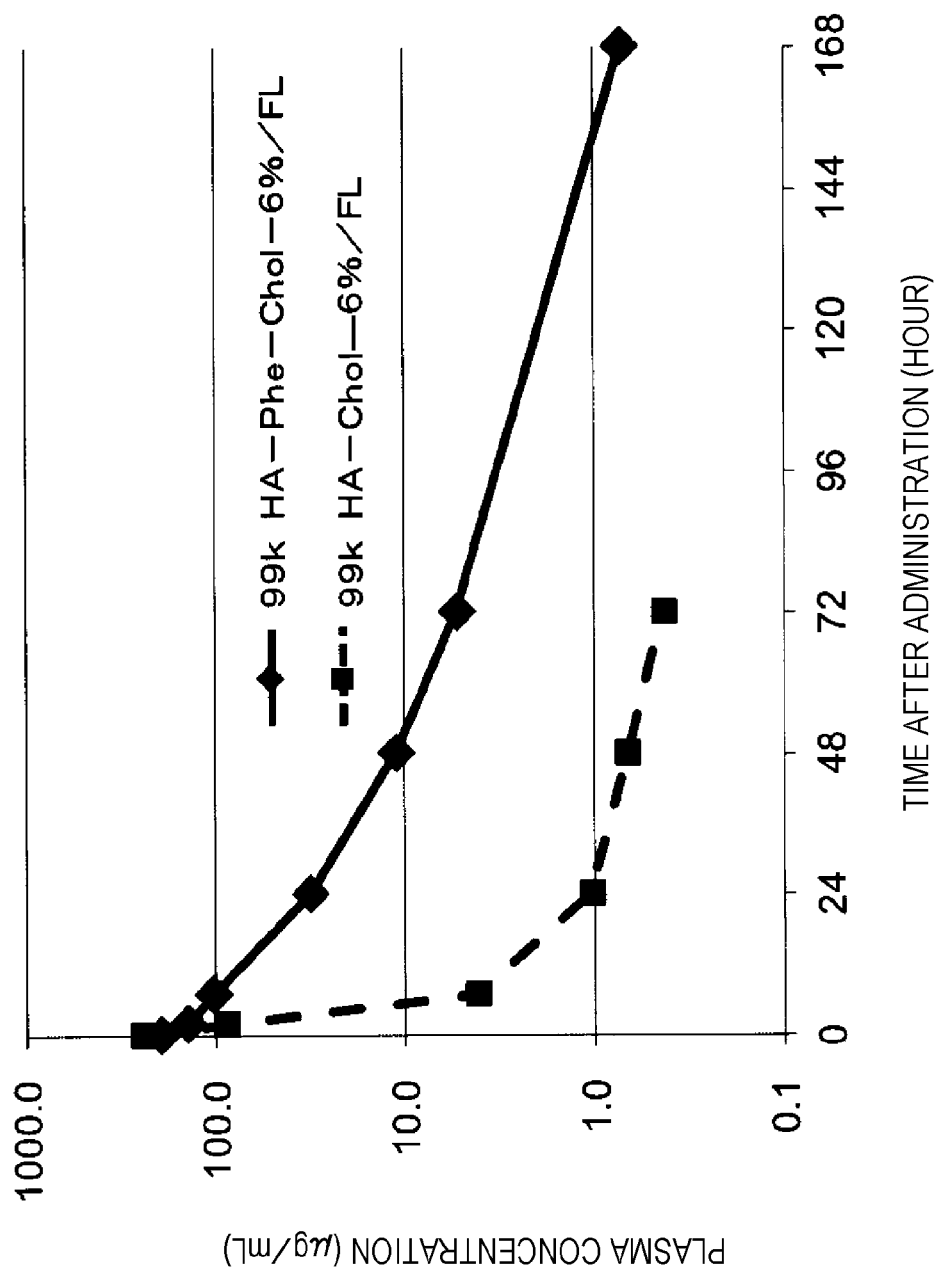

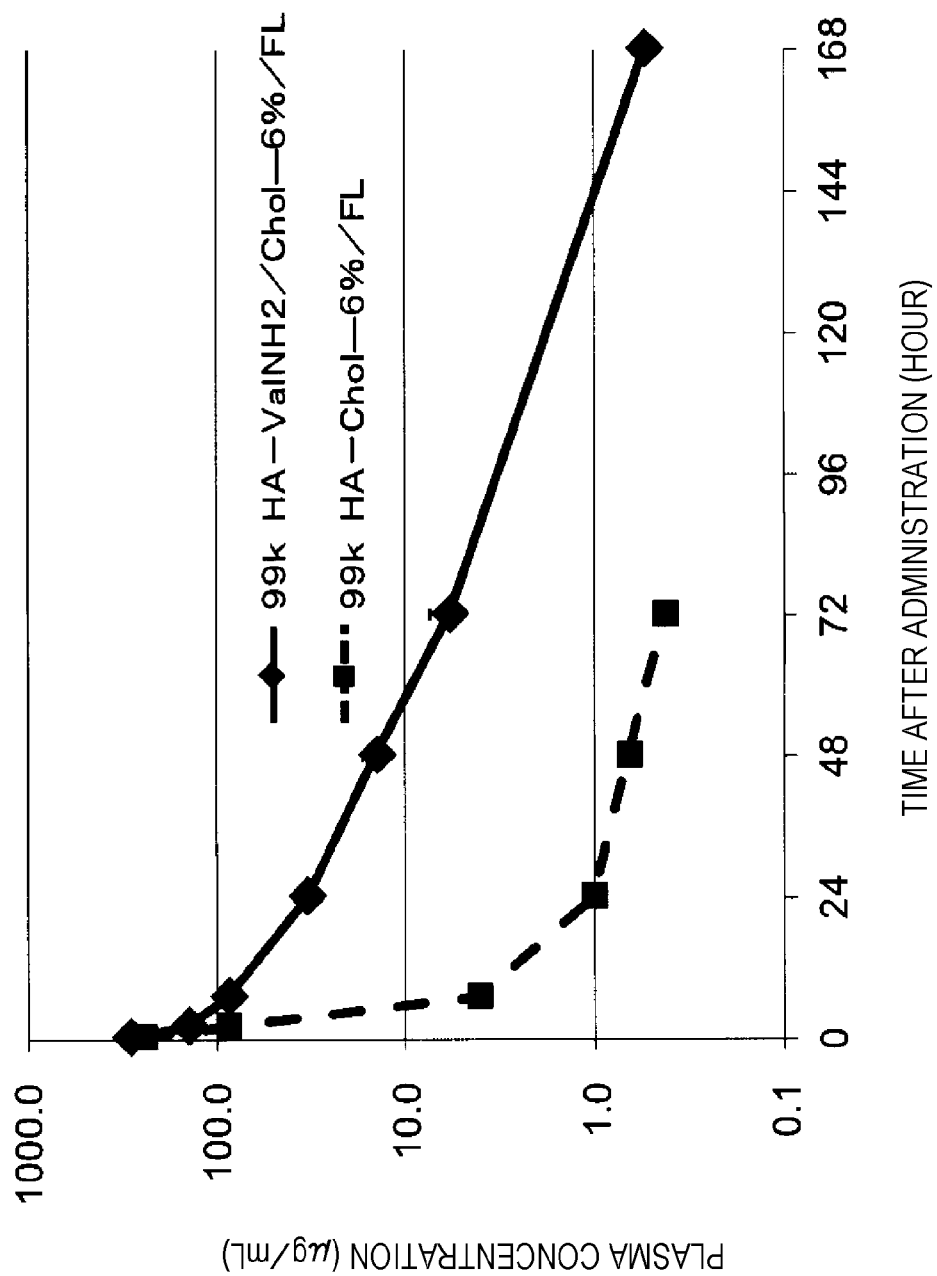

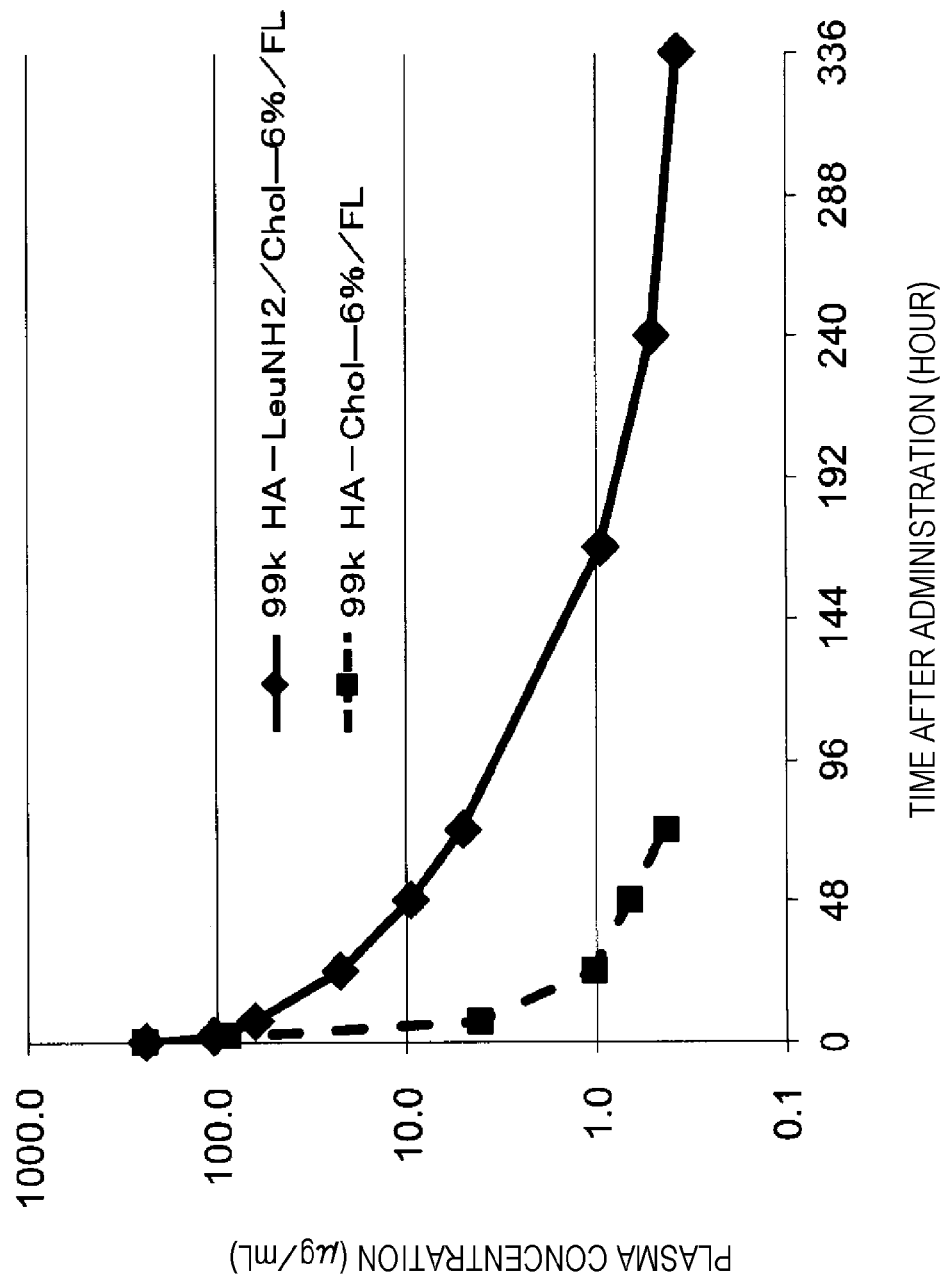

99k HA-Ala-Chol-30%/FL

50k HA-Ala-Chol-6%/FL

50k HA-Ala-Chol-22%/FL

50k HA-Ala-Chol-26%/FL

10k HA—Ala—Chol—16%/FL

99k HA—ThrNH$_2$/Chol—6%/FL

99k HA-Ser-Chol-6%/FL

99k HA-Gly-Chol-6%/FL

99k HA—Thr—Chol—6%/FL

99k HA—Asn—Chol—7%/FL

99k HA—Asp—Chol—6%/FL

99k HA—Ile—Chol—6%/FL

99k HA–Leu–Chol–6%/FL

99k HA–Val–Chol–6%/FL

99k HA−Phe−Chol−6%/FL

99k HA−ValNH$_2$/Chol−6%/FL

99k HA−GlyNH$_2$/Chol−6%/FL

99k HA−Ala/Chol−6%/FL

99k HA−Ser/Chol−6%/FL

HA−EDOBEA−Ac/FL

99k HA-Tyr-Chol-6%/FL

99k HA—AsnNH$_2$/Chol—6%/FL

99k HA—IleNH$_2$/Chol—6%/FL

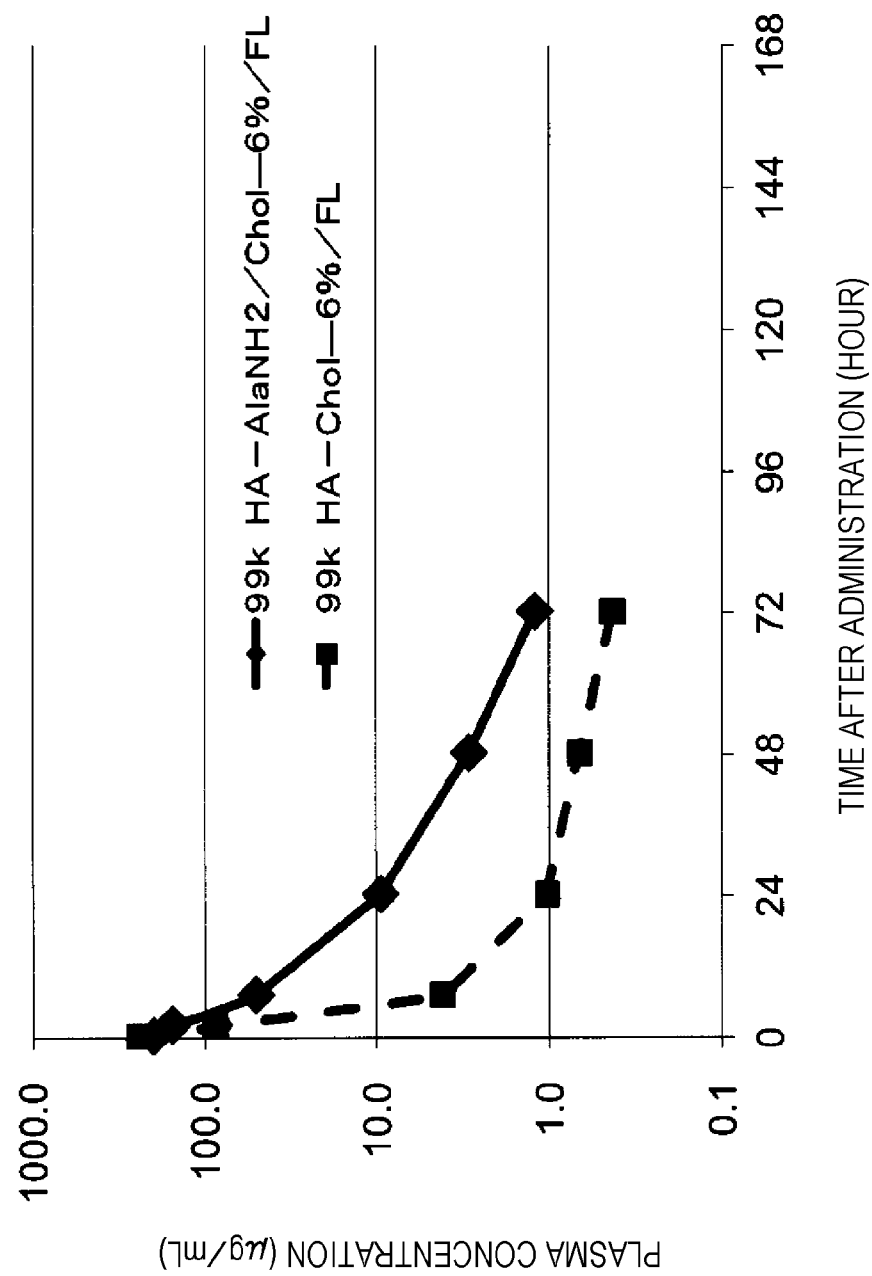

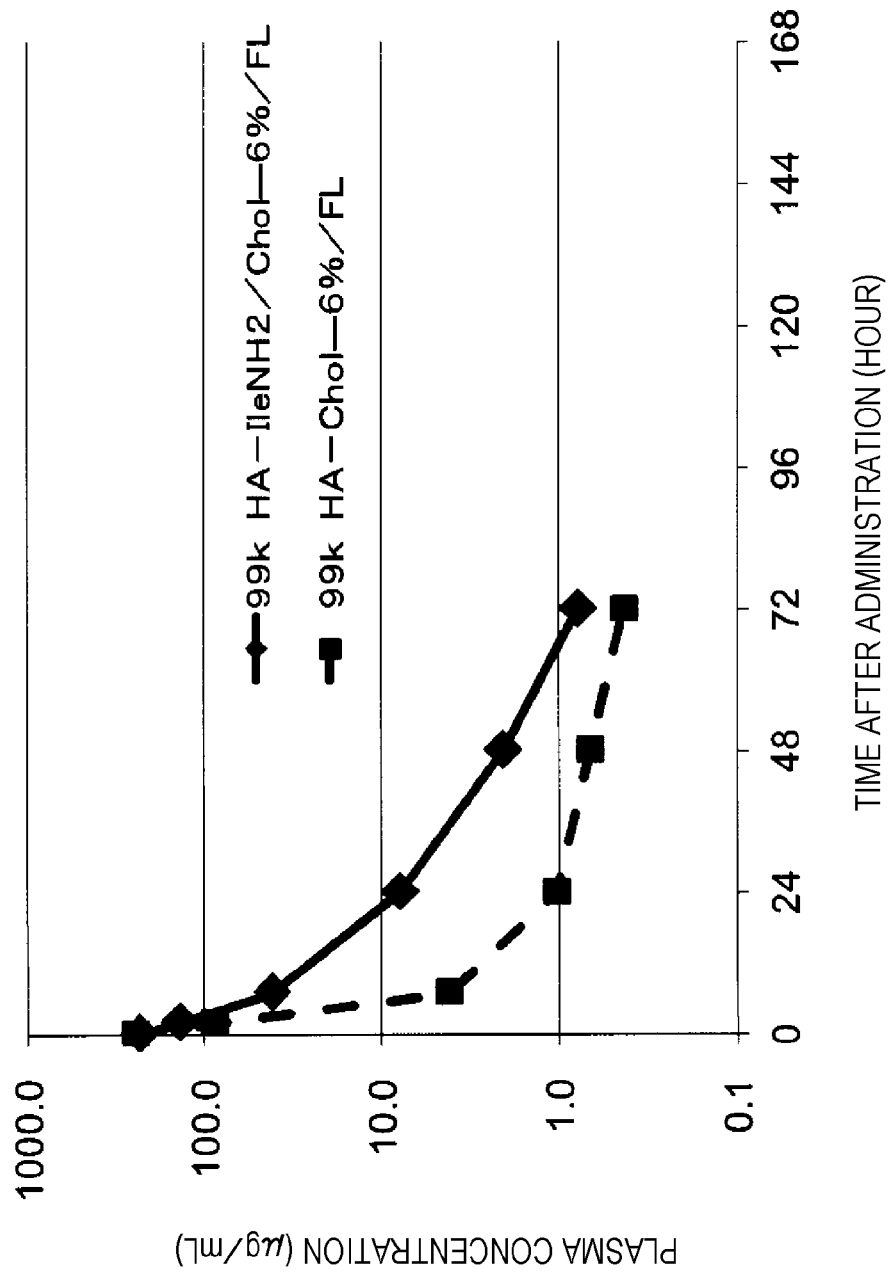

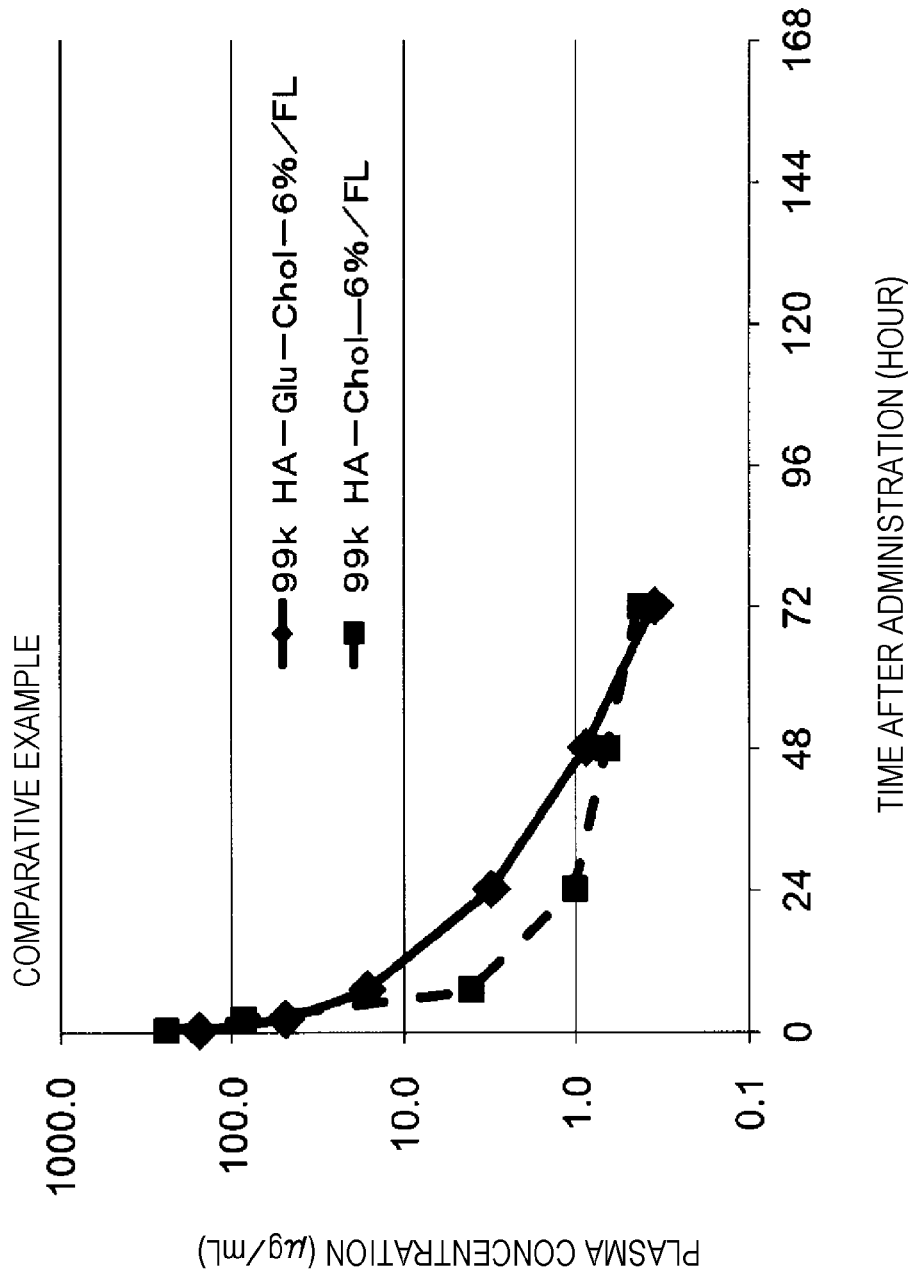

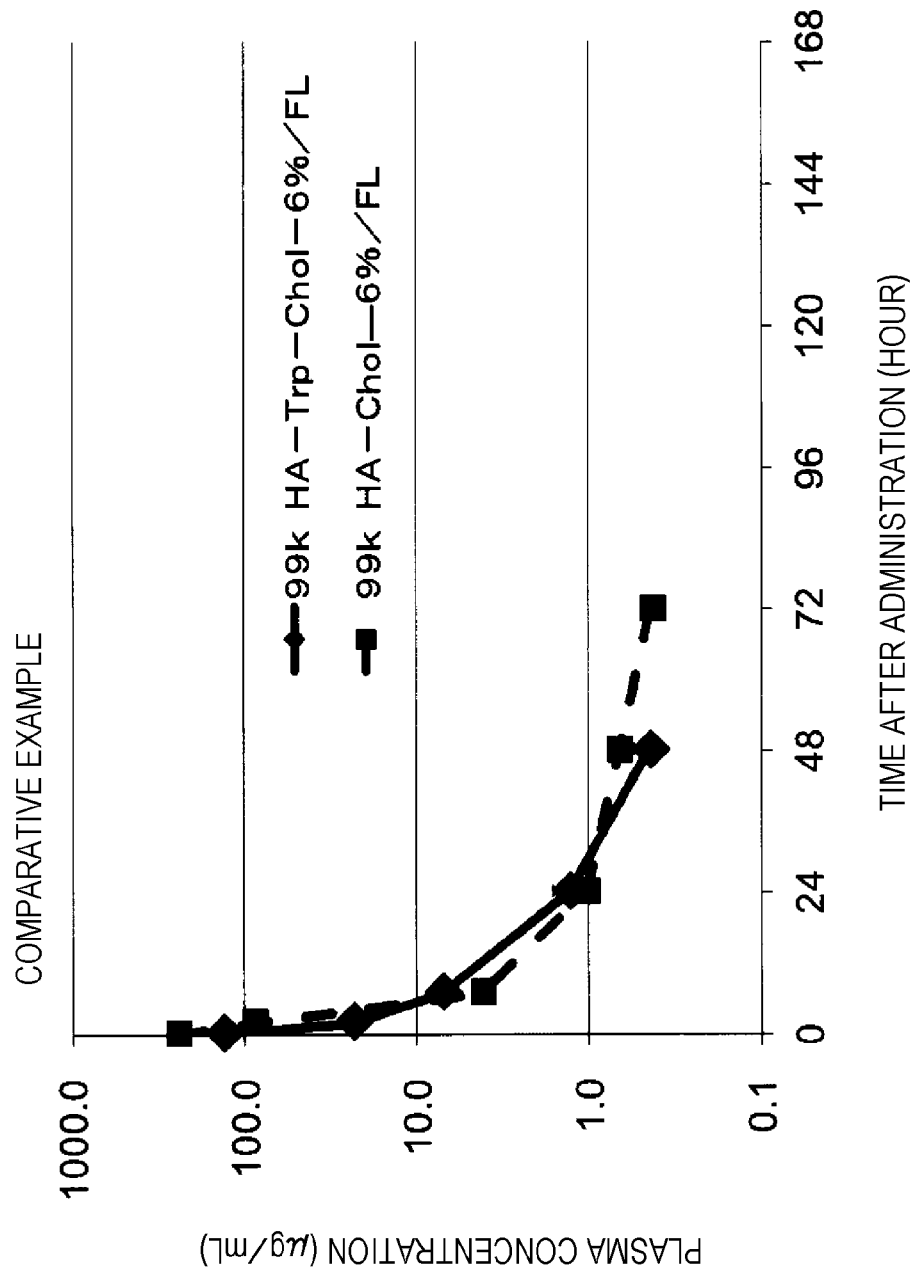

99k HA-Gln-Chol-6%/FL

99k HA-Met-Chol-6%/FL

99k HA−AlaNH$_2$/Chol−6%/FL

99k HA−AsnNH$_2$/Chol−6%/FL

99k HA−IleNH$_2$/Chol−6%/FL

99k HA−GlnNH$_2$/Chol−6%/FL

99k HA—MetNH$_2$/Chol—6%/FL

99k HA—Glu—Chol—6%/FL

99k HA-Trp-Chol-6%/FL

—— Liver sample
----- Standard

10k HA-Tyr-Chol-6%/FL

—— Liver sample
----- Standard

99k HA—Ala—$C_2$—Chol—6%

10k HA-Ala-$C_2$-Chol-7%

99k HA-Ala-$C_{12}$-Chol-7%

10k HA—Ala—$C_{12}$—Chol—7%

99k HA—Ala—$EO_2$—Chol—5%

10k HA—Ala—$EO_2$—Chol—6%

99k HA—Ala—CA—13%

HYALURONIC ACID DERIVATIVE HAVING AMINO ACID AND STERYL GROUP INTRODUCED THEREINTO

TECHNICAL FIELD

The present invention relates to hyaluronic acid derivatives that are modified with amino acids and have steryl groups introduced thereinto, complexes of the hyaluronic acid derivatives and drugs, and pharmaceutical compositions containing the hyaluronic acid derivatives and drugs.

BACKGROUND ART

Formulations containing proteins and peptides as active ingredients have been recently developed as a result of advancement of genetic recombination and chemical synthesis technologies, and the number of such formulations is increasing every year. However, proteins and peptides are not easily absorbed thorough the gastrointestinal tract, mucous membrane, etc. Furthermore, proteins and peptides are unstable in the body and have short halflives in the blood. Therefore, protein and peptide preparations need to be administered by frequent injections, which put a heavy burden on both patients and medical staff. There is a demand for a drug delivery system (DDS) matrix having a sustained release or targeting function for encapsulating a protein or a peptide without impairing its pharmacological activity. Further, in terms of administration efficiency, a matrix is preferred into which a maximal amount of protein and/or peptide can be encapsulated.

Pharmacological activities of proteins and peptides are known to be largely dependent on their conformations and impaired by degeneration and aggregation due to contact with an air interface or an organic solvent, or external conditions such as temperature, pressure, and pH. Denatured or aggregated protein is also known to increase risks, such as being antigenic, when administered into a body. For sustained release preparations containing a protein or a peptide as an active ingredient, the stability of the protein or the peptide needs to be ensured throughout the period from the formulation process, through the storage of the preparation, to the release of the active ingredient in the body after administration.

For low molecular weight drugs, issues concerning the stability of drugs are not big as compared with those for proteins and peptides, but there are yet strong needs for DDS matrices having a function of increasing the solubility of poorly soluble drugs, or a sustained release or targeting function.

In addition, matrices for pharmaceutical use have to be non-antigenic, non-mutagenic, non-toxic, and biodegradable for safety reasons.

Use of polysaccharides as matrices for pharmaceutical carriers has been recently reported. One of them, hyaluronic acid (HA) is a biomaterial (polysaccharide) which was isolated from the vitreous body in bull's eye by K. Meyer in 1934 and it has been known for a long time as a main component of the extracellular matrix. HA is a glycosaminoglycan composed of disaccharide units having D-glucuronic acid and N-acetylglucosamine connected by a β(1→3)glycosidic linkage. The structure of HA does not differ between species in the chemical and physical terms and humans also have a metabolic pathway for HA. Therefore, it is one of the safest biomaterials for medical use, also in terms of the immunity and toxicity.

Besides its properties as a safe material, properties of hyaluronic acid as a bioactive material in the induction of cell adhesion, proliferation, and motility have recently become a matter of interest. Furthermore, in terms of production, mass production of high molecular weight hyaluronic acid has become possible by using microorganisms. For these reasons, DDS studies on hyaluronic acid have been eagerly conducted. Conjugation of drug with hyaluronic acid has been reported to be successfully used in the drug targeting to cancerous tissue (PTL 1), the targeting to liver (PTL 2), and the reduction of anitigenecity (PTL 3). HA receptors, including CD44, RHAMM (Receptor for Hyaluronic Acid-Mediated Motility), LYVE-1 (Lymphe Vessel Endothelial HA Receptor-1), HARE (Hyaluronic acid Receptor for Endocytosis), have been reported to be present in the living body (NPL 7 and NPL 8). In particular, CD44 and RHAMM are overexpressed in many cancer cells. Therefore, attempts to use HA as a matrix of cancer targeting carrier have been made. Examples of such attempts include paclitaxel-HA conjugate (NPLs 9-11 and PTL 12), camptothecin-HA conjugate (PTL 13), doxorubicin-HPMA [N-(2-hydroxypropyl)methacrylamide]-HA conjugate (NPL 12), butyric acid-HA conjugate (NPL 13), doxorubicin containing HA-PEG-PLGA nanoparticle (NPL 14), siRNA-containing HA gel (NPL 15), and doxorubicin-containing HA-coated liposome (NPL 16). Furthermore, NPL 17 discloses a HA derivative conjugated with cholic acid via an ethylenediamine linker introduced by an amide linkage. These carriers containing HA as a matrix have been reported to be efficiently taken up in vitro by cells highly expressing CD44 (see, for example, NPL 9). However, HA systemically administered in vivo is known to be rapidly eliminated from the blood; immediately taken up via HARE receptors present on, for example, sinusoidal endothelial cells in the liver and metabolized (NPLs 18-20). This short retention time of hyaluronic acid in the blood is a disadvantage against its use for prolonged drug retention or as a DDS matrix for targeting. The receptors seem to recognize six consecutive sugar units in hyaluronic acid. Attempts were made to elongate the retention time in the blood by modifying carboxy (PTLs 4, 5, and 6).

Hyaluronic acid derivatives that have a longer retention time conferred by a high degree of modification of the carboxy in the glucuronic acid moiety in hyaluronic acid were developed and have been shown to be useful (PTL 7). In general, increasing the modification ratio of carboxy in the glucuronic acid moiety prolong the retention of the hyaluronic acid derivative in the blood. However, they do not show a linear correlation, but the retention abruptly changes at a certain threshold value.

Examples of the modification of carboxy in hyaluronic acid with amino acid include modifications with an ethyl ester of glycine by use of 4-(4,6-dimethoxy-1,3,5-triazine)-4-methylmorpholinium (hereinafter referred to as DMT-MM) as a condensation agent, which may be produced by, for example, reacting 2-chloro-4,6-dimethoxy-1,3,5-triazine in the presence of N-methylmorpholine, the modification ratio of which has been reported to be up to 20% (NPL 1). Examples in which a triazine-based compound is used as a condensation agent include hyaluronic acid modified with alanine, which have been reported to have an increased resistance to oxidative degradation and be potentially used as a viscous supplement (NPL 2). Modifications with other amino acids by similar methods have been reported (NPL 3, PTL 9). Examples include a preparation of water-insoluble biocompatible films, in which using 1-ethyl-3-(3-dimethylaminopropyl)carbodiimide hydrochloride (hereinafter referred to as EDC) as a condensation agent, hyaluronic acid is modified with methyl ester hydrochloride of leucine, methyl ester hydrochloride of valine, methyl ester hydrochloride of isoleucine, methyl ester hydrochloride of proline, methyl ester hydrochloride of phenylalanine, methyl ester hydrochloride of arginine, and methyl ester hydrochloride of histidine, and gel was made without deprotection; however, the modification ratio of which is not known (PTL 8). In addition, PTL 15, which was published after the priority date of the present application, discloses that a hyaluronic acid derivative obtained by modifying carboxy of hyaluronic acid with certain amino-carboxylic acid or an amide thereof has properties of both biodegradability and retention in the blood, and that it has an positive effect on the release of the drug from endosome to cytoplasm.

Further examples of drug carriers derived from polysaccharide include pullulan derivatives modified with a cholesteryl group, which has been reported to form nano-size fine particles in aqueous solution and function as host molecules that form complexes with hydrophobic low molecular weight molecules, peptides, and proteins (NPL 4). Thermodynamic analyses of the pullulan derivatives after protein uptake indicated that the taken-up protein is stabilized by hydrogen bonding with hydroxy groups of pullulan (NPL 5).

Further examples include carboxymethylcellulose (CMC; PTL 10) and chitosan modified with linoleic acid (NPL 6), which have been reported to be used as materials for making complexes with protein. In addition, PTL 11 discloses a composition containing a hyaluronic acid derivative having a crosslinking group and a hydrophilic polysaccharide derivative having a hydrophobic group, wherein the hyaluronic acid derivative having a crosslinking group is prepared by a crosslinking reaction of hyaluronic acid or a derivative thereof having a group capable of crosslinking in the presence of the hydrophilic polysaccharide derivative. PTL 14 discloses that a hyaluronic acid derivative into which a cholesteryl is introduced as a hydrophobic group forms fine particles by association and forms complexes with drugs in water.

CITATION LIST

Patent Literature

PTL 1: International publication No. 92/06714
PTL 2: Japanese Unexamined Patent Application Publication No. 2001-81103
PTL 3: Japanese Unexamined Patent Application Publication No. 2-273176
PTL 4: Japanese Unexamined Patent Application Publication No. 5-85942
PTL 5: International publication No. 01/05434
PTL 6: International publication No. 01/60412
PTL 7: International publication No. 2006/028110
PTL 8: International publication No. 92/20349
PTL 9: International publication No. 2011/148116
PTL 10: International Publication No. 2002/022154
PTL 11: International Publication No. 2008/136536
PTL 12: International Publication No. 2004/035629
PTL 13: International Publication No. 2009/074678
PTL 14: International Publication No. 2010/053140
PTL 15: International Publication No. 2012/118189

Non Patent Literature

NPL 1: Biomacromolecules, Vol. 8, p. 2190-2195, 2007
NPL 2: CARBOHYDRATE Polymers, Vol. 86, p. 747-752, 2011
NPL 3: CARBOHYDRATE Polymers, Vol. 87, p. 2211-2216, 2012
NPL 4: Macromolecules, Vol. 26, p. 3062-3068, 1993
NPL 5: Colloids and Surfaces, Vol. 112, p. 91-95, 1996
NPL 6: Carbohydrate Polymers, Vol. 62, p. 293-298, 2005
NPL 7: MOLECULAR PHARMACEUTICS, Vol. 5, p. 474-486, 2008
NPL 8: Journal of Drug Targeting, Vol. 16, p. 91-107, 2008
NPL 9: Bioconjugate Chem., Vol. 10, p. 755-763, 1999
NPL 10: Clinical Cancer Research, Vol. 14, p. 3598-3606, 2008
NPL 11: Bioconjugate Chem., Vol. 19, p. 1319-1325, 2008
NPL 12: Pharmaceutical Research, Vol. 19, p. 396-402, 2002
NPL 13: Clinical Cancer Research, Vol. 10, p. 4822-4830, 2004
NPL 14: Nanomedicine: Nanotechnology, Biology, and Medicine, Vol. 3, p. 246-257, 2007
NPL 15: Journal of Controlled Release, Vol. 119, p. 245-252, 2007
NPL 16: Neoplasia, Vol. 6, p. 343-353, 2004
NPL 17: Journal of Materials Chemistry, Vol. 19, p. 4102-4107, 2009
NPL 18: Cell and Tissue Research, Vol. 242, p. 505-510, 1985
NPL 19: THE JOURNAL OF BIOLOGICAL CHEMISTRY, Vol. 275, 37733-37741, 2000
NPL 20: The Biochemical Journal, Vol. 200, p. 415-424, 1981

SUMMARY OF INVENTION

Technical Problem

The retention of a hyaluronic acid derivative in the blood correlates with modification ratio of carboxy in its glucuronic acid moiety. But, it has been also found to change abruptly at a certain threshold value. Therefore, the retention of a hyaluronic acid derivative in the blood is difficult to keep within a desirable range merely by controlling the modification ratio of the carboxy. Accordingly, a simpler and more reliable way to control the retention in the blood is desired. In addition, reduction of hyaluronic acid recognition by hyaluronic acid receptors would make hyaluronic acid less susceptible to metabolism in the living body and decrease its biodegradability, an intrinsic property of hyaluronic acid. Therefore, a matrix having properties of both biodegradability (safety) and retention in the blood is desired.

An object of the invention is to provide a hyaluronic acid derivative having properties of both biodegradability and retention in the blood. Another object of the invention is to provide a complex of the hyaluronic acid derivative and a drug, and a pharmaceutical composition comprising the hyaluronic acid derivative, in particular, a complex of the hyaluronic acid derivative and the drug.

Solution to Problem

In the study aiming to achieve the objects, the present inventors found that a hyaluronic acid derivative obtained by further introduction of a steryl group into carboxy in the glucuronic acid moiety and/or carboxy in the amino acid moiety of the intermediate obtained by reacting carboxy in the glucuronic acid moiety of hyaluronic acid or a salt thereof with a certain amino acid or amino acid amide to convert the carboxy into amide has properties of biodegradability and retention in the blood and that a complex of the hyaluronic acid derivative and a drug has good properties as a pharmaceutical composition, thereby completing the present invention. Moreover, in the study, the present inventors found that derivatives with certain amino acid amides (those in which $R^a$ described later is $C_{1-6}$ alkyl substituted with aryl or heteroaryl, where the aryl is substituted with one or more hydroxy) such as tyrosinamide and tryptophanamide, which derivatives are modified with a steryl group, exhibit better dispersion in water in spite of the hydrophobicity of the steryl group, as compared to those without the steryl group introduction, thereby completing the present invention. Furthermore, the present inventors compared derivatives with phenylalaninamide (those in which $R^a$ described later is $C_{1-6}$ alkyl substituted with aryl, where the aryl is unsubstituted), which derivatives were further modified with a steryl group at an introduction ratio of 6% or less, with derivatives without phenylalaninamide, which derivatives were modified with a steryl group at an introduction ratio of 6% or less, and found that, while they were both dispersed in pure water, only the former was dispersed in saline and the latter aggregated to form precipitation and that the former is an excellent matrix for injections for sustained subcutaneous administration, thereby completing the present invention.

Accordingly, the present invention relates to hyaluronic acid derivatives having properties of both biodegradability and retention in the blood, to hyaluronic acid derivatives which exhibit better dispersion in water by introduction of a steryl group, and to complexes containing these hyaluronic acid derivatives and a compound having a pharmacological activity. Furthermore, the present invention relates to a method for producing the hyaluronic acid derivative and to a pharmaceutical composition containing a drug and the hyaluronic acid derivative and a method for producing the composition.

In an aspect of the present invention, hyaluronic acid derivatives according to the following (1) to (10) are provided.

(1) A hyaluronic acid derivative comprising a repeating unit represented by formula (I):

[Chemical Formula 1]

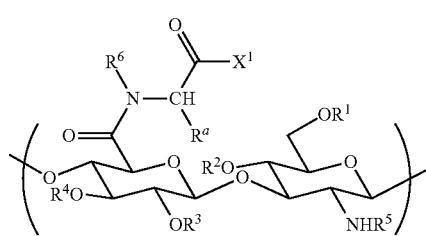

(I)

where $R^1$, $R^2$, $R^3$, and $R^4$ are independently selected from a hydrogen atom, $C_{1-6}$ alkyl, formyl, and $C_{1-6}$ alkylcarbonyl;
$R^5$ is a hydrogen atom, formyl, or $C_{1-6}$ alkylcarbonyl;
$X^1$ is hydroxy, $C_{1-6}$ alkoxy, $-O^-Q^+$, $-NR^7R^8$, or $-NR^9-Z^1-Z^2$;
$Q^+$ represents a counter cation;
$R^6$, $R^7$, $R^8$, and $R^9$ are independently selected from a hydrogen atom and $C_{1-6}$ alkyl;

$R^a$ is a hydrogen atom or $C_{1-6}$ alkyl, where the alkyls may be independently substituted by one or more groups selected from hydroxy, carboxy, carbamoyl, $C_{1-6}$ alkylthio, aryl, and heteroaryl, where the aryl may be substituted with one or more hydroxy groups;
$Z^1$ is $C_{2-30}$ alkylene or $-(CH_2CH_2O)_m-CH_2CH_2-$, where into the alkylene 1 to 5 groups independently selected from $-O-$, $-NR^g-$, and $-S-S-$ may be inserted, and $m$ is an integer selected from 1 to 100;
$Z^2$ is selected from groups represented by the following formulas:
$-NR^b-Z^3$,
$-NR^b-COO-Z^3$,
$-NR^b-CO-Z^3$,
$-NR^b-CO-NR^c-Z^3$,
$-COO-Z^3$,
$-CO-NR^c-Z^3$,
$-O-CO-NR^c-Z^3$,
$-O-COO-Z^c$,
$-S-Z^3$,
$-CO-Z^a-S-Z^3$,
$-O-CO-Z^b-S-Z^3$,
$-NR^b-CO-Z^b-S-Z^3$, and
$-S-S-Z^3$;

$R^b$ and $R^c$ are independently selected from a hydrogen atom, $C_{1-20}$ alkyl, amino $C_{2-20}$ alkyl, and hydroxy $C_{2-20}$ alkyl, where into the alkyl moieties of the groups 1 to 3 groups independently selected from $-O-$ and $-NR^f-$ may be inserted;

$R^f$ is independently selected from a hydrogen atom, $C_{1-12}$ alkyl, amino $C_{2-12}$ alkyl, and hydroxy $C_{2-12}$ alkyl, and into the alkyl moieties of the groups 1 to 2 groups independently selected from $-O-$ and $-NH-$ may be inserted;

$R^g$ is independently selected from a hydrogen atom, $C_{1-20}$ alkyl, amino $C_{2-20}$ alkyl, or hydroxy $C_{2-20}$ alkyl, and into the alkyl moieties of the groups 1 to 3 groups independently selected from $-O-$ and $-NH-$ may be inserted;

$Z^3$ is a steryl group;
$Z^a$ is $C_{1-5}$ alkylene; and
$Z^b$ is $C_{2-8}$ alkylene or $C_{2-8}$ alkenylene; and wherein if the hyaluronic acid derivative comprises no repeating units represented by formula (I), in which $X^1$ is $-NR^9-Z^1-Z^2$, then the hyaluronic acid derivative further comprises a repeating unit represented by formula (II):

[Chemical Formula 2]

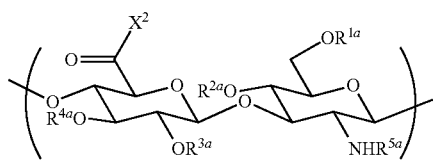

(II)

where $R^{1a}$, $R^{2a}$, $R^{3a}$, and $R^{4a}$ are independently selected from a hydrogen atom, $C_{1-6}$ alkyl, formyl, and $C_{1-6}$ alkylcarbonyl;

$R^{5a}$ is a hydrogen atom, formyl, or $C_{1-6}$ alkylcarbonyl; and $X^2$ is $-NR^9-Z^1-Z^2$, where $R^9$, $Z^1$, and $Z^2$ are as defined above.

(2) The hyaluronic acid derivative according to the above (1), further comprising a repeating unit represented by formula (IIb):

[Chemical Formula 3]

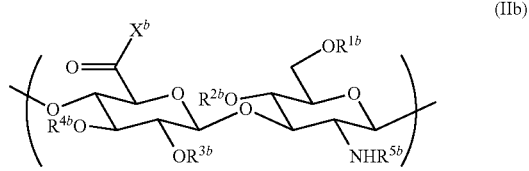

(IIb)

where $R^{1b}$, $R^{2b}$, $R^{3b}$, and $R^{4b}$ are independently selected from a hydrogen atom, $C_{1-6}$ alkyl, formyl, and $C_{1-6}$ alkylcarbonyl;
$R^{5b}$ is selected from a hydrogen atom, formyl, and $C_{1-6}$ alkylcarbonyl; and
$X^b$ is selected from hydroxy and $-O^-Q^+$, where $Q^+$ represents a counter cation.

(3) The hyaluronic acid derivative according to the above (1) or (2), wherein $X^1$ is $-NR^9-Z^1-Z^2$ in formula (I).

(4) The hyaluronic acid derivative according to any of the above (1) to (3), wherein a percentage of the disaccharide unit represented by formula (I) in existing disaccharide repeating units is 70 to 100%.

(5) The hyaluronic acid derivative according to any of the above (1) to (4), wherein a percentage of the disaccharide unit comprising the group $-NR^9-Z^1-Z^2$ in existing disaccharide repeating units is 3 to 50%.

(6) The hyaluronic acid derivative according to the above (1) or (2), comprising no repeating unit represented by formula (I), wherein $X^1$ is $-NR^9-Z^1-Z^2$.

(7) The hyaluronic acid derivative according to any of (1), (2), and (6), wherein a sum of percentages of the repeating unit represented by (I) and the repeating unit represented by formula (II) in existing disaccharide repeating units is 70 to 100%.

(8) The hyaluronic acid derivative according to any of the above (1) to (7), wherein the hyaluronic acid derivative is produced by using hyaluronic acid exclusively consisting of the disaccharide unit represented by formula (IIb) according to (2), and has a weight average molecular weight of 3 kilo Daltons to 1,500 kilo Daltons when $R^{1b}$, $R^{2b}$, $R^{3b}$, and $R^{4b}$ are all hydrogen atoms, $R^{5b}$ is acetyl, and $X^b$ is $-O^-Na^+$.

(9) The hyaluronic acid derivative according to any of (1) to (8), wherein $Z^1$ is $C_{2-10}$ alkylene, $Z^2$ is $-NH-COO-Z^3$, and $Z^3$ is a cholesteryl group.

(10) The hyaluronic acid derivative according to any of the above (1) to (9), wherein the hyaluronic acid derivative is obtained by reacting a hyaluronic acid derivative comprising a repeating unit represented by formula (IIb) and a repeating unit represented by formula (Ia),

[Chemical Formula 4]

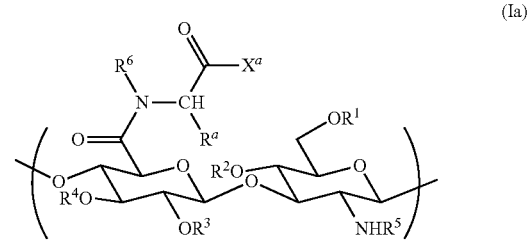

(Ia)

where $X^a$ is selected from hydroxy, $-O^-Q^+$, $C_{1-6}$ alkoxy, and $-NR^1R^8$ and $R^1$, $R^2$, $R^3$, $R^4$, $R^5$, $R^6$, $R^7$, $R^8$, $Q^+$, and $R^a$ are as defined in the above (1), with a compound represented by formula $HNR^9-Z^1-Z^2$, where $R^9$, $Z^1$, and $Z^2$ are as defined in the above (1).

In another aspect of the present invention, pharmaceutical compositions according to the following (11) and (12) are provided.

(11) A pharmaceutical composition comprising the hyaluronic acid derivative according to any of the above (1) to (10) and a drug.

(12) The pharmaceutical composition according to the above (11), wherein the drug is held by forming a complex with the hyaluronic acid derivative.

In yet another aspect of the present invention, a hyaluronic acid derivative-drug complex, wherein the drug is held in the hyaluronic acid derivative according to any of the above (1) to (10) is provided. Preferably, a hyaluronic acid derivative-drug complex, wherein the hyaluronic acid derivative forms fine particles by association in water and holds the drug is provided.

Furthermore, in another aspect of the present invention, a biodegradable drug carrier comprising the hyaluronic acid derivative according to any of the (1) to (10) is provided.

Furthermore, in another aspect of the present invention, a method for administering a drug, comprising administering a therapeutically efficient amount of a drug with the hyaluronic acid derivative according to any of the above (1) to (10) is provided.

The aryl (optionally substituted with one or more hydroxy) in $R^a$ is preferably unsubstituted if $X^1$ is hydroxy, $-O^-Q^+$ or $-NR^9-Z^1-Z^2$.

Advantageous Effects of Invention

By using a hyaluronic acid derivative of the present invention, a sustained release preparation containing a large amount of a drug, in particular, a low molecular weight compound or a protein or a peptide having an efficacy while maintaining its bioactivities can be provided. In addition, hyaluronic acid derivatives are excellent in terms of the safety and have especially excellent properties as a carrier for pharmaceutical preparations and as a matrix for injections for sustained subcutaneous administration in terms of both the retention of drug in the blood and the biodegradability. In addition, pharmacokinetics of preparations produced with the derivatives can be controlled by regulating the modification degree of carboxy, i.e. the percentage of the introduction of the group $-NR^9-Z^1-Z^2$ and/or amino acid (including amino acid amide), in the hyaluronic acid derivatives of the present invention.

BRIEF DESCRIPTION OF DRAWINGS

FIG. 1-2 illustrates an example of $^1$H-NMR spectra (solvent: $D_2O$) of TBA salt of hyaluronic acid (HA-TBA) produced from the starting material 99 kDa HA-Na prepared in Example 1-3.

FIG. 1-3 illustrates an example of $^1$H-NMR spectra of HA-Ala produced from the starting material 99 kDa HA-Na prepared in Example 1-4.

FIG. 1-4 illustrates an example of $^1$H-NMR spectra of HA-Ala-Chol/FL produced from the starting material 99 kDa HA-Na prepared in Example 1-4 (introduction ratio of cholesteryl group: 7%).

FIG. 1-5 illustrates an example of $^1$H-NMR spectra of HA-ThrNH$_2$/Chol/FL produced from the starting material 99 kDa HA-Na prepared in Example 1-5 (introduction ratio of cholesteryl group: 6%).

FIG. 1-6 illustrates an example of $^1$H-NMR spectra of HA-Ser-OEt prepared in Example 1-6.

FIG. 1-7 illustrates an example of $^1$H-NMR spectra of HA-Ser prepared in Example 1-6.

FIG. 1-8 illustrates an example of $^1$H-NMR spectra of HA-Ser-Chol/FL prepared in Example 1-6 (introduction ratio of cholesteryl group: 6%).

FIG. 1-9 illustrates an example of $^1$H-NMR spectra of HA-Gly-OEt prepared in Example 1-7.

FIG. 1-10 illustrates an example of $^1$H-NMR spectra of HA-Gly prepared in Example 1-7.

FIG. 1-11 illustrates an example of $^1$H-NMR spectra of HA-Gly-Chol/FL prepared in Example 1-7 (introduction ratio of cholesteryl group: 6%).

FIG. 1-12 illustrates an example of $^1$H-NMR spectra of HA-Thr prepared in Example 1-8.

FIG. 1-13 illustrates an example of $^1$H-NMR spectra of HA-Thr-Chol/FL prepared in Example 1-8 (introduction ratio of cholesteryl group: 6%).

FIG. 1-14 illustrates an example of $^1$H-NMR spectra of HA-Asn prepared in Example 1-9.

FIG. 1-15 illustrates an example of $^1$H-NMR spectra of HA-Asn-Chol/FL prepared in Example 1-9 (introduction ratio of cholesteryl group: 7%).

FIG. 1-16 illustrates an example of $^1$H-NMR spectra of HA-Asp prepared in Example 1-10.

FIG. 1-17 illustrates an example of $^1$H-NMR spectra of HA-Asp-Chol/FL prepared in Example 1-10 (introduction ratio of cholesteryl group: 6%).

FIG. 1-18 illustrates an example of $^1$H-NMR spectra of HA-Ile prepared in Example 1-11.

FIG. 1-19 illustrates an example of $^1$H-NMR spectra of HA-Ile-Chol/FL prepared in Example 1-11 (introduction ratio of cholesteryl group: 6%).

FIG. 1-20 illustrates an example of $^1$H-NMR spectra of HA-Leu prepared in Example 1-12.

FIG. 1-21 illustrates an example of $^1$H-NMR spectra of HA-Leu-Chol/FL prepared in Example 1-12 (introduction ratio of cholesteryl group: 6%).

FIG. 1-22 illustrates an example of $^1$H-NMR spectra of HA-Val prepared in Example 1-13.

FIG. 1-23 illustrates an example of $^1$H-NMR spectra of HA-Val-Chol/FL prepared in Example 1-13 (introduction ratio of cholesteryl group: 6%).

FIG. 1-24 illustrates an example of $^1$H-NMR spectra of HA-Phe prepared in Example 1-14.

FIG. 1-25 illustrates an example of $^1$H-NMR spectra of HA-Phe-Chol/FL prepared in Example 1-14 (introduction ratio of cholesteryl group: 6%).

FIG. 1-26 illustrates an example of $^1$H-NMR spectra (solvent: 0.02 N DCl DMSO-d$_6$/D$_2$O mixed solution) of HA-SerNH$_2$/Chol/FL prepared in Example 1-15 (introduction ratio of cholesteryl group: 6%).

FIG. 1-27 illustrates an example of $^1$H-NMR spectra (solvent: D$_2$O) of HA-SerNH$_2$/Chol/FL prepared in Example 1-15 (introduction ratio of cholesteryl group: 6%).

FIG. 1-28 illustrates an example of $^1$H-NMR spectra (solvent: 0.02 N DCl DMSO-d$_6$/D$_2$O mixed solution) of HA-GlyNH$_2$/Chol/FL prepared in Example 1-16 (introduction ratio of cholesteryl group: 6%).

FIG. 1-29 illustrates an example of $^1$H-NMR spectra (solvent: D$_2$O) of HA-GlyNH$_2$/Chol/FL prepared in Example 1-16 (introduction ratio of cholesteryl group: 6%).

FIG. 1-30 illustrates an example of $^1$H-NMR spectra of HA-LeuNH$_2$/Chol/FL prepared in Example 1-17 (introduction ratio of cholesteryl group: 6%).

FIG. 1-31 illustrates an example of $^1$H-NMR spectra of HA-ValNH$_2$/Chol/FL prepared in Example 1-18 (introduction ratio of cholesteryl group: 6%).

FIG. 1-32 illustrates an example of $^1$H-NMR spectra of HA-Ala/Chol/FL prepared in Example 1-19 (introduction ratio of cholesteryl group: 6%).

FIG. 1-33 illustrates an example of $^1$H-NMR spectra of HA-Ser-OEt/Chol/FL prepared in Example 1-20.

FIG. 1-34 illustrates an example of $^1$H-NMR spectra of HA-Ser/Chol/FL prepared in Example 1-20 (introduction ratio of cholesteryl group: 6%).

FIG. 1-35 illustrates an example of $^1$H-NMR spectra of HA-Chol/FL prepared in Comparative Example 1-1 (introduction ratio of cholesteryl group: 6%).

FIG. 1-36 illustrates an example of $^1$H-NMR spectra of HA-EDOBEA prepared in Comparative Example 1-2.

FIG. 1-37 illustrates an example of $^1$H-NMR spectra of HA-EDOBEA-Ac/FL prepared in Comparative Example 1-2.

FIG. 1-38 illustrates an example of $^1$H-NMR spectra of HA-Tyr prepared in Comparative Example 1-3.

FIG. 1-39 illustrates an example of $^1$H-NMR spectra of HA-Tyr-Chol/FL prepared in Comparative Example 1-3 (introduction ratio of cholesteryl group: 6%).

FIG. 2-1-1 is a graph illustrating changes of plasma concentrations of 99 k HA-Ala-Chol-7%/FL (Table 9: sample 2-1) and 99 k HA-Chol-6%/FL (Table 9: comparative sample 2-1) (Example 2-2).

FIG. 2-1-2 is a graph illustrating changes of plasma concentrations of 99 k HA-Ala-Chol-24%/FL (Table 9: sample 2-2) and 99 k HA-Chol-24%/FL (Table 9: comparative sample 2-2) (Example 2-2).

FIG. 2-1-3 is a graph illustrating changes of plasma concentrations of 99 k HA-Ala-Chol-30%/FL (Table 9: sample 2-3) and 99 k HA-Chol-25%/FL (Table 9: comparative sample 2-3) (Example 2-2).

FIG. 2-1-4 is a graph illustrating changes of plasma concentrations of 50 k HA-Ala-Chol-6%/FL (Table 9: sample 2-4) and 50 k HA-Chol-6%/FL (Table 9: comparative sample 2-4) (Example 2-2)

FIG. 2-1-5 is a graph illustrating changes of plasma concentrations of 50 k HA-Ala-Chol-22%/FL (Table 9: sample 2-5) and 50 k HA-Chol-20%/FL (Table 9: comparative sample 2-5) (Example 2-2).

FIG. 2-1-6 is a graph illustrating changes of plasma concentrations of 50 k HA-Ala-Chol-26%/FL (Table 9: sample 2-6) and 50 k HA-Chol-27%/FL (Table 9: comparative sample 2-6) (Example 2-2)

FIG. 2-1-7 is a graph illustrating changes of plasma concentrations of 10 k HA-Ala-Chol-16%/FL (Table 9: sample 2-7) and 10 k HA-Chol-15%/FL (Table 9: comparative sample 2-7) (Example 2-2)

FIG. 2-1-8 is a graph illustrating changes of plasma concentrations of 99 k HA-ThrNH$_2$/Chol-6%/FL (Table 9: sample 2-8) and 99 k HA-Chol-6%/FL (Table 9: comparative sample 2-1) (Example 2-2)

FIG. 2-1-9 is a graph illustrating changes of plasma concentrations of 99 k HA-ThrNH$_2$/Chol-24%/FL (Table 9: sample 2-9) and 99 k HA-Chol-24%/FL (Table 9: comparative sample 2-2) (Example 2-2)

FIG. 2-1-10 is a graph illustrating changes of plasma concentrations of 99 k HA-ThrNH$_2$/Chol-31%/FL (Table 9: sample 2-10) and 99 k HA-Chol-25%/FL (Table 9: comparative sample 2-3) (Example 2-2)

FIG. 2-1-11 is a graph illustrating changes of plasma concentrations of 99 k HA-Ser-Chol-6%/FL (Table 9: sample 2-11) and 99 k HA-Chol-6%/FL (Table 9: comparative sample 2-1) (Example 2-2)

FIG. 2-1-12 is a graph illustrating changes of plasma concentrations of 99 k HA-Gly-Chol-6%/FL (Table 9: sample 2-12) and 99 k HA-Chol-6%/FL (Table 9: comparative sample 2-1) (Example 2-2)

FIG. 2-1-13 is a graph illustrating changes of plasma concentrations of 99 k HA-Thr-Chol-6%/FL (Table 9: sample 2-13) and 99 k HA-Chol-6%/FL (Table 9: comparative sample 2-1) (Example 2-2)

FIG. 2-1-14 is a graph illustrating changes of plasma concentrations of 99 k HA-Asn-Chol-7%/FL (Table 9: sample 2-14) and 99 k HA-Chol-6%/FL (Table 9: comparative sample 2-1) (Example 2-2)

FIG. 2-1-15 is a graph illustrating changes of plasma concentrations of 99 k HA-Asp-Chol-6%/FL (Table 9: sample 2-15) and 99 k HA-Chol-6%/FL (Table 9: comparative sample 2-1) (Example 2-2)

FIG. 2-1-16 is a graph illustrating changes of plasma concentrations of 99 k HA-Ile-Chol-6%/FL (Table 9: sample 2-16) and 99 k HA-Chol-6%/FL (Table 9: comparative sample 2-1) (Example 2-2)

FIG. 2-1-17 is a graph illustrating changes of plasma concentrations of 99 k HA-Leu-Chol-6%/FL (Table 9: sample 2-17) and 99 k HA-Chol-6%/FL (Table 9: comparative sample 2-1) (Example 2-2).

FIG. 2-1-18 is a graph illustrating changes of plasma concentrations of 99 k HA-Val-Chol-6%/FL (Table 9: sample 2-18) and 99 k HA-Chol-6%/FL (Table 9: comparative sample 2-1) (Example 2-2)

FIG. 2-1-19 is a graph illustrating changes of plasma concentrations of 99 k HA-Phe-Chol-6%/FL (Table 9: sample 2-19) and 99 k HA-Chol-6%/FL (Table 9: comparative sample 2-1) (Example 2-2)

FIG. 2-1-20 is a graph illustrating changes of plasma concentrations of 99 k HA-ValNH$_2$/Chol-6%/FL (Table 9: sample 2-20) and 99 k HA-Chol-6%/FL (Table 9: comparative sample 2-1) (Example 2-2)

FIG. 2-1-21 is a graph illustrating changes of plasma concentrations of 99 k HA-SerNH$_2$/Chol-6%/FL (Table 9: sample 2-21) and 99 k HA-Chol-6%/FL (Table 9: comparative sample 2-1) (Example 2-2)

FIG. 2-1-22 is a graph illustrating changes of plasma concentrations of 99 k HA-LeuNH$_2$/Chol-6%/FL (Table 9: sample 2-22) and 99 k HA-Chol-6%/FL (Table 9: comparative sample 2-1) (Example 2-2)

FIG. 2-1-23 is a graph illustrating changes of plasma concentrations of 99 k HA-GlyNH$_2$/Chol-6%/FL (Table 9: sample 2-23) and 99 k HA-Chol-6%/FL (Table 9: comparative sample 2-1) (Example 2-2)

FIG. 2-1-24 is a graph illustrating changes of plasma concentrations of 99 k HA-Ala/Chol-6%/FL (Table 9: sample 2-24) and 99 k HA-Chol-6%/FL (Table 9: comparative sample 2-1) (Example 2-2).

FIG. 2-1-25 is a graph illustrating changes of plasma concentrations of 99 k HA-Ser/Chol-6%/FL (Table 9: sample 2-25) and 99 k HA-Chol-6%/FL (Table 9: comparative sample 2-1) (Example 2-2).

FIG. 2-1-26 is a graph illustrating changes of plasma concentrations of 99 k HA-Tyr-Chol-6%/FL (Table 9: comparative sample 2-8) and 99 k HA-Chol-6%/FL (Table 9: comparative sample 2-1) (Example 2-2).

FIG. 2-2-1 illustrates a size exclusion chromatography analysis of 99 k HA-Ala-Chol-7%/FL (Table 9: sample 2-1) and a liver sample of a mouse having received the sample, which indicates metabolism of the administered sample in the murine liver (Example 2-3).

FIG. 2-2-2 illustrates a size exclusion chromatography analysis of 99 k HA-Ala-Chol-24%/FL (Table 9: sample 2-2) and a liver sample of a mouse having received the sample, which indicates metabolism of the administered sample in the murine liver (Example 2-3).

FIG. 2-2-3 illustrates a size exclusion chromatography analysis of 99 k HA-Ala-Chol-30%/FL (Table 9: sample 2-3) and a liver sample of a mouse having received the sample, which indicates metabolism of the administered sample in the murine liver (Example 2-3).

FIG. 2-2-4 illustrates a size exclusion chromatography analysis of 50K HA-Ala-Chol-6%/FL (Table 9: sample 2-4) and a liver sample of a mouse having received the sample, which indicates metabolism of the administered sample in the murine liver (Example 2-3)

FIG. 2-2-5 illustrates a size exclusion chromatography analysis of 50K HA-Ala-Chol-22%/FL (Table 9: sample 2-5) and a liver sample of a mouse having received the sample, which indicates metabolism of the administered sample in the murine liver (Example 2-3)

FIG. 2-2-6 illustrates a size exclusion chromatography analysis of 50K HA-Ala-Chol-26%/FL (Table 9: sample 2-6) and a liver sample of a mouse having received the sample, which indicates metabolism of the administered sample in the murine liver (Example 2-3)

FIG. 2-2-7 illustrates a size exclusion chromatography analysis of 10 k HA-Ala-Chol-16%/FL (Table 9: sample 2-7) and a liver sample of a mouse having received the sample, which indicates metabolism of the administered sample in the murine liver (Example 2-3)

FIG. 2-2-8 illustrates a size exclusion chromatography analysis of 99 k HA-ThrNH$_2$/Chol-6%/FL (Table 9: sample 2-8) and a liver sample of a mouse having received the sample, which indicates metabolism of the administered sample in the murine liver (Example 2-3)

FIG. 2-2-9 illustrates a size exclusion chromatography analysis of 99 k HA-ThrNH$_2$/Chol-24%/FL (Table 9: sample 2-9) and a liver sample of a mouse having received the sample, which indicates metabolism of the administered sample in the murine liver (Example 2-3).

FIG. 2-2-10 illustrates a size exclusion chromatography analysis of 99 k HA-ThrNH$_2$/Chol-31%/FL (Table 9: sample 2-10) and a liver sample of a mouse having received the sample, which indicates metabolism of the administered sample in the murine liver (Example 2-3).

FIG. 2-2-11 illustrates a size exclusion chromatography analysis of 99 k HA-Ser-Chol-6%/FL (Table 9: sample 2-11) and a liver sample of a mouse having received the sample, which indicates metabolism of the administered sample in the murine liver (Example 2-3).

FIG. 2-2-12 illustrates a size exclusion chromatography analysis of 99 k HA-Gly-Chol-6%/FL (Table 9: sample 2-12) and a liver sample of a mouse having received the sample, which indicates metabolism of the administered sample in the murine liver (Example 2-3).

FIG. 2-2-13 illustrates a size exclusion chromatography analysis of 99 k HA-Thr-Chol-6%/FL (Table 9: sample 2-13) and a liver sample of a mouse having received the sample, which indicates metabolism of the administered sample in the murine liver (Example 2-3).

FIG. 2-2-14 illustrates a size exclusion chromatography analysis of 99 k HA-Asn-Chol-7%/FL (Table 9: sample 2-14) and a liver sample of a mouse having received the sample, which indicates metabolism of the administered sample in the murine liver (Example 2-3).

FIG. 2-2-15 illustrates a size exclusion chromatography analysis of 99 k HA-Asp-Chol-6%/FL (Table 9: sample 2-15) and a liver sample of a mouse having received the sample, which indicates metabolism of the administered sample in the murine liver (Example 2-3).

FIG. 2-2-16 illustrates a size exclusion chromatography analysis of 99 k HA-Ile-Chol-6%/FL (Table 9: sample 2-16) and a liver sample of a mouse having received the sample, which indicates metabolism of the administered sample in the murine liver (Example 2-3).

FIG. 2-2-17 illustrates a size exclusion chromatography analysis of 99 k HA-Leu-Chol-6%/FL (Table 9: sample 2-17) and a liver sample of a mouse having received the sample, which indicates metabolism of the administered sample in the murine liver (Example 2-3).

FIG. 2-2-18 illustrates a size exclusion chromatography analysis of 99 k HA-Val-Chol-6%/FL (Table 9: sample 2-18) and a liver sample of a mouse having received the sample, which indicates metabolism of the administered sample in the murine liver (Example 2-3).

FIG. 2-2-19 illustrates a size exclusion chromatography analysis of 99 k HA-Phe-Chol-6%/FL (Table 9: sample 2-19) and a liver sample of a mouse having received the sample, which indicates metabolism of the administered sample in the murine liver (Example 2-3).

FIG. 2-2-20 illustrates a size exclusion chromatography analysis of 99 k HA-ValNH$_2$/Chol-6%/FL (Table 9: sample 2-20) and a liver sample of a mouse having received the sample, which indicates metabolism of the administered sample in the murine liver (Example 2-3)

FIG. 2-2-21 illustrates a size exclusion chromatography analysis of 99 k HA-SerNH$_2$/Chol-6%/FL (Table 9: sample 2-21) and a liver sample of a mouse having received the sample, which indicates metabolism of the administered sample in the murine liver (Example 2-3)

FIG. 2-2-22 illustrates a size exclusion chromatography analysis of 99 k HA-LeuNH$_2$/Chol-6%/FL (Table 9: sample 2-22) and a liver sample of a mouse having received the sample, which indicates metabolism of the administered sample in the murine liver (Example 2-3)

FIG. 2-2-23 illustrates a size exclusion chromatography analysis of 99 k HA-GlyNH$_2$/Chol-6%/FL (Table 9: sample 2-23) and a liver sample of a mouse having received the sample, which indicates metabolism of the administered sample in the murine liver (Example 2-3)

FIG. 2-2-24 illustrates a size exclusion chromatography analysis of 99 k HA-Ala/Chol-6%/FL (Table 9: sample 2-24) and a liver sample of a mouse having received the sample, which indicates metabolism of the administered sample in the murine liver (Example 2-3)

FIG. 2-2-25 illustrates a size exclusion chromatography analysis of 99 k HA-Ser/Chol-6%/FL (Table 9: sample 2-25) and a liver sample of a mouse having received the sample, which indicates metabolism of the administered sample in the murine liver (Example 2-3)

FIG. 2-2-26 illustrates a size exclusion chromatography analysis of 99 k HA-EDOBEA-Ac/FL (Comparative Example 1-2) and a liver sample of a mouse having received the sample, which indicates that the administered sample is not metabolized (Example 2-3).

FIG. 2-2-27 illustrates a size exclusion chromatography analysis of 99 k HA-Tyr-Chol-6%/FL (Table 9: comparative sample 2-8) and a liver sample of a mouse having received the sample, which indicates metabolism of the administered sample in the murine liver (Example 2-3).

FIG. 2-3-1 illustrates a size exclusion chromatography analysis of urine samples of a mouse having received 99 k HA-Ala-Chol-7%/FL (Table 9: sample 2-1), in which chromatograms at time points in a same scale are shown to the left and those normalized with the highest peaks are shown to the right (Example 2-4).

FIG. 2-3-2 illustrates a size exclusion chromatography analysis of urine samples of a mouse having received 99 k HA-Ala-Chol-24%/FL (Table 9: sample 2-2), in which chromatograms at time points in a same scale are shown to the left and those normalized with the highest peaks are shown to the right (Example 2-4).

FIG. 2-3-3 illustrates a size exclusion chromatography analysis of urine samples of a mouse having received 99 k HA-Ala-Chol-30%/FL (Table 9: sample 2-3), in which chromatograms at time points in a same scale are shown to the left and those normalized with the highest peaks are shown to the right (Example 2-4).

FIG. 2-3-4 illustrates a size exclusion chromatography analysis of urine samples of a mouse having received 50 k HA-Ala-Chol-6%/FL (Table 9: sample 2-4), in which chromatograms at time points in a same scale are shown to the left and those normalized with the highest peaks are shown to the right (Example 2-4).

FIG. 2-3-5 illustrates a size exclusion chromatography analysis of urine samples of a mouse having received 50 k HA-Ala-Chol-22%/FL (Table 9: sample 2-5), in which chromatograms at time points in a same scale are shown to the left and those normalized with the highest peaks are shown to the right (Example 2-4).

FIG. 2-3-6 illustrates a size exclusion chromatography analysis of urine samples of a mouse having received 50 k HA-Ala-Chol-26%/FL (Table 9: sample 2-6), in which chromatograms at time points in a same scale are shown to the left and those normalized with the highest peaks are shown to the right (Example 2-4).

FIG. 2-3-7 illustrates a size exclusion chromatography analysis of urine samples of a mouse having received 10 k HA-Ala-Chol-16%/FL (Table 9: sample 2-7), in which chromatograms at time points in a same scale are shown to the left and those normalized with the highest peaks are shown to the right (Example 2-4).

FIG. 2-3-8 illustrates a size exclusion chromatography analysis of urine samples of a mouse having received 99 k HA-ThrNH$_2$/Chol-6%/FL (Table 9: sample 2-8) in which chromatograms at time points in a same scale are shown to the left and those normalized with the highest peaks are shown to the right (Example 2-4).

FIG. 2-3-9 illustrates a size exclusion chromatography analysis of urine samples of a mouse having received 99 k HA-ThrNH$_2$/Chol-24%/FL (Table 9: sample 2-9), in which chromatograms at time points in a same scale are shown to the left and those normalized with the highest peaks are shown to the right (Example 2-4).

FIG. 2-3-10 illustrates a size exclusion chromatography analysis of urine samples of a mouse having received 99 k HA-ThrNH$_2$/Chol-31%/FL (Table 9: sample 2-10), in which chromatograms at time points in a same scale are shown to the left and those normalized with the highest peaks are shown to the right (Example 2-4).

FIG. 2-3-11 illustrates a size exclusion chromatography analysis of urine samples of a mouse having received 99 k HA-Ser-Chol-6%/FL (Table 9: sample 2-11), in which chromatograms at time points in a same scale are shown to the left and those normalized with the highest peaks are shown to the right (Example 2-4).

FIG. 2-3-12 illustrates a size exclusion chromatography analysis of urine samples of a mouse having received 99 k HA-Gly-Chol-6%/FL (Table 9: sample 2-12), in which chromatograms at time points in a same scale are shown to the left and those normalized with the highest peaks are shown to the right (Example 2-4).

FIG. 2-3-13 illustrates a size exclusion chromatography analysis of urine samples of a mouse having received 99 k HA-Thr-Chol-6%/FL (Table 9: sample 2-13), in which chromatograms at time points in a same scale are shown to the left and those normalized with the highest peaks are shown to the right (Example 2-4)

FIG. 2-3-14 illustrates a size exclusion chromatography analysis of urine samples of a mouse having received 99 k HA-Asn-Chol-7%/FL (Table 9: sample 2-14), in which chromatograms at time points in a same scale are shown to the left and those normalized with the highest peaks are shown to the right (Example 2-4)

FIG. 2-3-15 illustrates a size exclusion chromatography analysis of urine samples of a mouse having received 99 k HA-Asp-Chol-6%/FL (Table 9: sample 2-15), in which chromatograms at time points in a same scale are shown to the left and those normalized with the highest peaks are shown to the right (Example 2-4)

FIG. 2-3-16 illustrates a size exclusion chromatography analysis of urine samples of a mouse having received 99 k HA-Ile-Chol-6%/FL (Table 9: sample 2-16), in which chromatograms at time points in a same scale are shown to the left and those normalized with the highest peaks are shown to the right (Example 2-4)

FIG. 2-3-17 illustrates a size exclusion chromatography analysis of urine samples of a mouse having received 99 k HA-Leu-Chol-6%/FL (Table 9: sample 2-17), in which chromatograms at time points in a same scale are shown to the left and those normalized with the highest peaks are shown to the right (Example 2-4).

FIG. 2-3-18 illustrates a size exclusion chromatography analysis of urine samples of a mouse having received 99 k HA-Val-Chol-6%/FL (Table 9: sample 2-18) in which chromatograms at time points in a same scale are shown to the left and those normalized with the highest peaks are shown to the right (Example 2-4).

FIG. 2-3-19 illustrates a size exclusion chromatography analysis of urine samples of a mouse having received 99 k HA-Phe-Chol-6%/FL (Table 9: sample 2-19), in which chromatograms at time points in a same scale are shown to the left and those normalized with the highest peaks are shown to the right (Example 2-4).

FIG. 2-3-20 illustrates a size exclusion chromatography analysis of urine samples of a mouse having received 99 k HA-ValNH$_2$/Chol-6%/FL (Table 9: sample 2-20), in which chromatograms at time points in a same scale are shown to the left and those normalized with the highest peaks are shown to the right (Example 2-4).

FIG. 2-3-21 illustrates a size exclusion chromatography analysis of urine samples of a mouse having received 99 k HA-SerNH$_2$/Chol-6%/FL (Table 9: sample 2-21), in which chromatograms at time points in a same scale are shown to the left and those normalized with the highest peaks are shown to the right (Example 2-4).

FIG. 2-3-22 illustrates a size exclusion chromatography analysis of urine samples of a mouse having received 99 k HA-LeuNH$_2$/Chol-6%/FL (Table 9: sample 2-22), in which chromatograms at time points in a same scale are shown to the left and those normalized with the highest peaks are shown to the right (Example 2-4).

FIG. 2-3-23 illustrates a size exclusion chromatography analysis of urine samples of a mouse having received 99 k HA-GlyNH$_2$/Chol-6%/FL (Table 9: sample 2-23), in which chromatograms at time points in a same scale are shown to the left and those normalized with the highest peaks are shown to the right (Example 2-4).

FIG. 2-3-24 illustrates a size exclusion chromatography analysis of urine samples of a mouse having received 99 k HA-Ala/Chol-6%/FL (Table 9: sample 2-24), in which chromatograms at time points in a same scale are shown to the left and those normalized with the highest peaks are shown to the right (Example 2-4).

FIG. 2-3-25 illustrates a size exclusion chromatography analysis of urine samples of a mouse having received 99 k HA-Ser/Chol-6%/FL (Table 9: sample 2-25), in which chromatograms at time points in a same scale are shown to the left and those normalized with the highest peaks are shown to the right (Example 2-4).

FIG. 2-3-26 illustrates a size exclusion chromatography analysis of urine samples of a mouse having received 99 k HA-EDOBEA-Ac/FL (Comparative Example 1-2), in which chromatograms at time points in a same scale are shown to the left and those normalized with the highest peaks are shown to the right (Example 2-4).

FIG. 2-3-27 illustrates a size exclusion chromatography analysis of urine samples of a mouse having received 99 k HA-Tyr-Chol-6%/FL (Table 9: comparison sample 2-8), in which chromatograms at time points in a same scale are shown to the left and those normalized with the highest peaks are shown to the right (Example 2-4).

FIG. 3-1 illustrates an example of NMR spectra of HA-Gln prepared in Example 3-1.

FIG. 3-2 illustrates an example of NMR spectra of HA-Gln-Chol/FL prepared in Example 3-1 (introduction ratio of cholesteryl group: 6%).

FIG. 3-3 illustrates an example of NMR spectra of HA-Met prepared in Example 3-2.

FIG. 3-4 illustrates an example of NMR spectra of HA-Met-Chol/FL prepared in Example 3-2 (introduction ratio of cholesteryl group: 6%).

FIG. 3-5 illustrates an example of NMR spectra of HA-AlaNH$_2$/Chol/FL prepared in Example 3-3 (introduction ratio of cholesteryl group: 6%).

FIG. 3-6 illustrates an example of NMR spectra of HA-AsnNH$_2$/Chol/FL prepared in Example 3-4 (introduction ratio of cholesteryl group: 6%).

FIG. 3-7 illustrates an example of NMR spectra of HA-AsnNH$_2$/Chol/FL prepared in Example 3-4 (introduction ratio of cholesteryl group: 6%).

FIG. 3-8 illustrates an example of NMR spectra of HA-IleNH$_2$/Chol/FL prepared in Example 3-5 (introduction ratio of cholesteryl group: 6%).

FIG. 3-9 illustrates an example of NMR spectra of HA-GlnNH$_2$/Chol/FL prepared in Example 3-6 (introduction ratio of cholesteryl group: 6%).

FIG. 3-10 illustrates an example of NMR spectra of HA-MetNH$_2$/Chol/FL prepared in Example 3-7 (introduction ratio of cholesteryl group: 6%).

FIG. 3-11 illustrates an example of NMR spectra of HA-Glu prepared in Comparative Example 3-1.

FIG. 3-12 illustrates an example of NMR spectra of HA-Glu-Chol/FL prepared in Comparative Example 3-1 (introduction ratio of cholesteryl group: 6%).

FIG. 3-13 illustrates an example of NMR spectra of HA-Trp prepared in Comparative Example 3-2.

FIG. 3-14 illustrates an example of NMR spectra of HA-Trp-Chol/FL prepared in Comparative Example 3-2 (introduction ratio of cholesteryl group: 6%).

Figure 1:
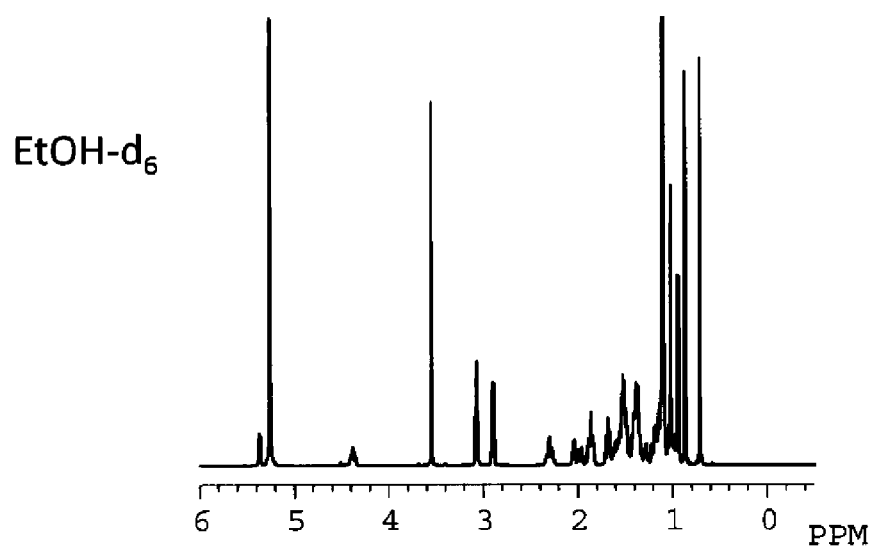
FIG. 1-1 illustrates an example of $^1$H-NMR spectra of hydrochloride salt of cholesteryl 6-aminohexylcarbamate (Chol-$C_6$) prepared in Example 1-1.
Figures 1, 2:
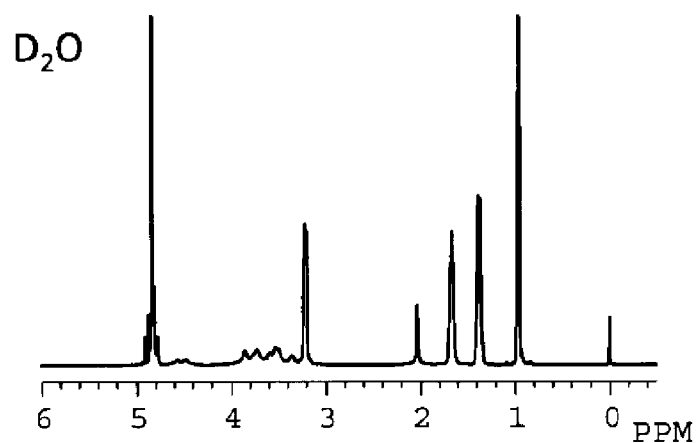
Figures 1, 2, 3:
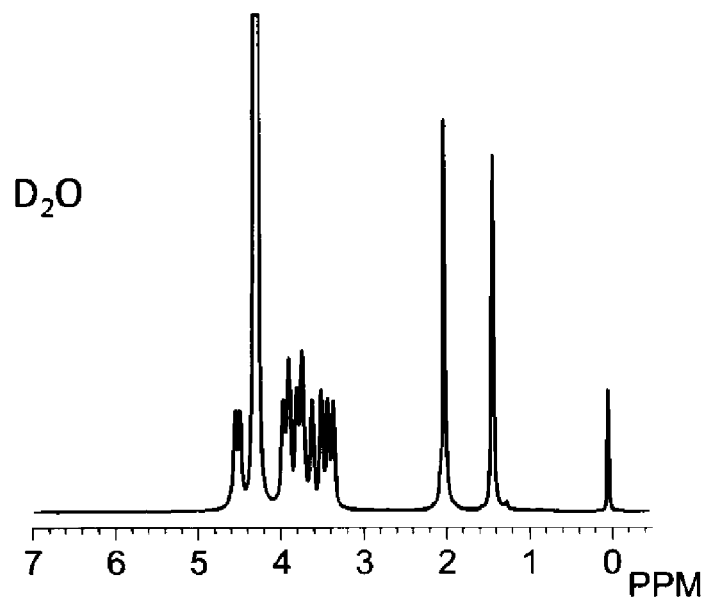
Figures 1, 2, 3, 4:
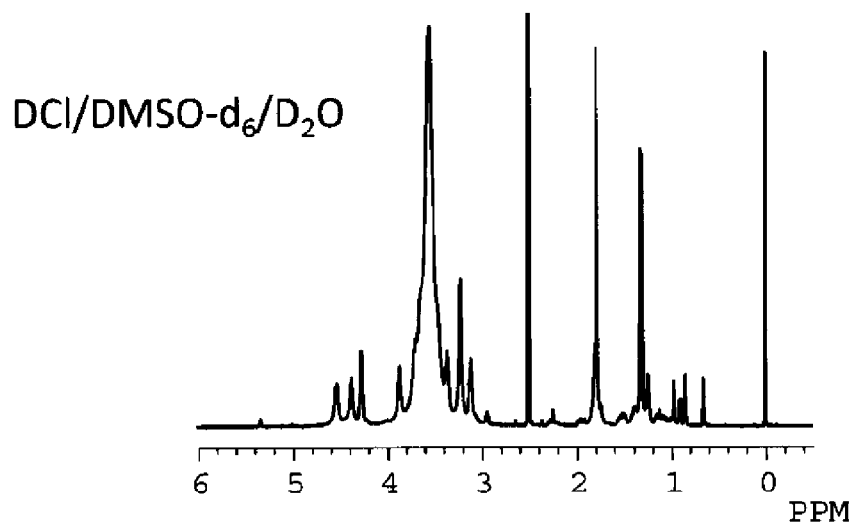

FIG. 4-1-1 is a graph illustrating changes of plasma concentrations of 99 k HA-Gln-Chol-6%/FL (Table 15:

sample 4-1) and 99 k HA-Chol-6%/FL (Table 9: comparative sample 2-1) (Example 4-2).

FIG. 4-1-2 is a graph illustrating changes of plasma concentrations of 99 k HA-Met-Chol-6%/FL (Table 15: sample 4-2) and 99 k HA-Chol-6%/FL (Table 9: comparative sample 2-1) (Example 4-2)

FIG. 4-1-3 is a graph illustrating changes of plasma concentrations of 99 k HA-AlaNH$_2$/Chol-6%/FL (Table 15: sample 4-3) and 99 k HA-Chol-6%/FL (Table 9: comparative sample 2-1) (Example 4-2)

FIG. 4-1-4 is a graph illustrating changes of plasma concentrations of 99 k HA-AsnNH$_2$/Chol-6%/FL (Table 15: sample 4-4) and 99 k HA-Chol-6%/FL (Table 9: comparative sample 2-1) (Example 4-2)

Figures 1, 2, 3, 4, 5:
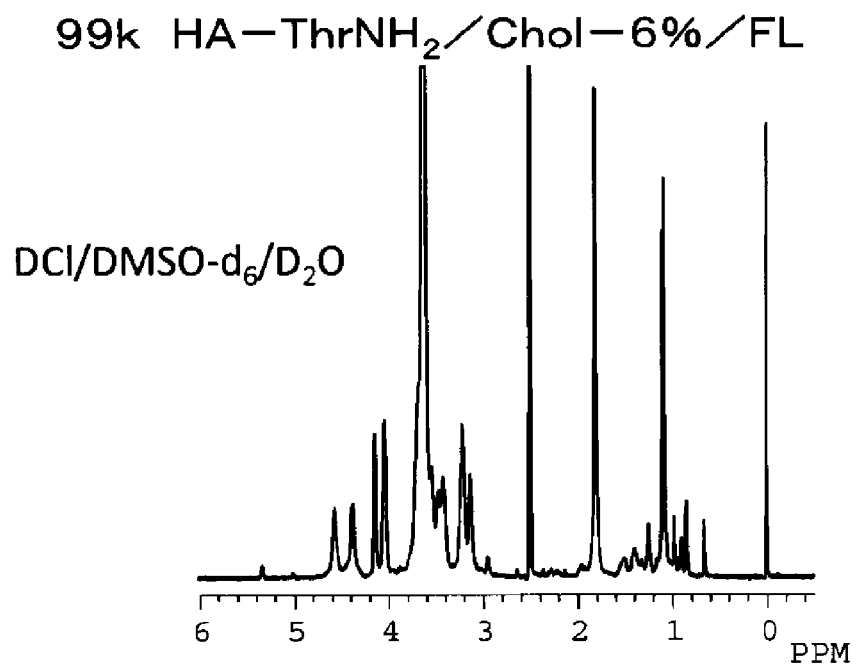

FIG. 4-1-5 is a graph illustrating changes of plasma concentrations of 99 k HA-IleNH$_2$/Chol-6%/FL (Table 15: sample 4-5) and 99 k HA-Chol-6%/FL (Table 9: comparative sample 2-1) (Example 4-2)

Figures 1, 2, 3, 4, 5, 6:
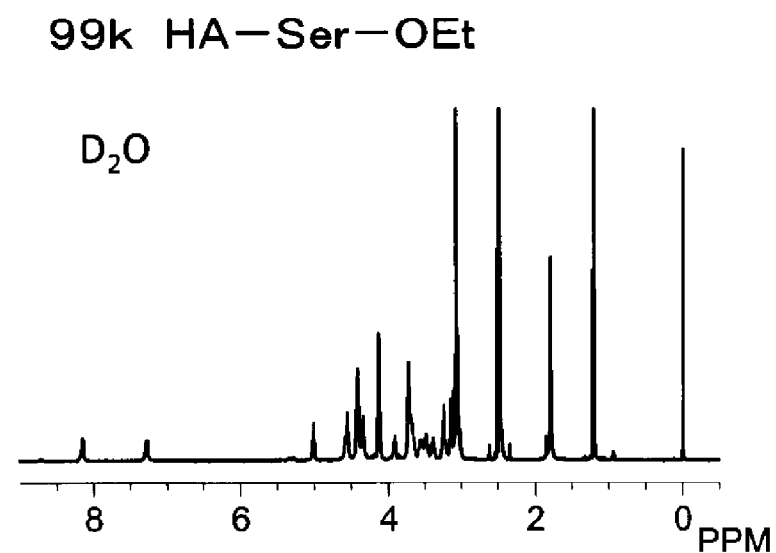

FIG. 4-1-6 is a graph illustrating changes of plasma concentrations of 99 k HA-GlnNH$_2$/Chol-6%/FL (Table 15: sample 4-6) and 99 k HA-Chol-6%/FL (Table 9: comparative sample 2-1) (Example 4-2)

Figures 1, 2, 3, 4, 5, 6, 7:
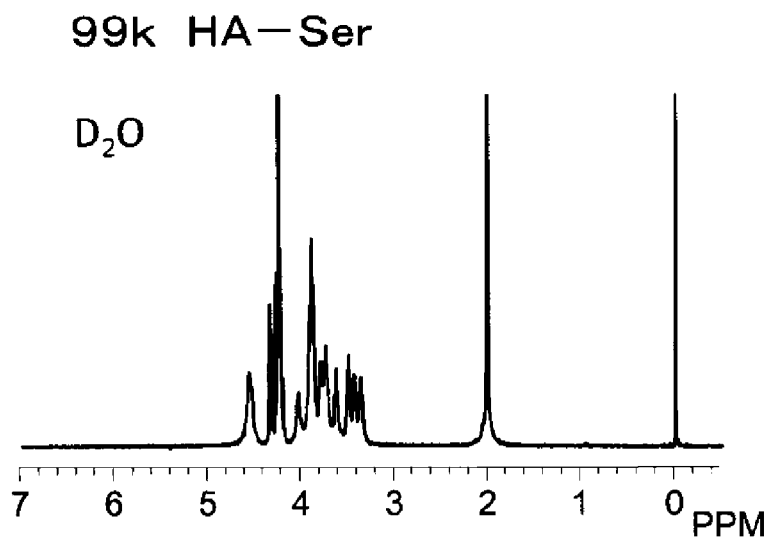

FIG. 4-1-7 is a graph illustrating changes of plasma concentrations of 99 k HA-MetNH$_2$/Chol-6%/FL (Table 15: sample 4-7) and 99 k HA-Chol-6%/FL (Table 9: comparative sample 2-1) (Example 4-2)

Figures 1, 2, 3, 4, 5, 6, 7, 8:
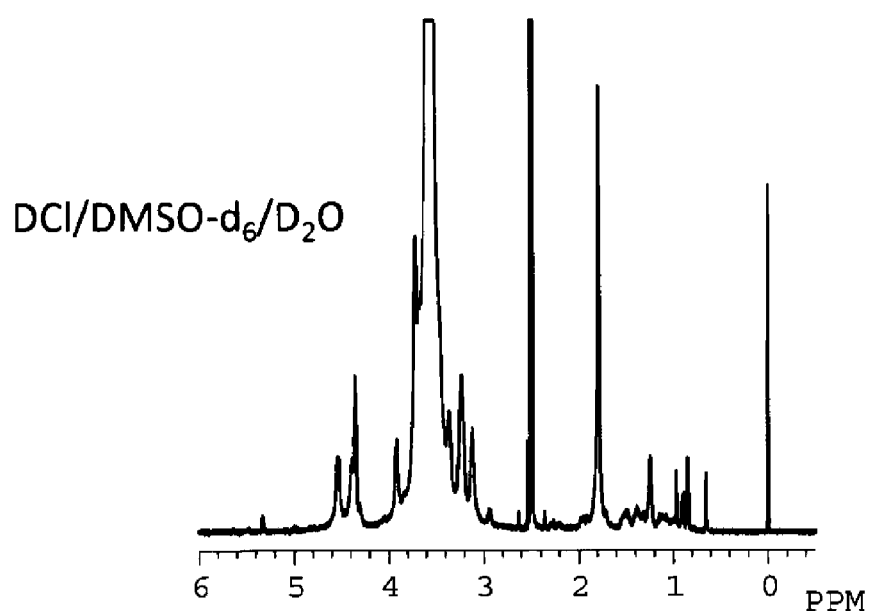

FIG. 4-1-8 is a graph illustrating changes of plasma concentrations of 99 k HA-Glu-Chol-6%/FL (Table 15: comparative sample 4-1) and 99 k HA-Chol-6%/FL (Table 9: comparative sample 2-1) (Example 4-2).

Figures 1, 2, 3, 4, 5, 6, 7, 8, 9:
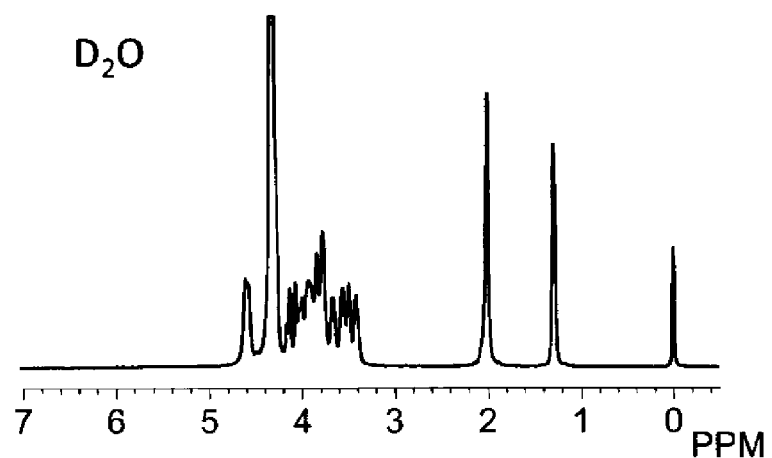

FIG. 4-1-9 is a graph illustrating changes of plasma concentrations of 99 k HA-Trp-Chol-6%/FL (Table 15: comparative sample 4-2) and 99 k HA-Chol-6%/FL (Table 9: comparative sample 2-1) (Example 4-2).

Figures 1, 2, 3, 4, 5, 6, 7, 8, 9, 10:
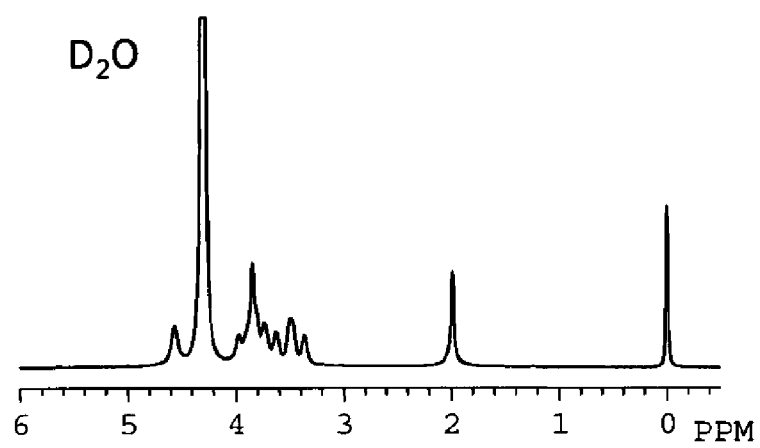
Figures 1, 2, 3, 4, 5, 6, 7, 8, 9, 10, 11:
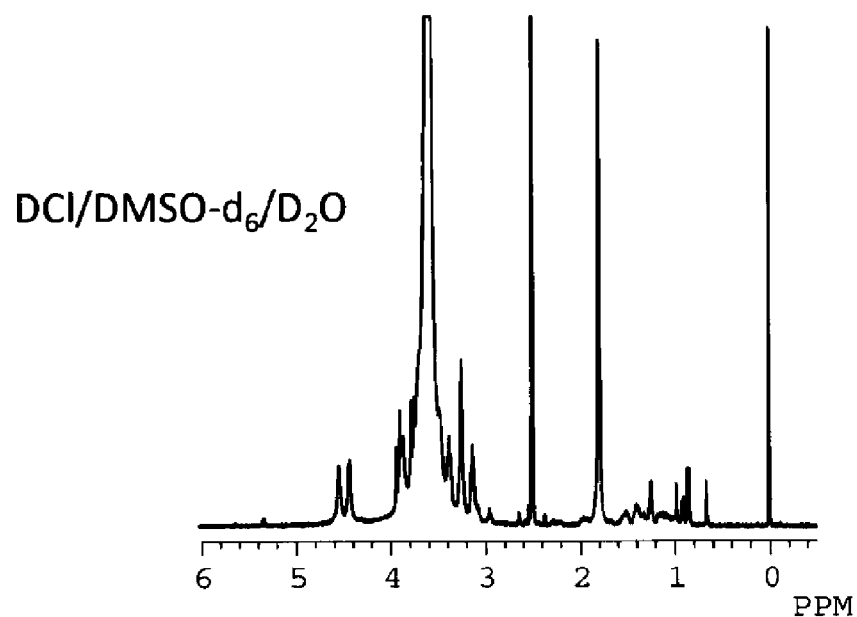
Figures 1, 2, 3, 4, 5, 6, 7, 8, 9, 10, 11, 12:
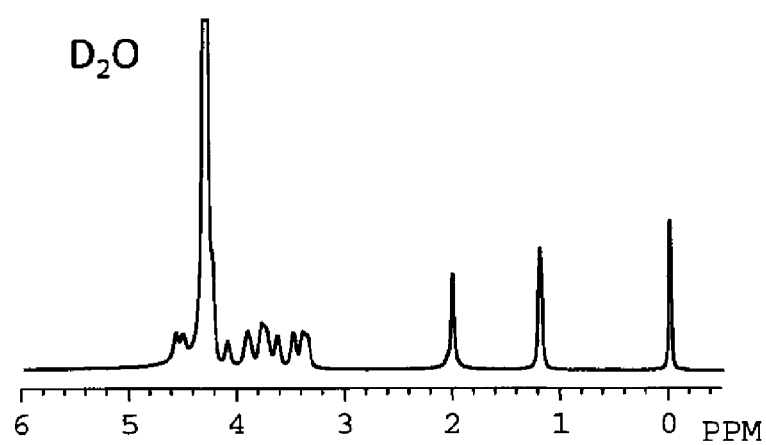
Figures 1, 2, 3, 4, 5, 6, 7, 8, 9, 10, 11, 12, 13:
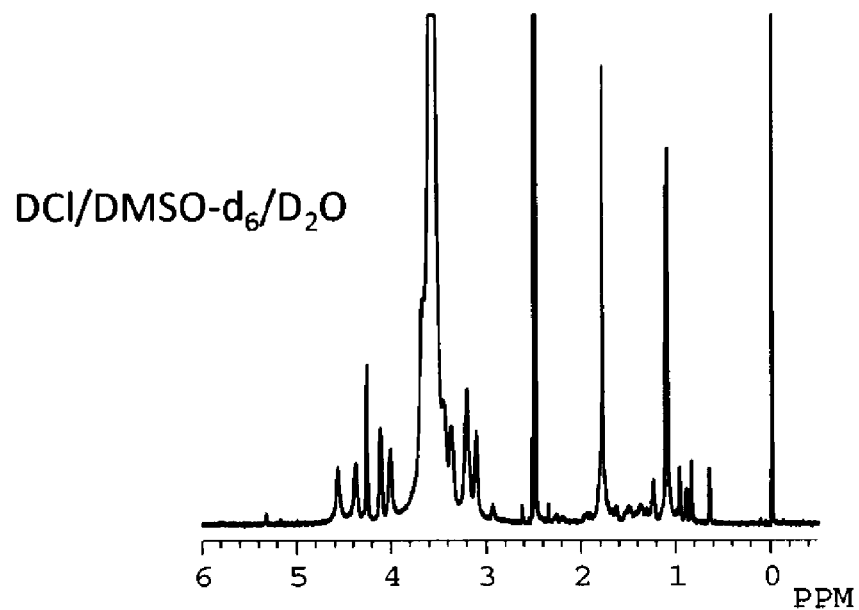
Figures 1, 2, 3, 4, 5, 6, 7, 8, 9, 10, 11, 12, 13, 14:
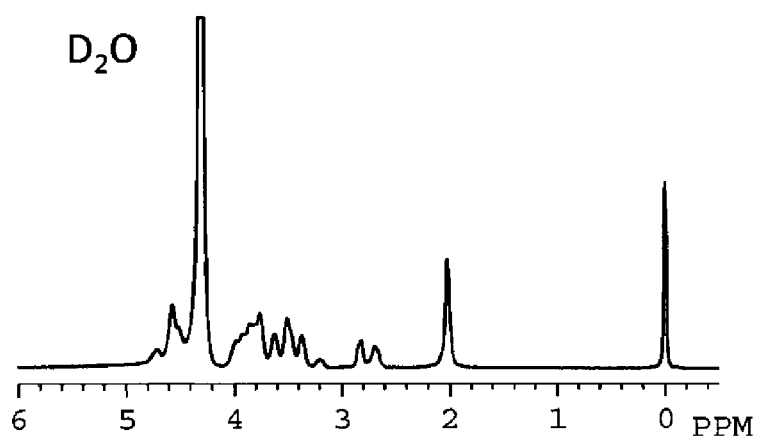
Figures 1, 2, 3, 4, 5, 6, 7, 8, 9, 10, 11, 12, 13, 14, 15:
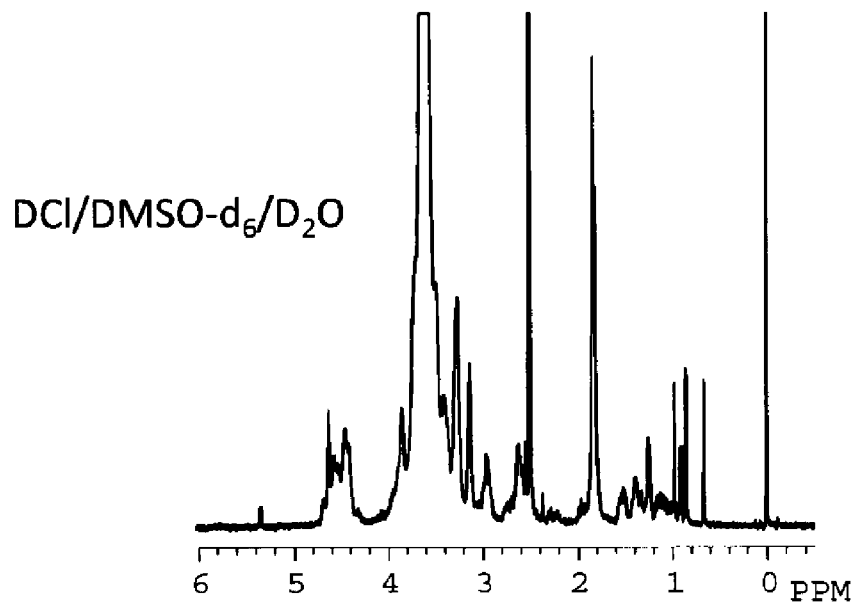
Figures 1, 2, 3, 4, 5, 6, 7, 8, 9, 10, 11, 12, 13, 14, 15, 16:
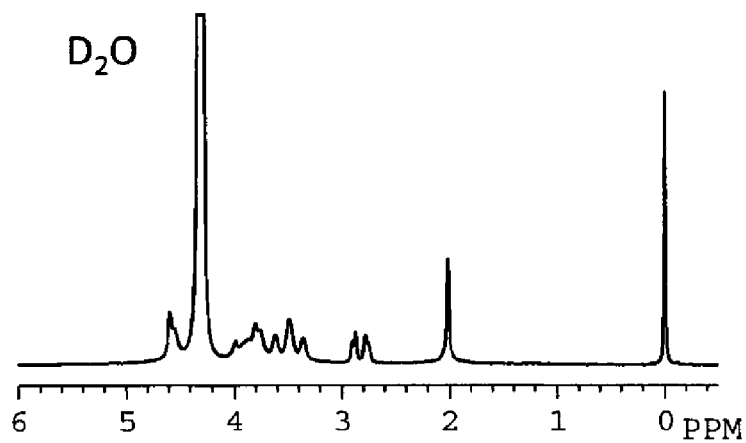
Figures 1, 2, 3, 4, 5, 6, 7, 8, 9, 10, 11, 12, 13, 14, 15, 16, 17:
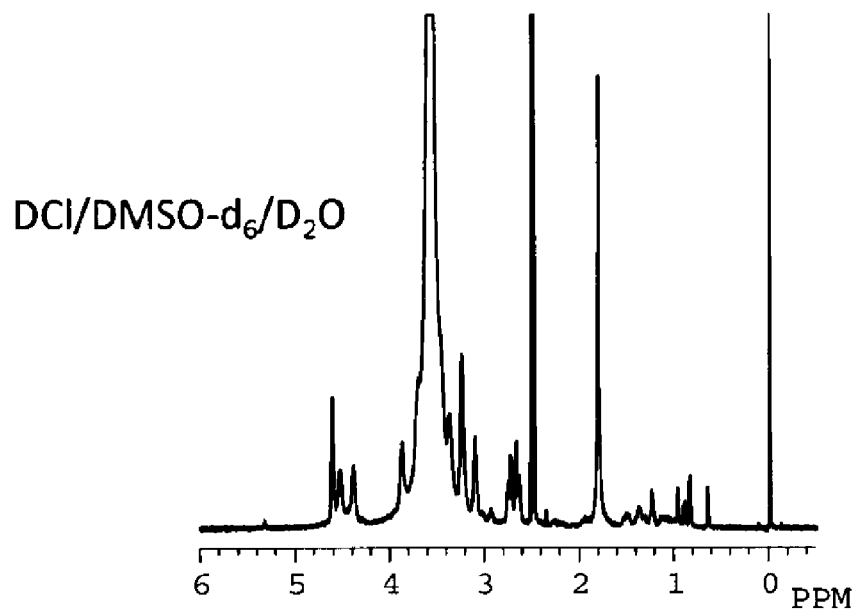
Figures 1, 2, 3, 4, 5, 6, 7, 8, 9, 10, 11, 12, 13, 14, 15, 16, 17, 18:
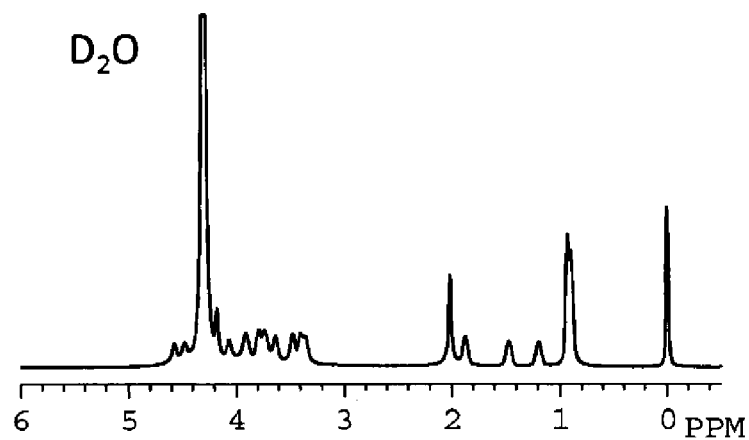
Figures 1, 2, 3, 4, 5, 6, 7, 8, 9, 10, 11, 12, 13, 14, 15, 16, 17, 18, 19:
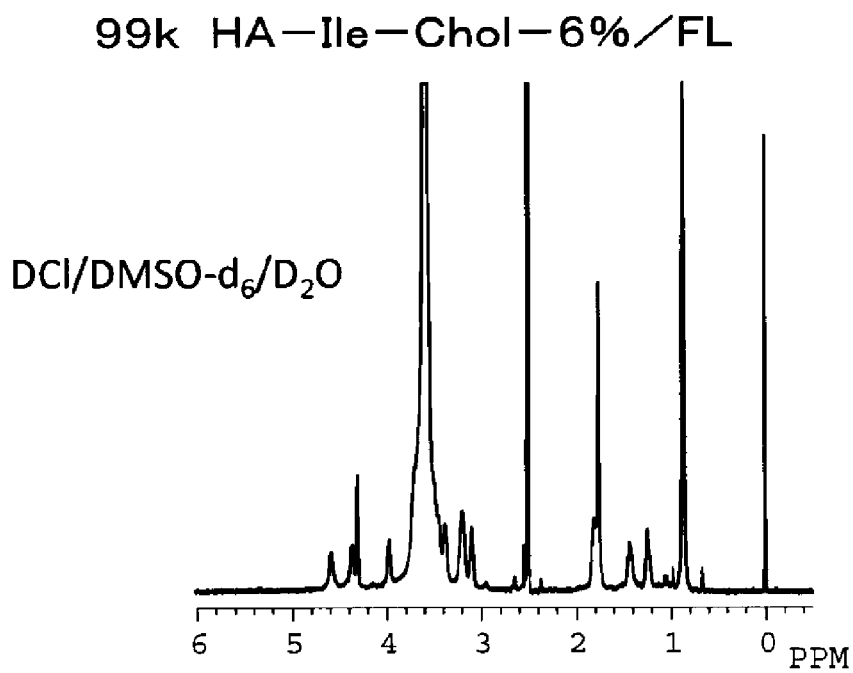
Figures 1, 2, 3, 4, 5, 6, 7, 8, 9, 10, 11, 12, 13, 14, 15, 16, 17, 18, 19, 20:
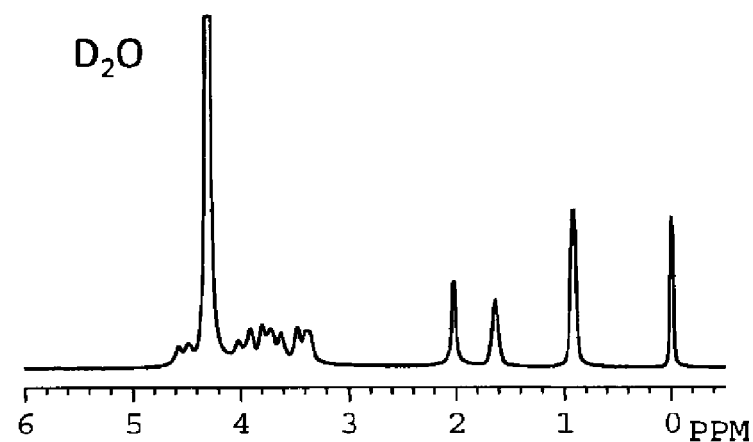
Figures 1, 2, 3, 4, 5, 6, 7, 8, 9, 10, 11, 12, 13, 14, 15, 16, 17, 18, 19, 20, 21:
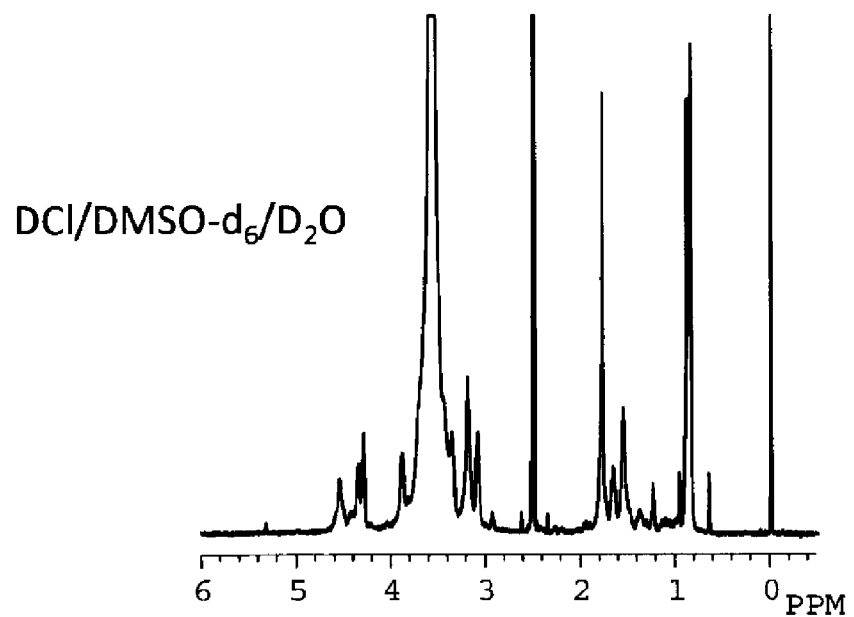
Figures 1, 2, 3, 4, 5, 6, 7, 8, 9, 10, 11, 12, 13, 14, 15, 16, 17, 18, 19, 20, 21, 22:
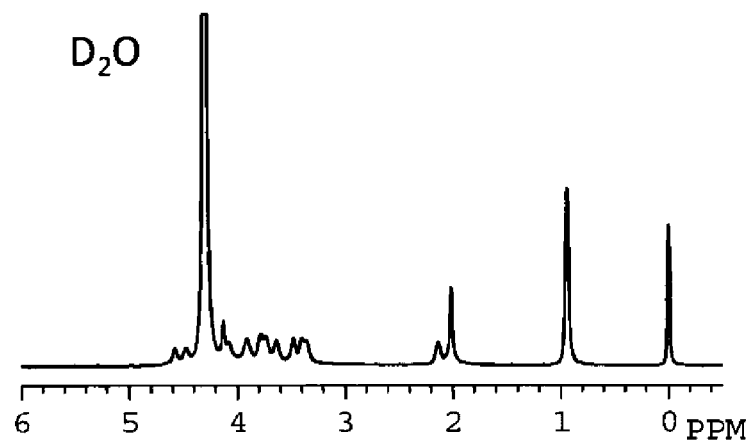
Figures 1, 2, 3, 4, 5, 6, 7, 8, 9, 10, 11, 12, 13, 14, 15, 16, 17, 18, 19, 20, 21, 22, 23:
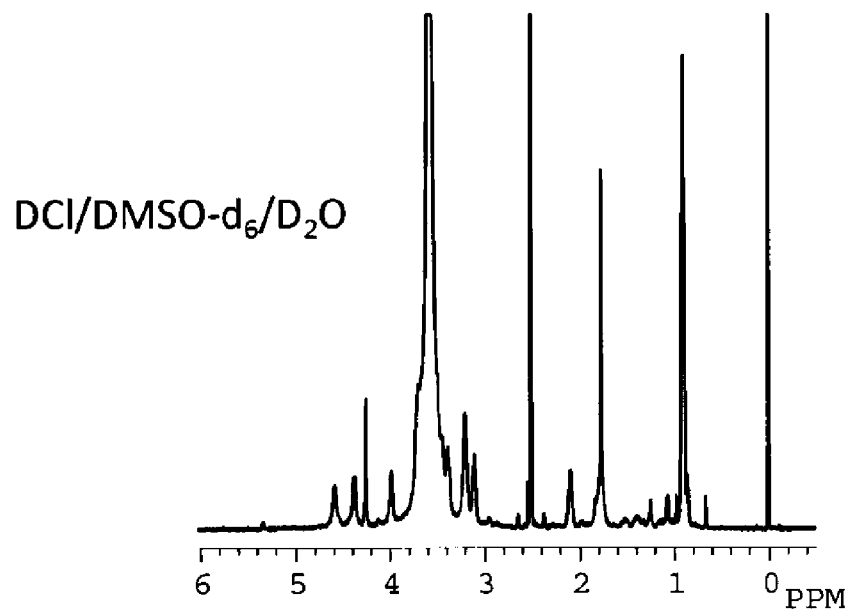
Figures 1, 2, 3, 4, 5, 6, 7, 8, 9, 10, 11, 12, 13, 14, 15, 16, 17, 18, 19, 20, 21, 22, 23, 24:
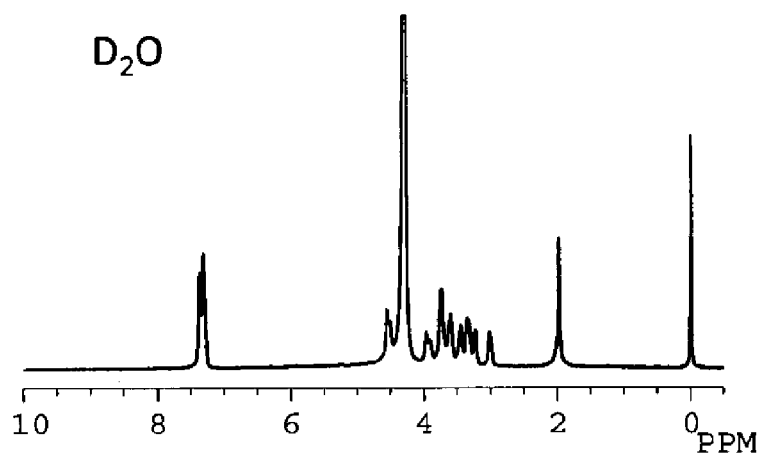
Figures 1, 2, 3, 4, 5, 6, 7, 8, 9, 10, 11, 12, 13, 14, 15, 16, 17, 18, 19, 20, 21, 22, 23, 24, 25:
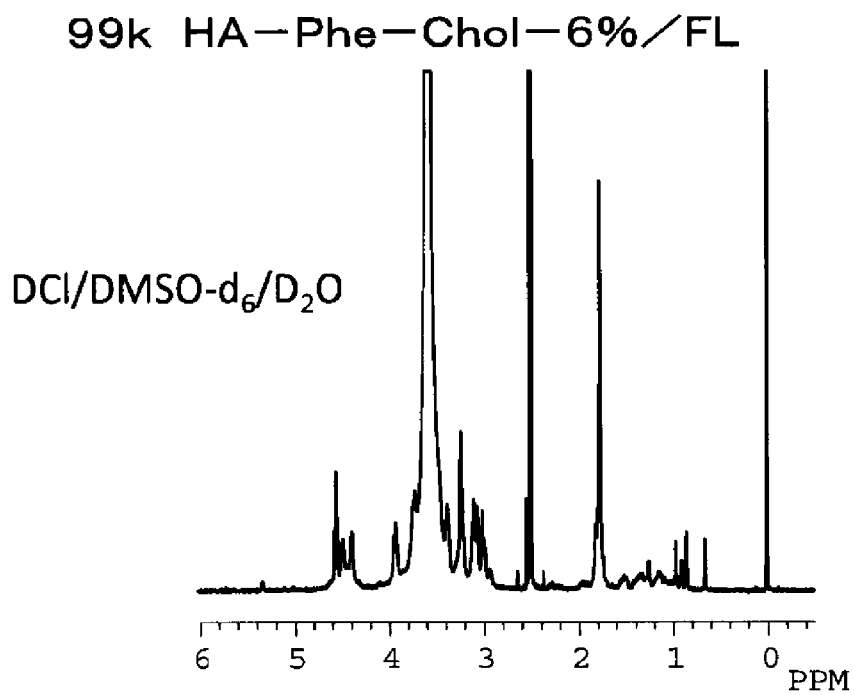
Figures 1, 2, 3, 4, 5, 6, 7, 8, 9, 10, 11, 12, 13, 14, 15, 16, 17, 18, 19, 20, 21, 22, 23, 24, 25, 26:
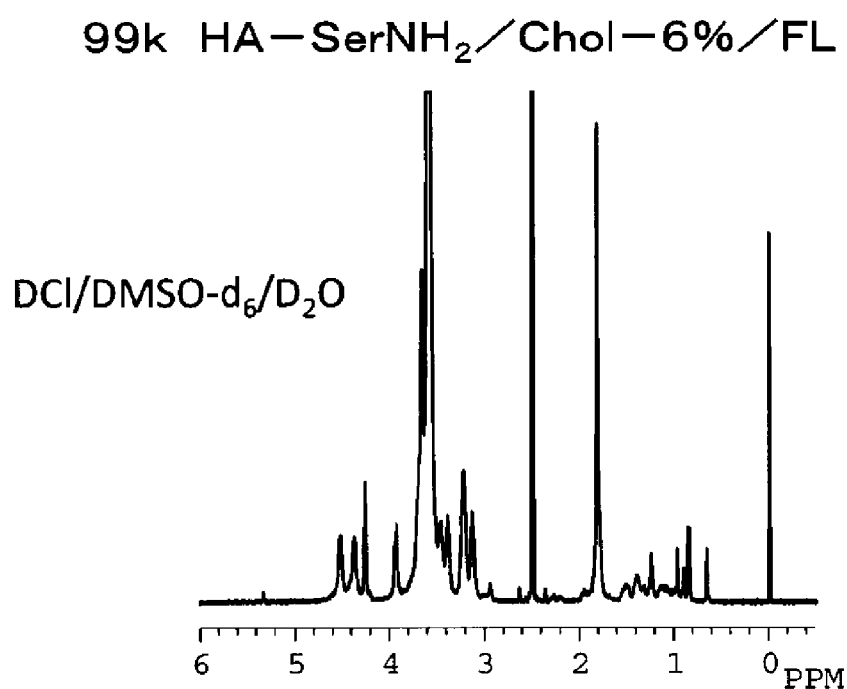
Figures 1, 2, 3, 4, 5, 6, 7, 8, 9, 10, 11, 12, 13, 14, 15, 16, 17, 18, 19, 20, 21, 22, 23, 24, 25, 26, 27:
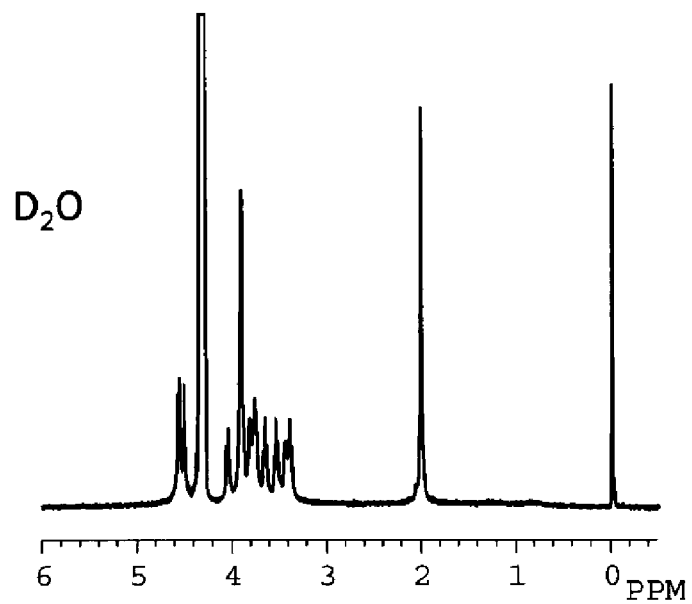
Figures 1, 2, 3, 4, 5, 6, 7, 8, 9, 10, 11, 12, 13, 14, 15, 16, 17, 18, 19, 20, 21, 22, 23, 24, 25, 26, 27, 28:
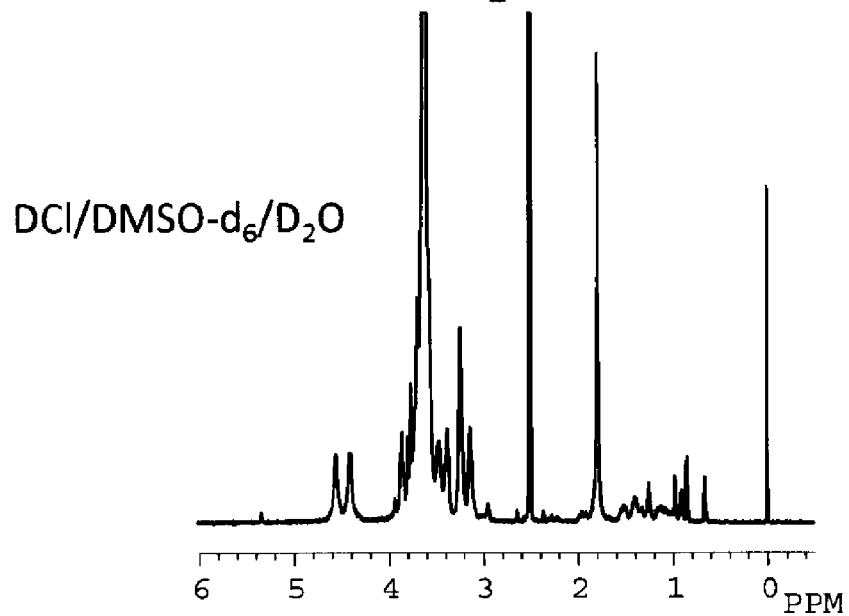
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29:
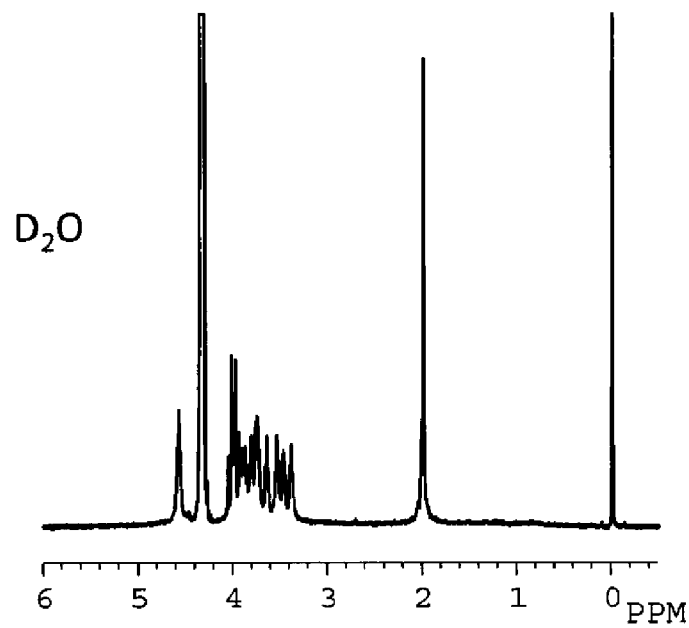
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30:
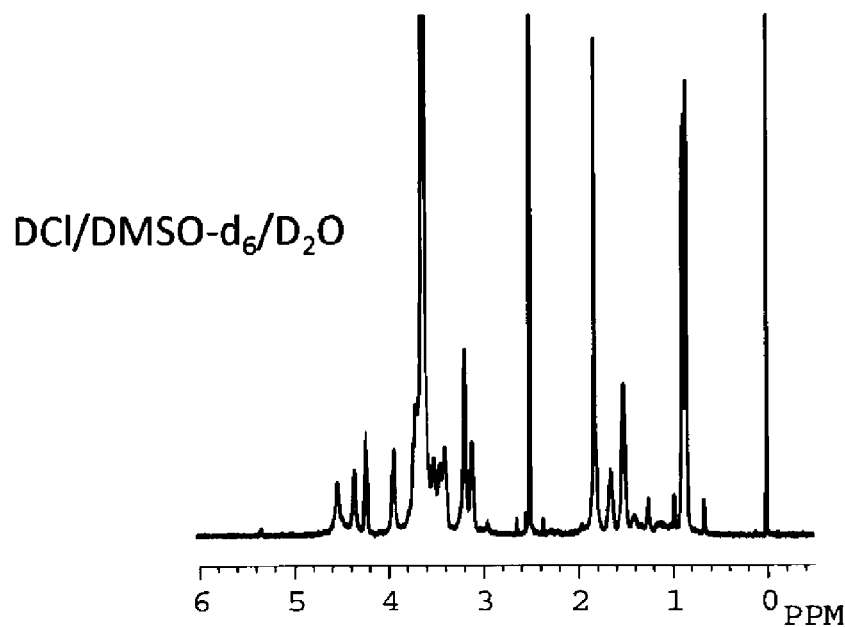
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31:
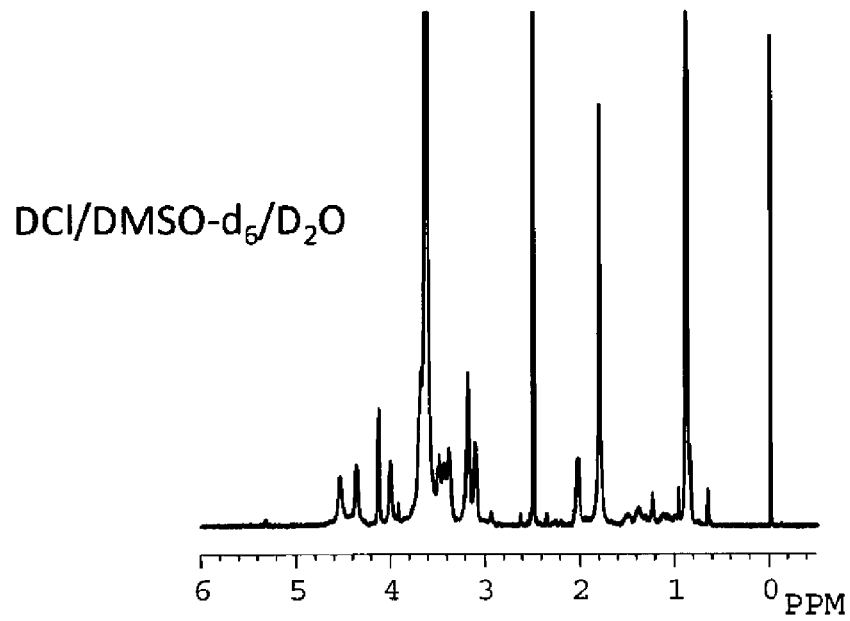
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32:
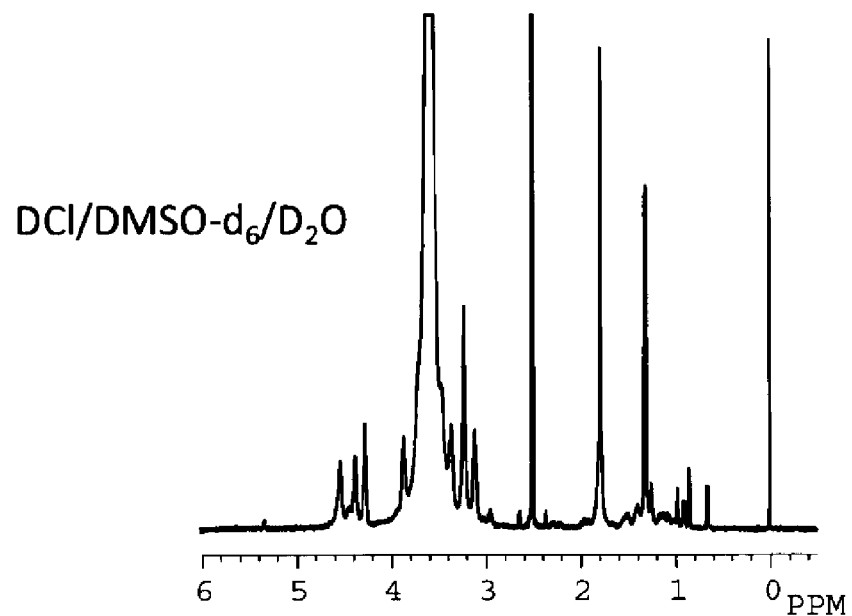
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33:
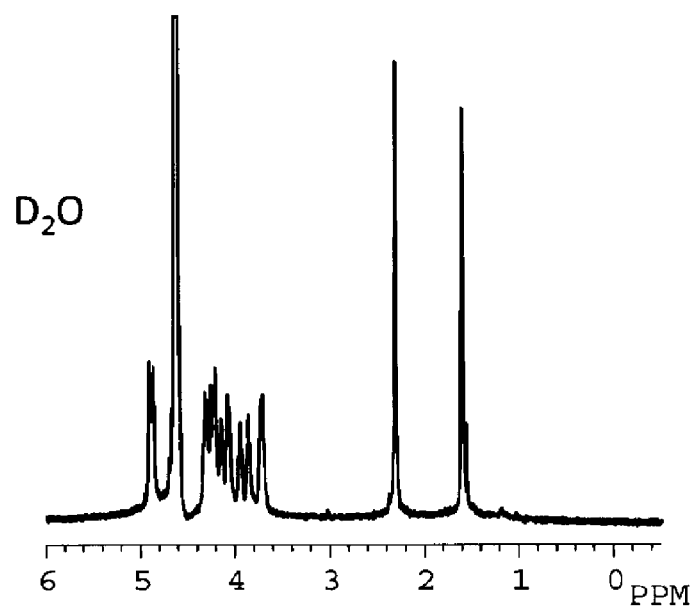
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34:
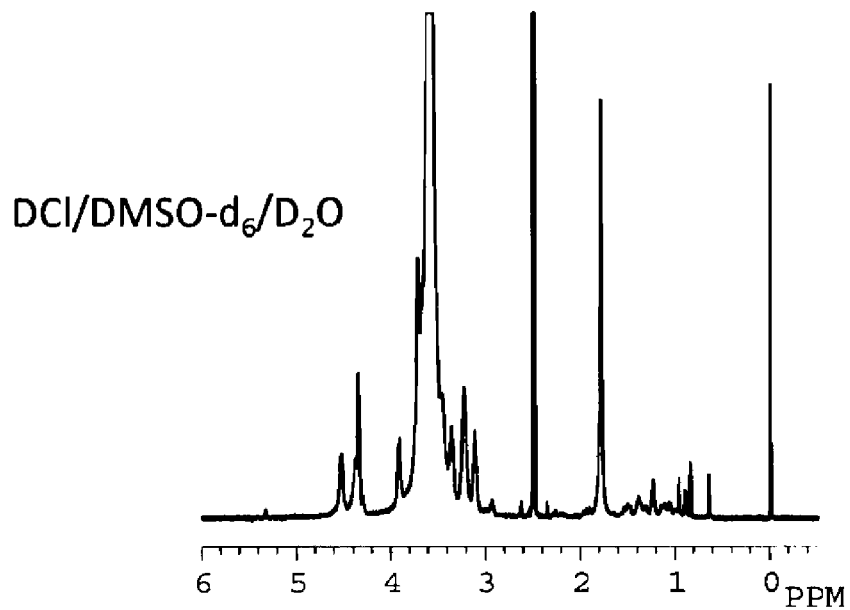
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35:
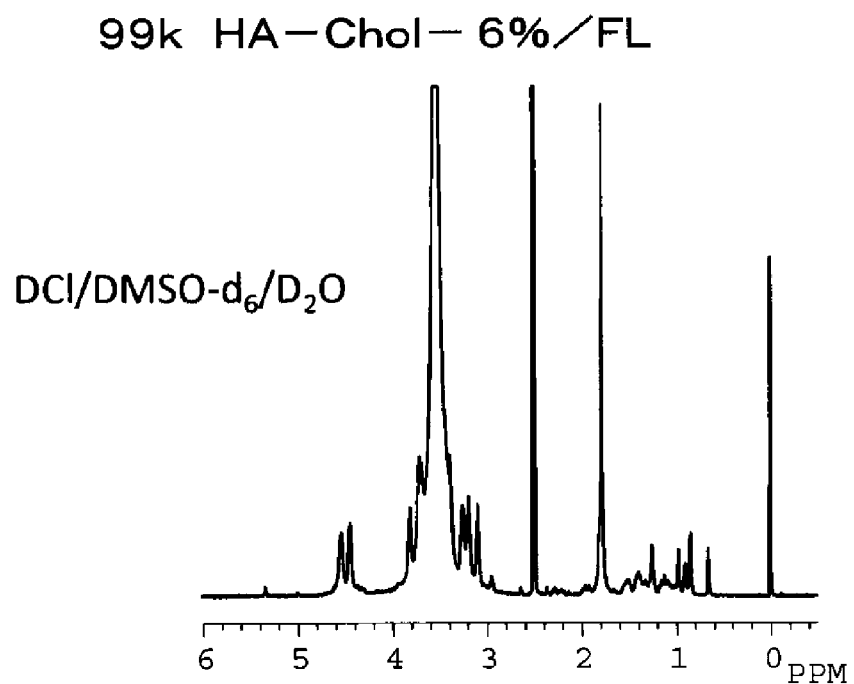
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36:
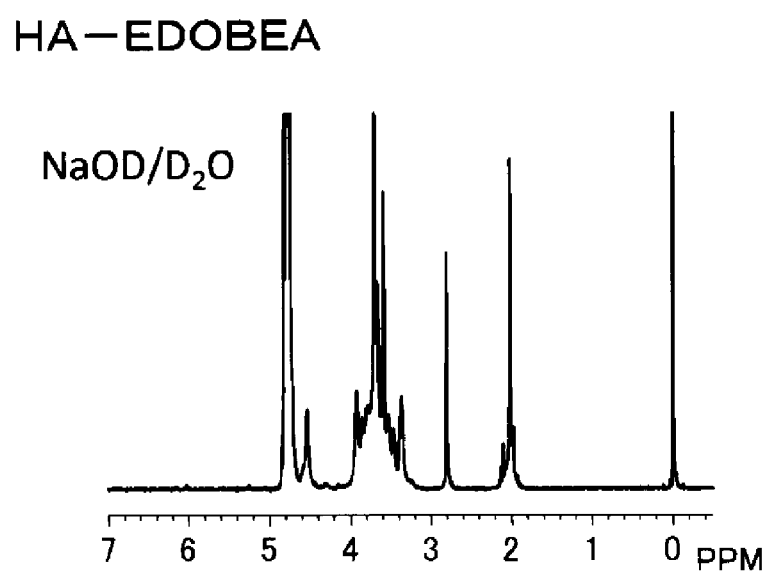
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37:
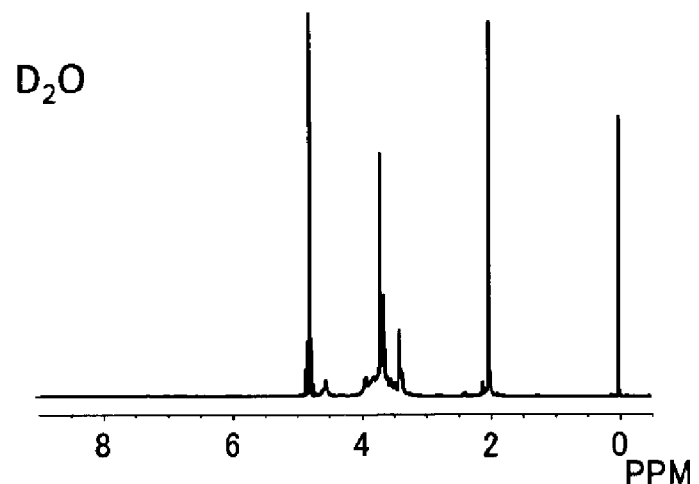
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38:
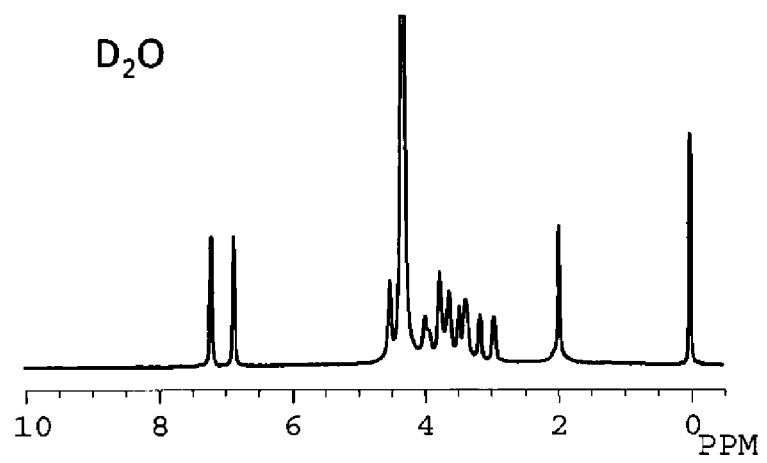
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39:
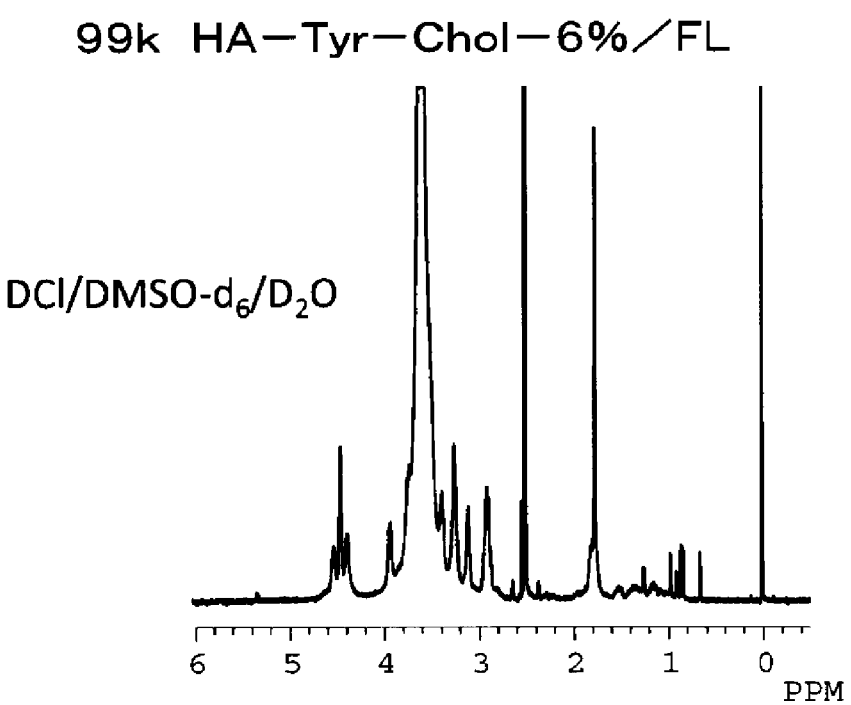
Figures 1, 2:
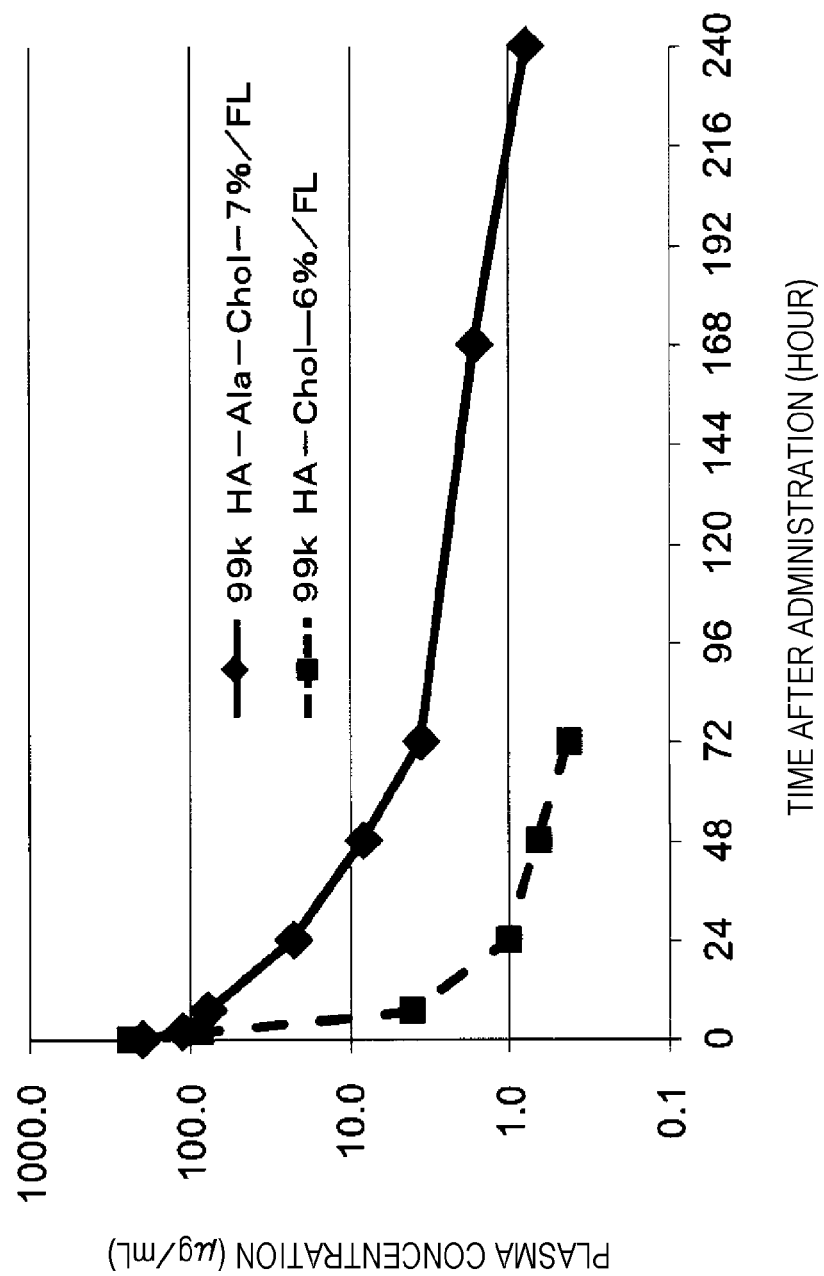
Figures 1, 2:
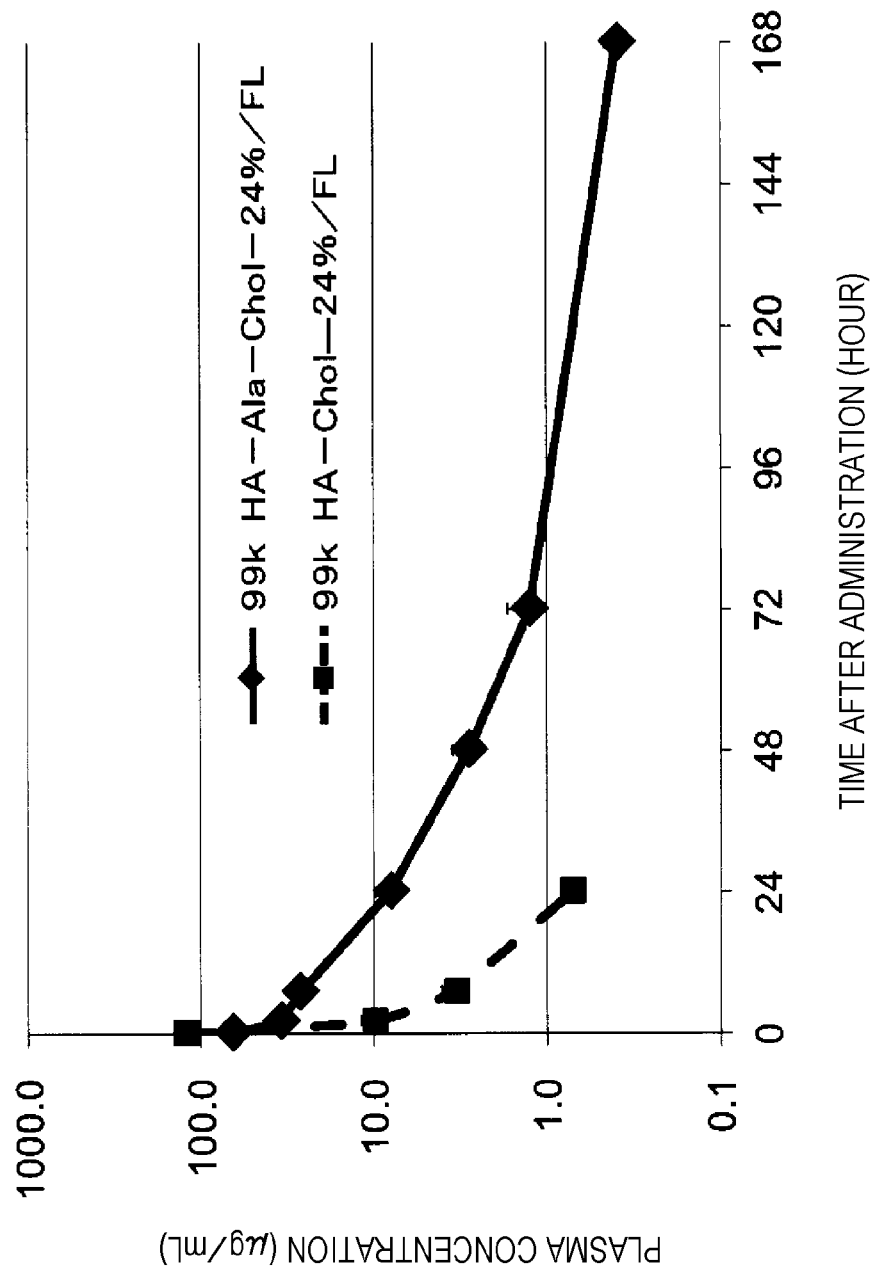
Figures 1, 2, 3:
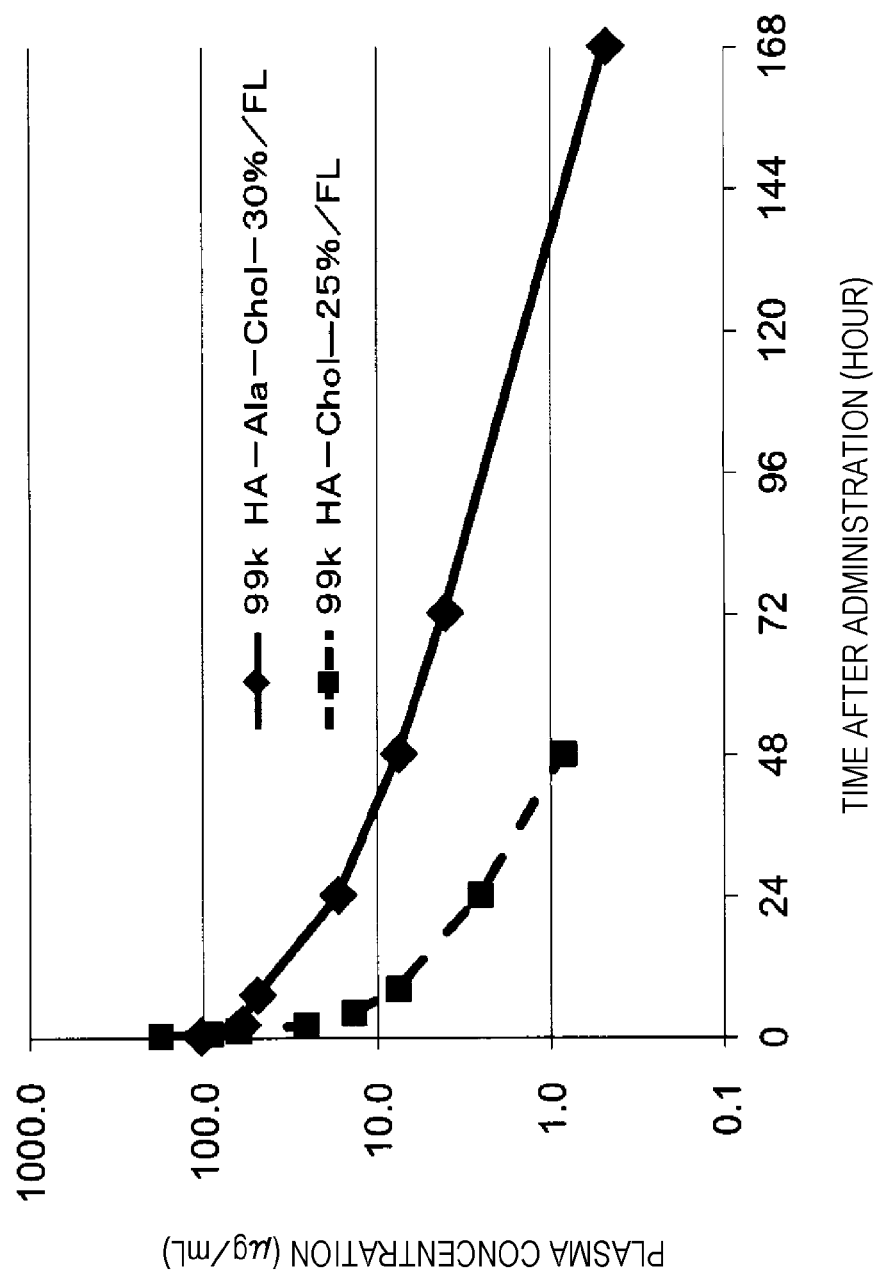
Figures 1, 2, 4:
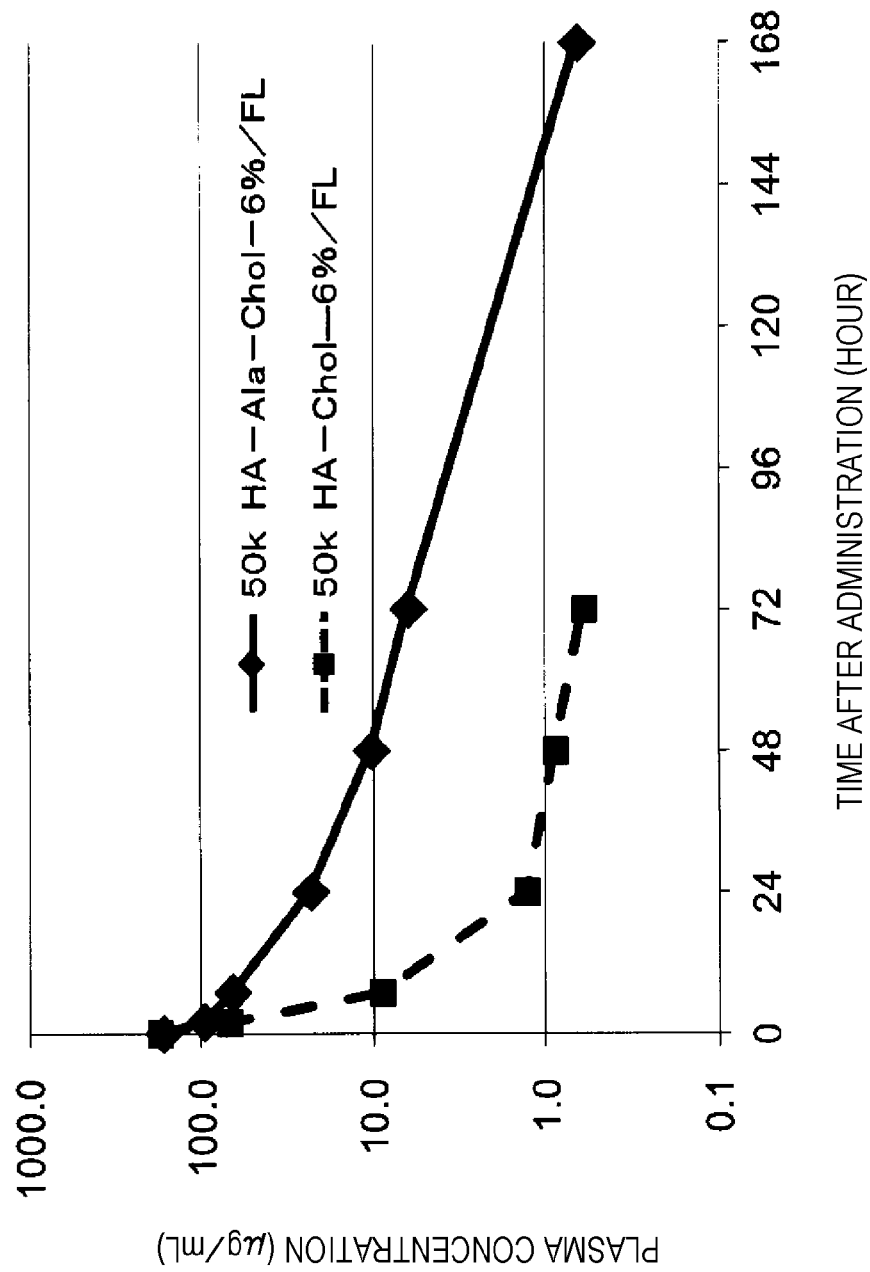
Figures 1, 2, 6:
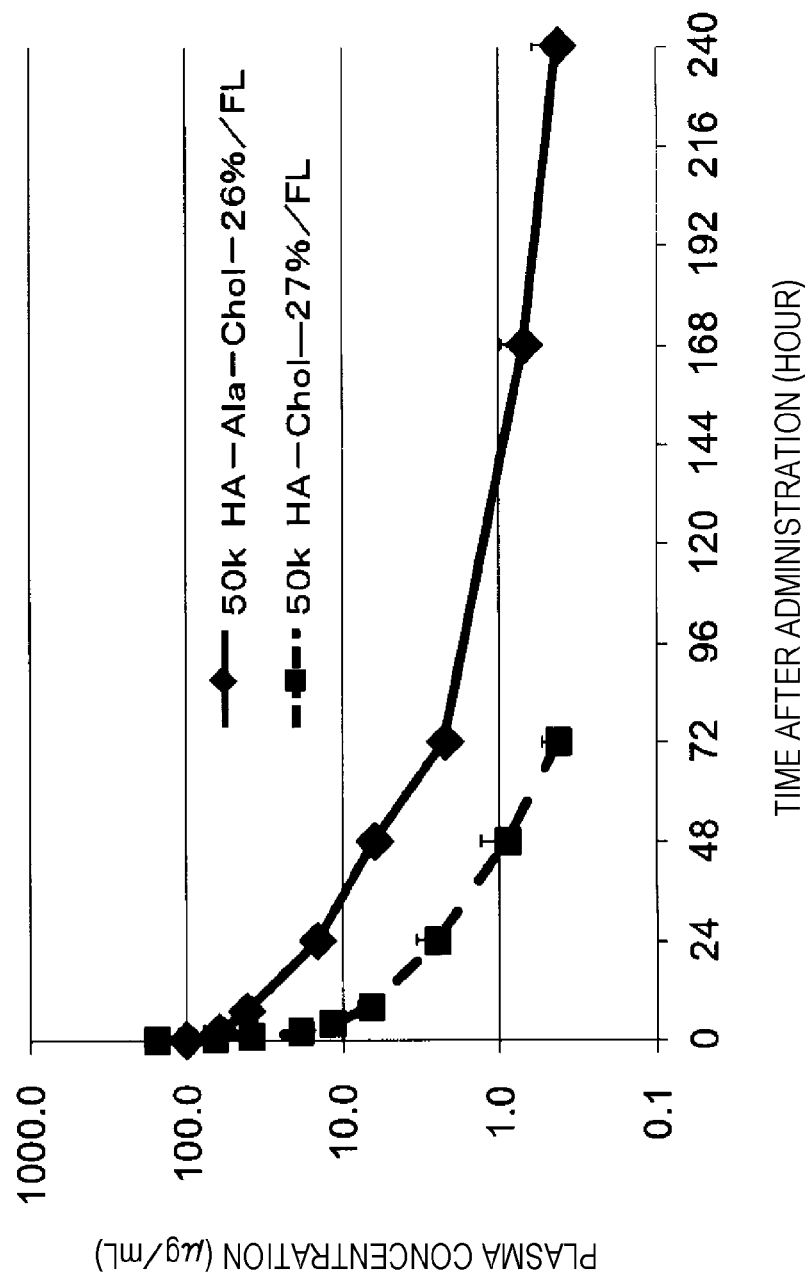
Figures 1, 2, 7:
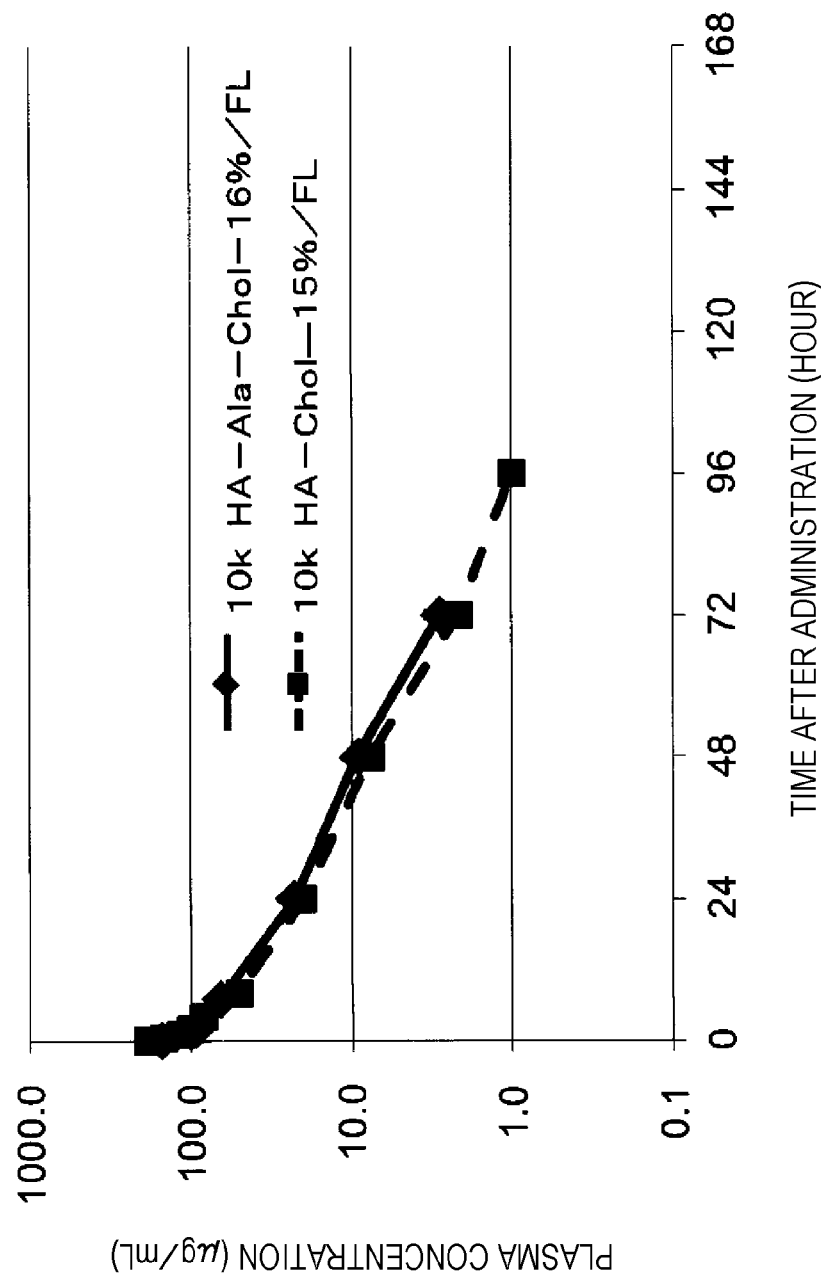
Figures 1, 2, 8:
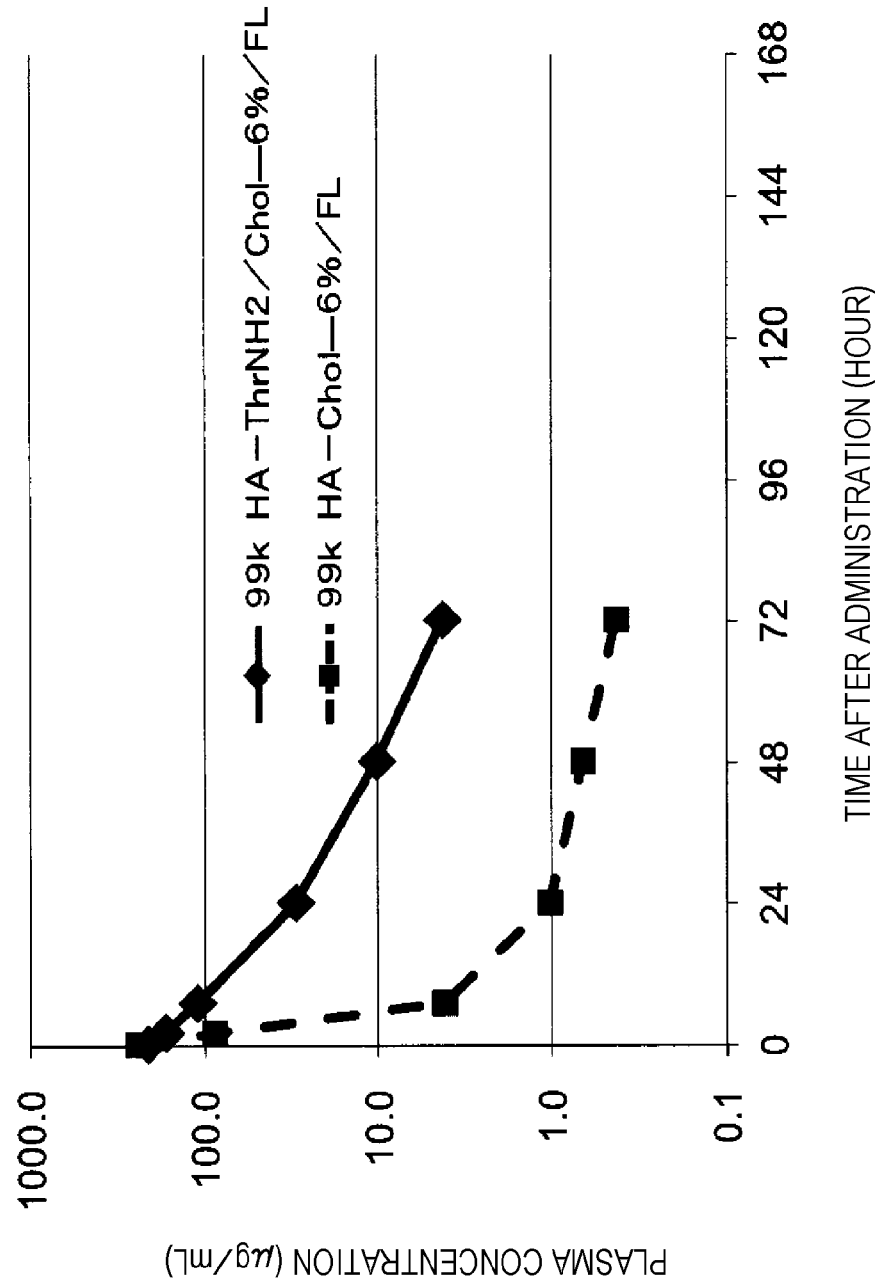
Figures 1, 2, 10:
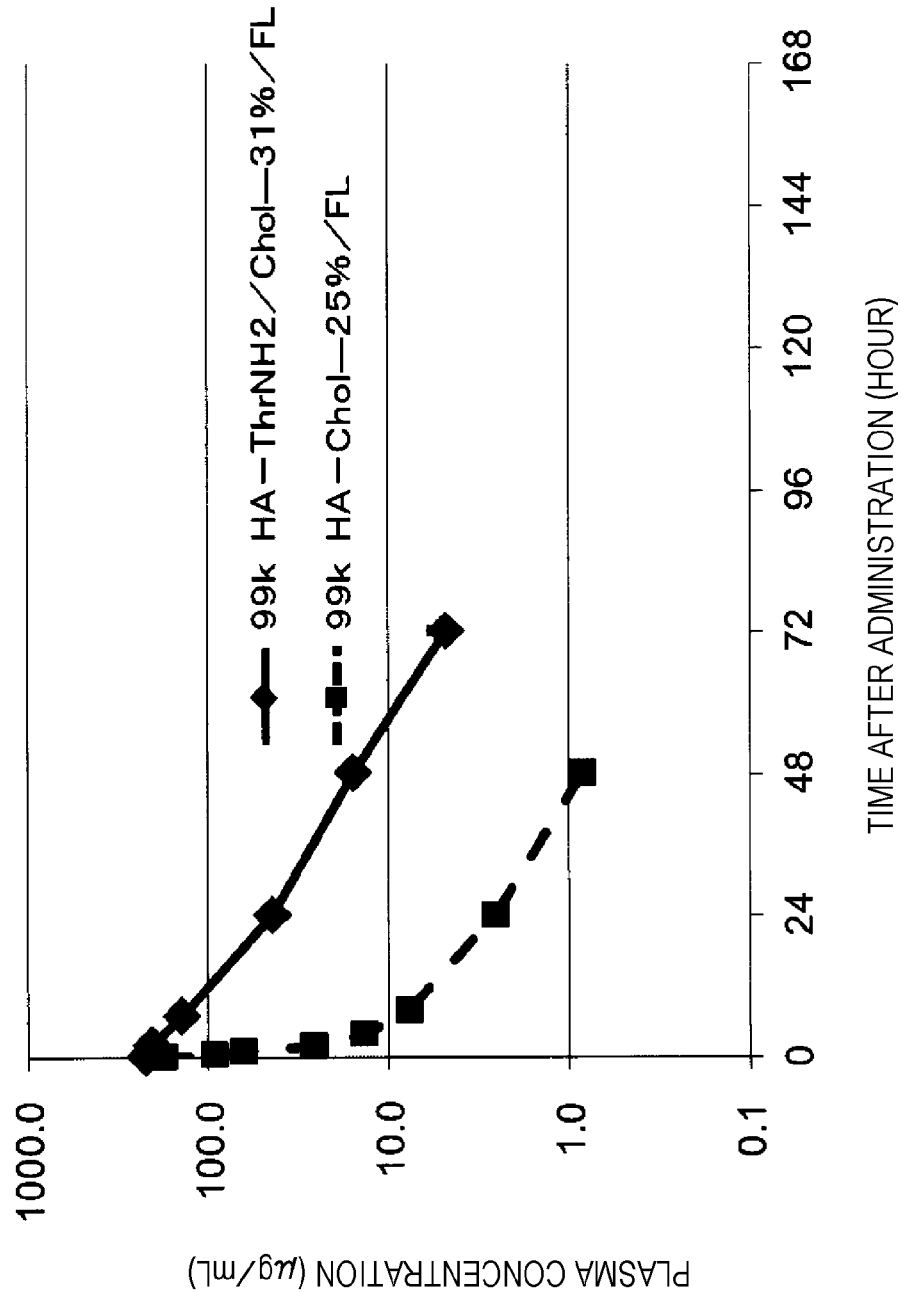
Figures 1, 2, 11:
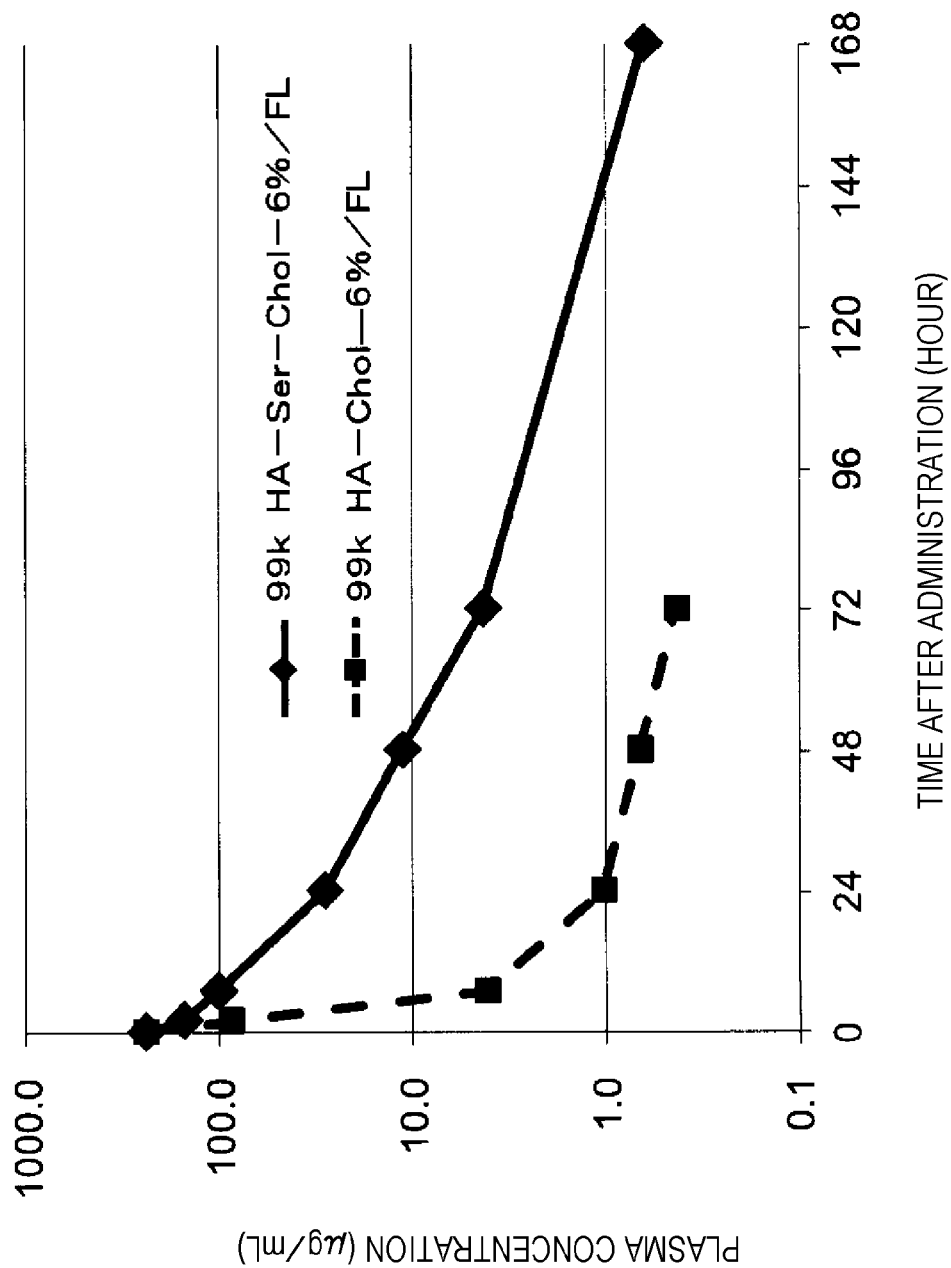
Figures 1, 2, 13:
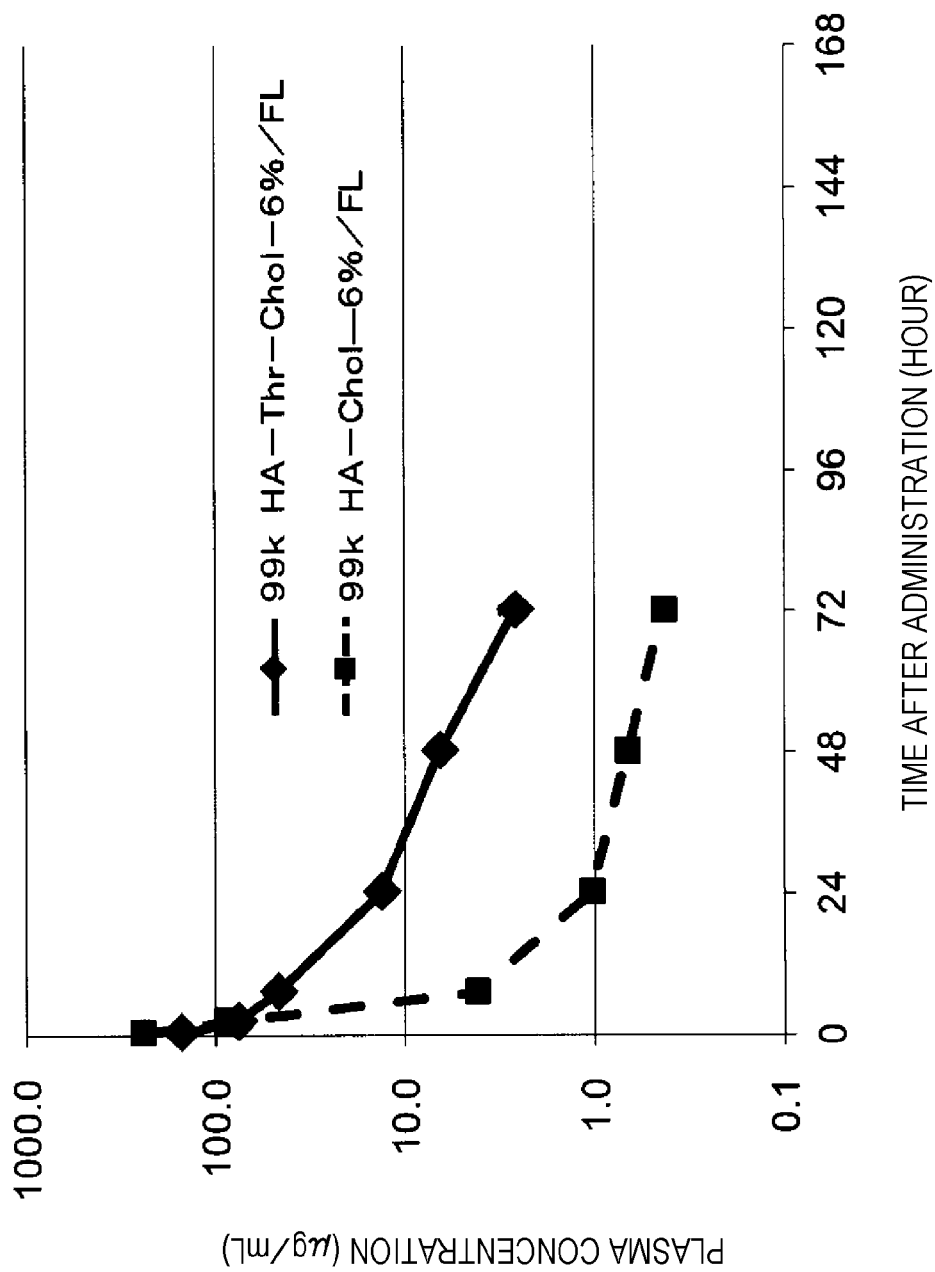
Figures 1, 2, 15:
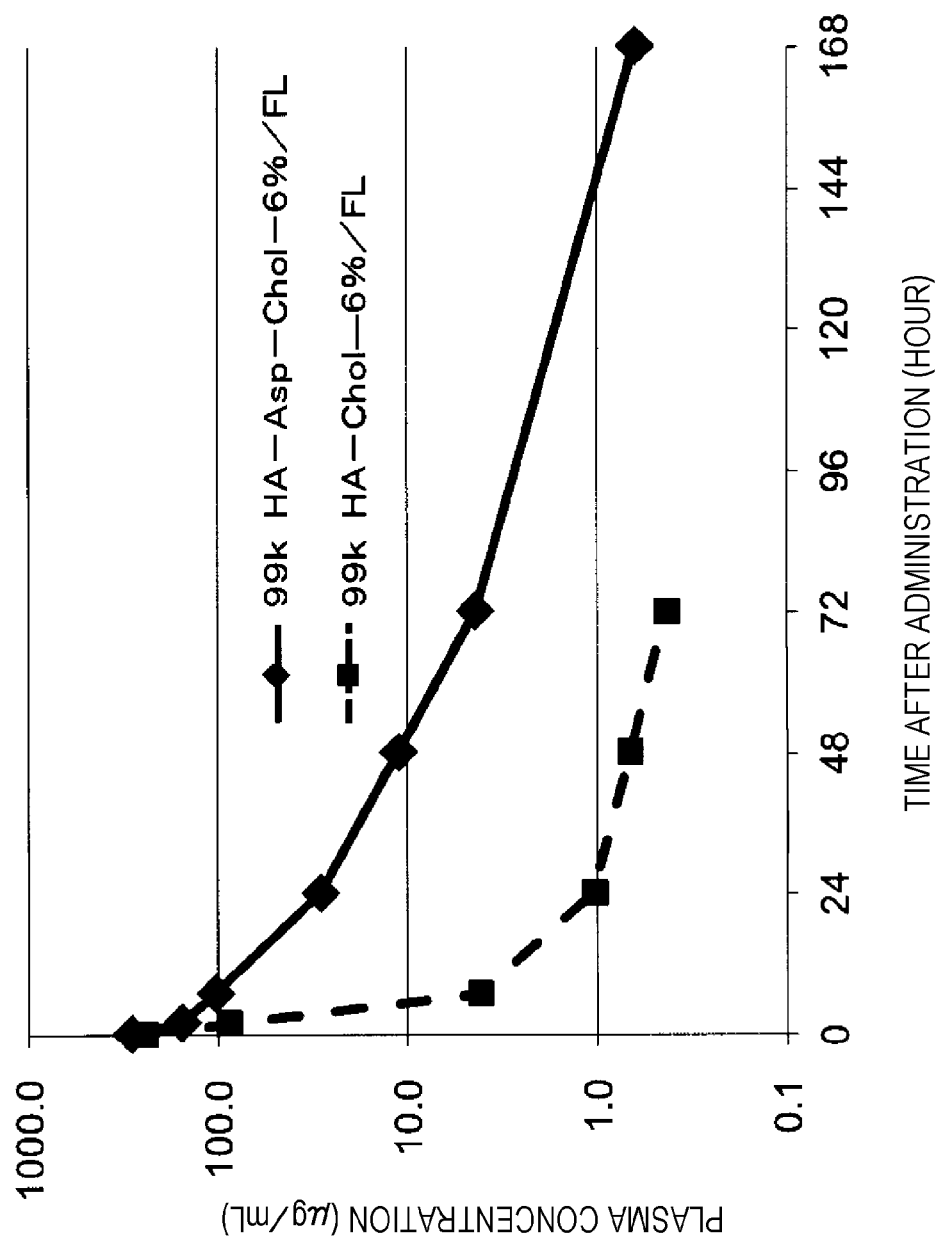
Figures 1, 2, 16:
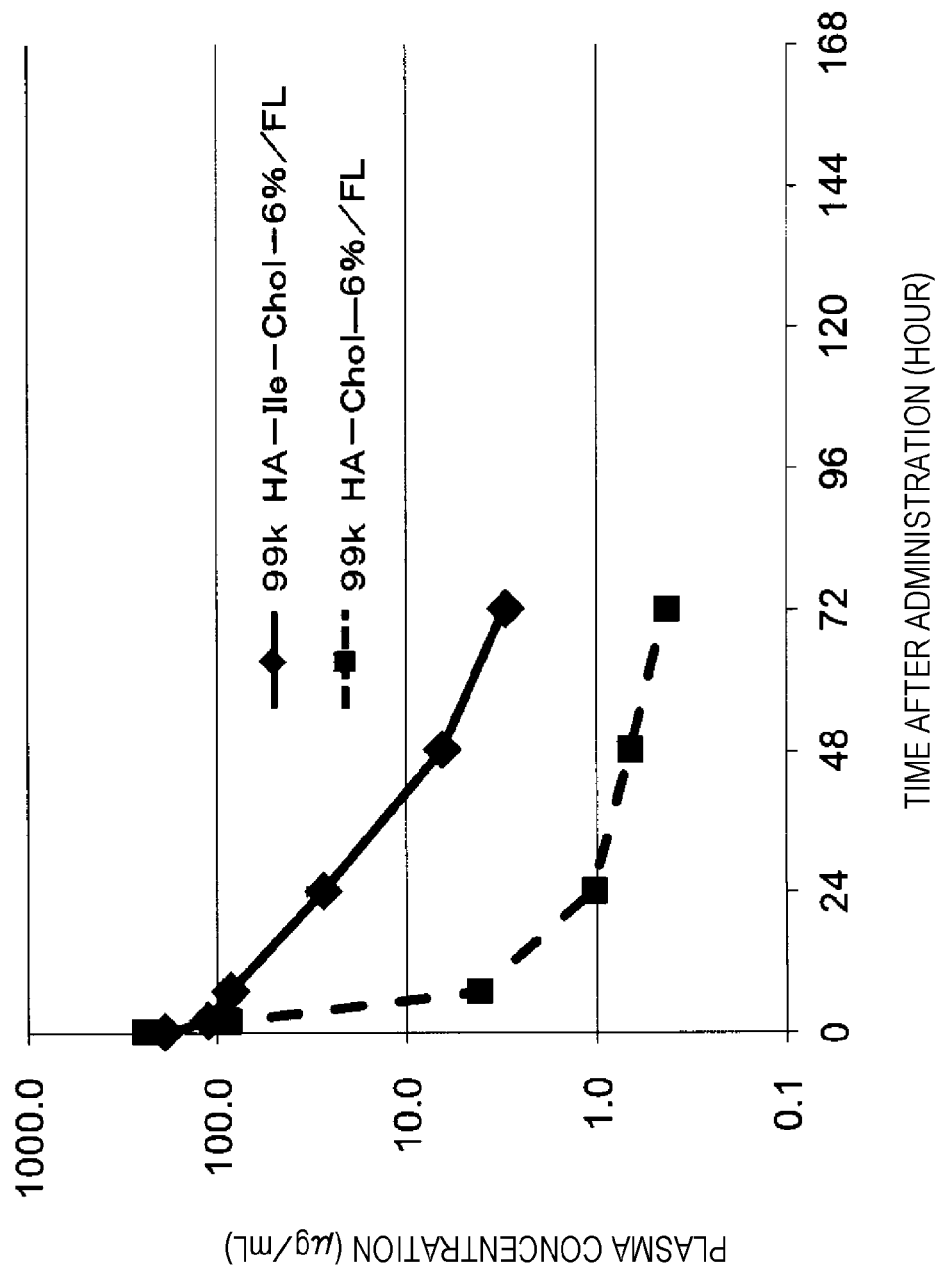
Figures 1, 2, 17:
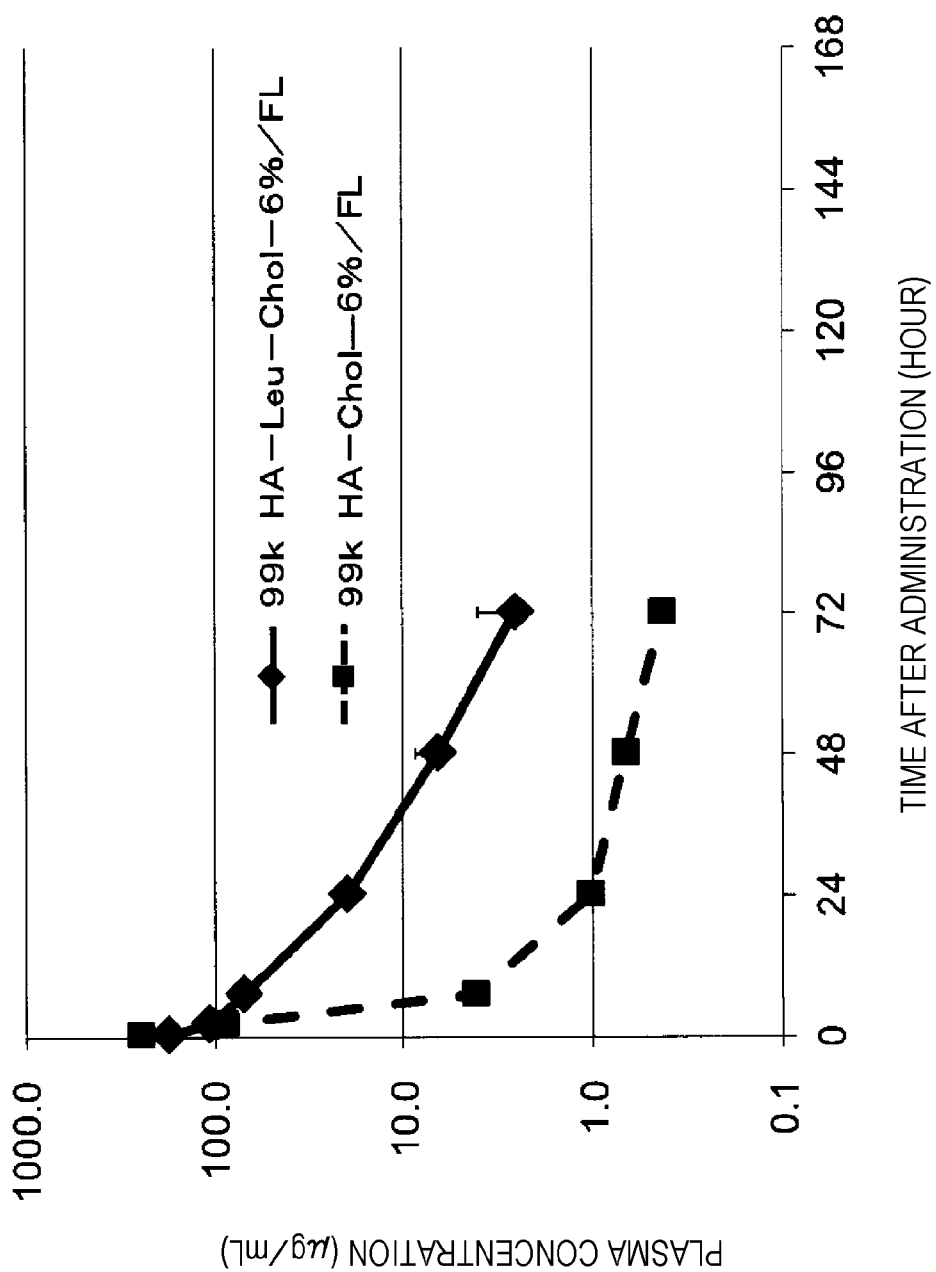
Figures 1, 2, 18:
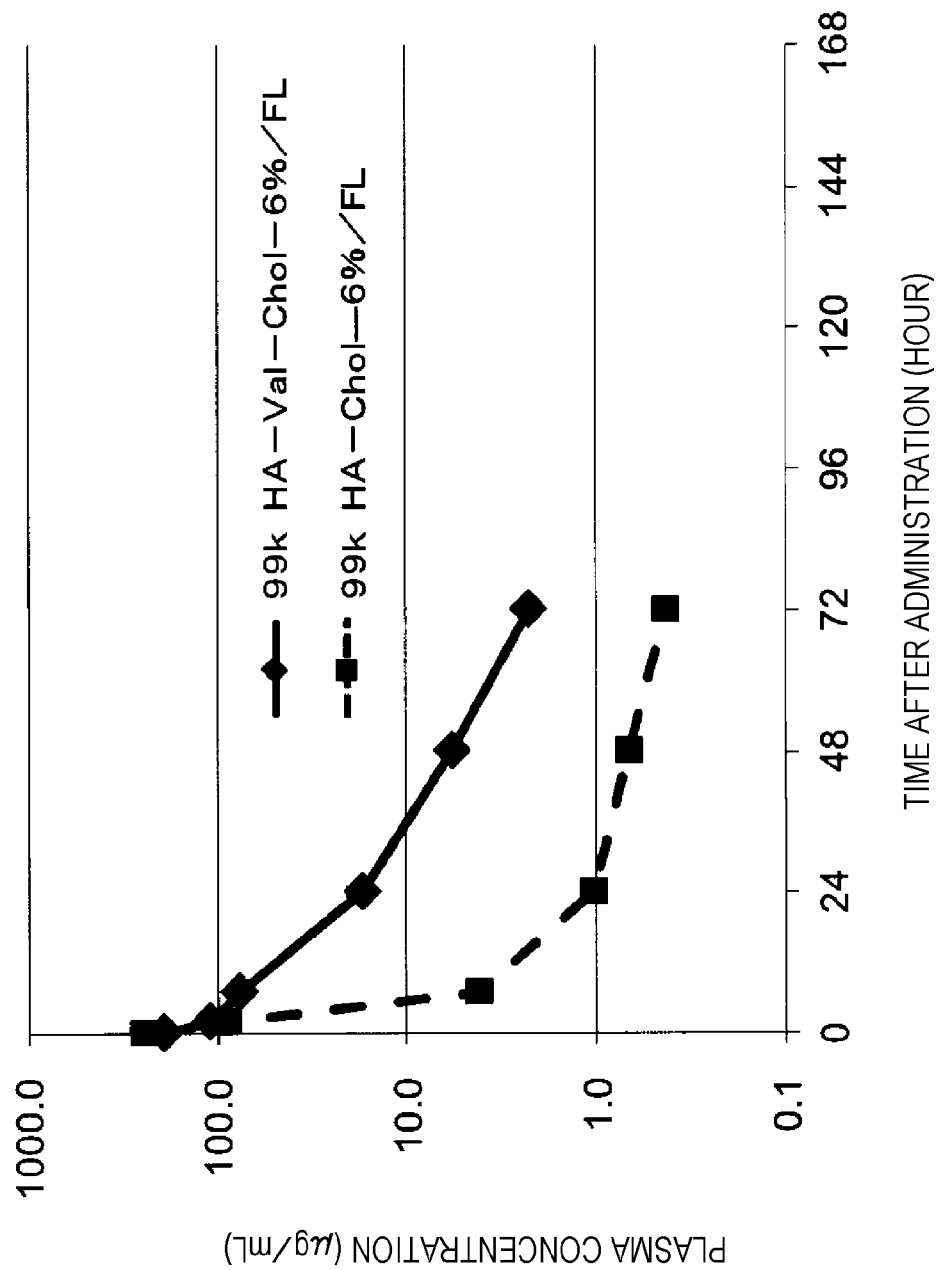
Figures 1, 2, 21:
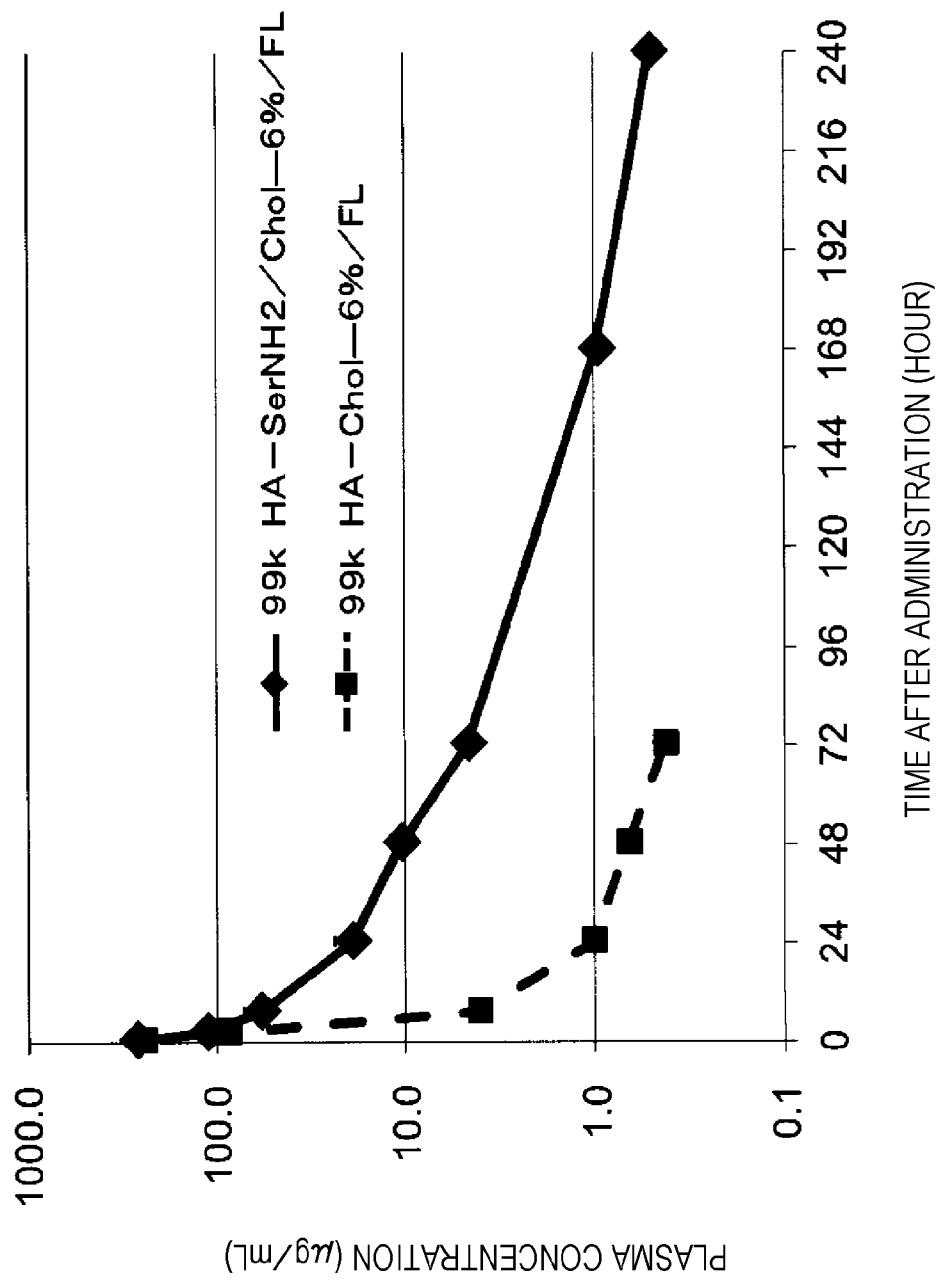
Figures 1, 2, 23:
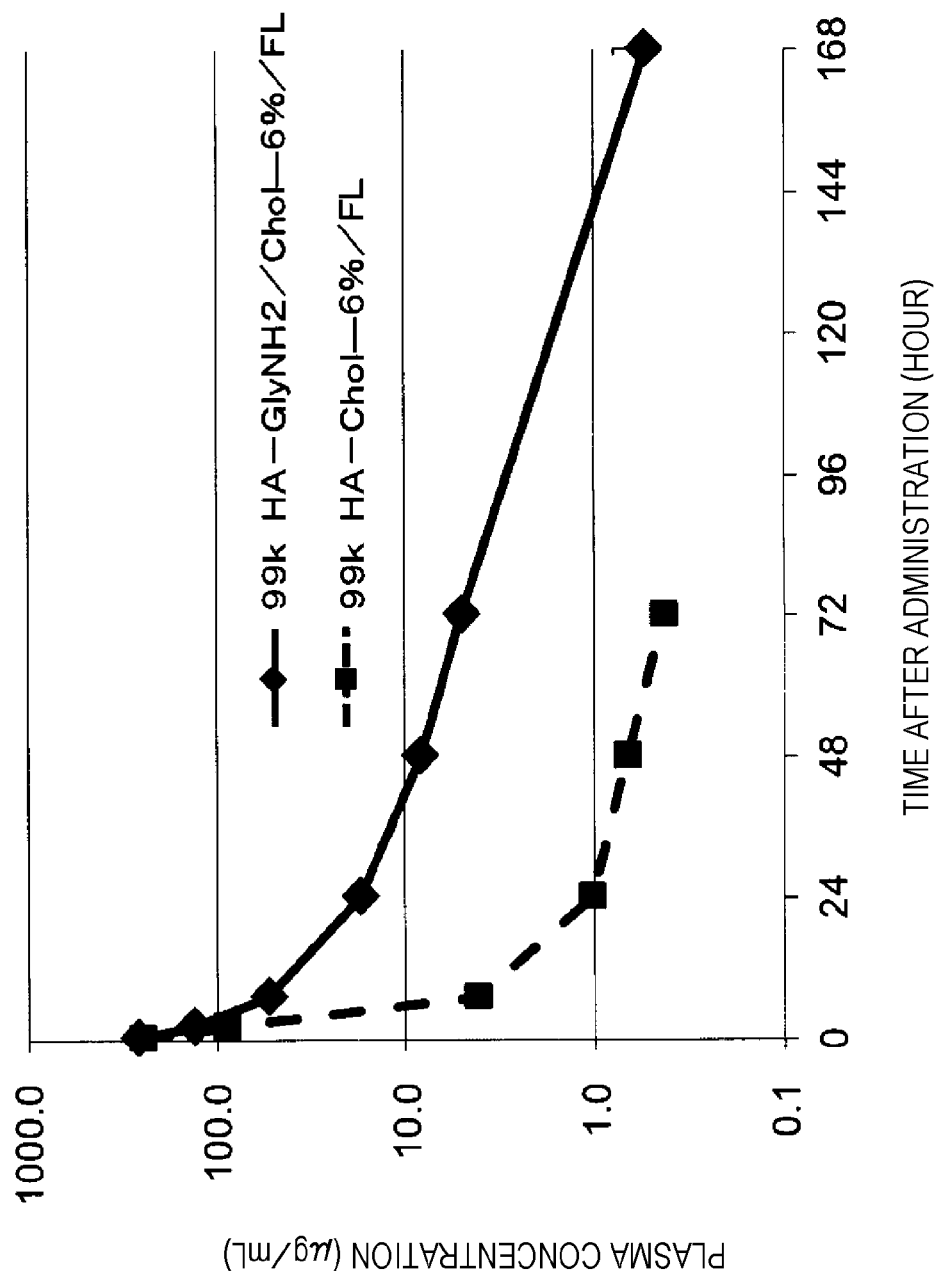
Figures 1, 2, 24:
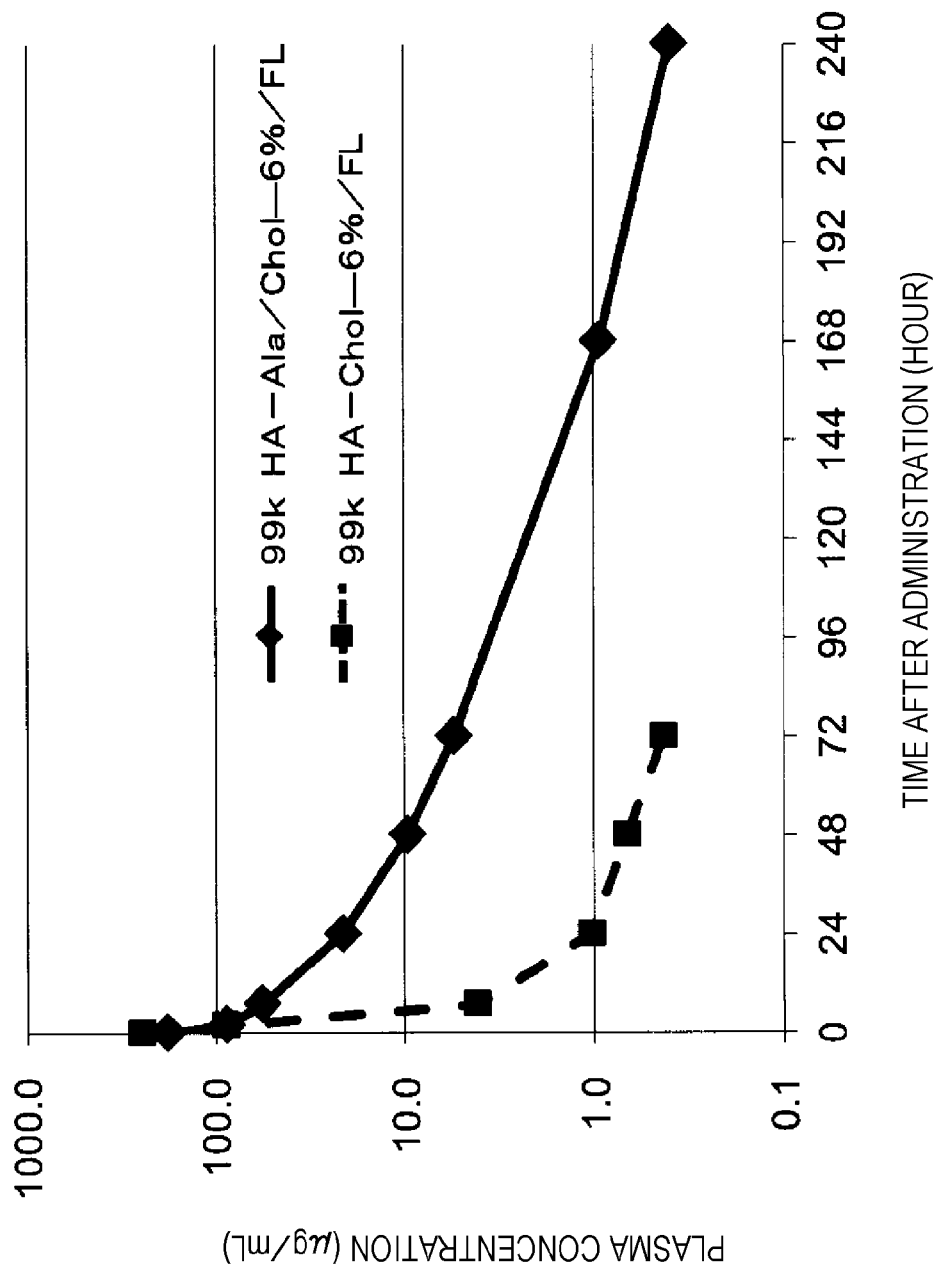
Figures 1, 2, 25:
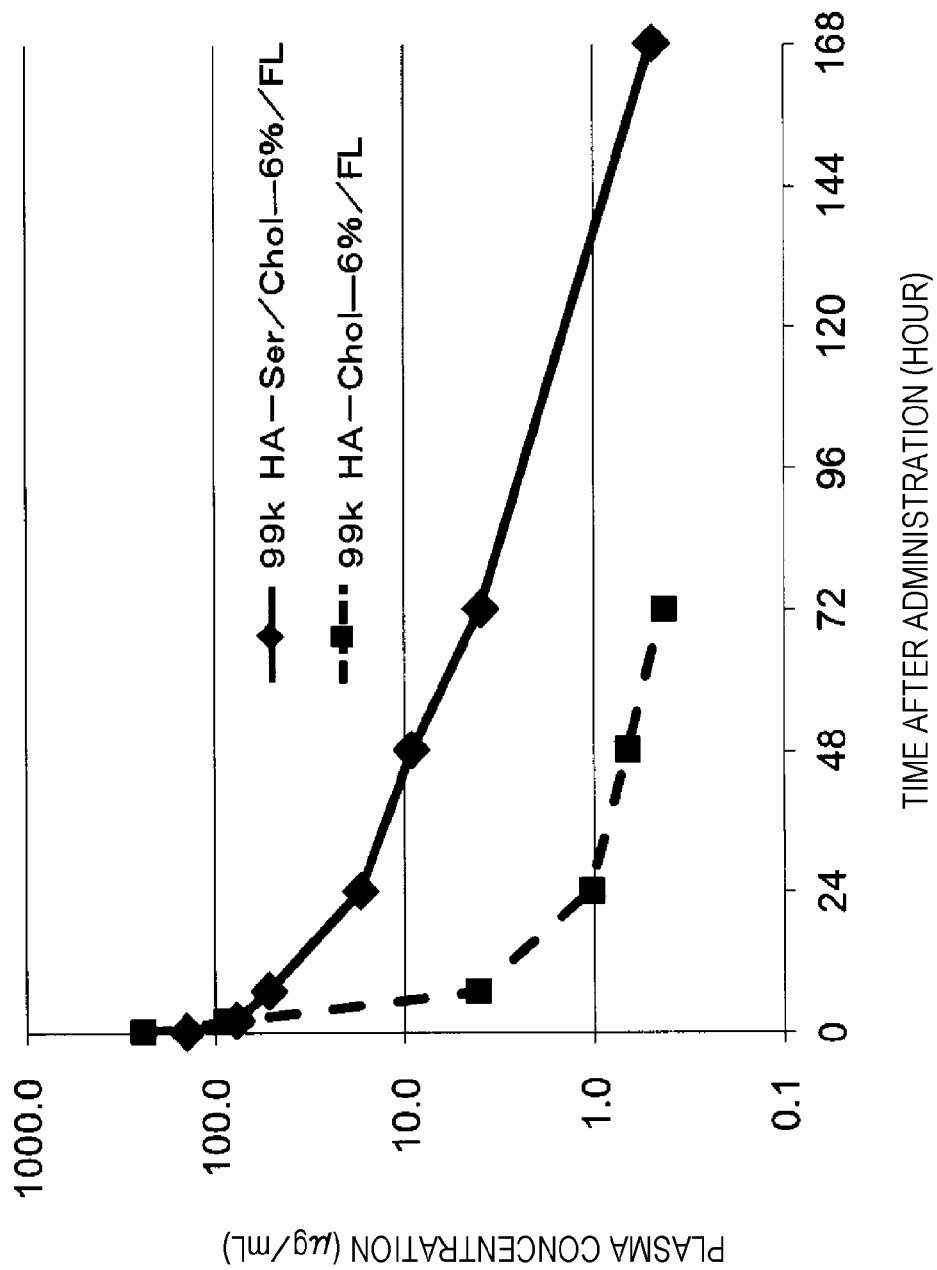
Figures 1, 2, 26:
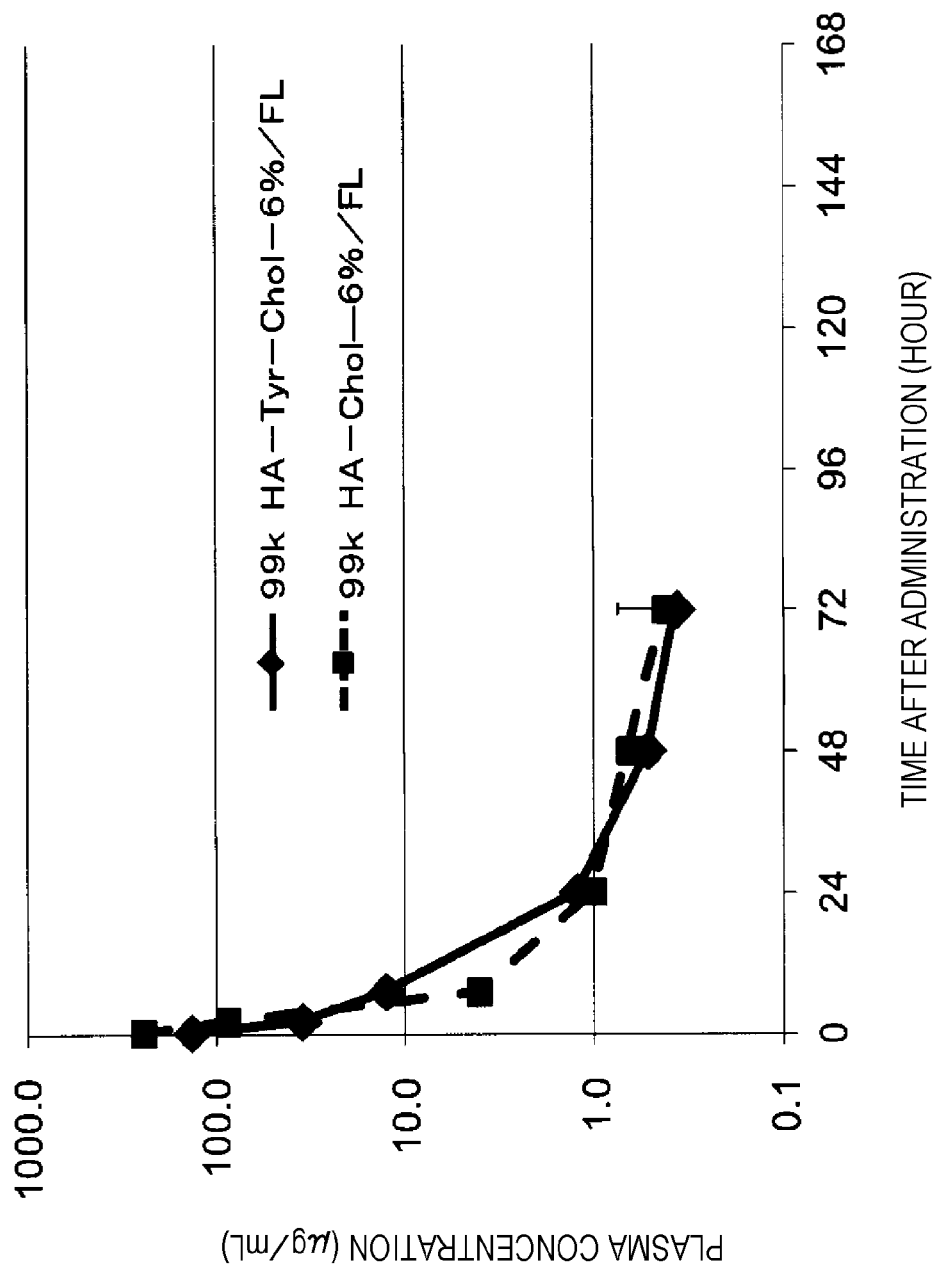
Figures 1, 2:
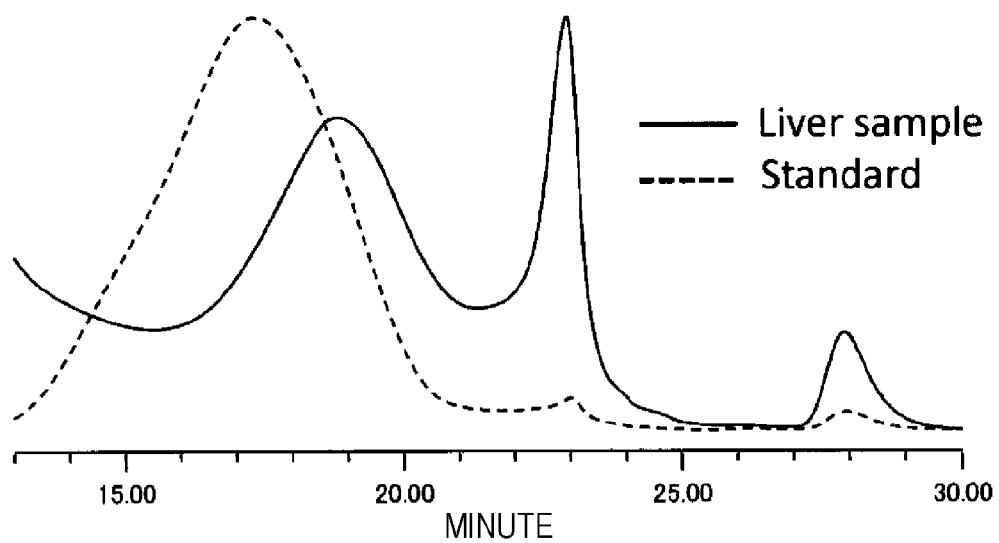
Figure 2:
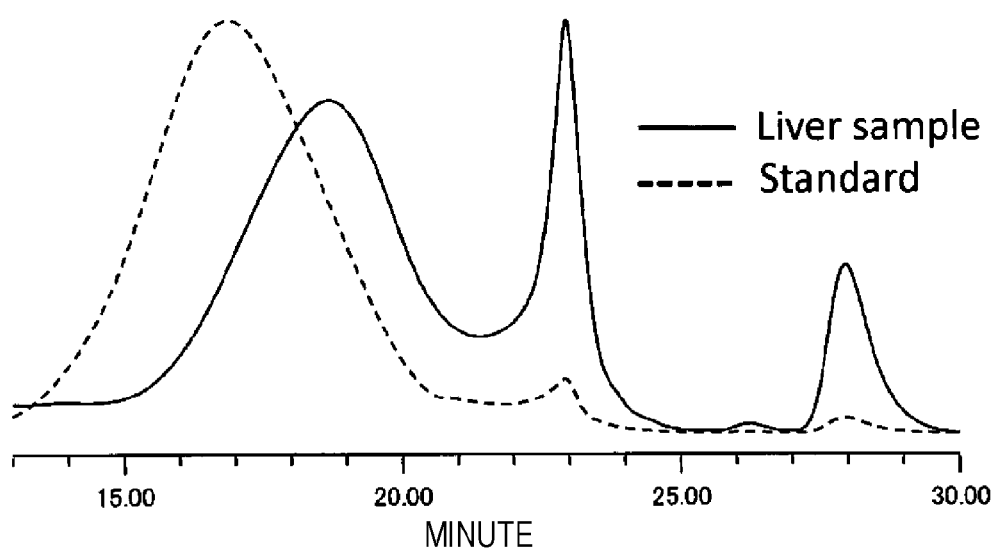
Figures 2, 3:
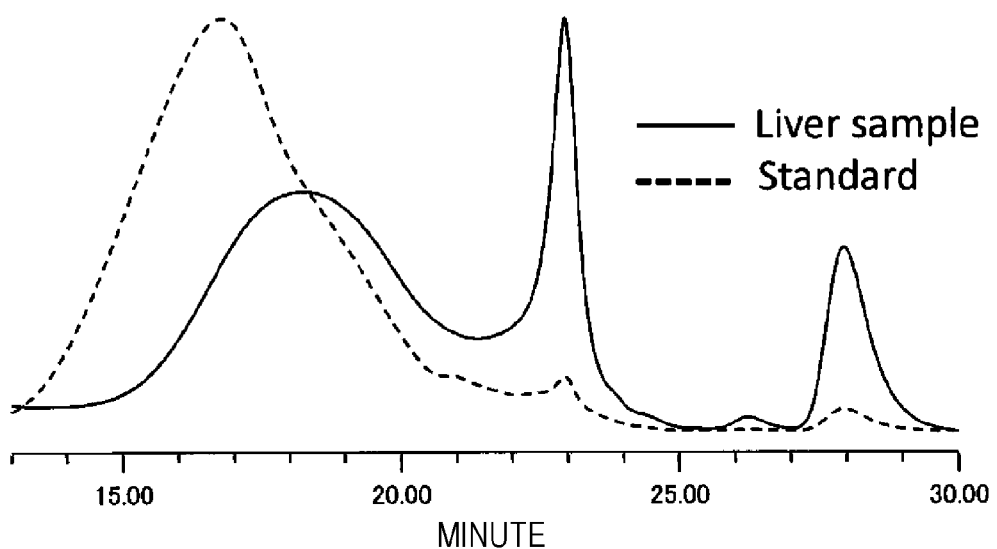
Figures 2, 4:
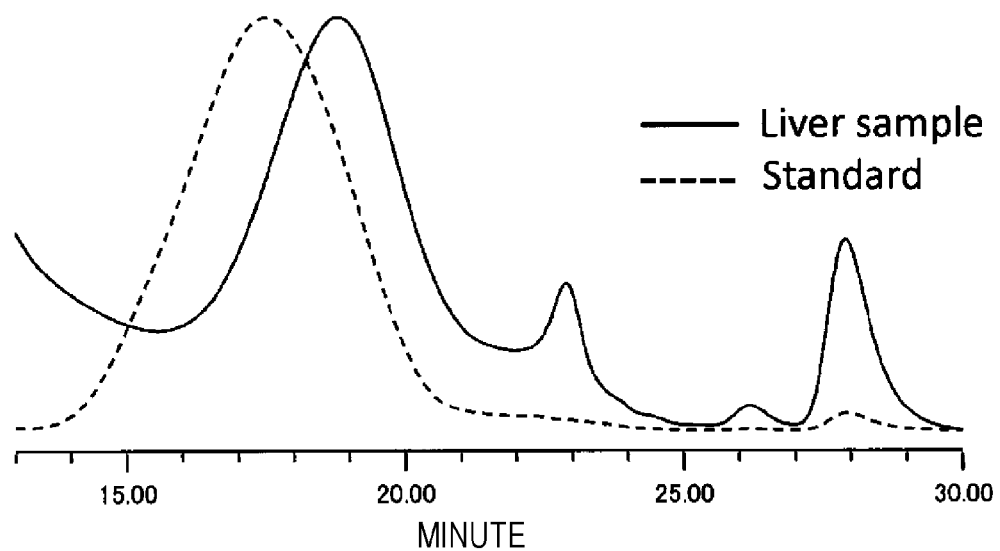
Figures 2, 5:
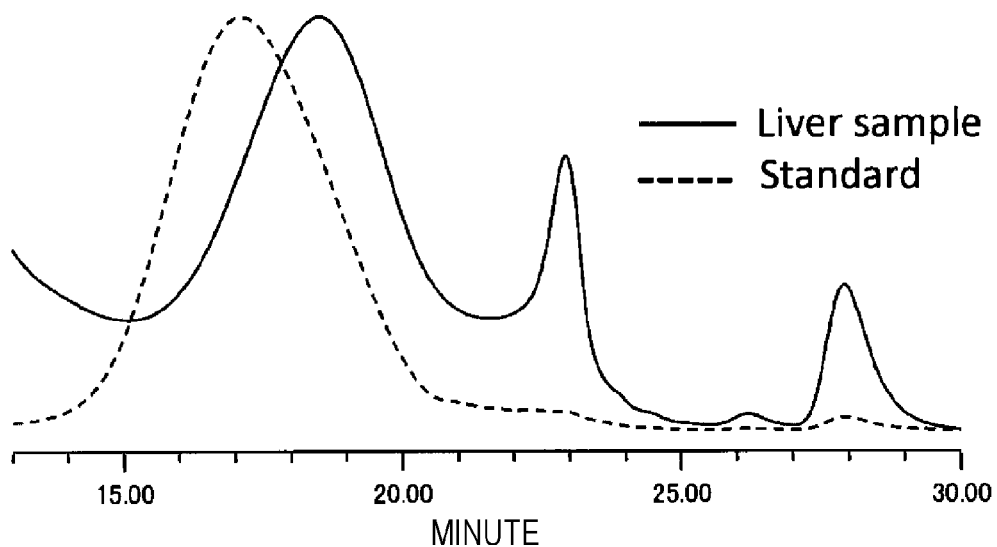
Figures 2, 6:
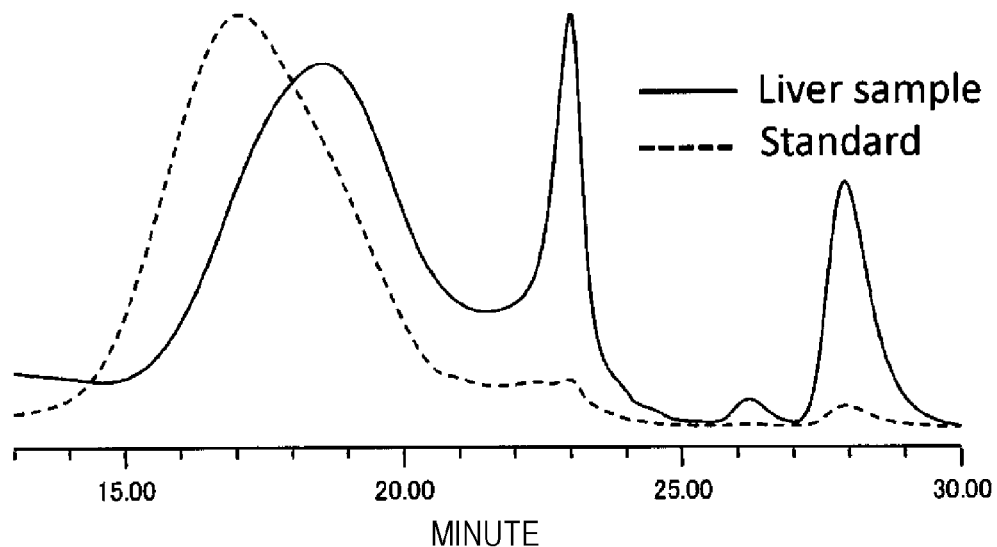
Figures 2, 7:
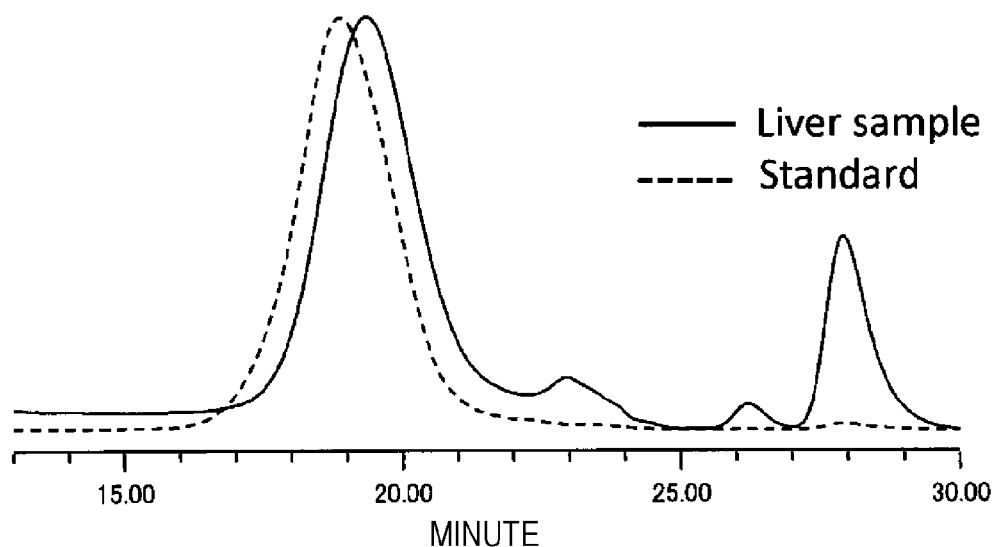
Figures 2, 8:
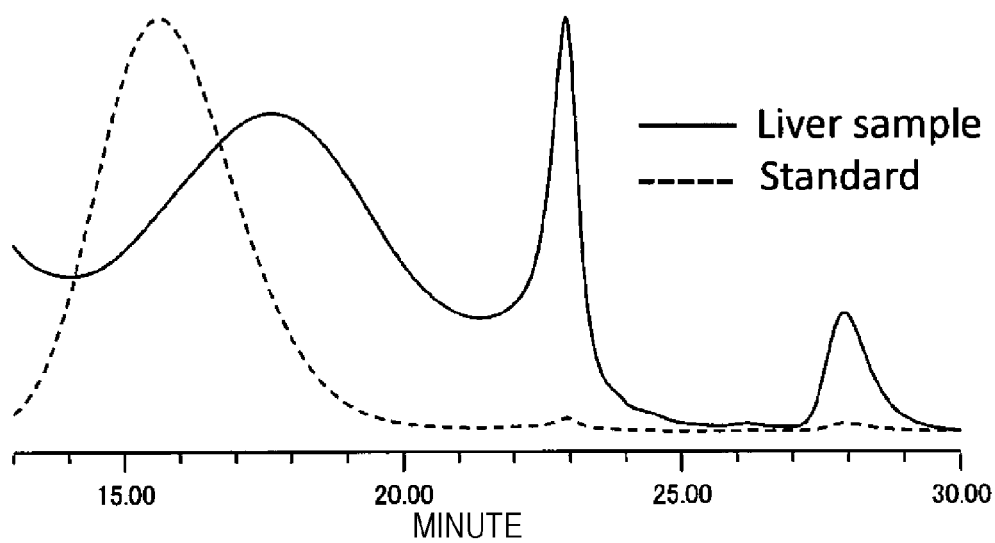
Figures 2, 9:
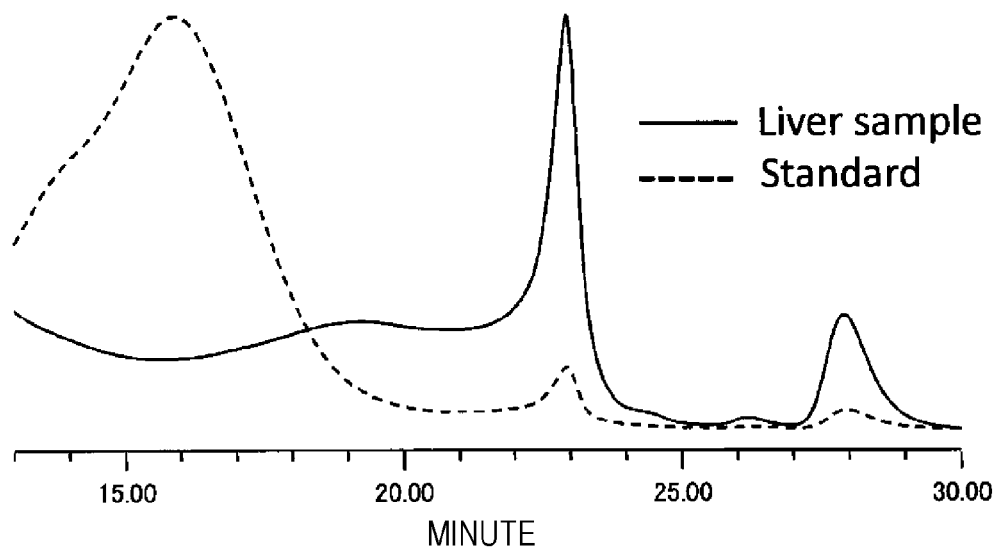
Figures 2, 10:
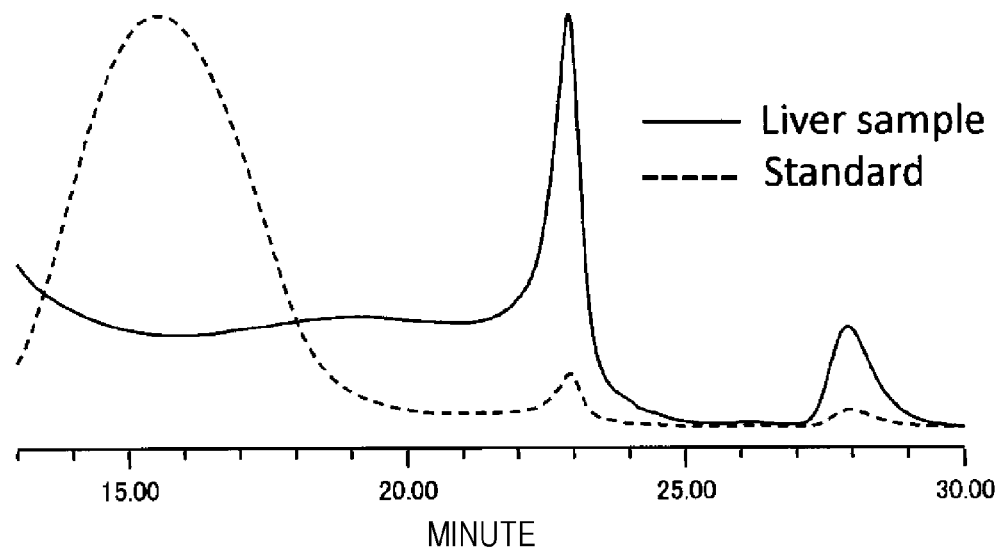
Figures 2, 11:
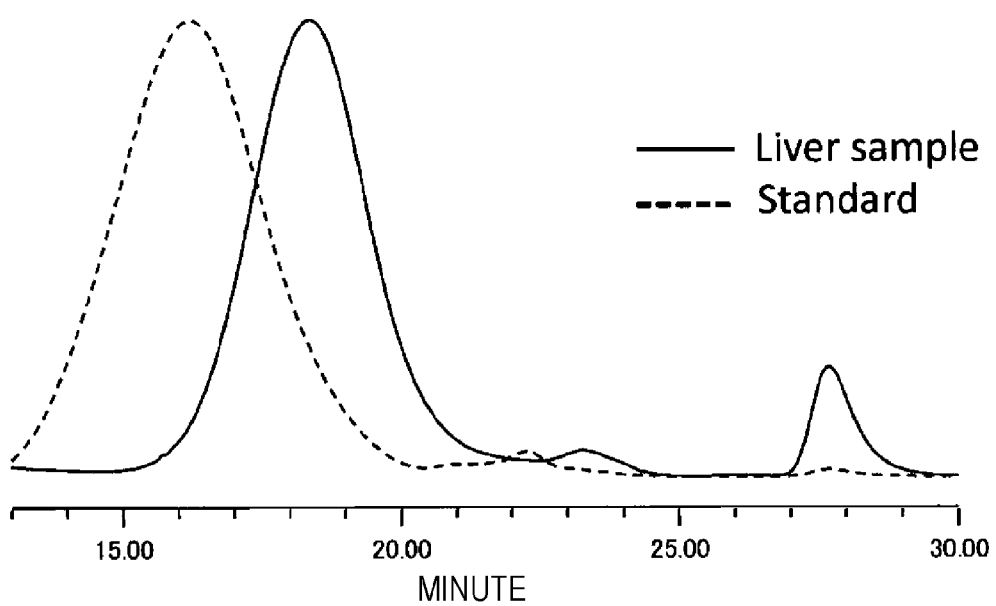
Figures 2, 12:
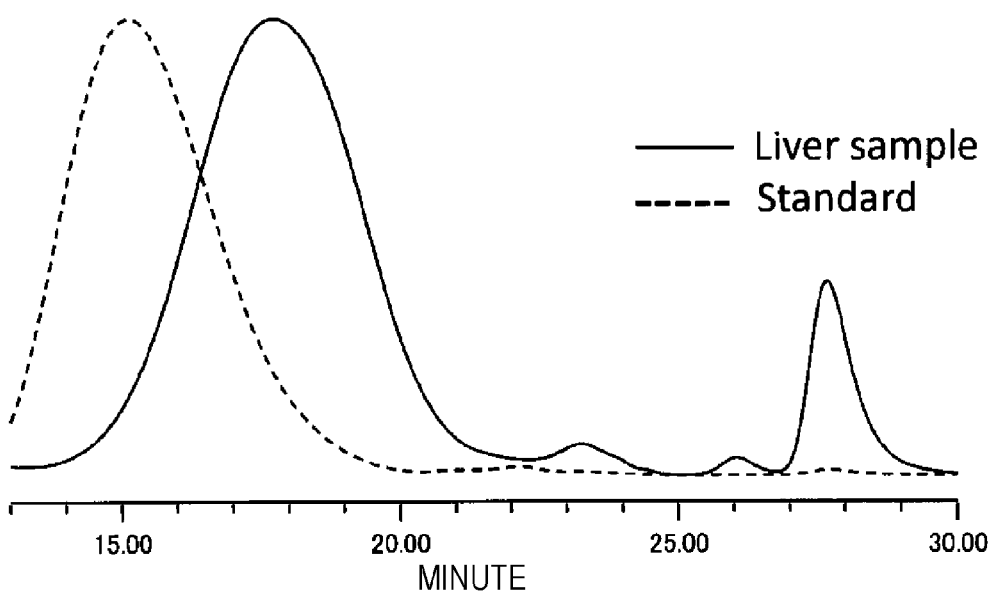
Figures 2, 13:
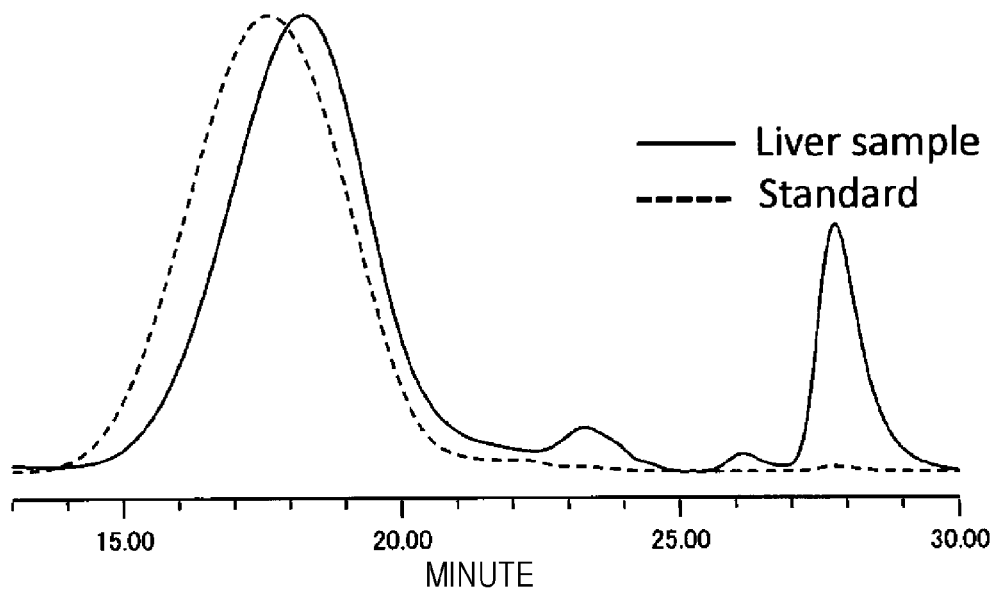
Figures 2, 14:
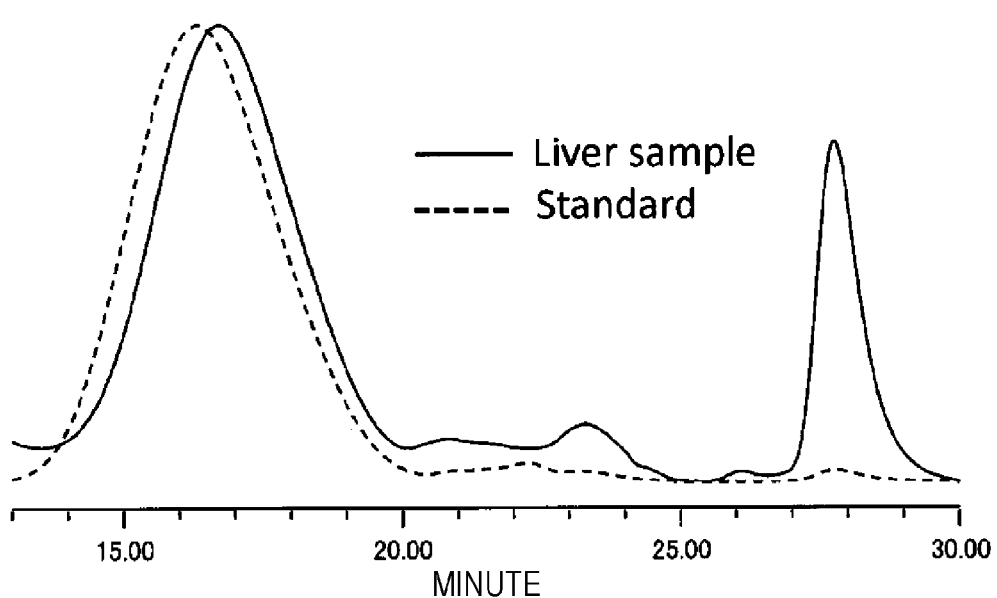
Figures 2, 15:
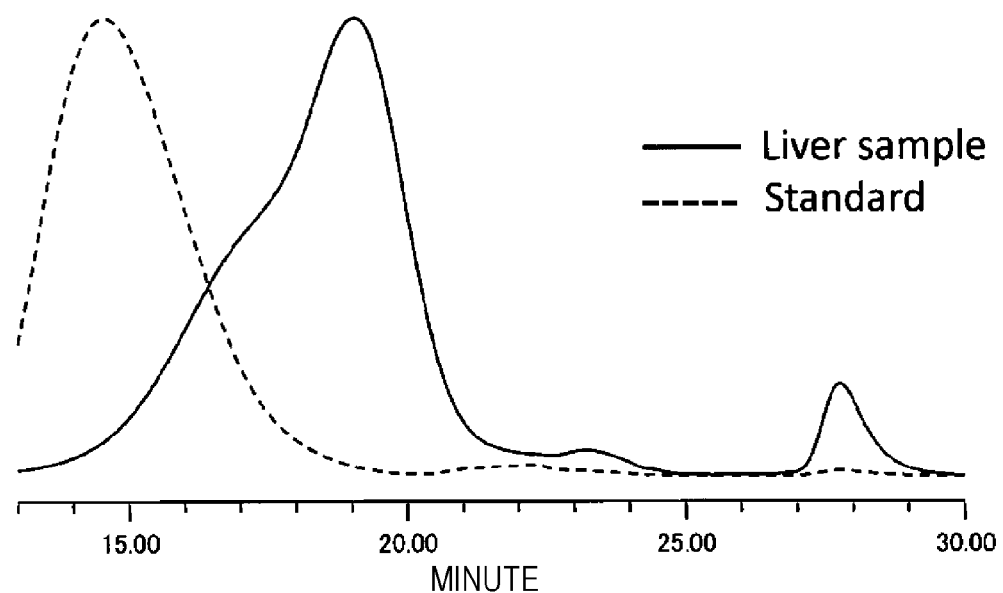
Figures 2, 16:
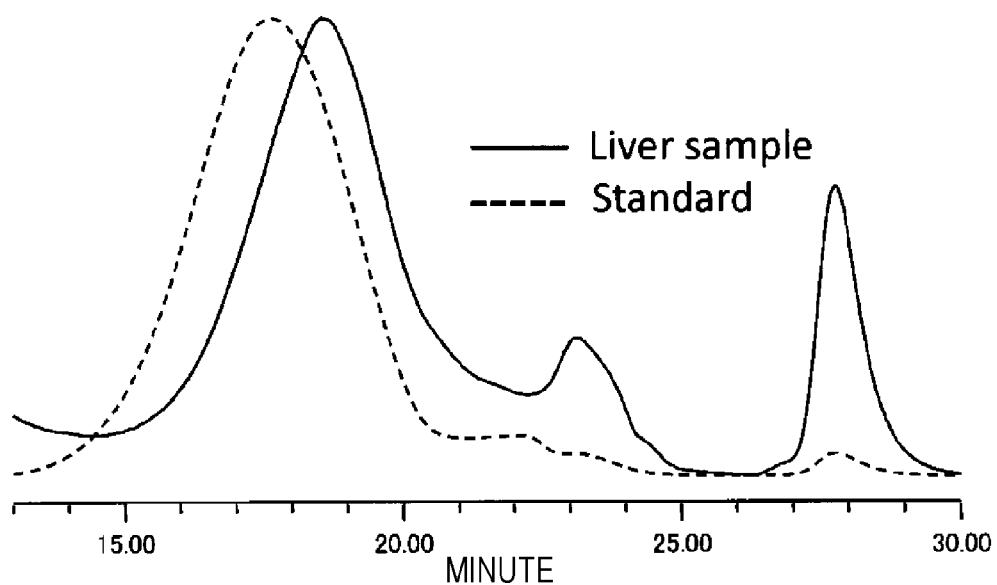
Figures 2, 17:
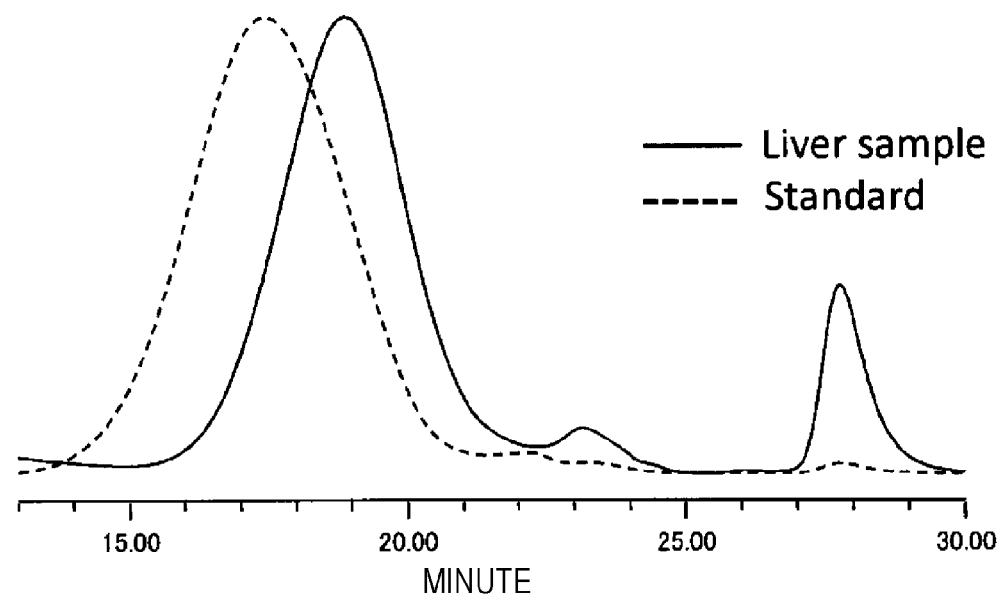
Figures 2, 18:
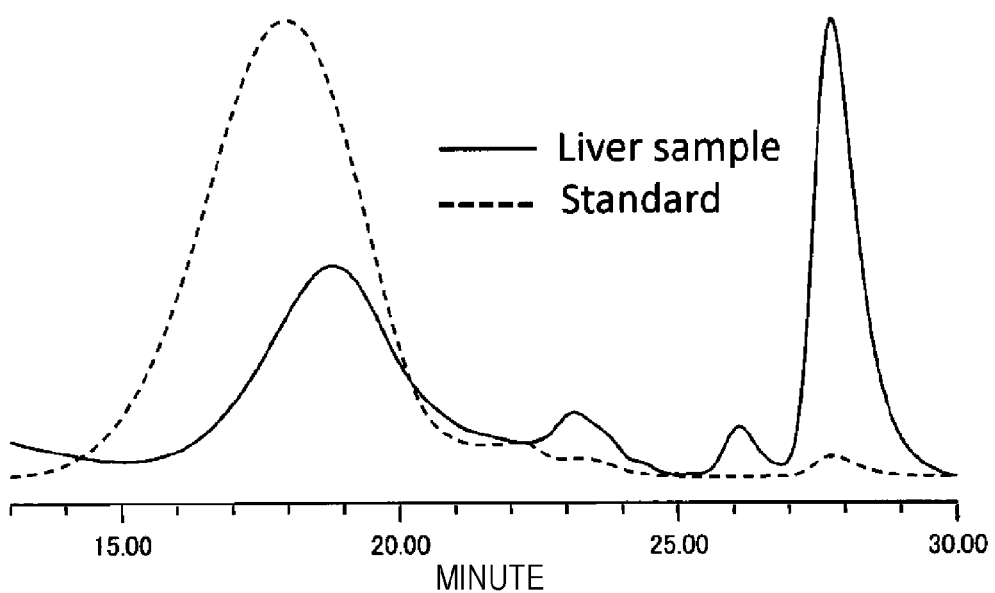
Figures 2, 19:
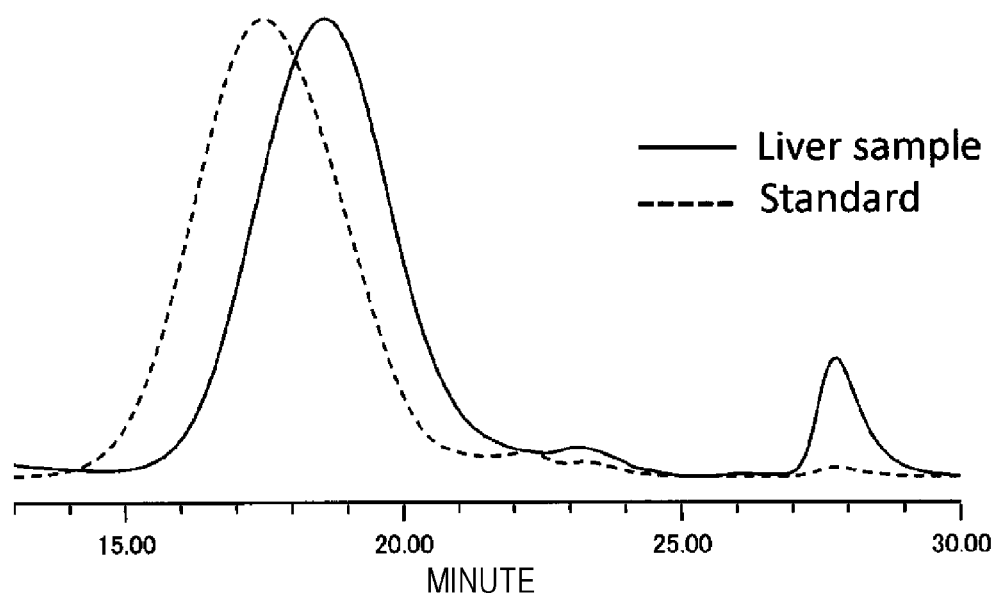
Figures 2, 20:
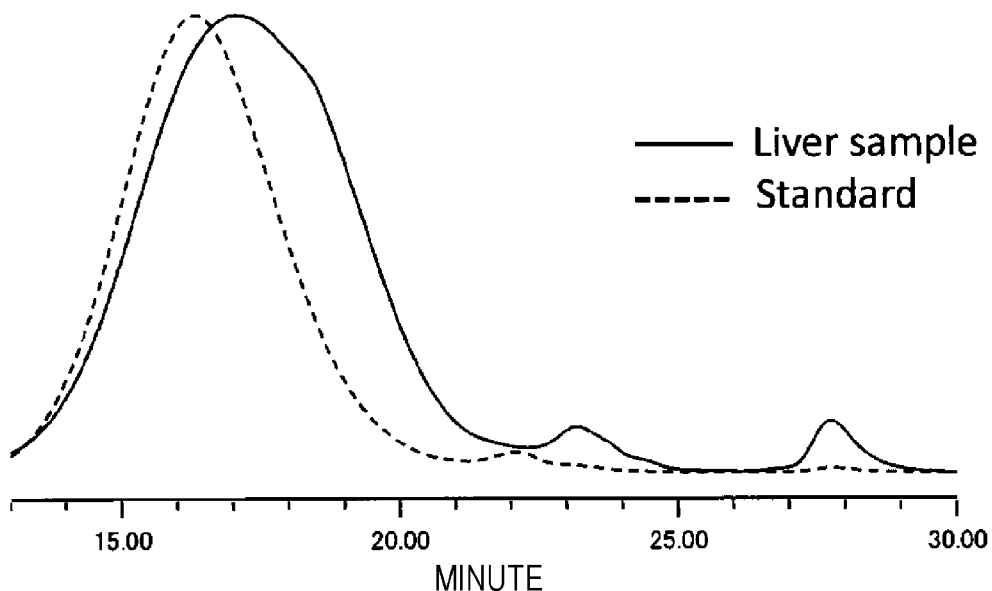
Figures 2, 21:
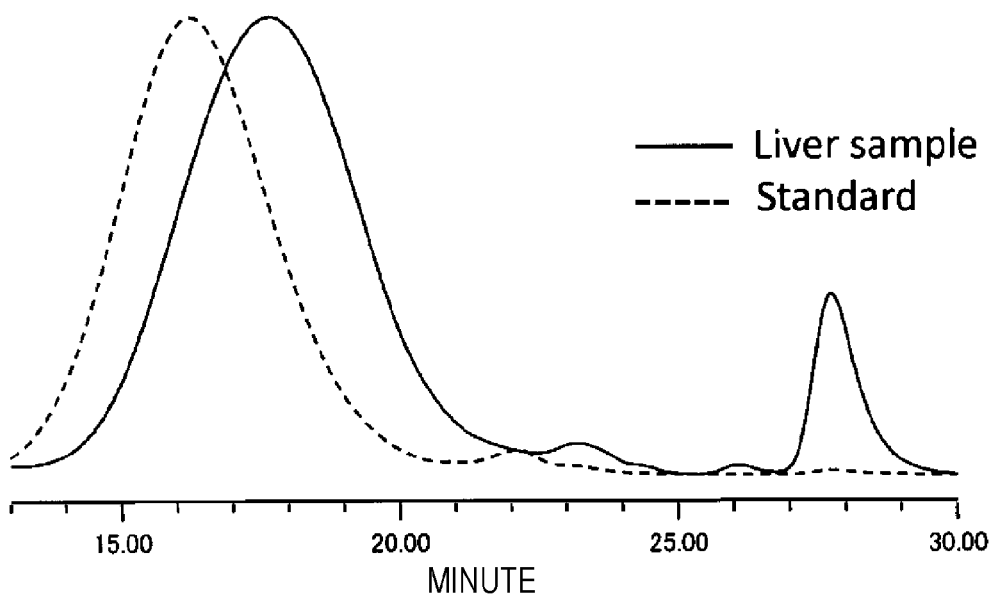
Figures 2, 22:
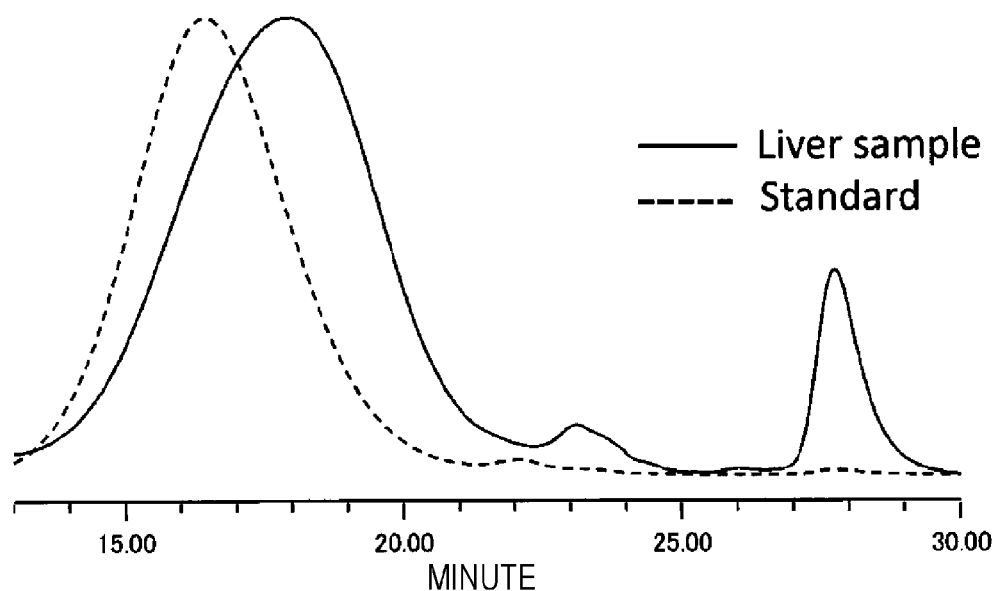
Figures 2, 23:
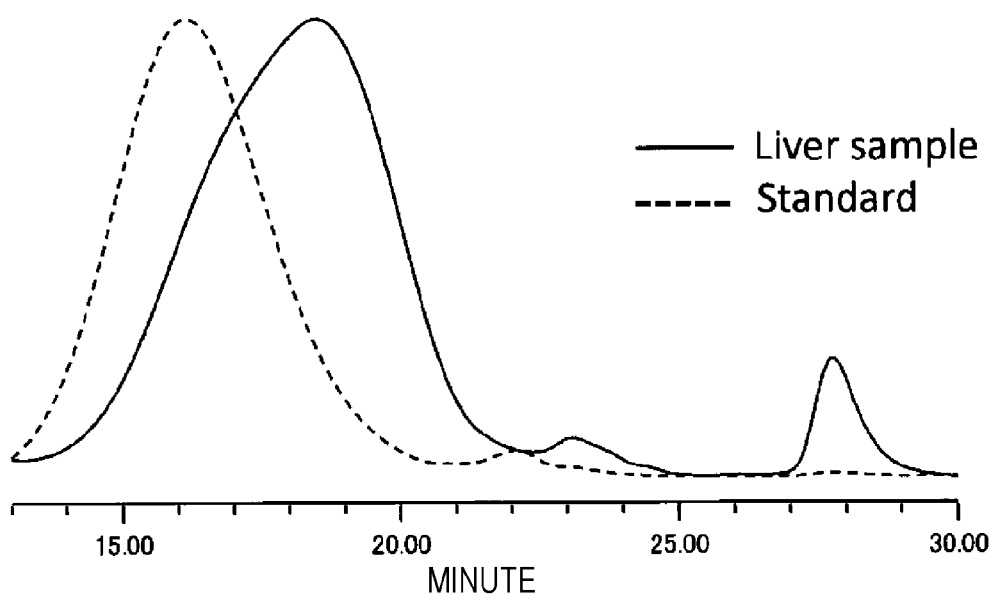
Figures 2, 24:
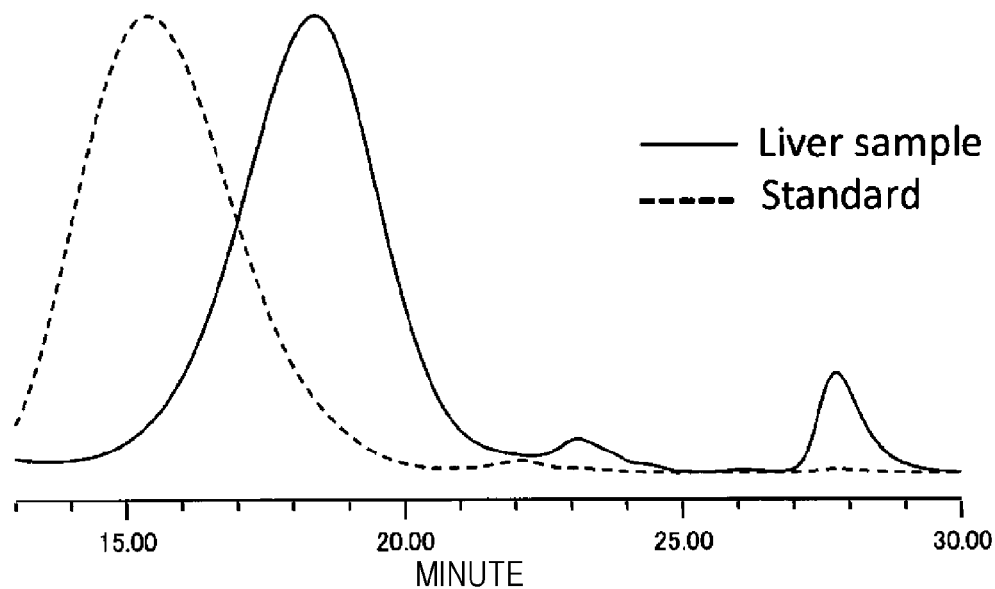
Figures 2, 25:
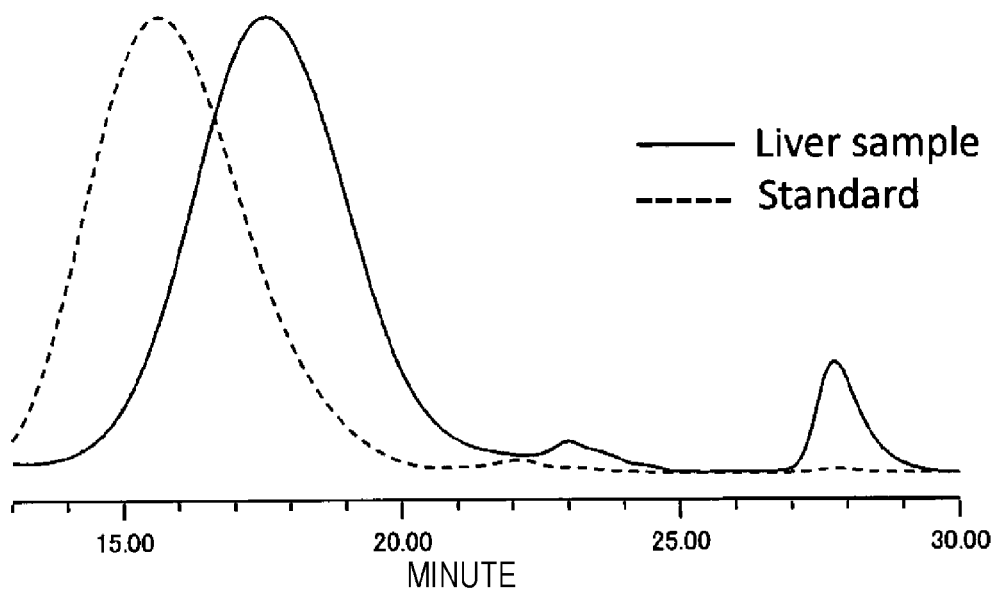
Figures 2, 26:
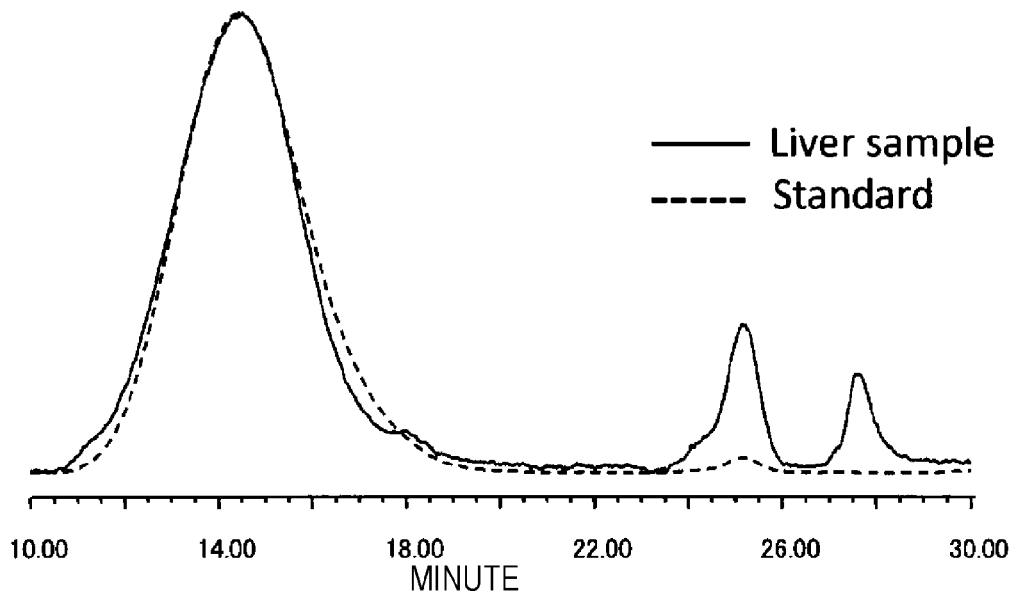
Figures 2, 27:
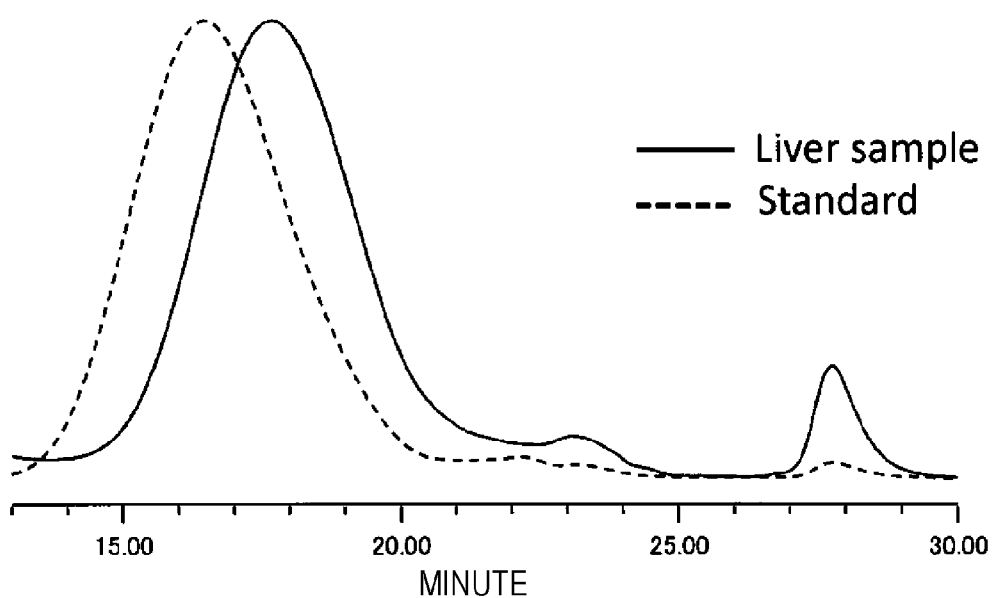
Figures 1, 2, 3:
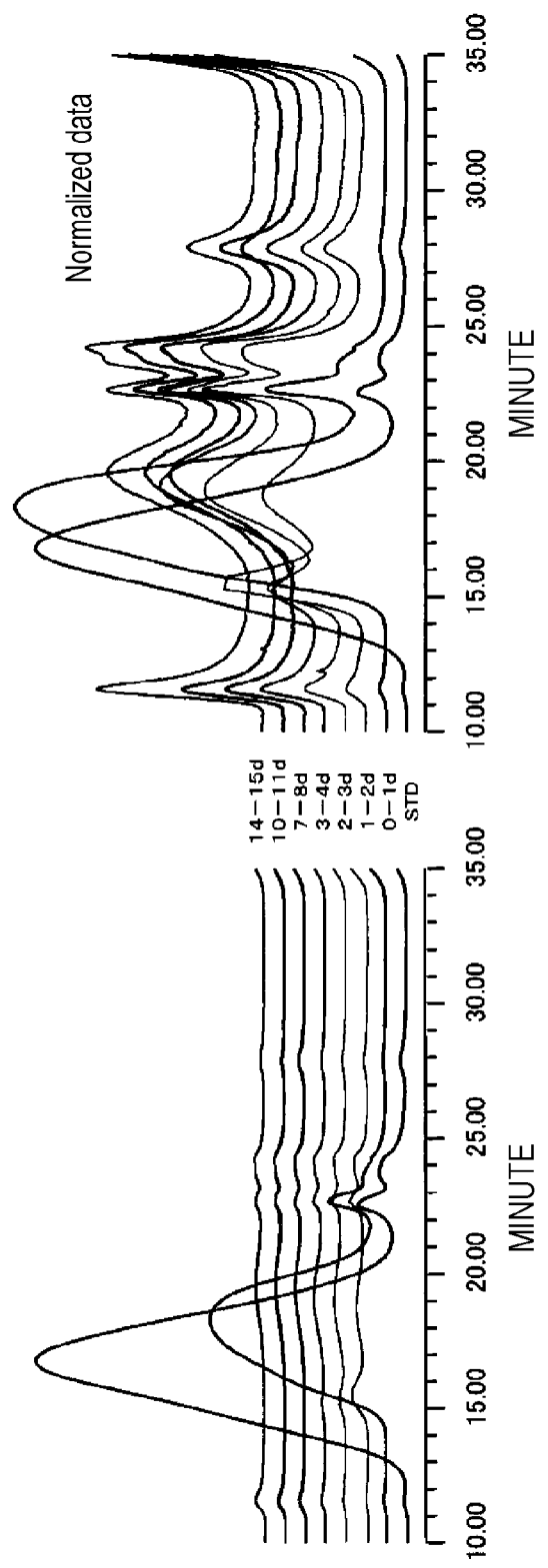
Figures 2, 3:
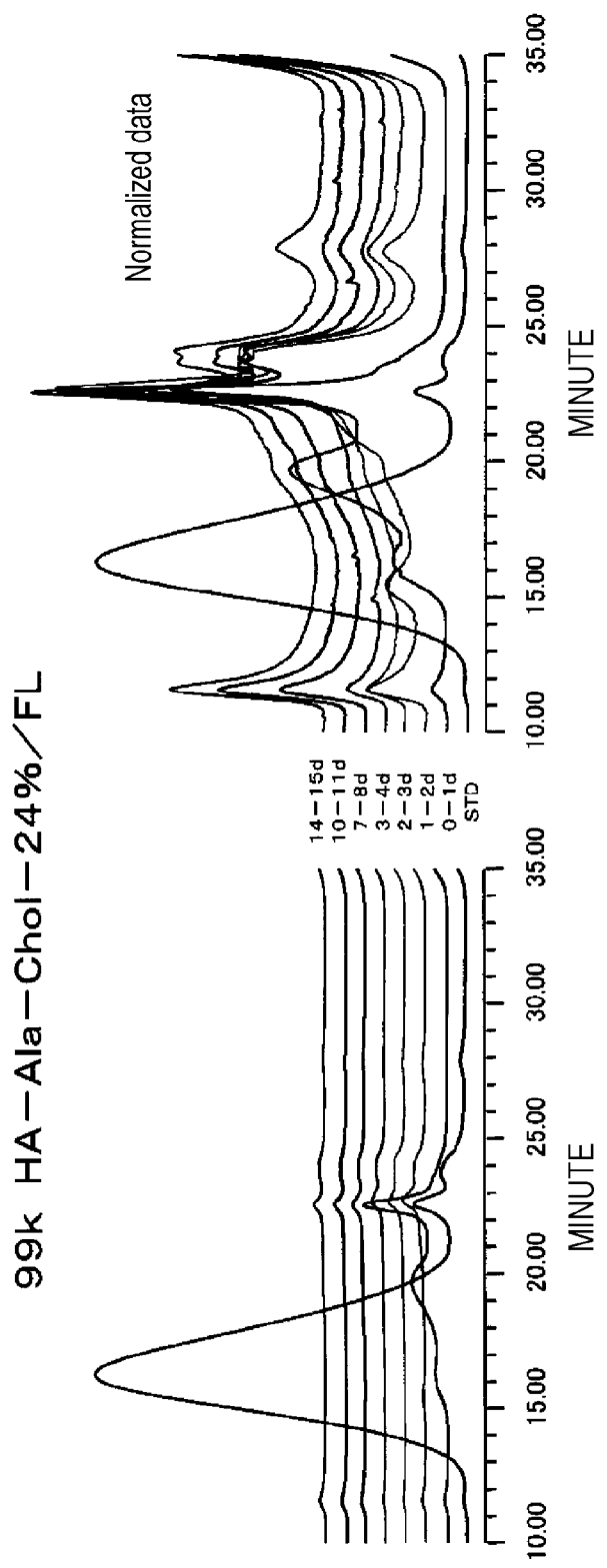
Figures 2, 3:
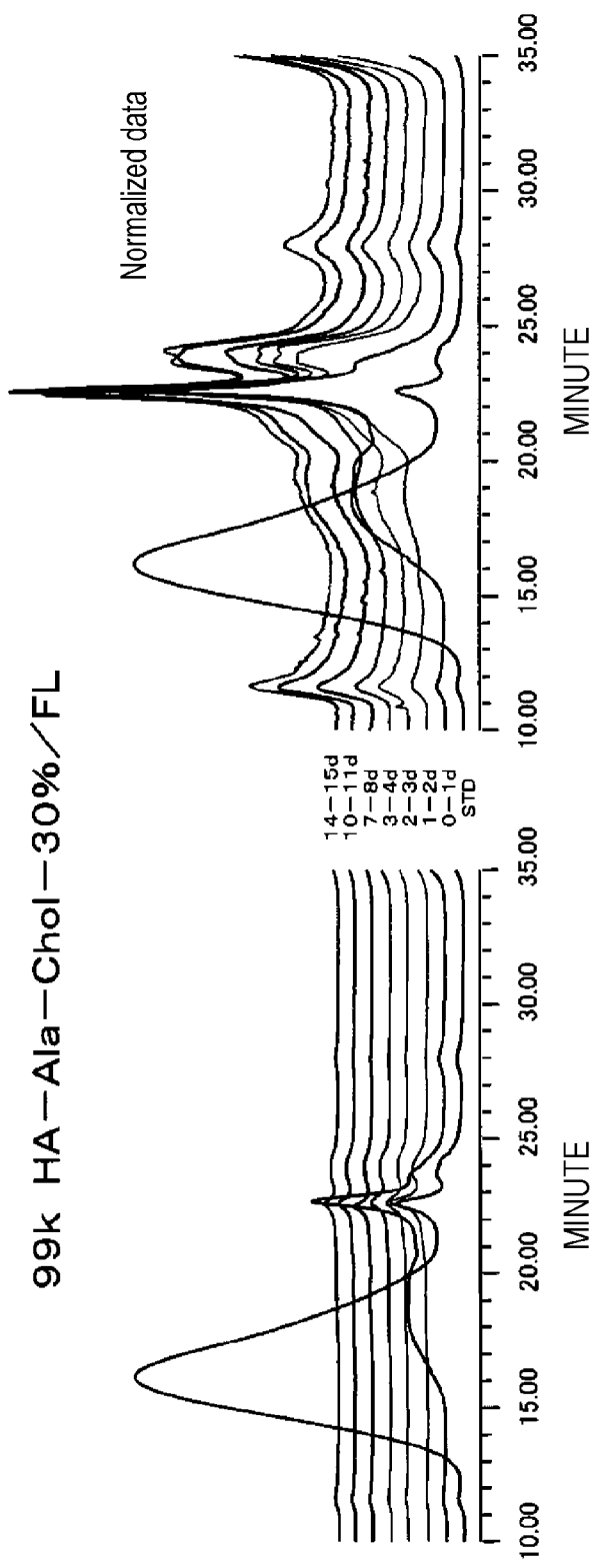
Figures 2, 3, 4:
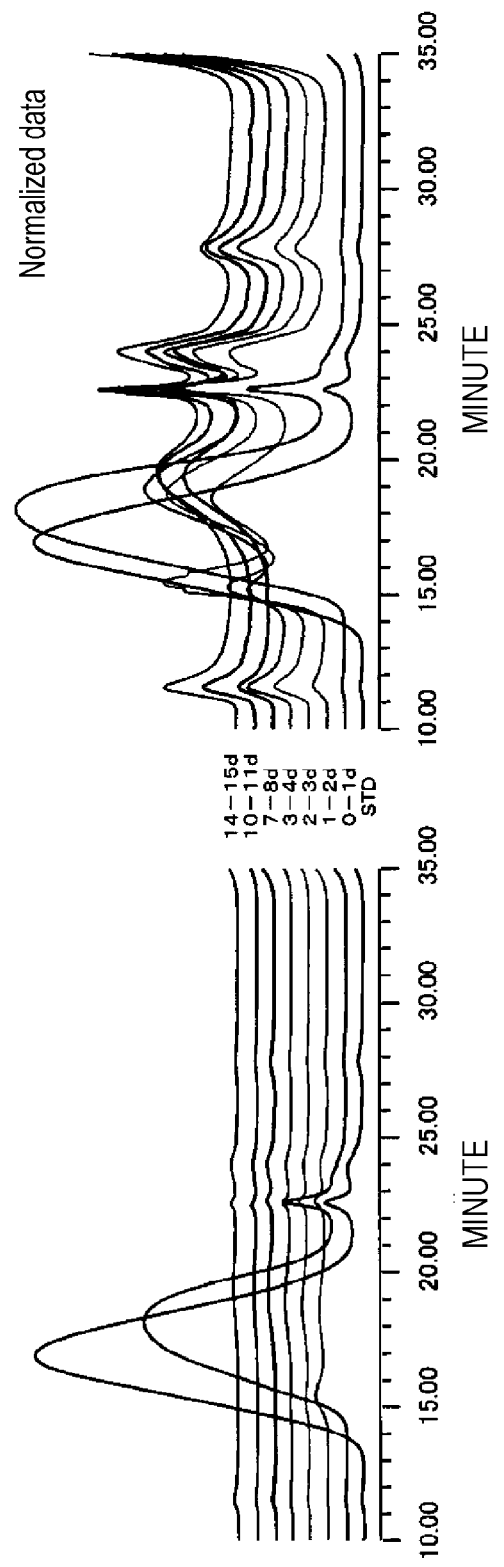
Figures 2, 3, 5:
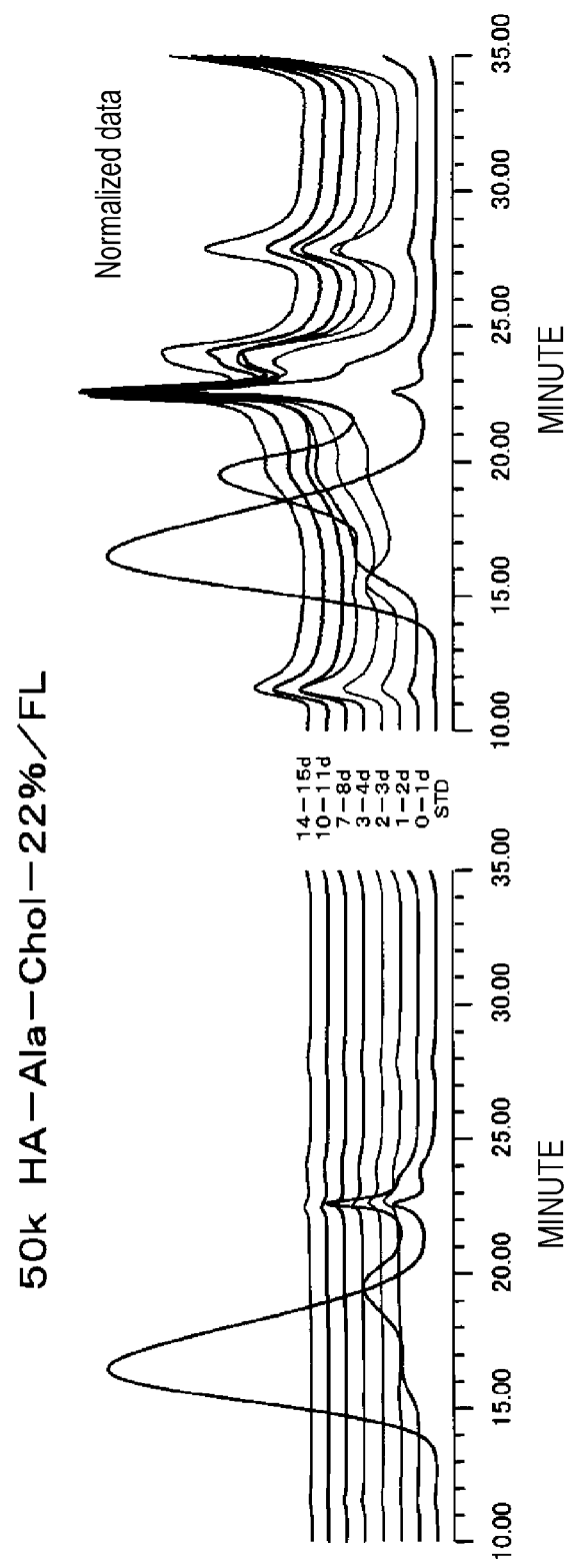
Figures 2, 3, 6:
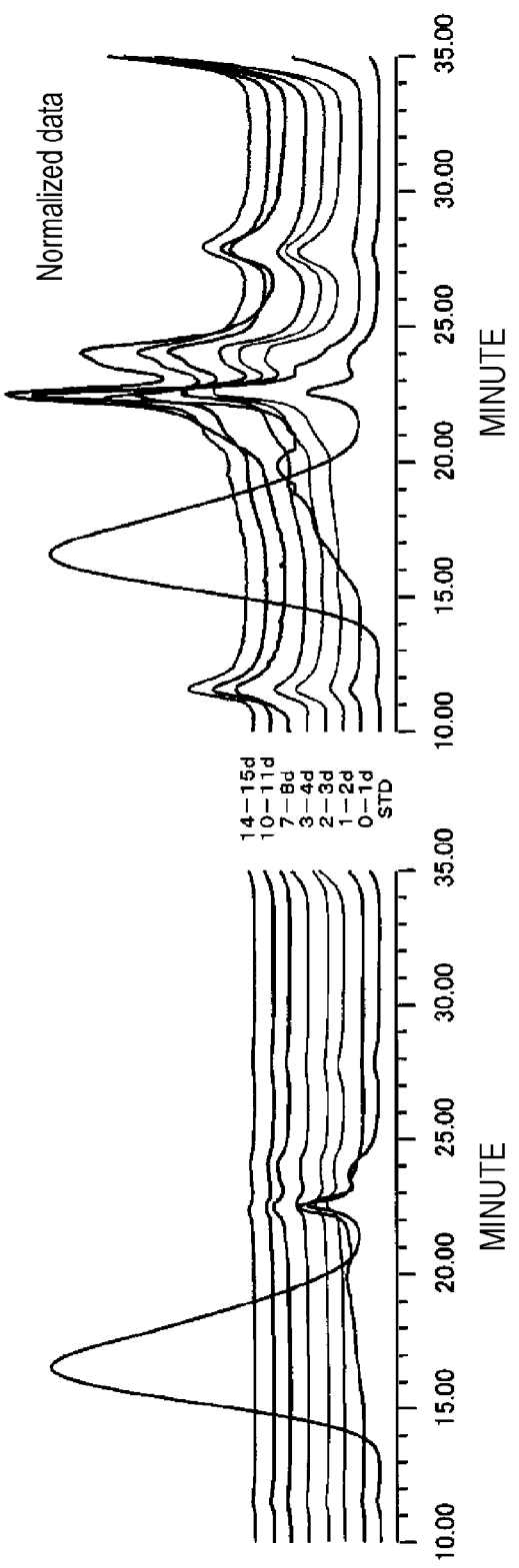
Figures 2, 3, 7:
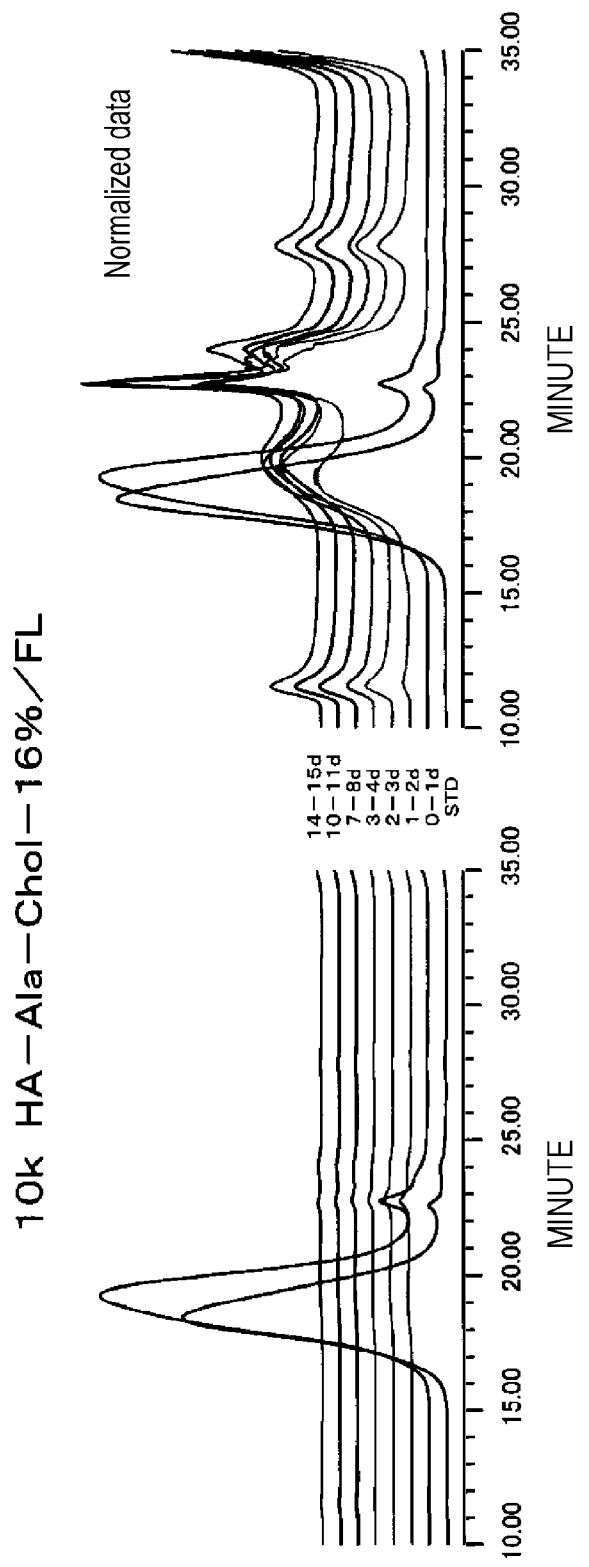
Figures 2, 3, 8:
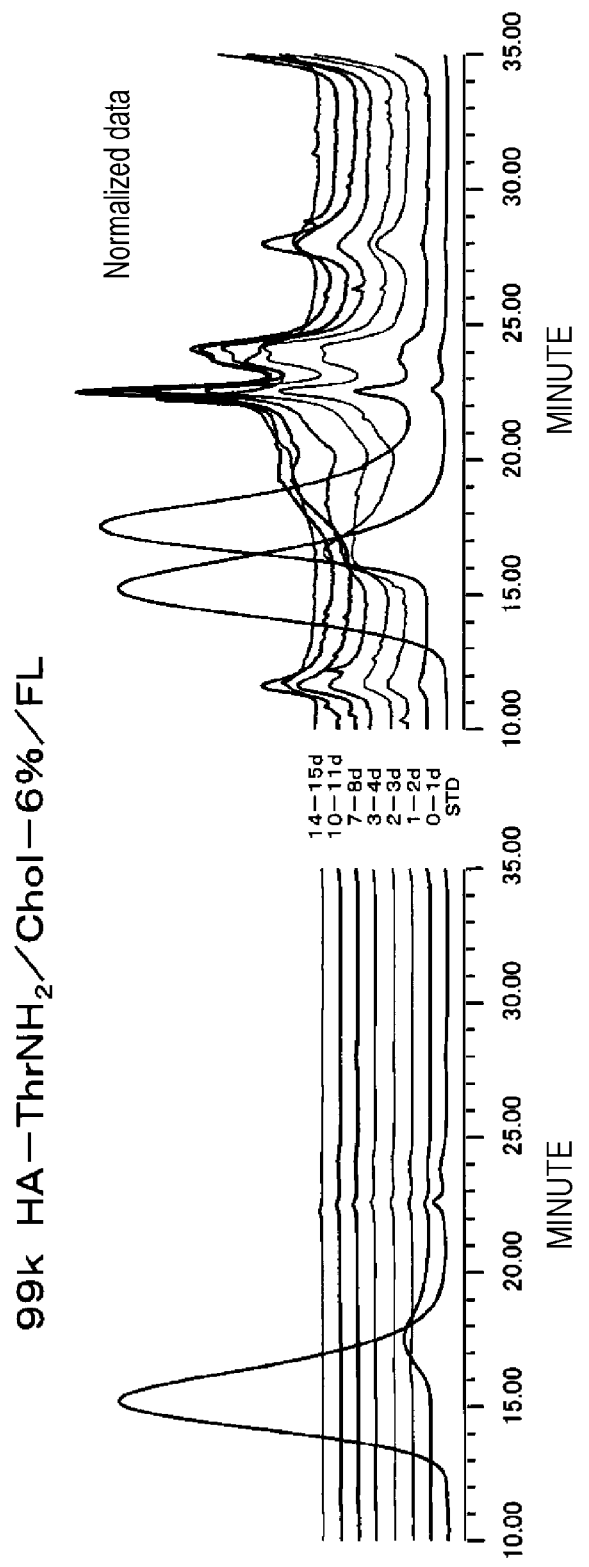
Figures 2, 3, 9:
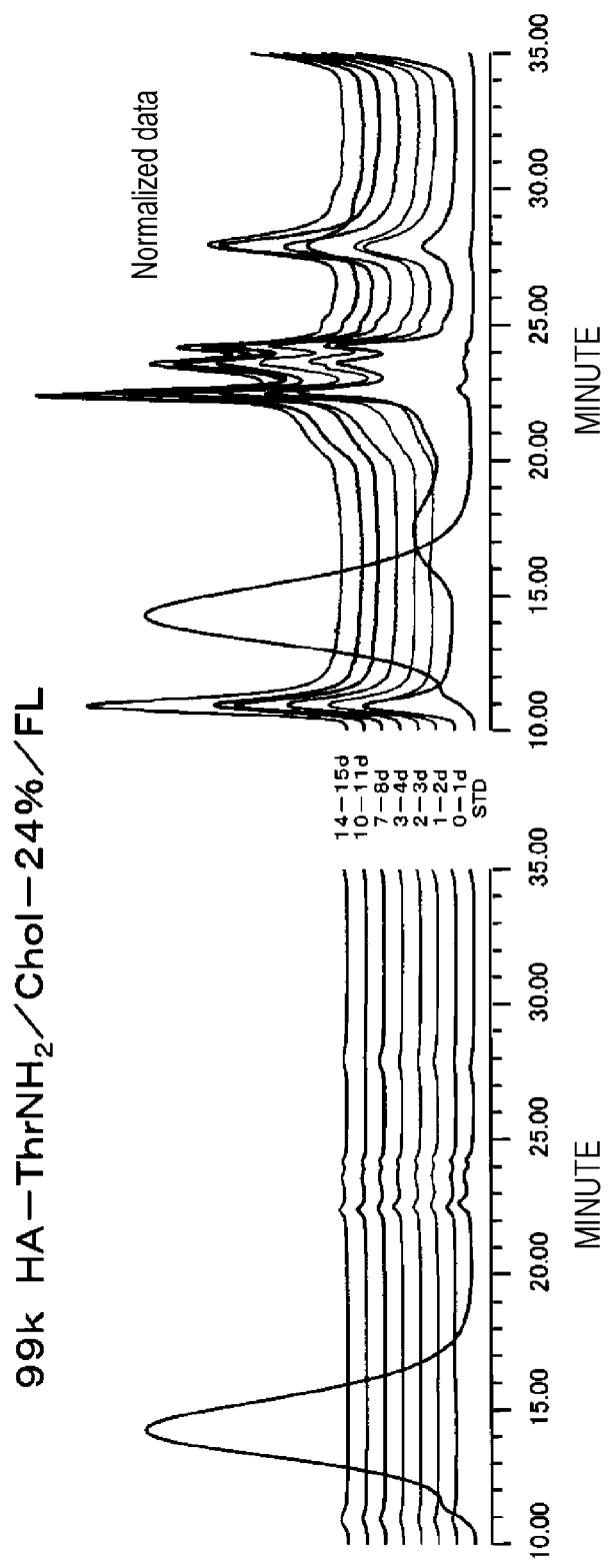
Figures 2, 3, 10:
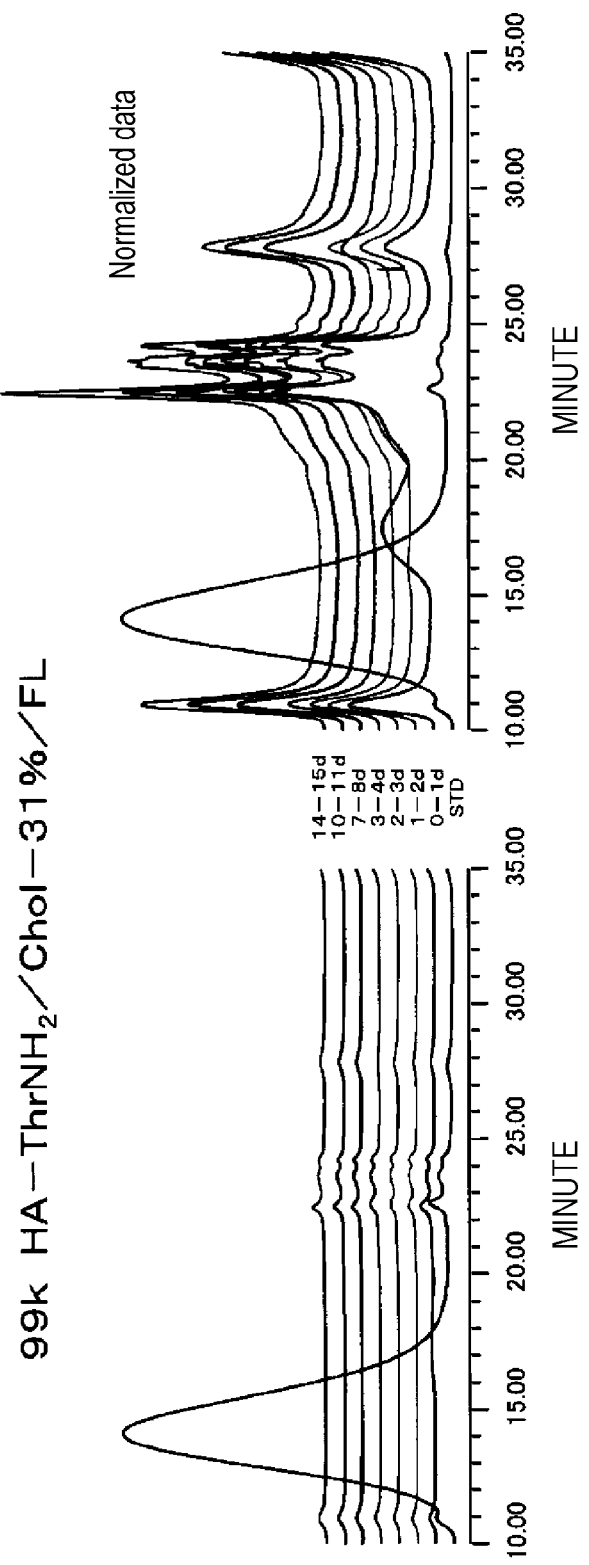
Figures 2, 3, 11:
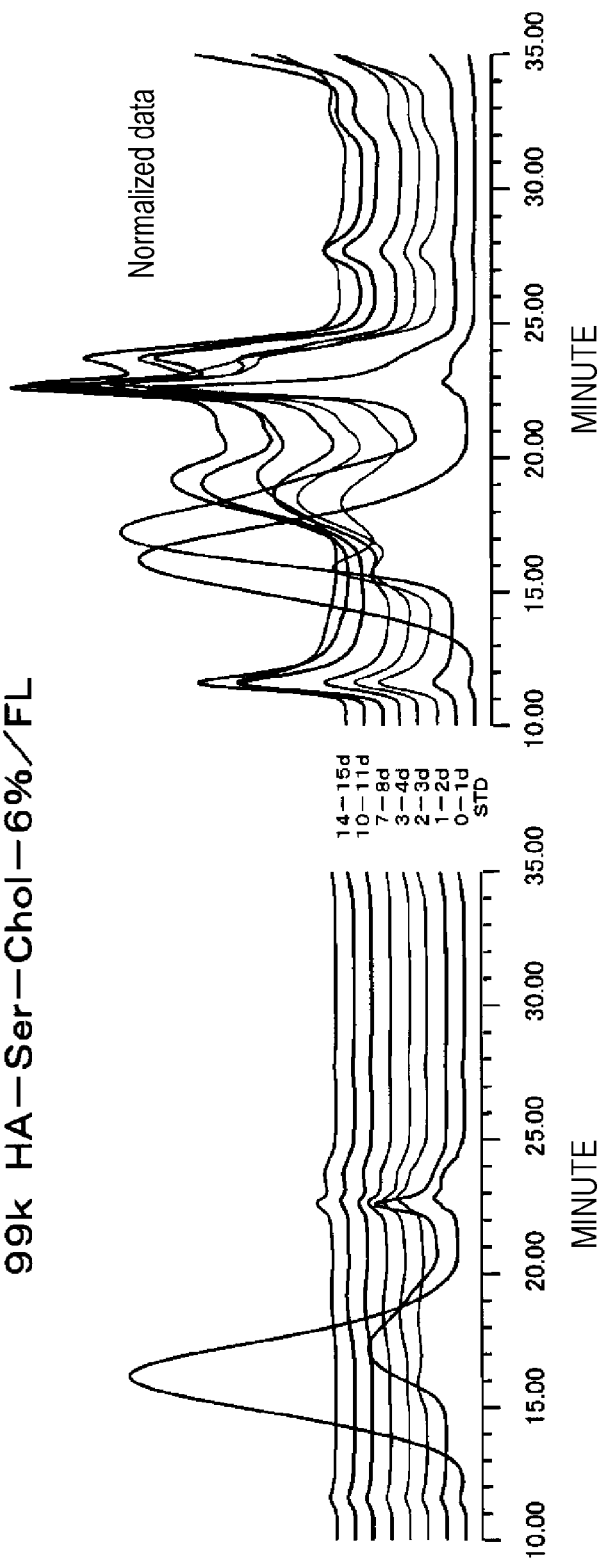
Figures 2, 3, 12:
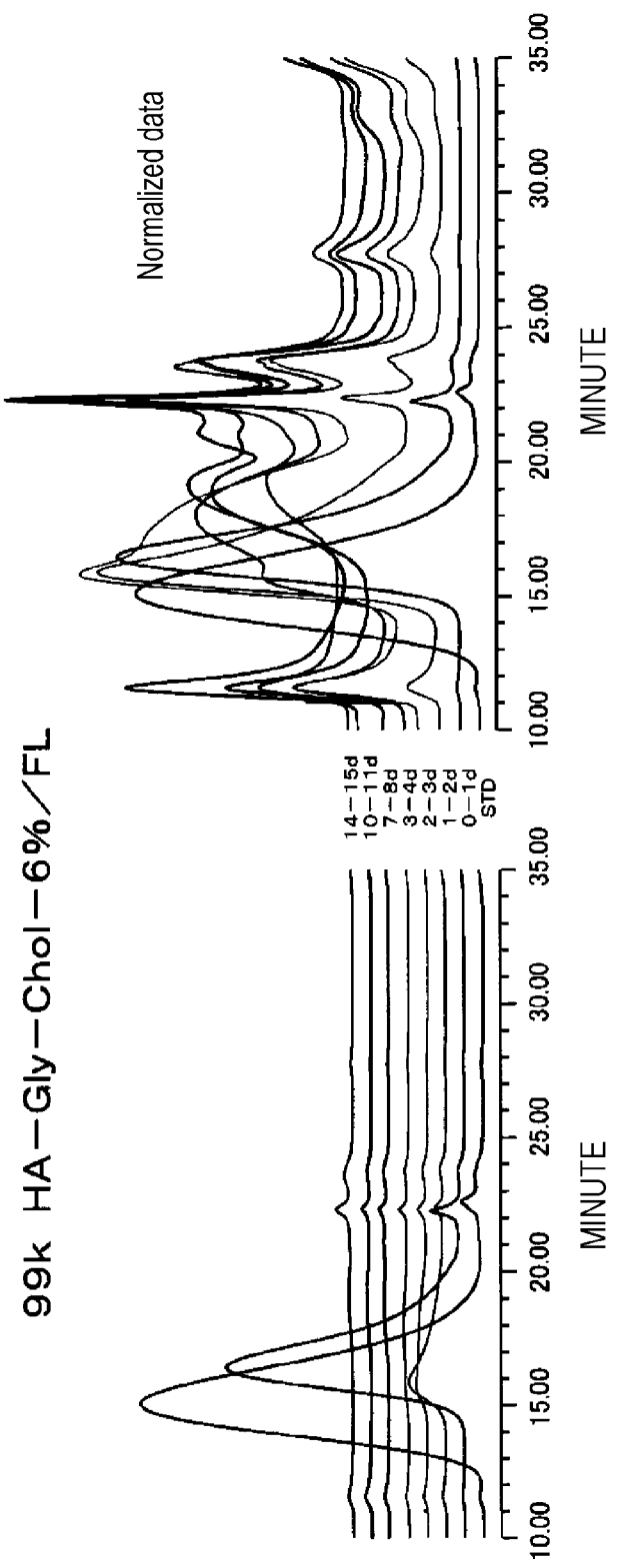
Figures 2, 3, 13:
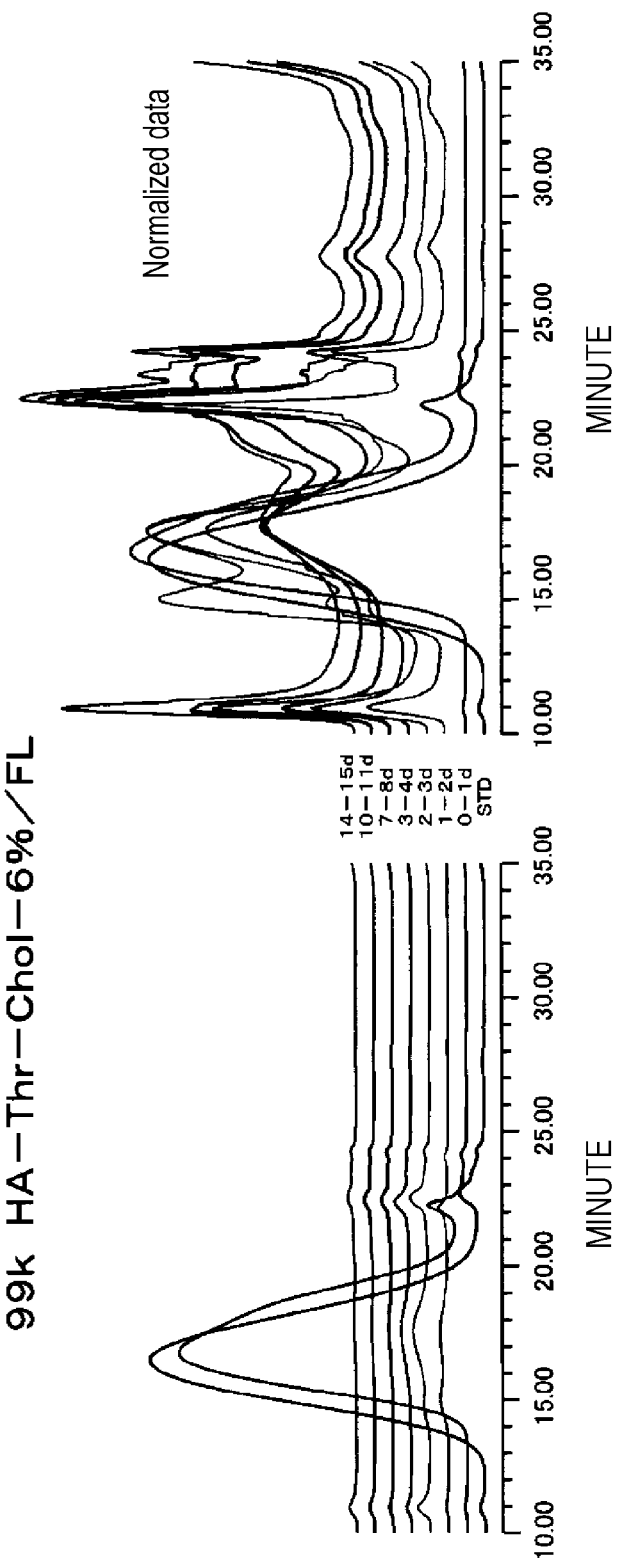
Figures 2, 3, 14:
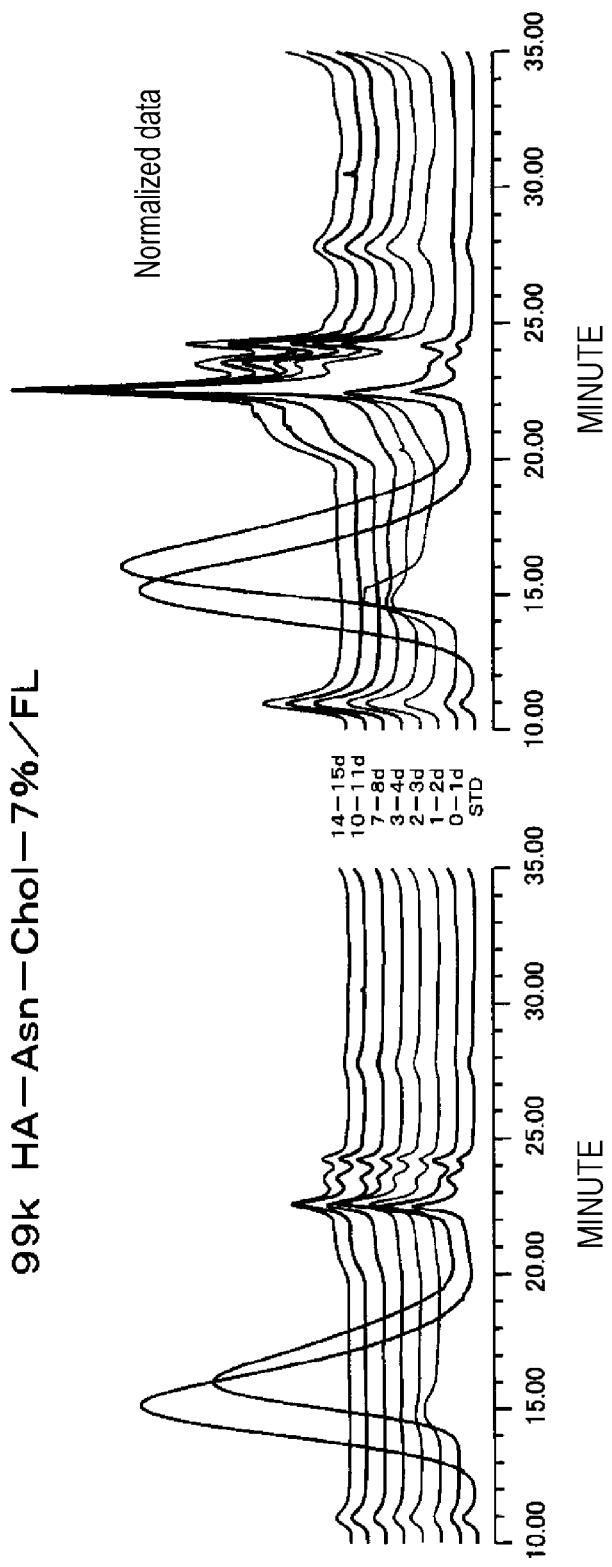
Figures 2, 3, 15:
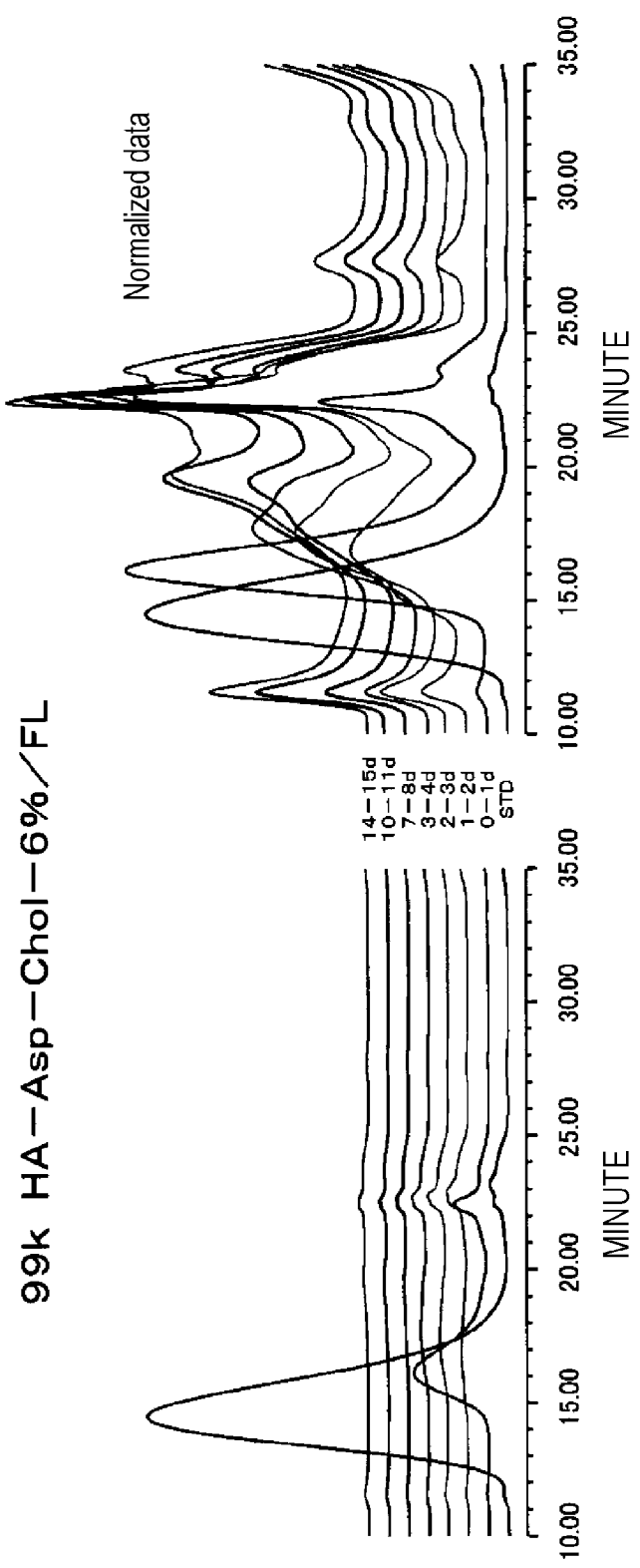
Figures 2, 3, 16:
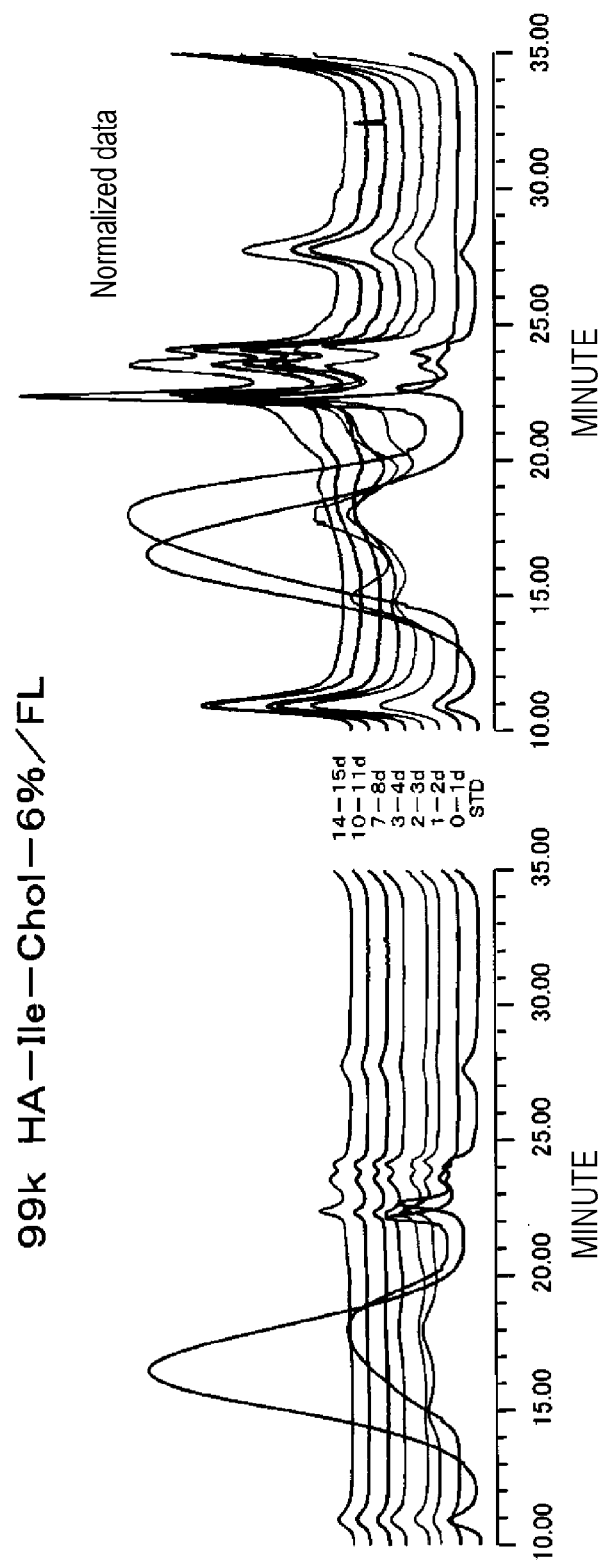
Figures 2, 3, 17:
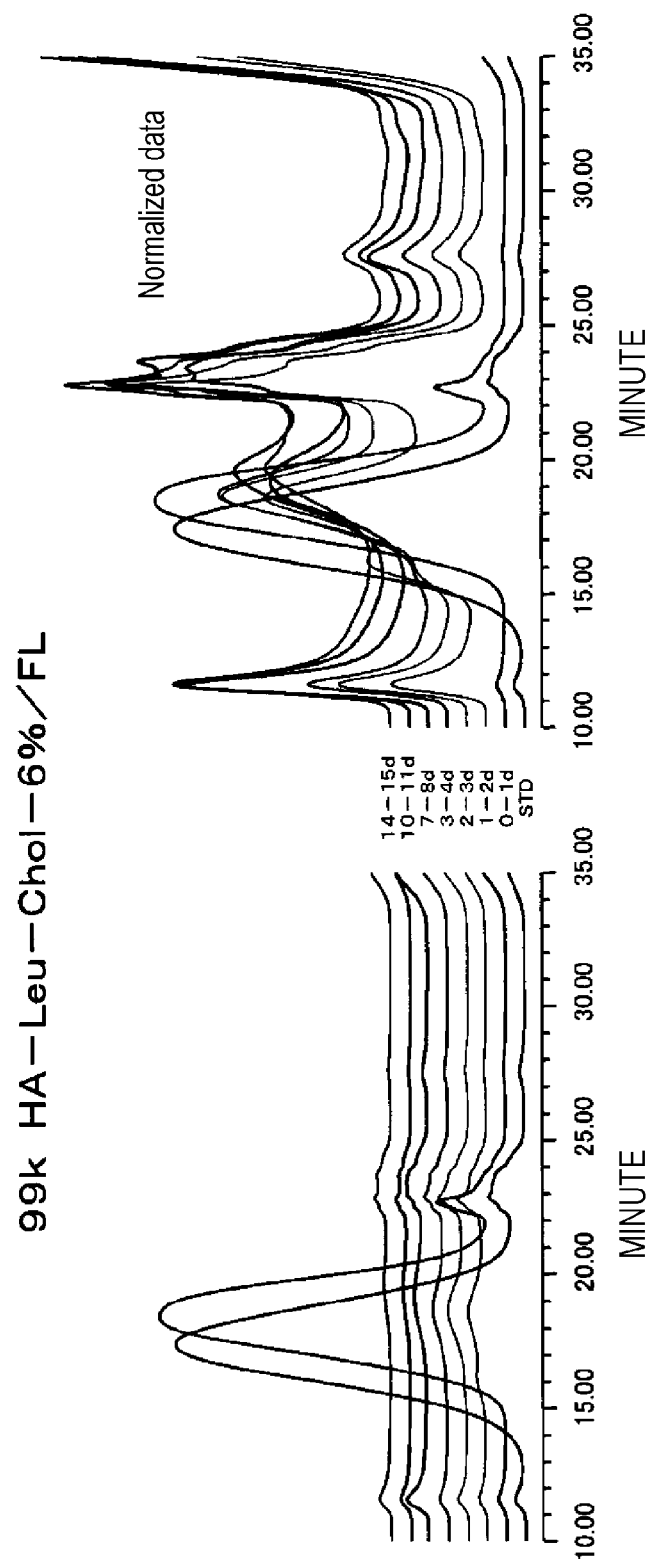
Figures 2, 3, 18:
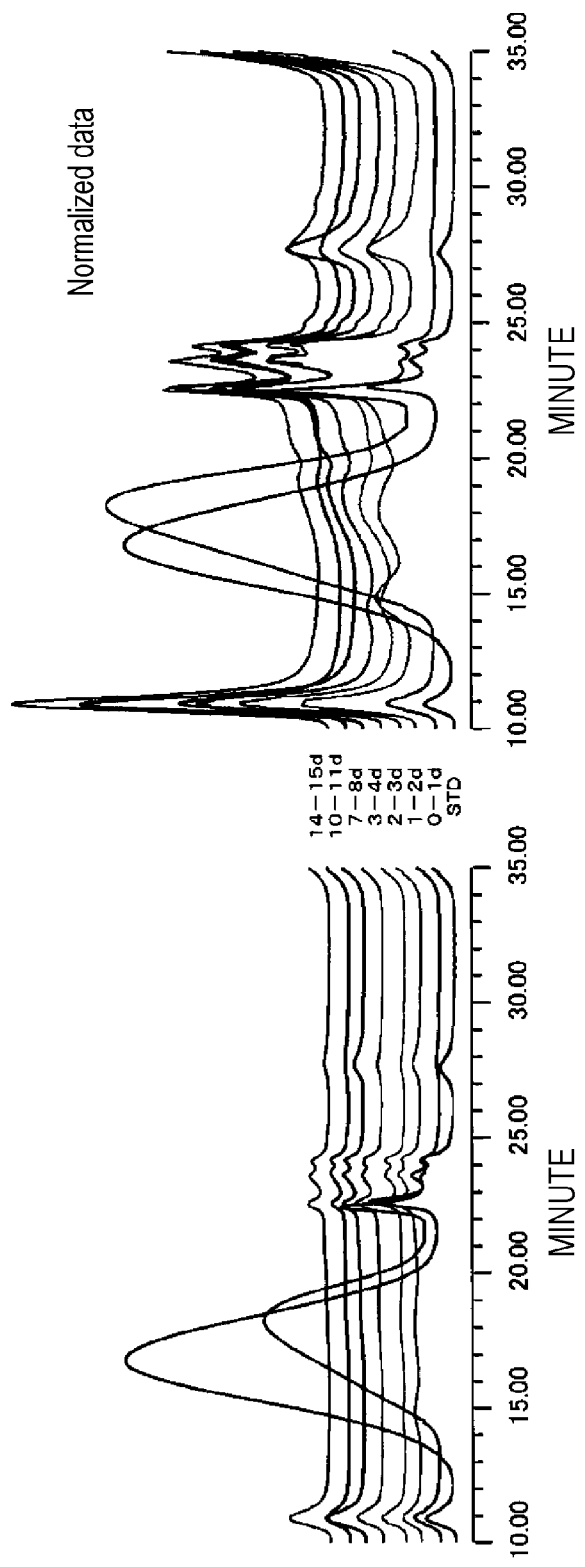
Figures 2, 3, 19:
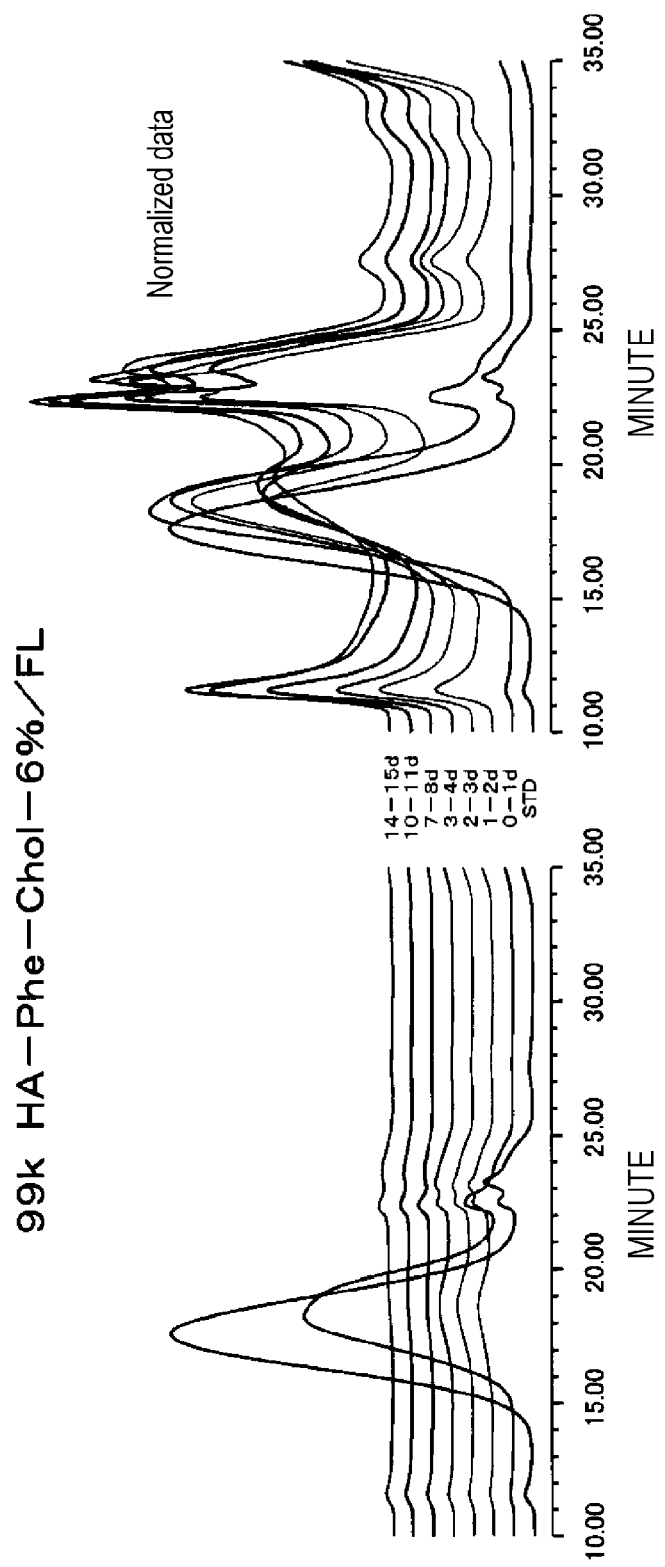
Figures 2, 3, 20:
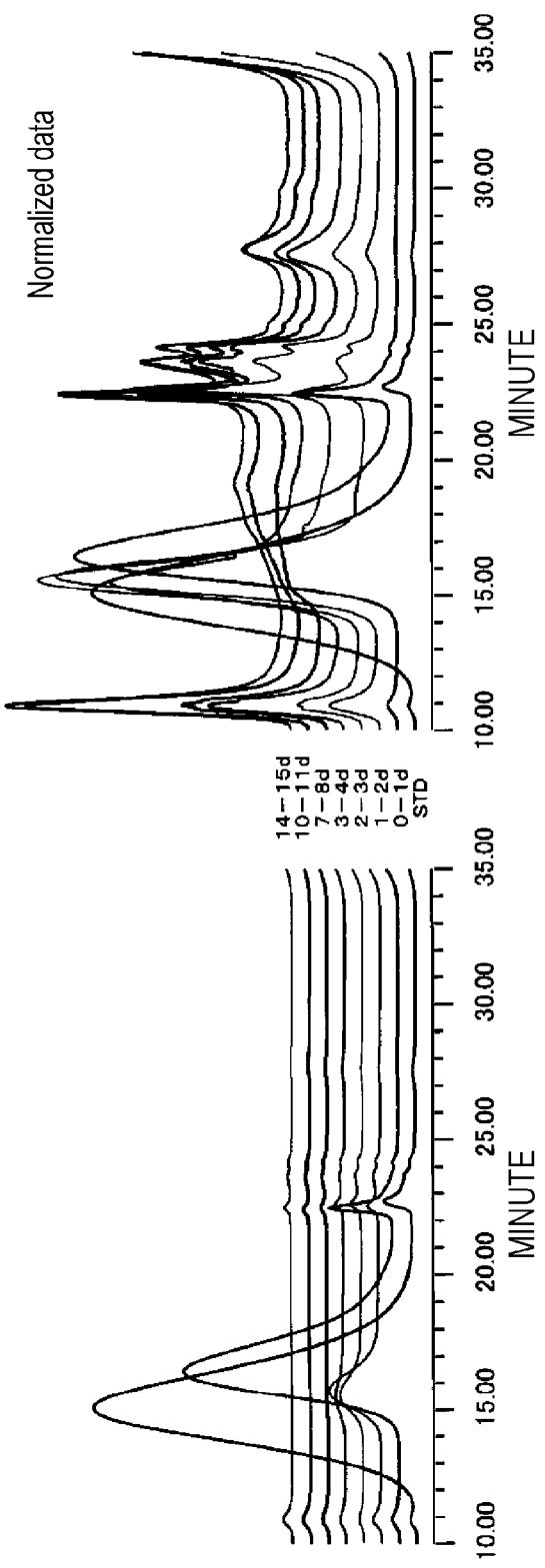
Figures 2, 3, 21:
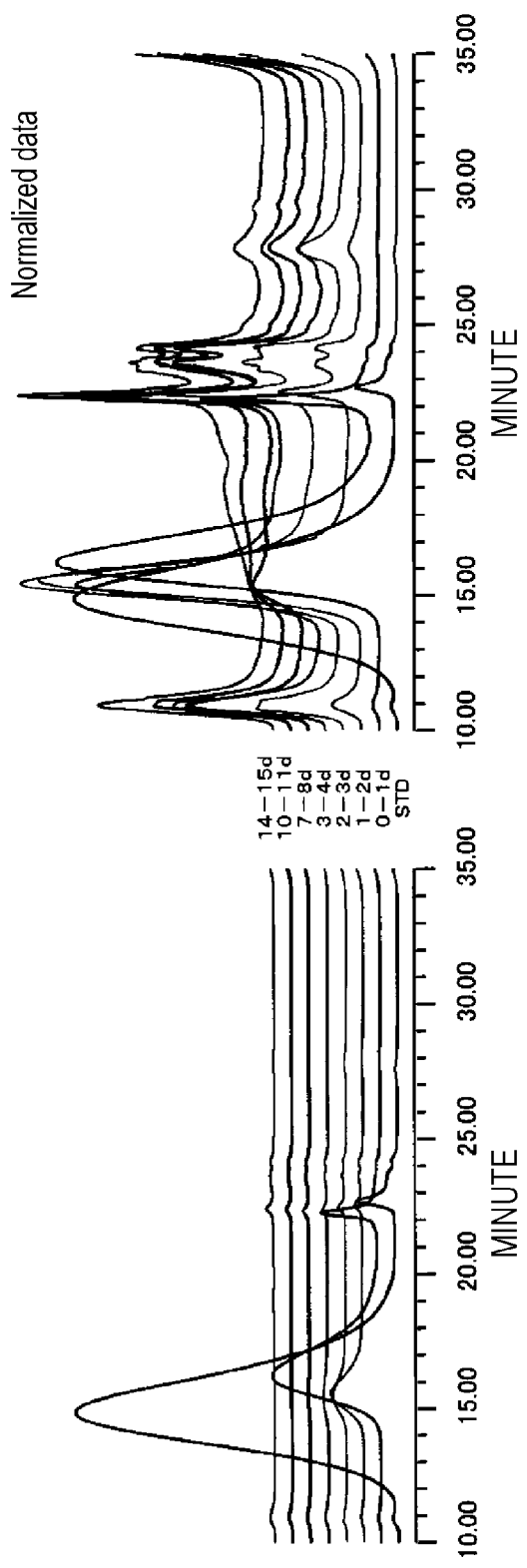
Figures 2, 3, 22:
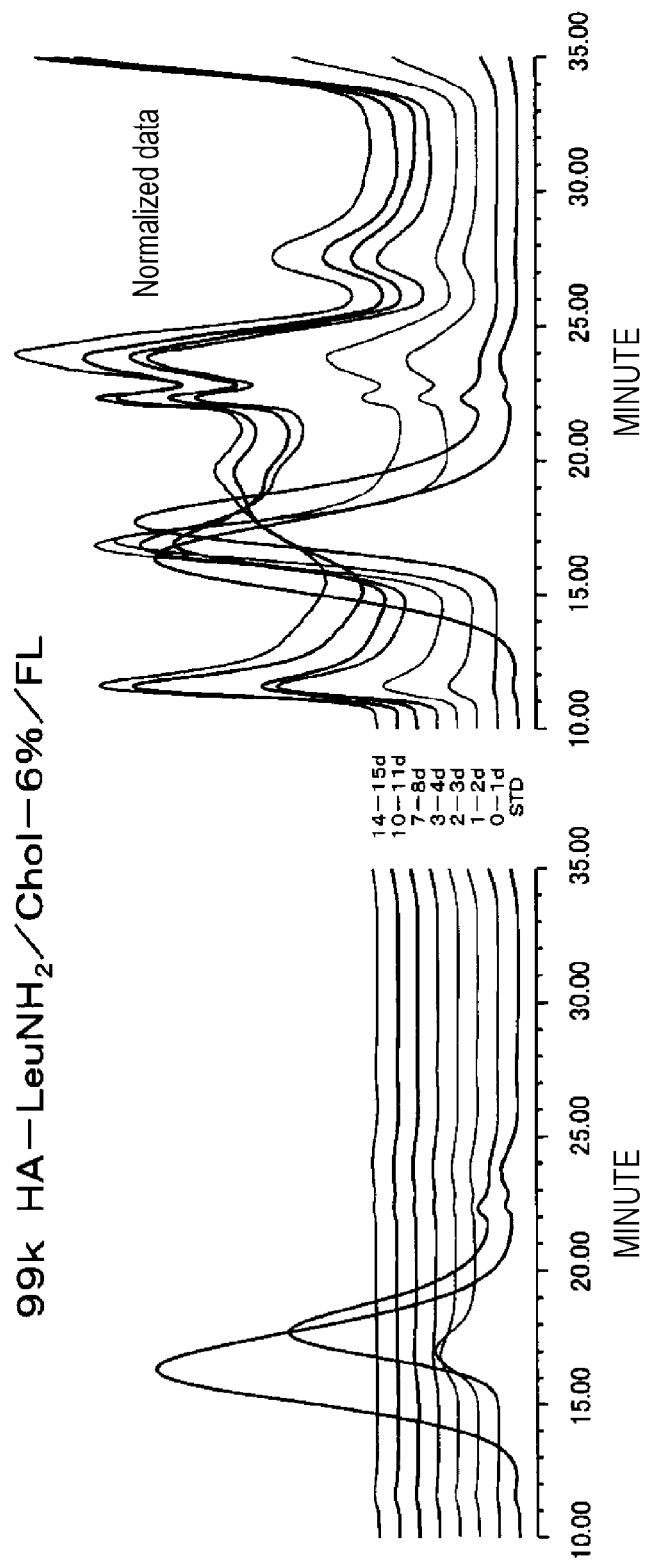
Figures 2, 3, 23:
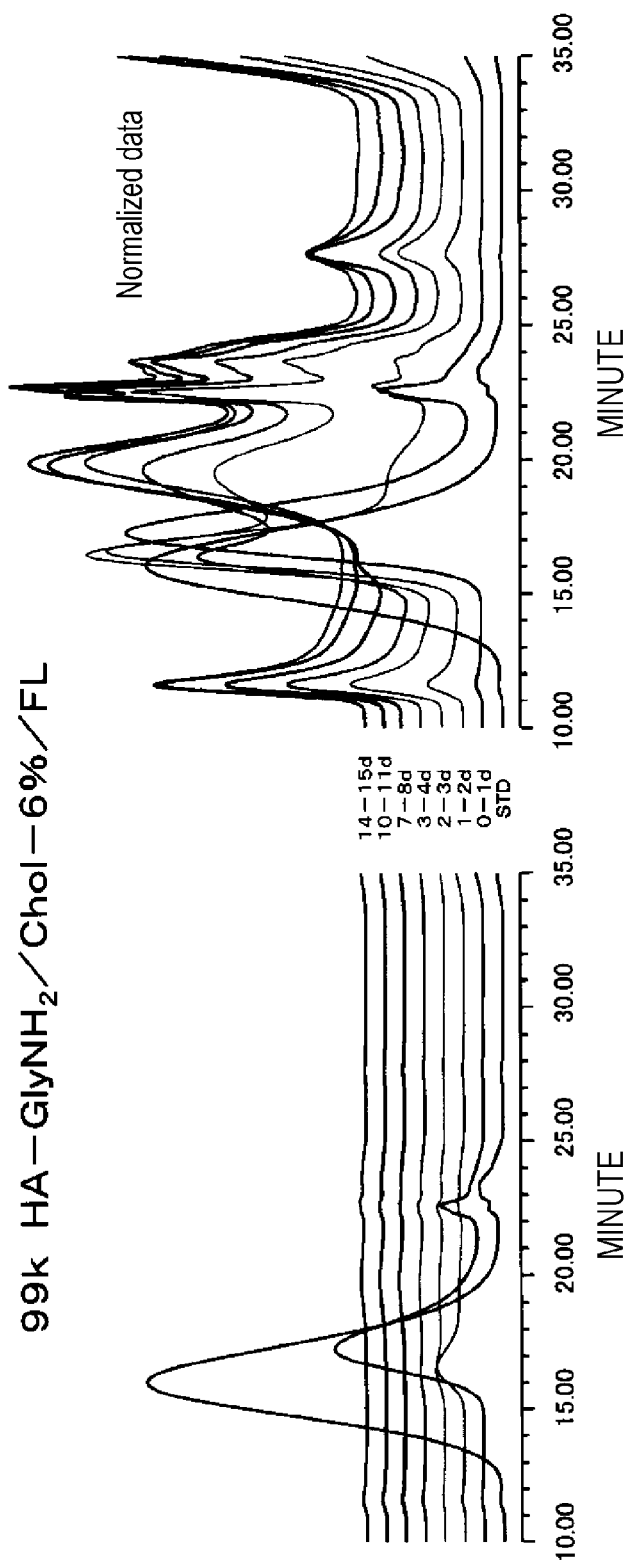
Figures 2, 3, 24:
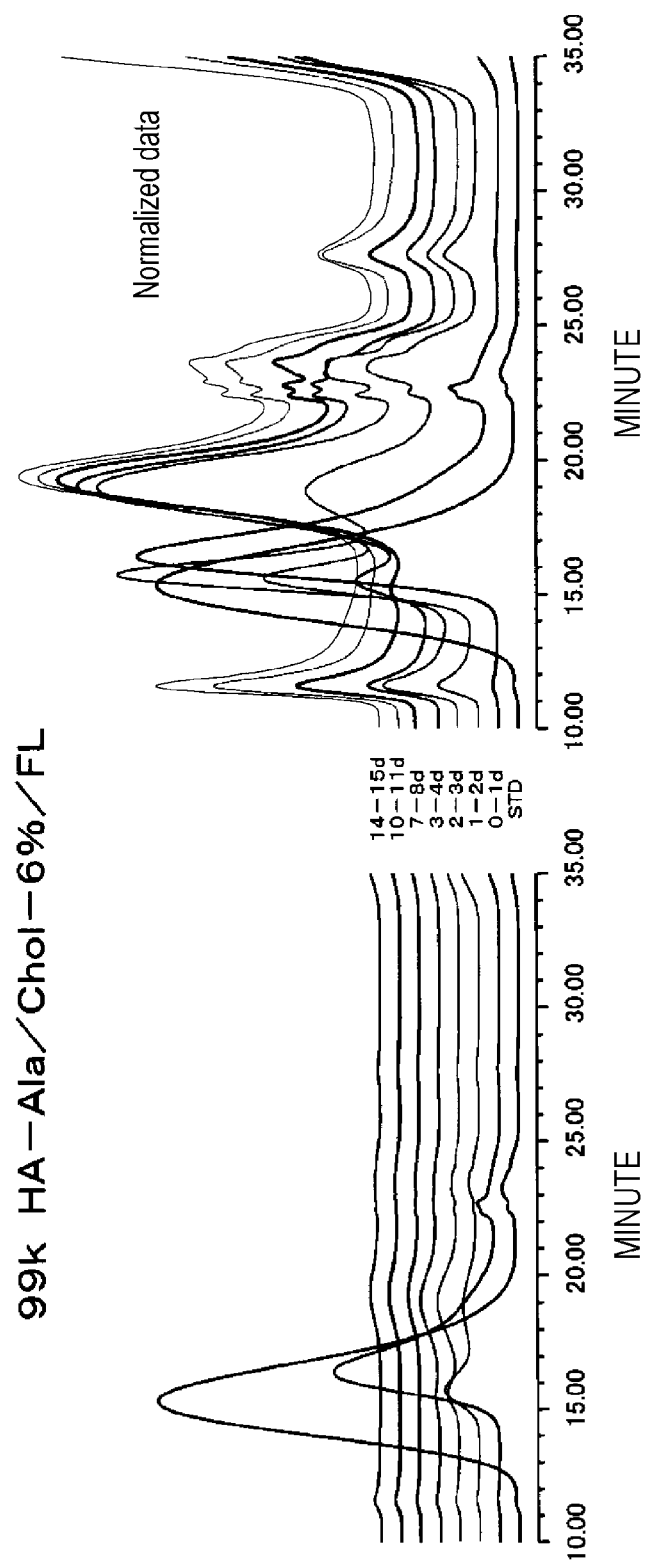
Figures 2, 3, 25:
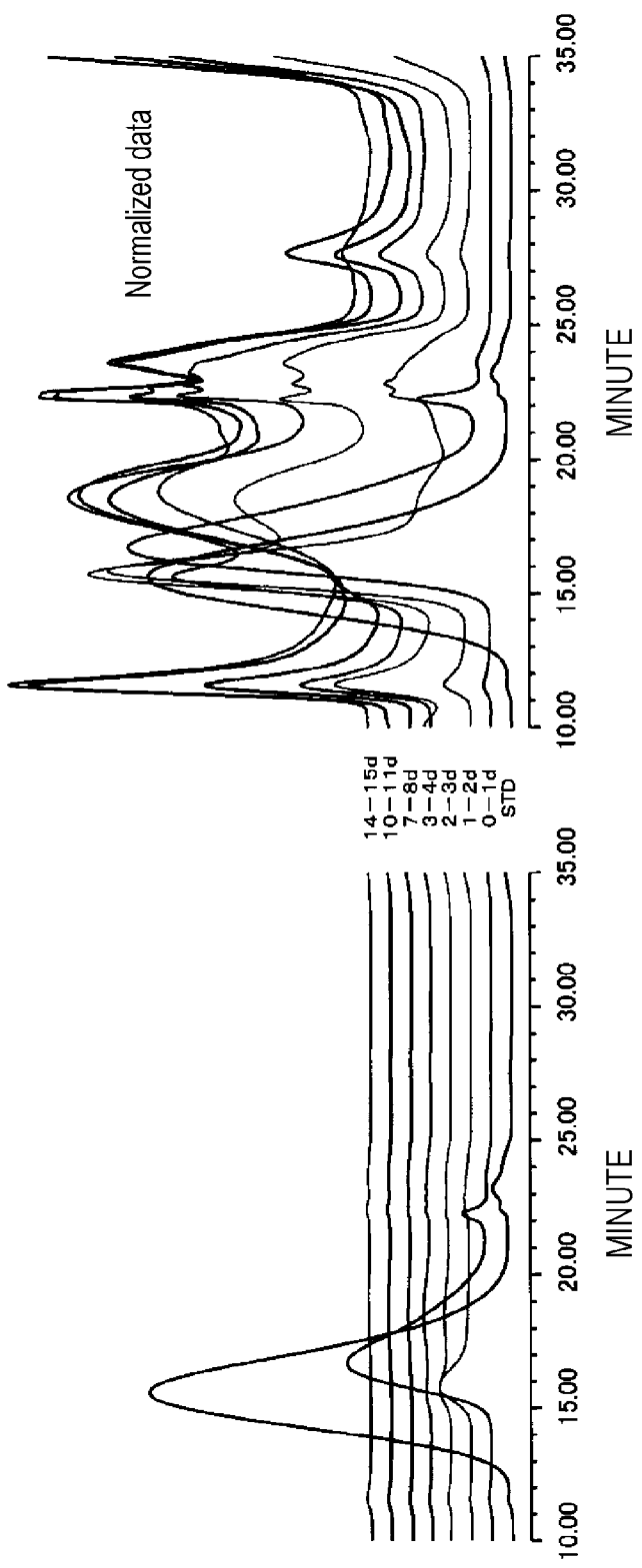
Figures 2, 3, 26:
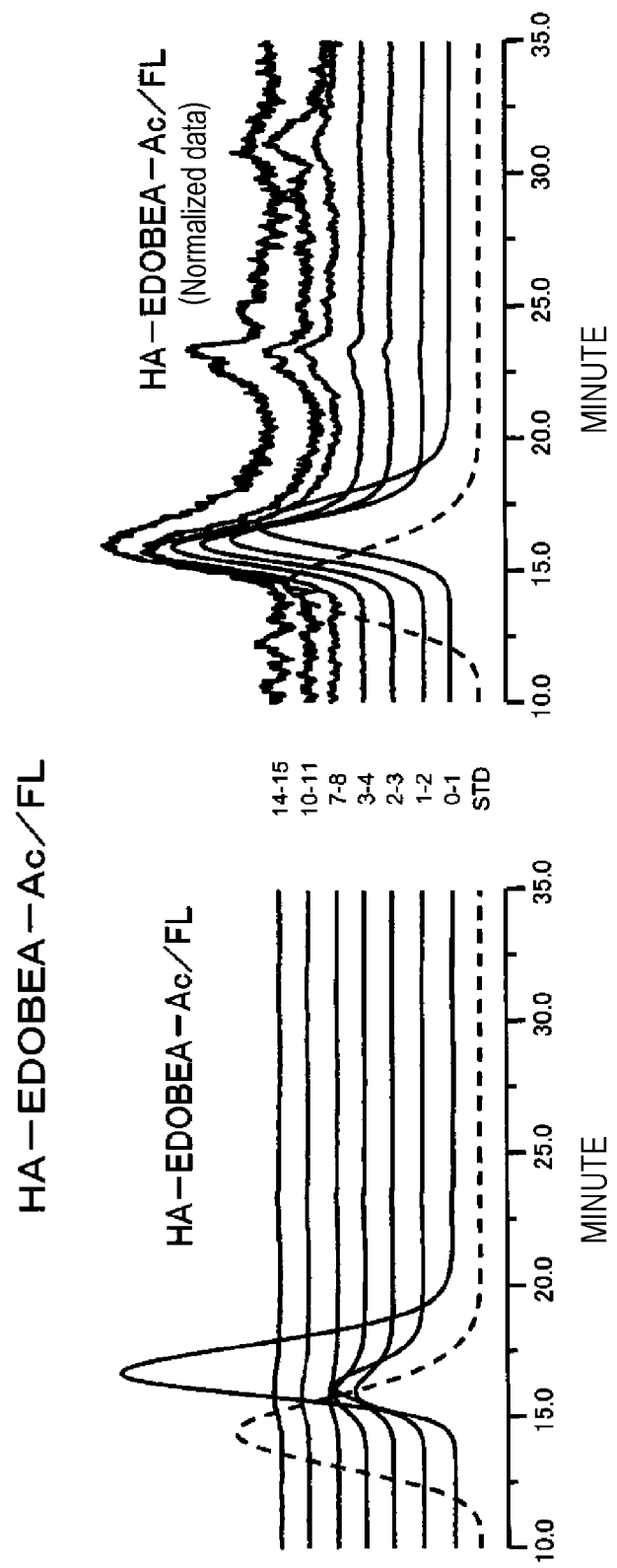
Figures 2, 3, 27:
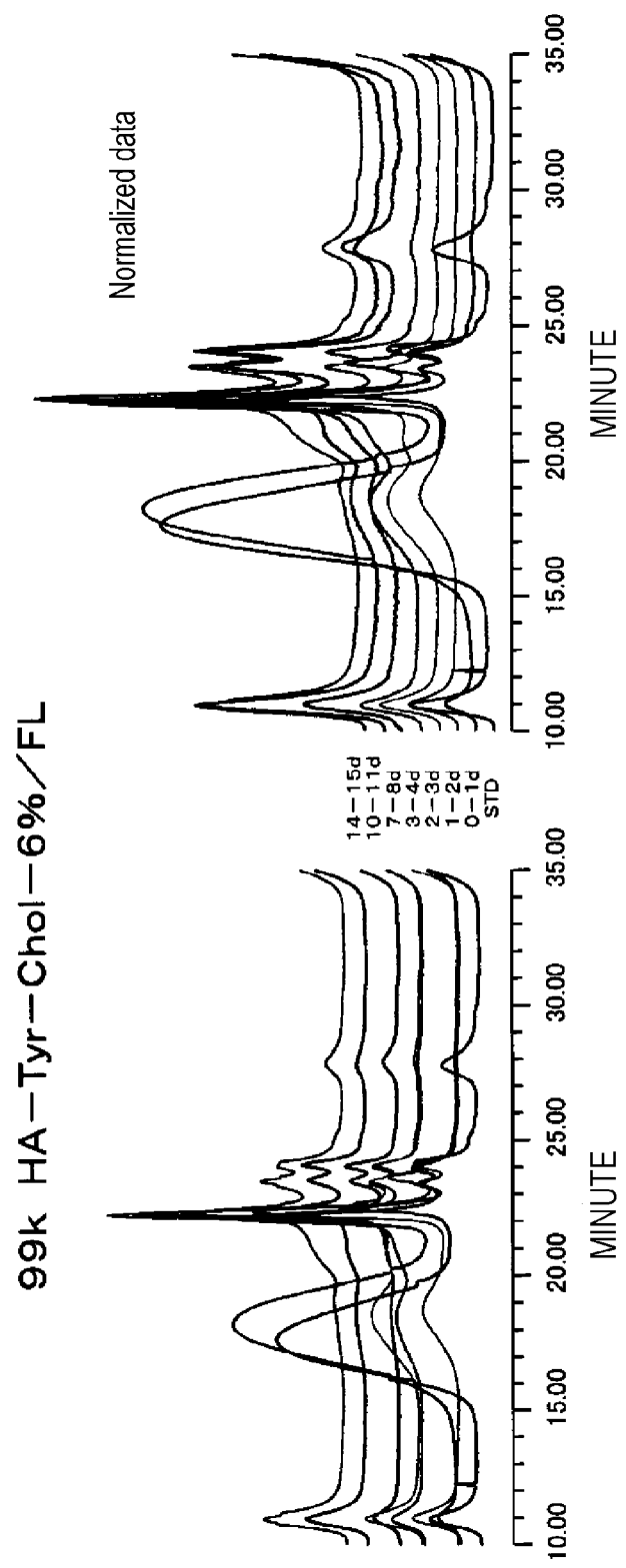
Figures 1, 3:
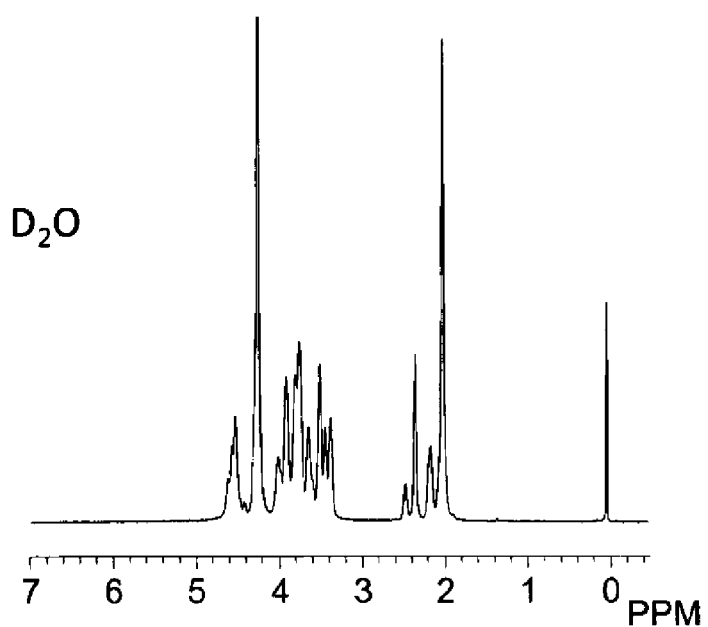
Figures 2, 3:
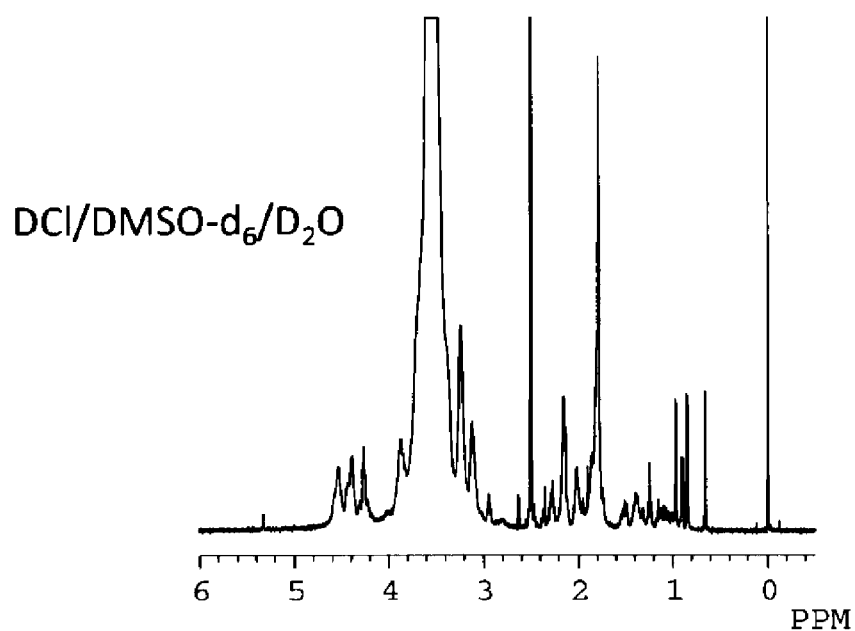
Figure 3:
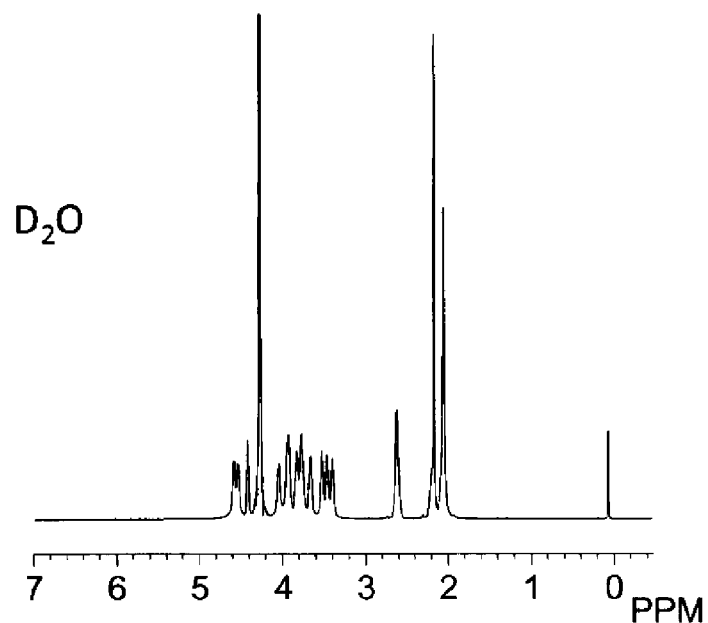
Figures 3, 4:
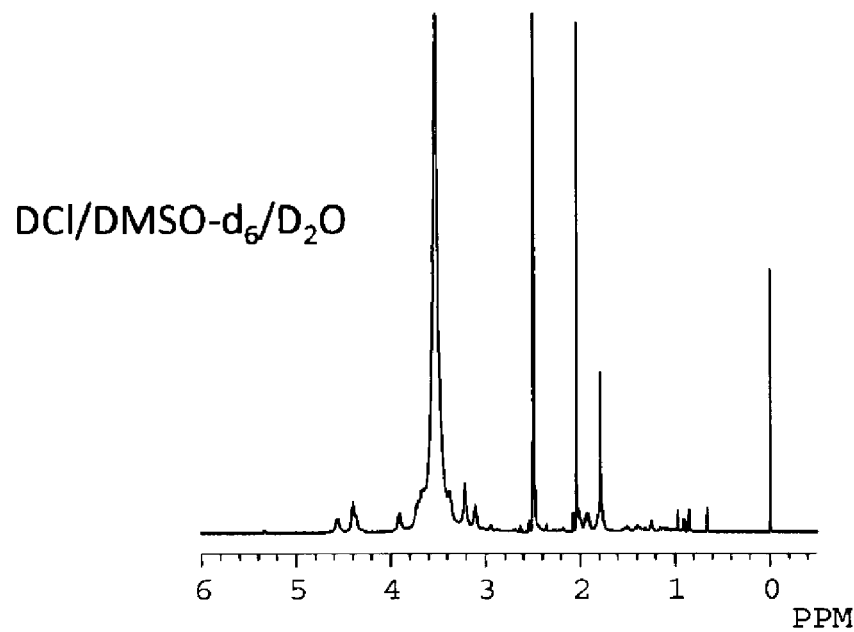
Figures 3, 4, 5:
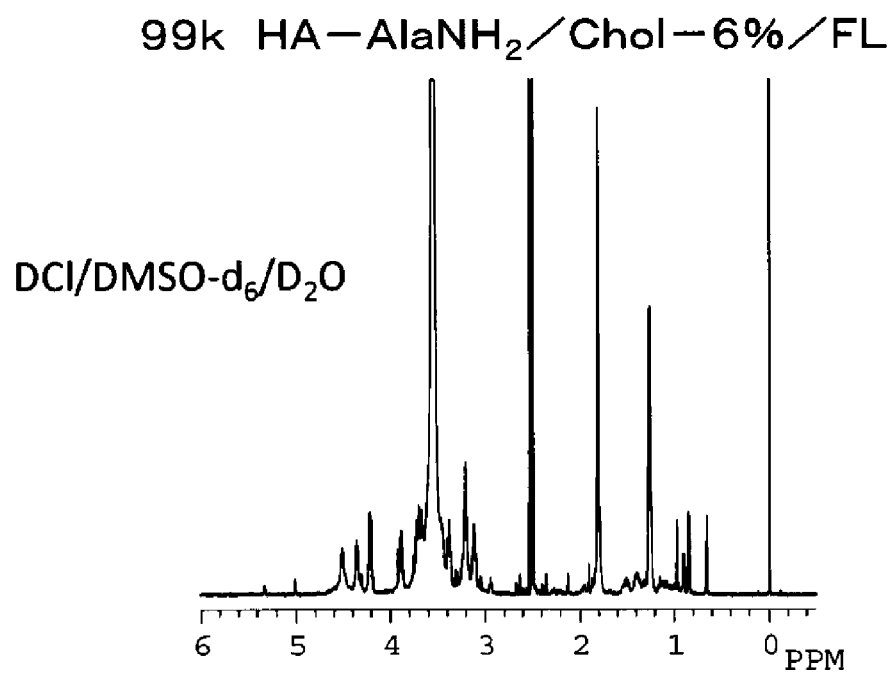
Figures 3, 4, 5, 6:
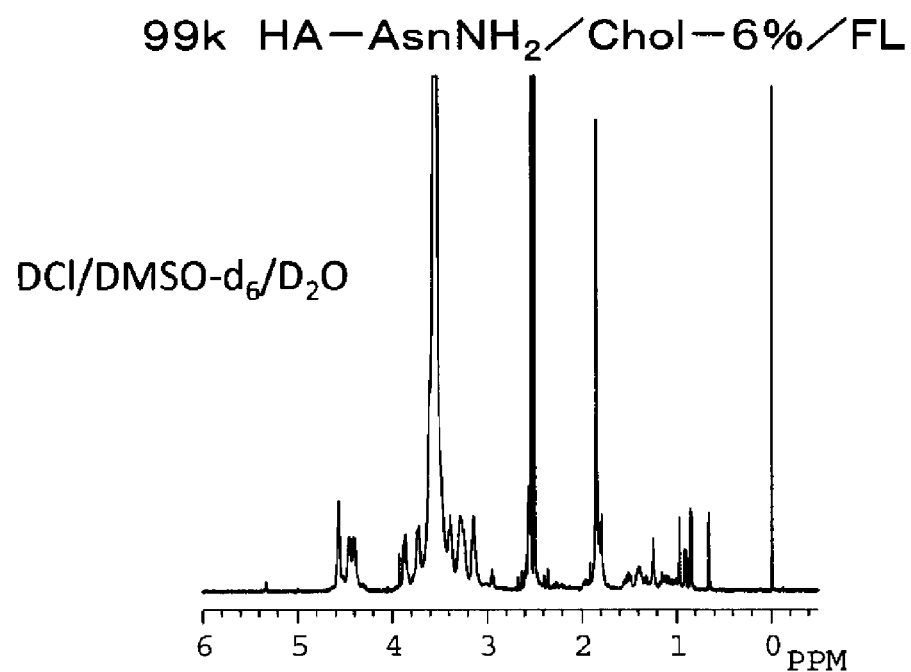
Figures 3, 4, 5, 6, 7:
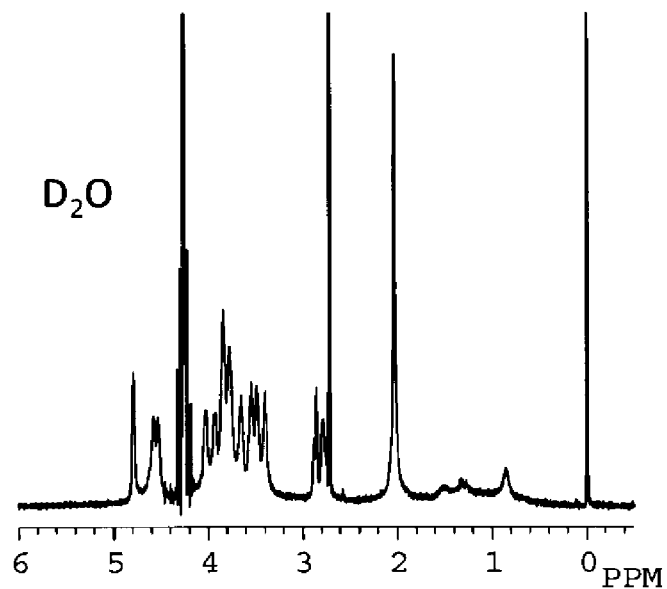
Figures 3, 4, 5, 6, 7, 8:
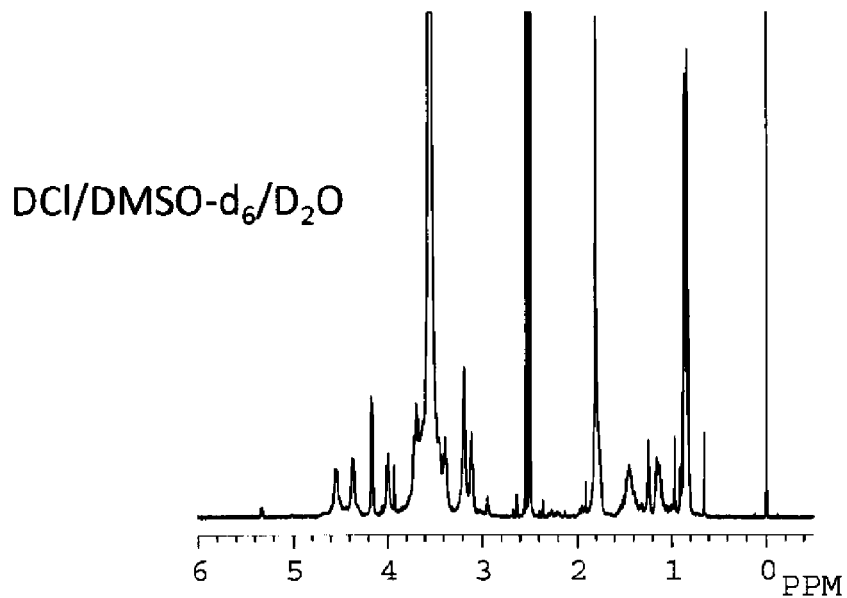
Figures 3, 4, 5, 6, 7, 8, 9:
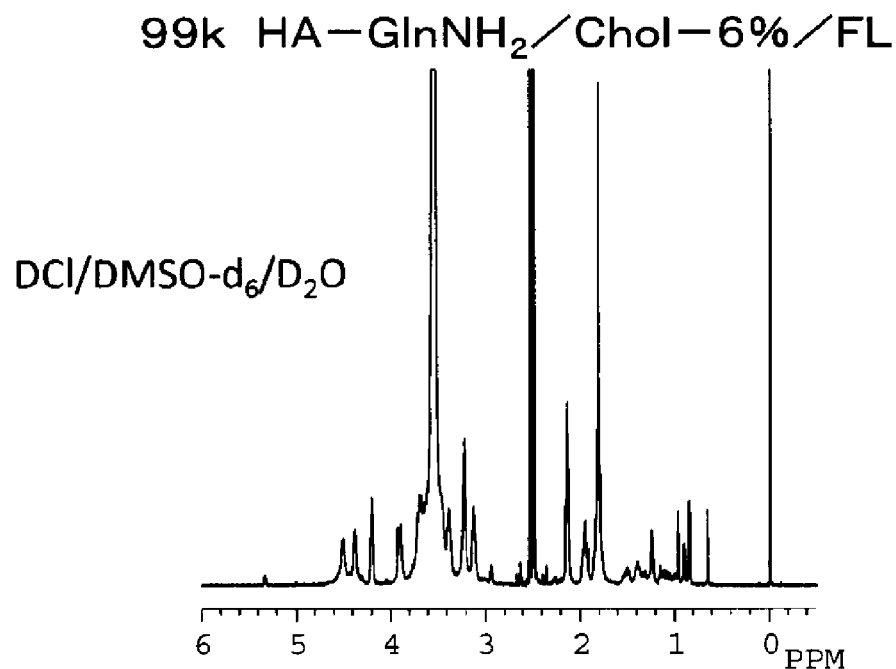
Figures 3, 4, 5, 6, 7, 8, 9, 10:
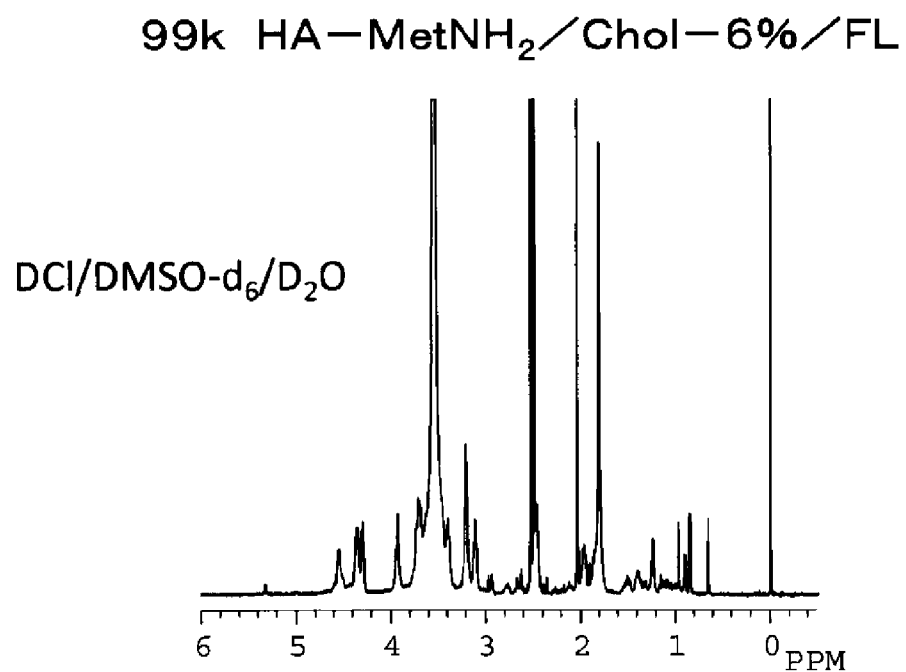
Figures 3, 4, 5, 6, 7, 8, 9, 10, 11:
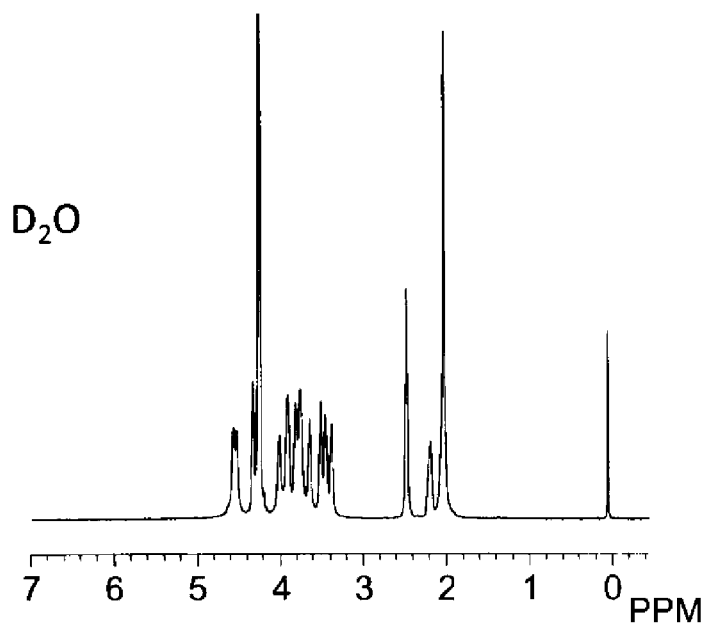
Figures 3, 4, 5, 6, 7, 8, 9, 10, 11, 12:
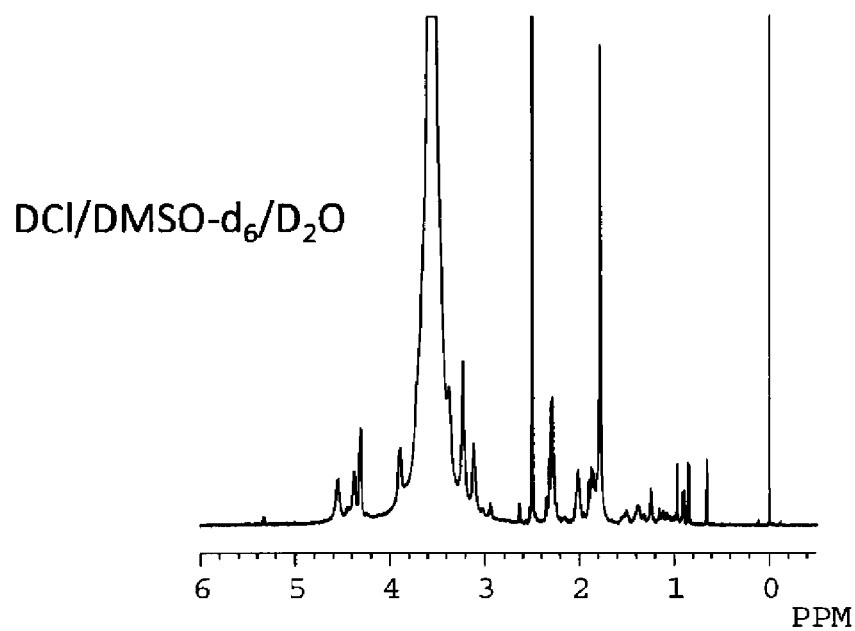
Figures 3, 4, 5, 6, 7, 8, 9, 10, 11, 12, 13:
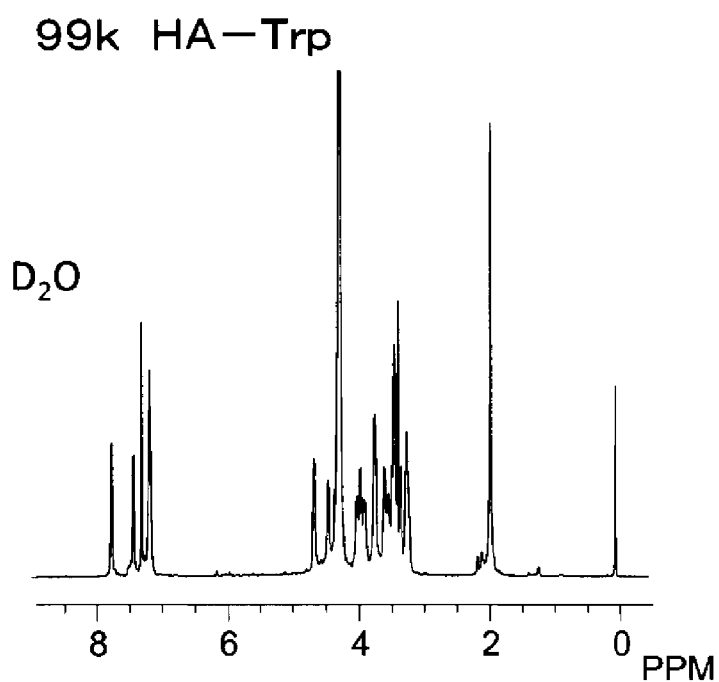
Figures 3, 4, 5, 6, 7, 8, 9, 10, 11, 12, 13, 14:
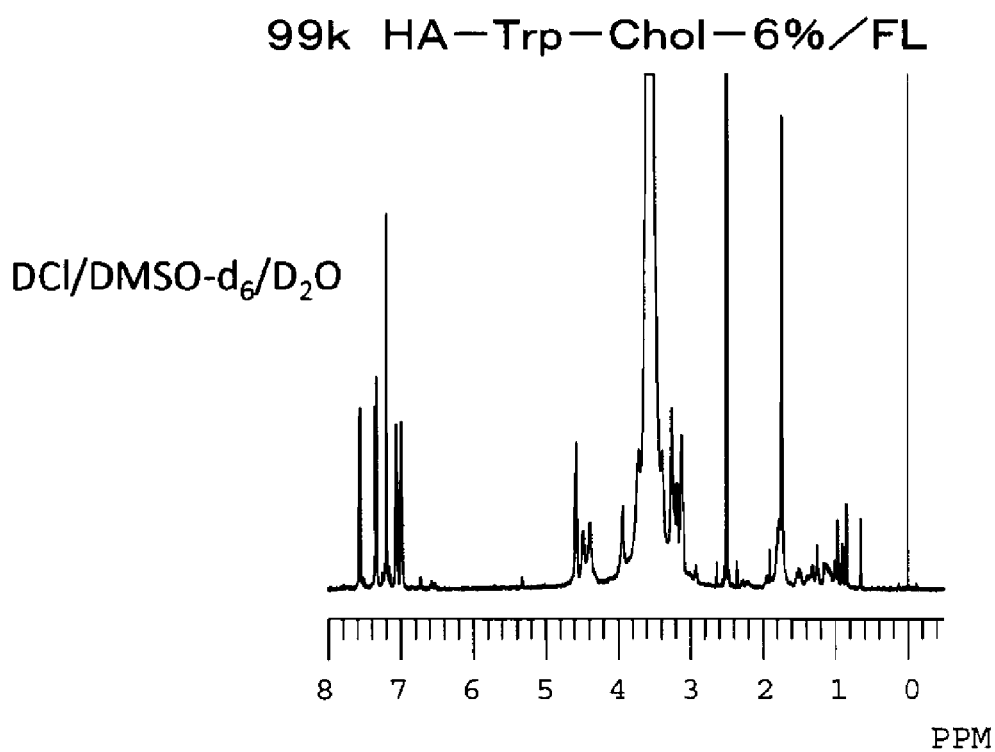
Figures 1, 4:
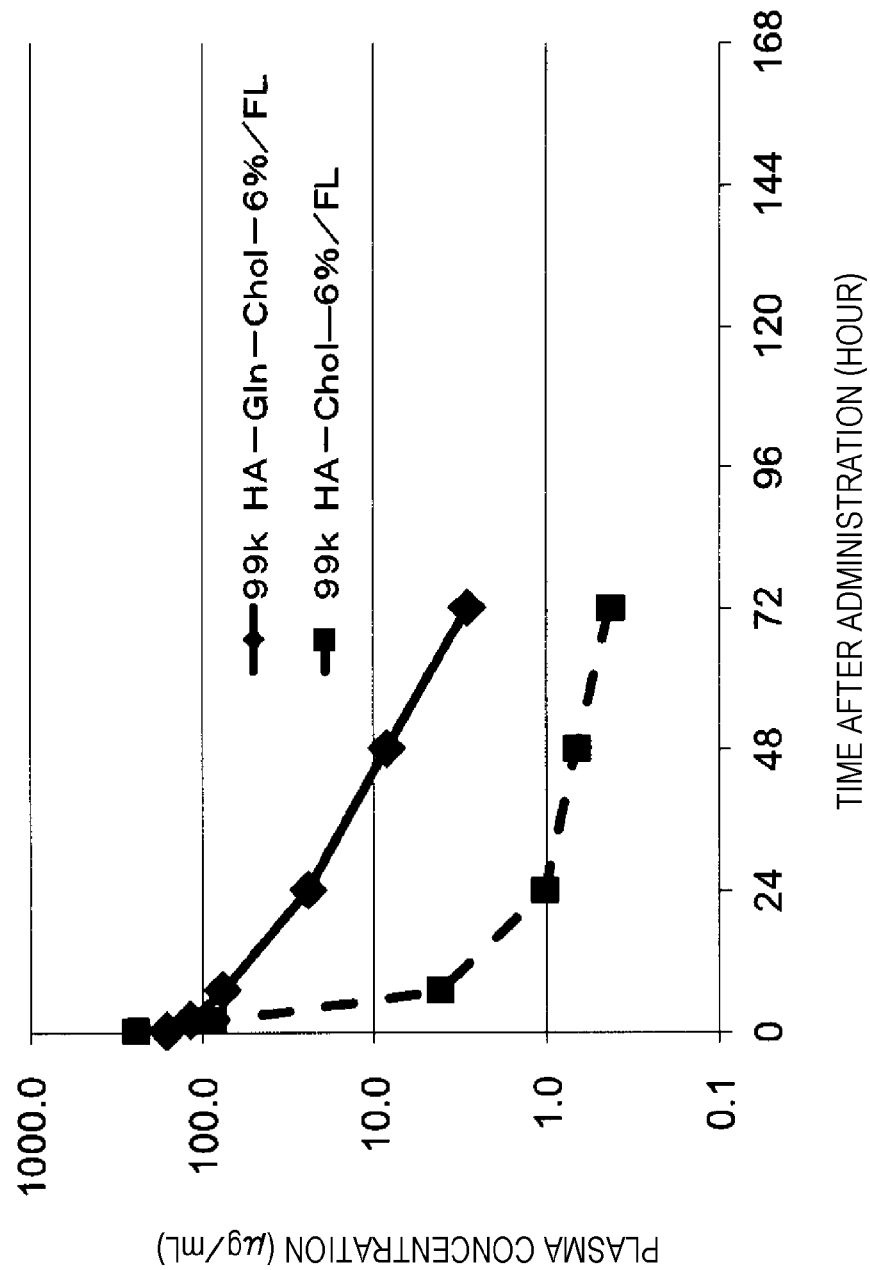
Figures 1, 2, 4:
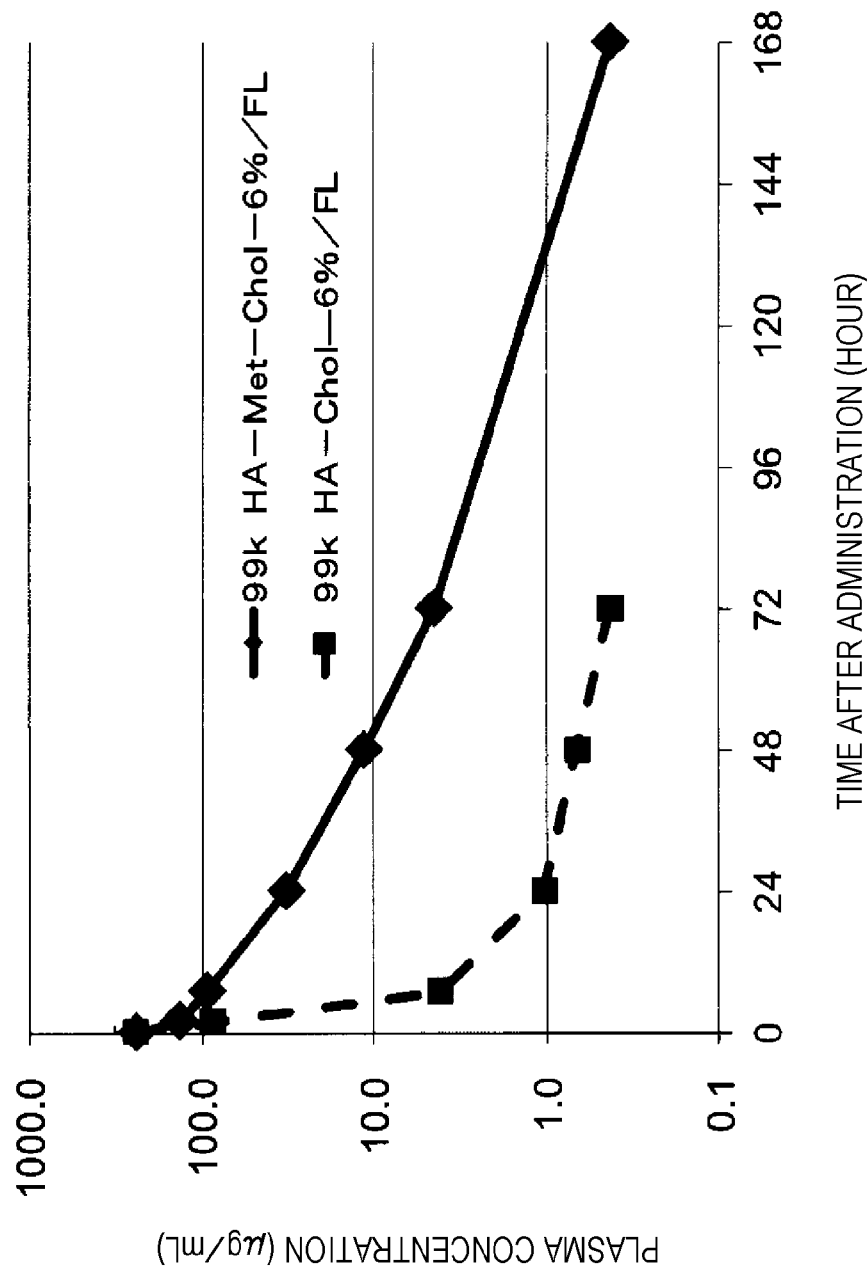
Figures 1, 4:
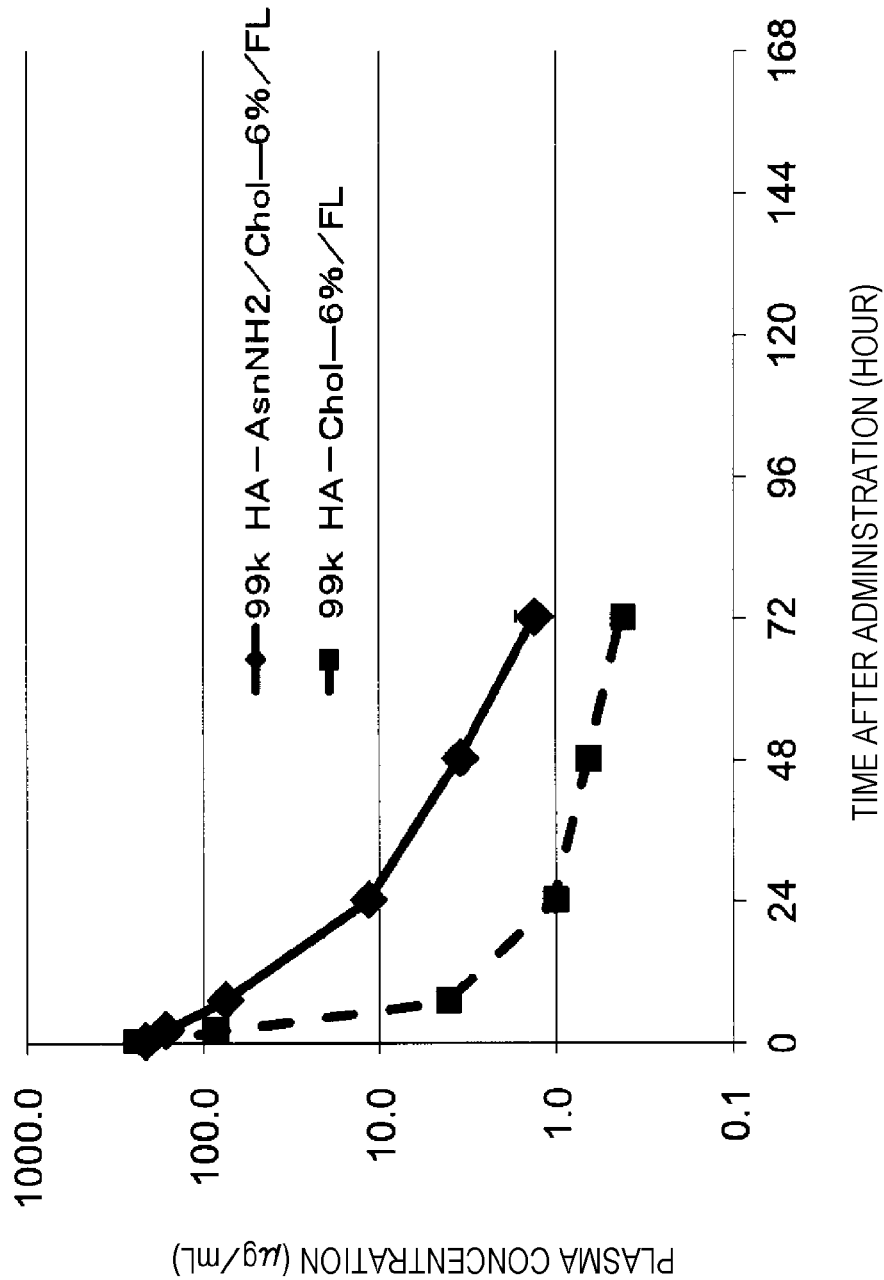
Figures 1, 4, 6:
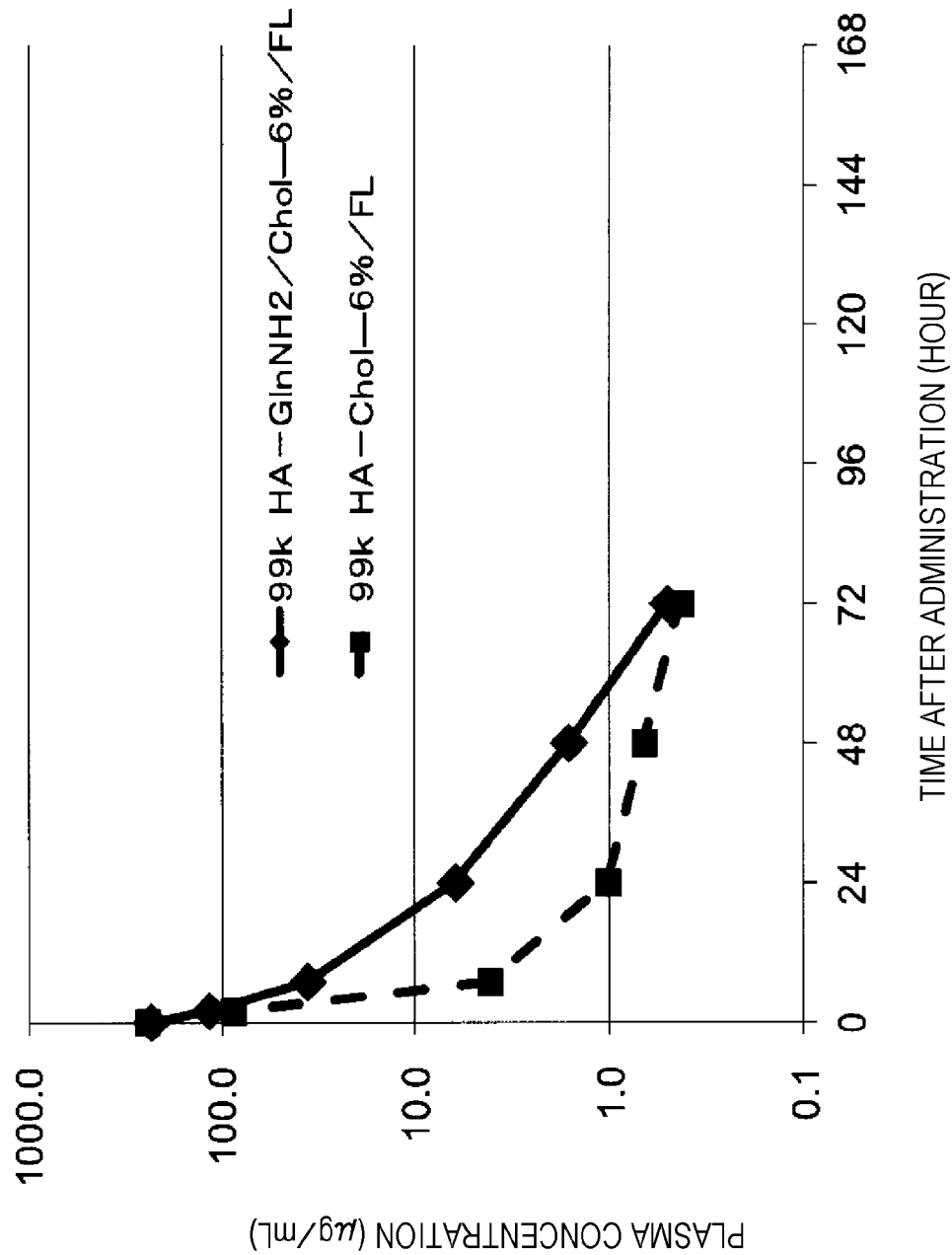
Figures 1, 4, 7:
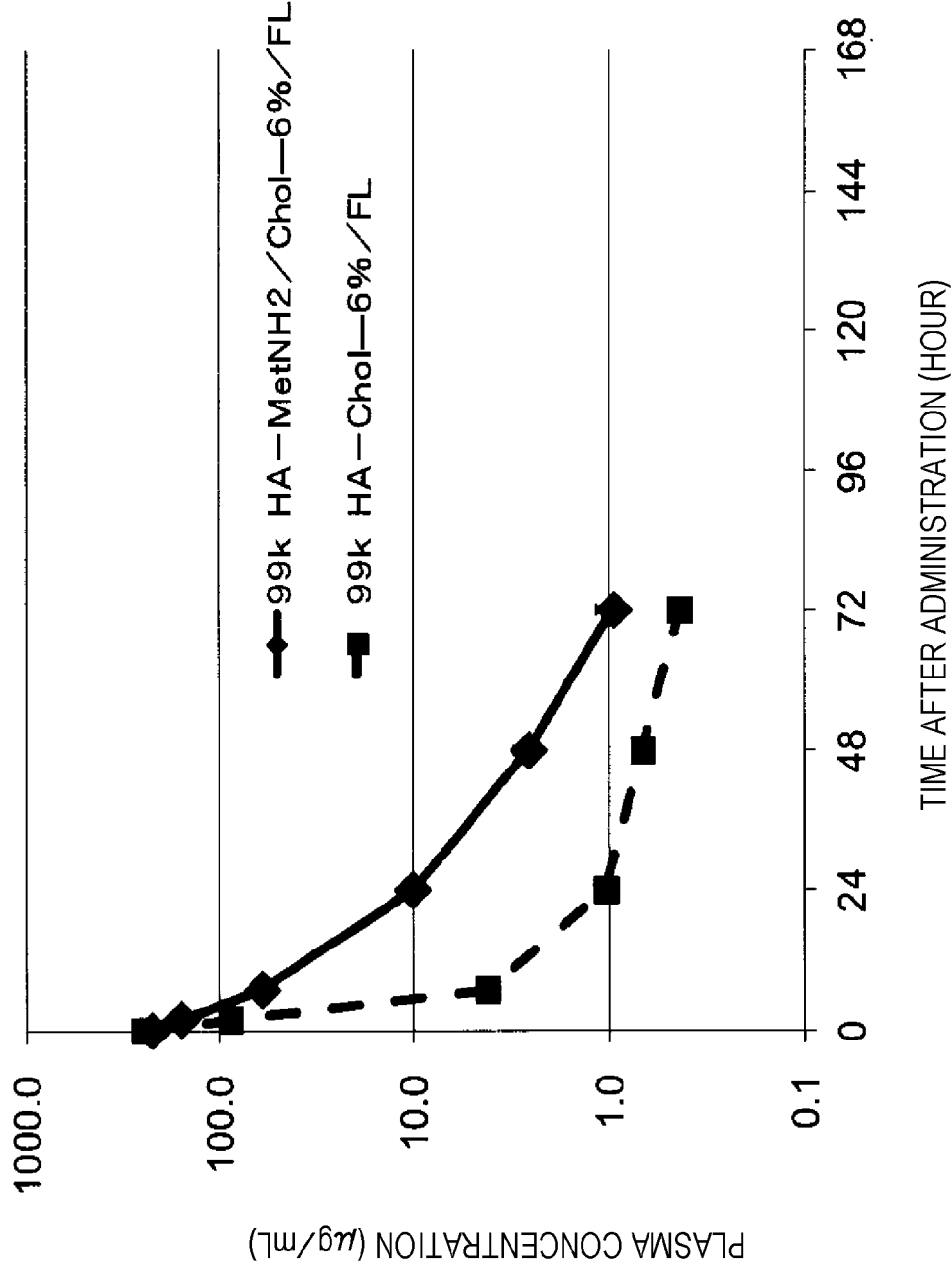
Figures 1, 4, 10:
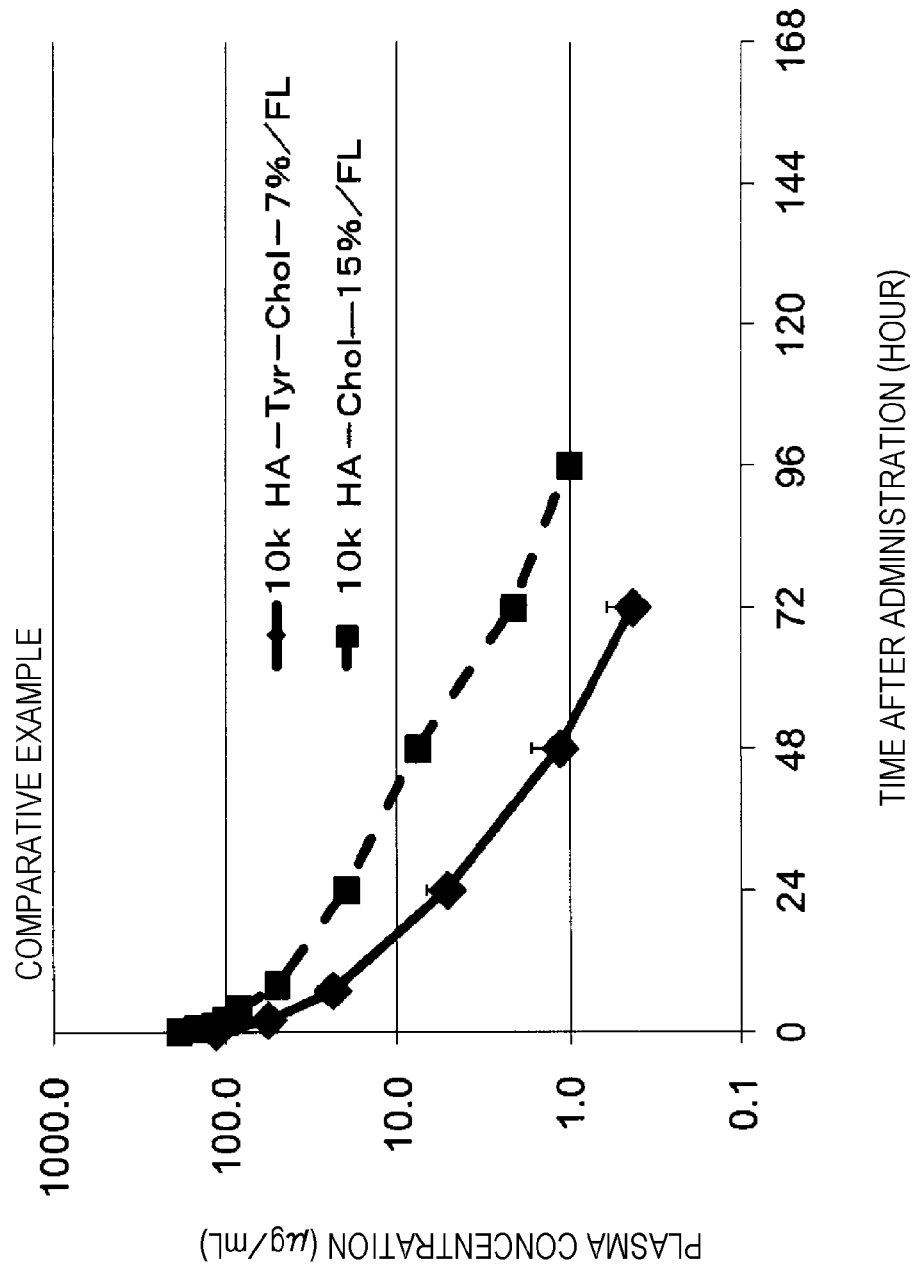
Figures 1, 2, 4:
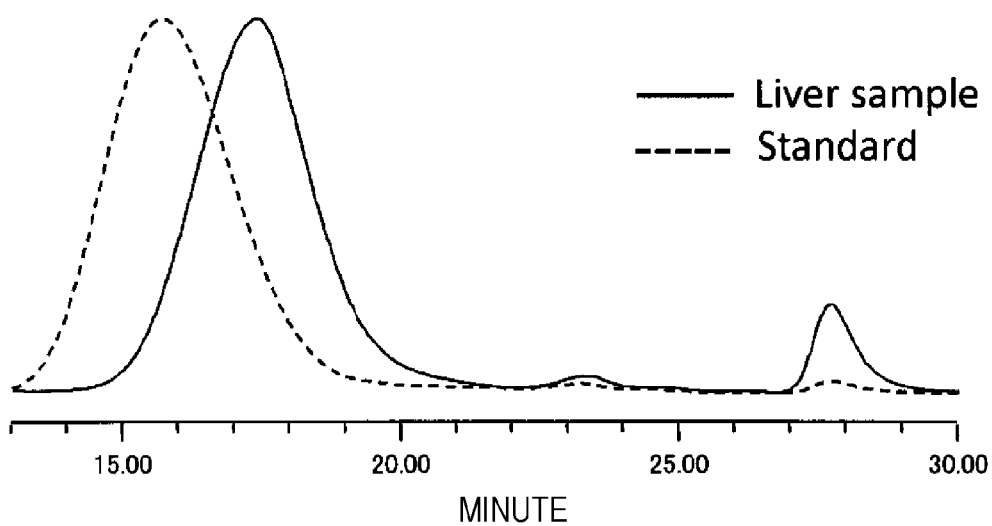
Figures 2, 4:
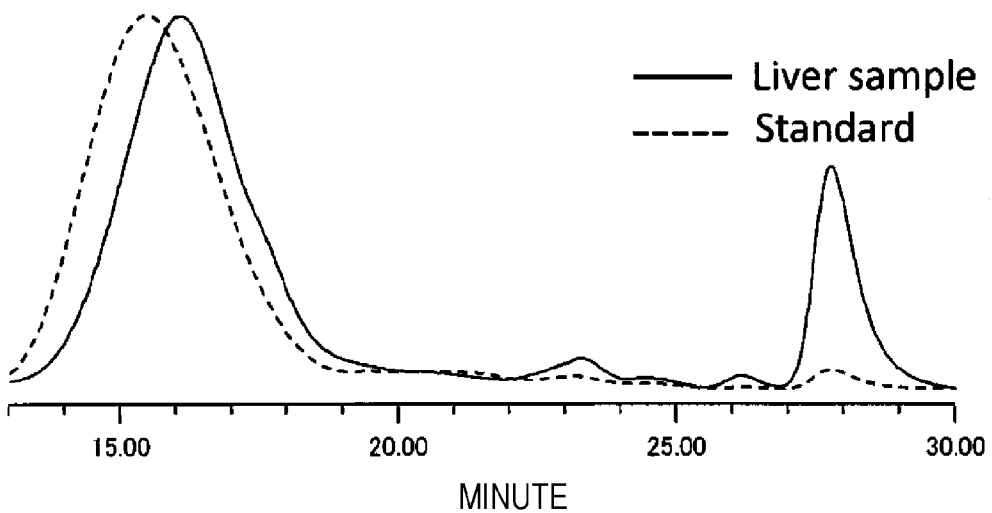
Figures 2, 3, 4:
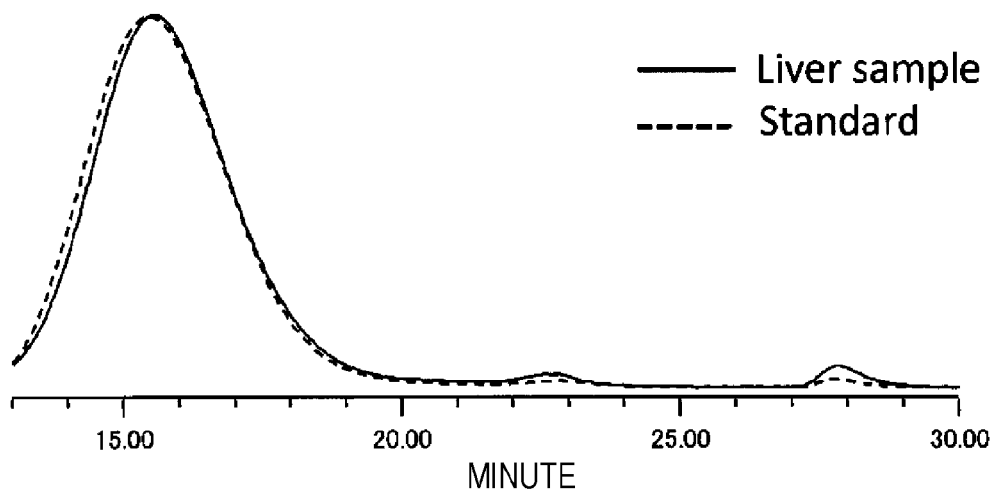
Figures 2, 4:
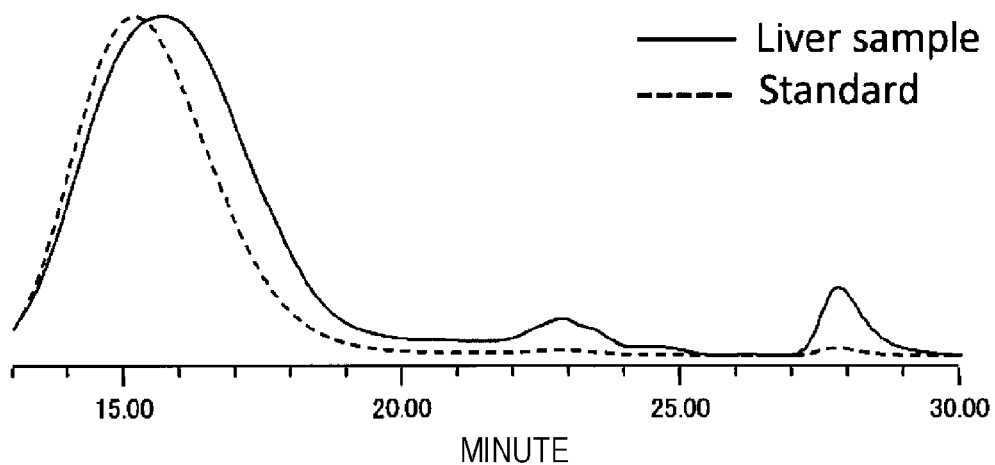
Figures 2, 4, 5:
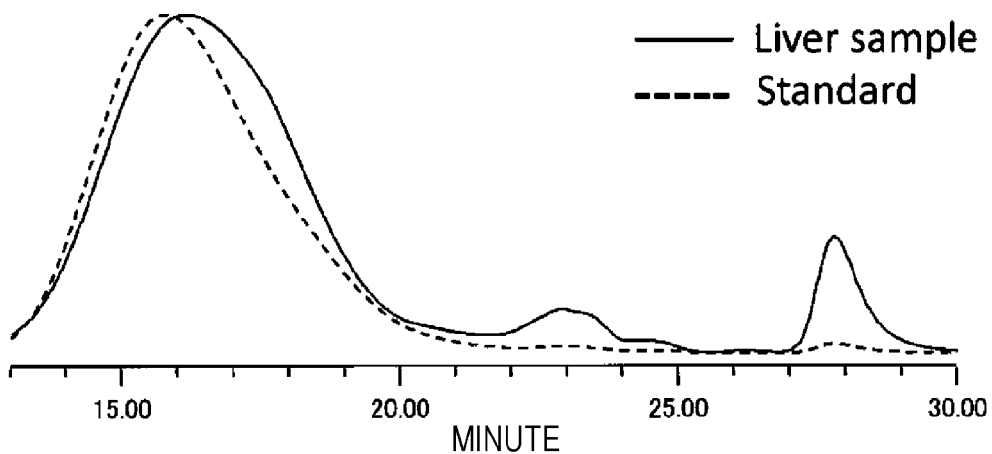
Figures 2, 4, 6:
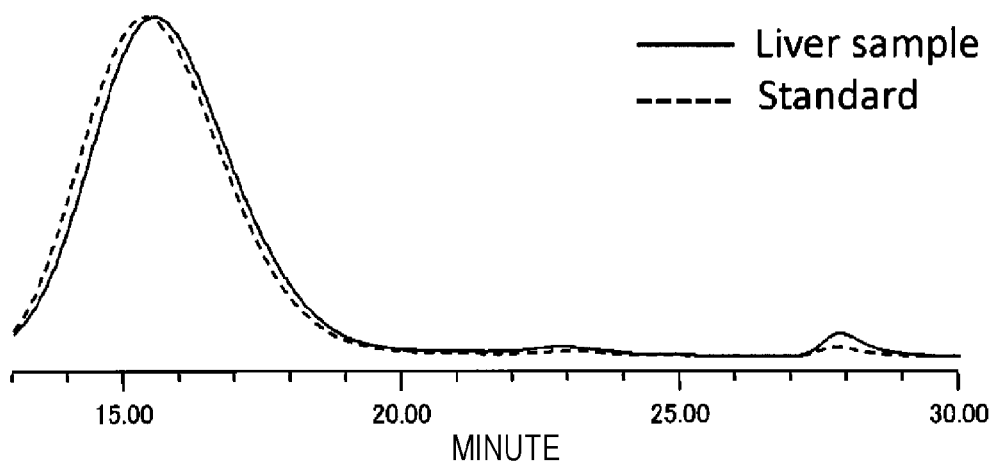
Figures 2, 4, 7:
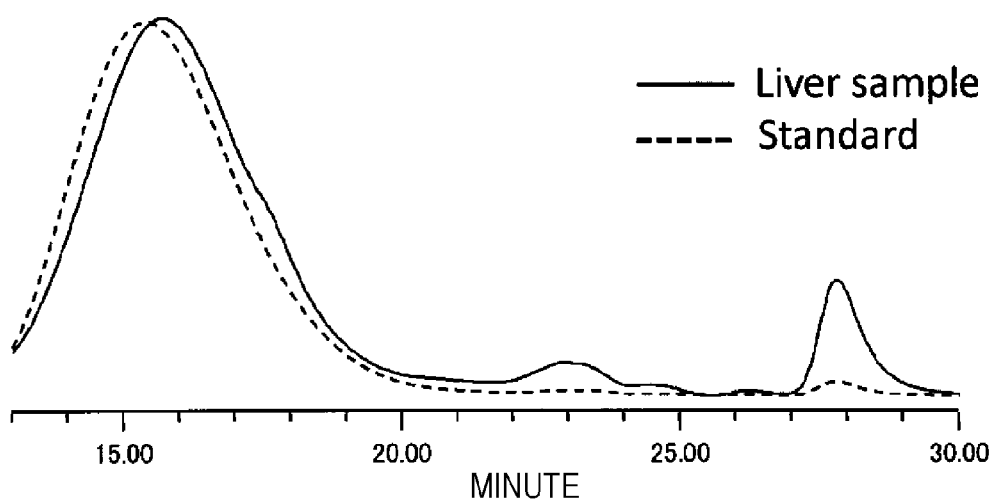
Figures 2, 4, 8:
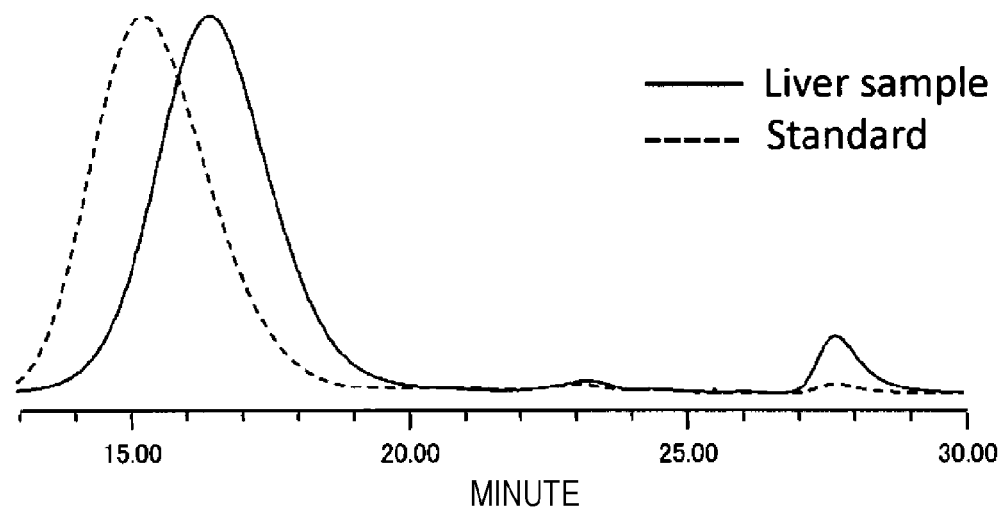
Figures 2, 4, 9:
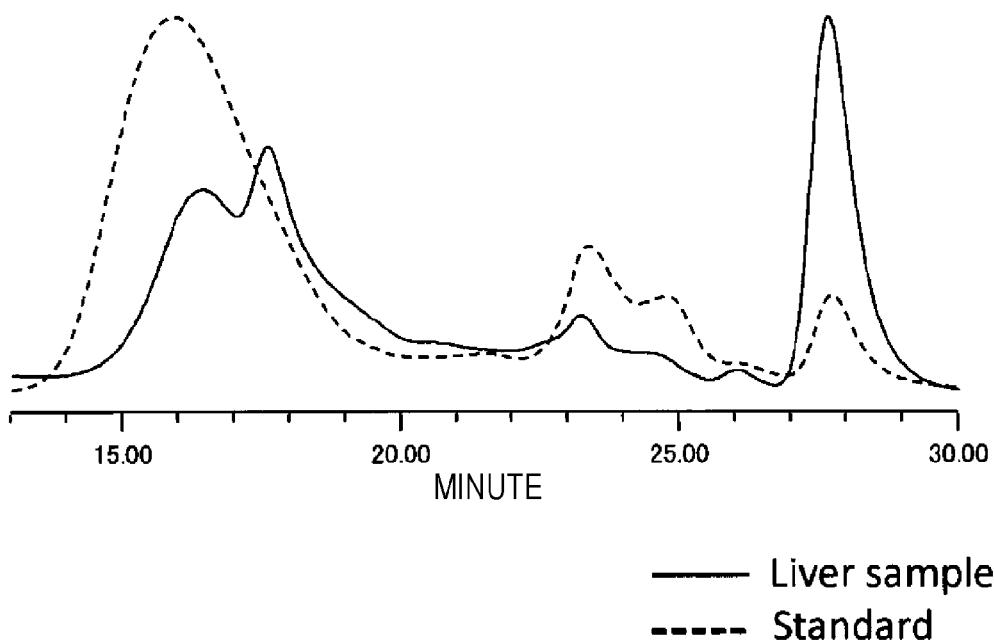
Figures 2, 4, 10:
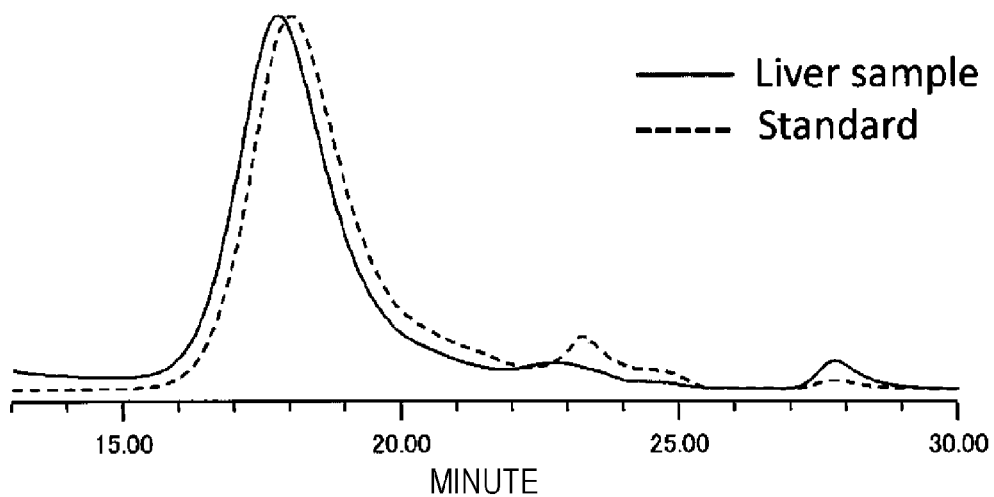
Figures 1, 5:
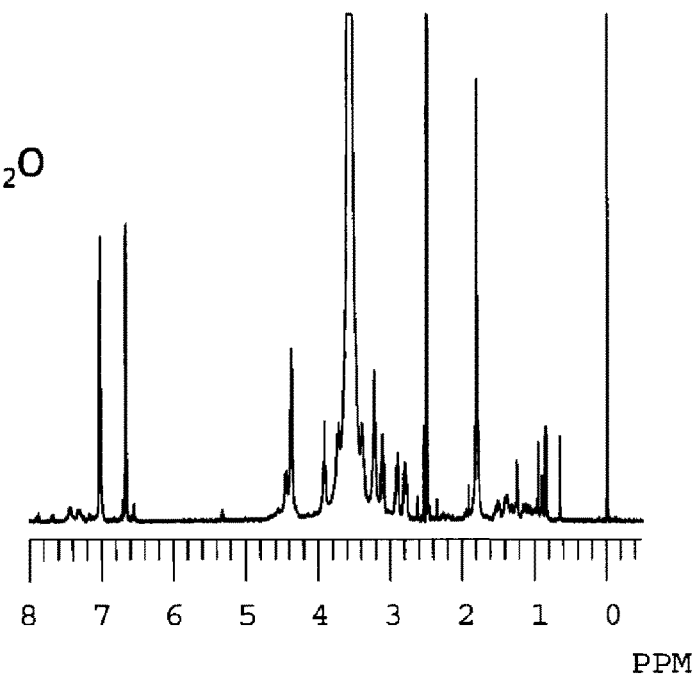
Figures 2, 5:
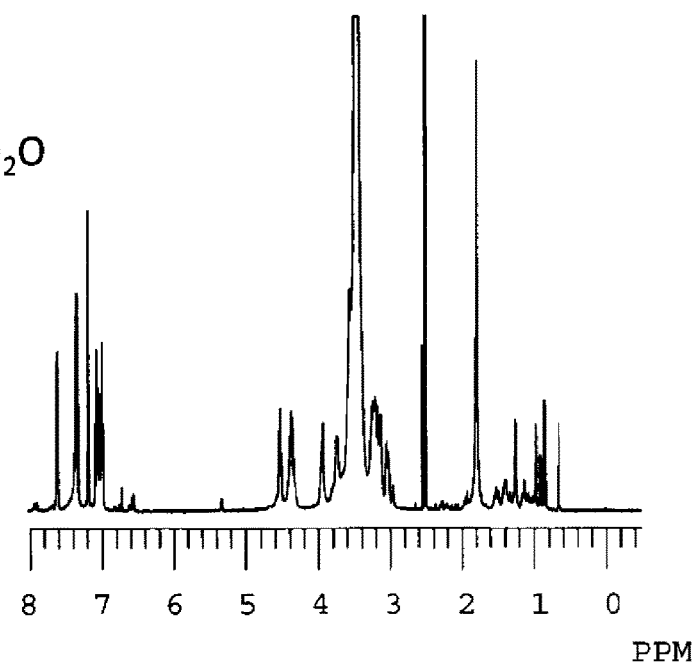
Figures 3, 5:
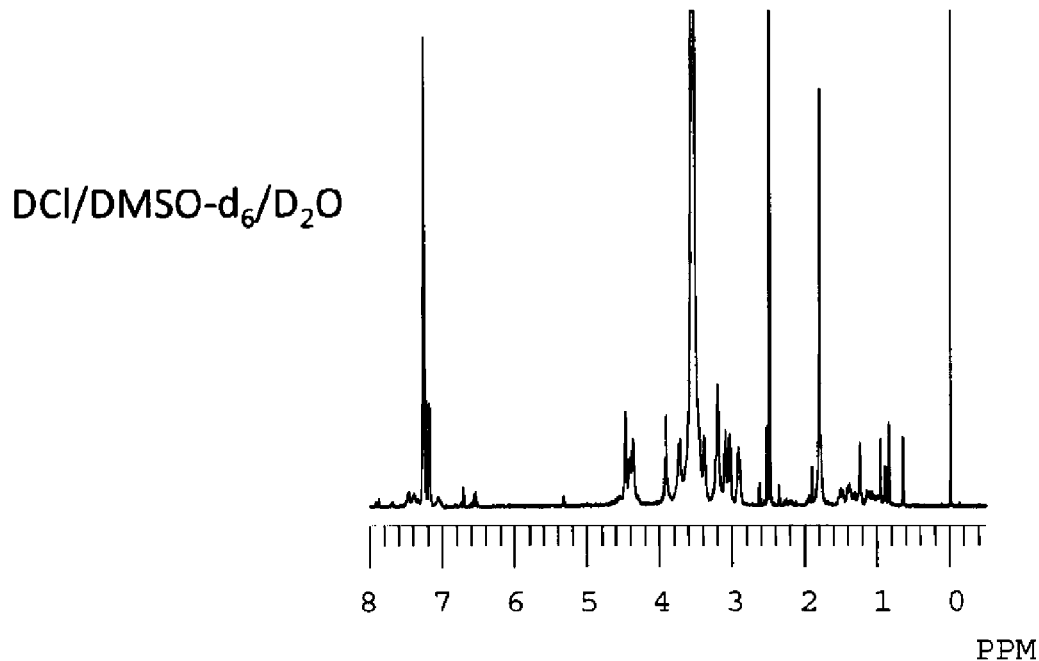
Figures 1, 6:
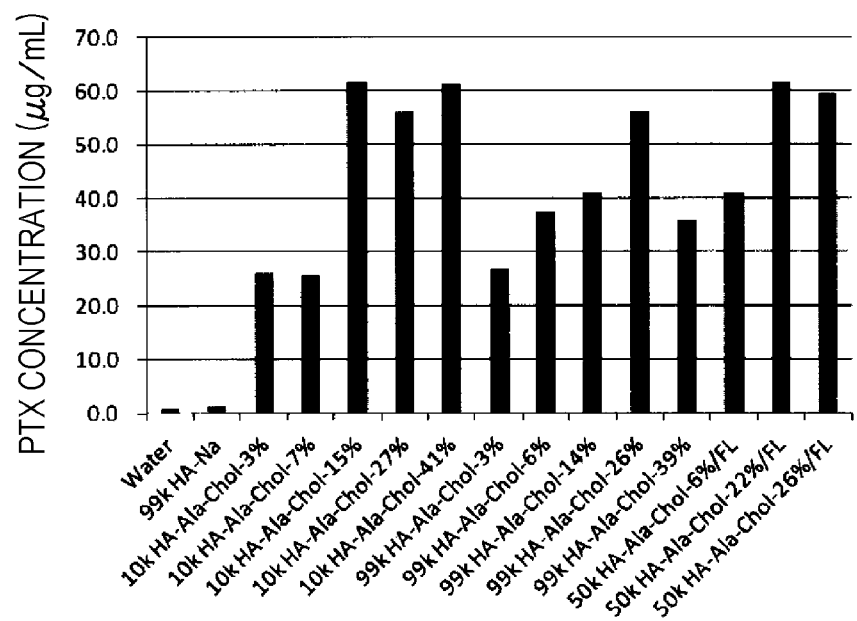
Figures 1, 2, 6:
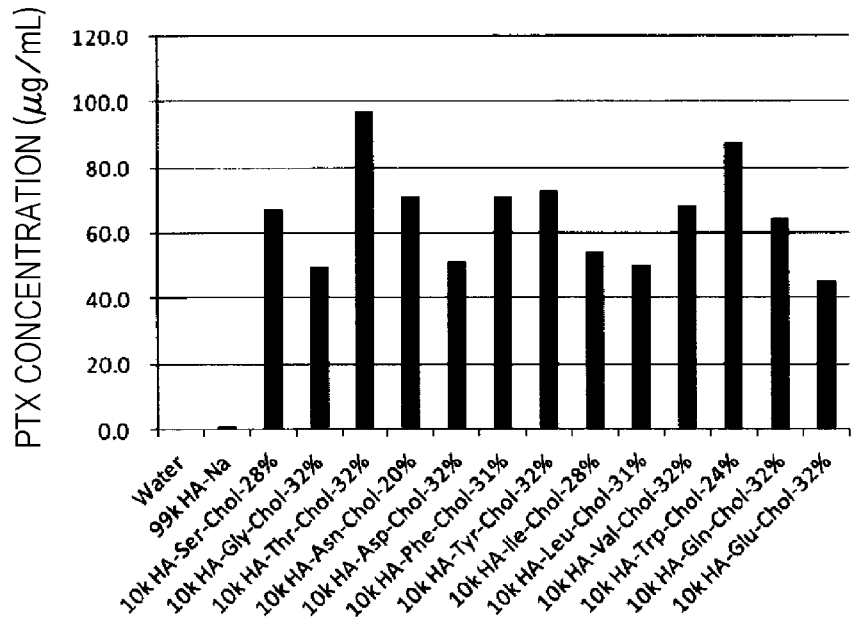
Figures 1, 3, 6:
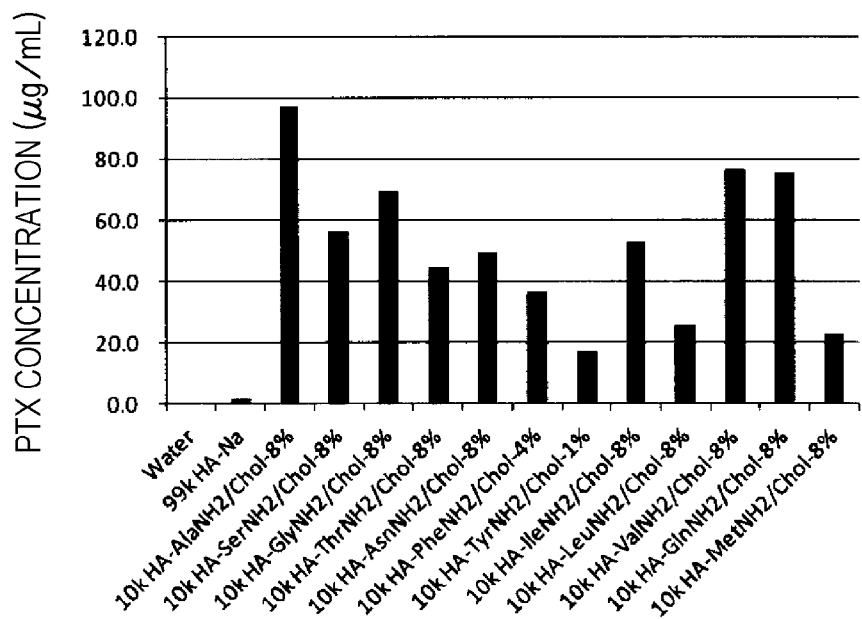
Figures 1, 4, 6:
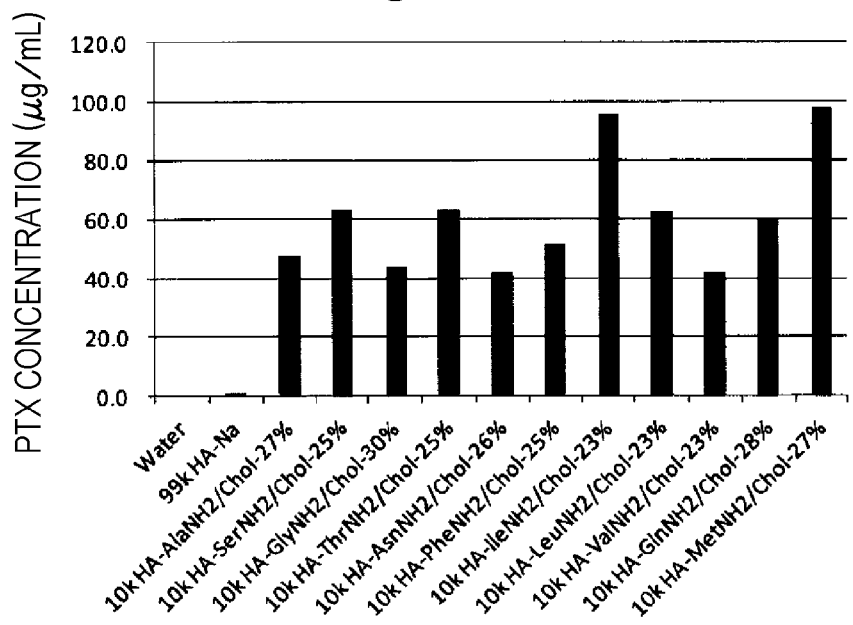
Figures 1, 2, 6:
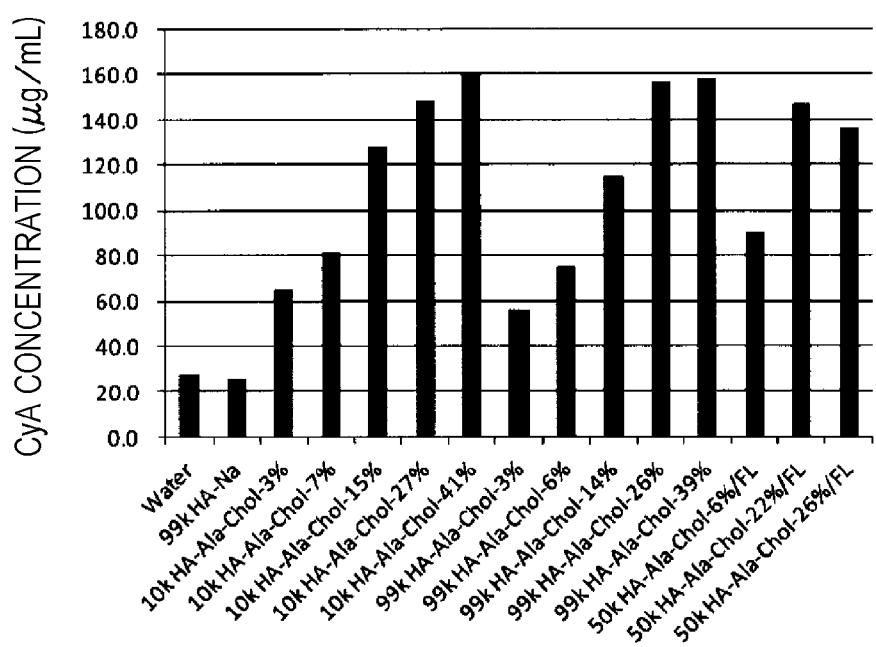
Figures 2, 6:
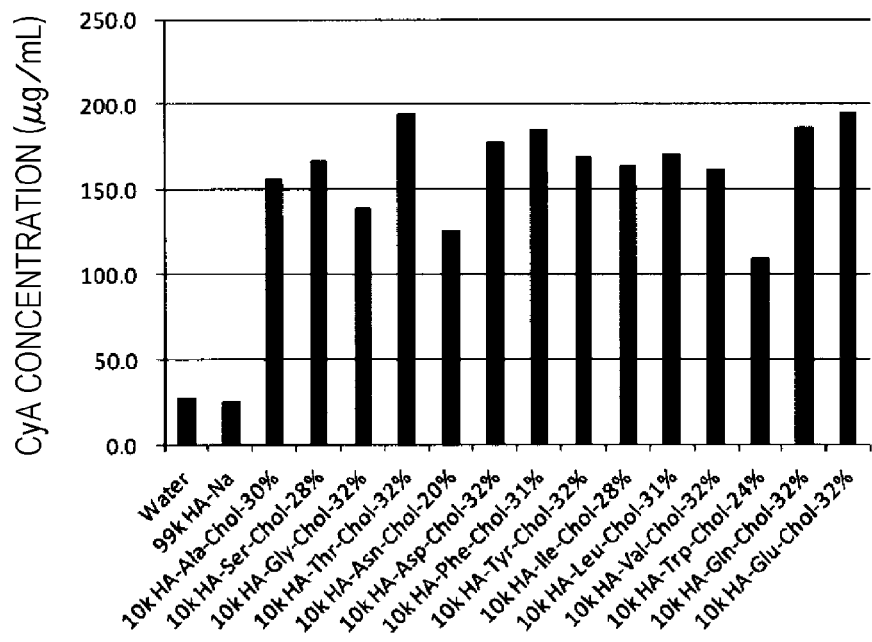
Figures 2, 3, 6:
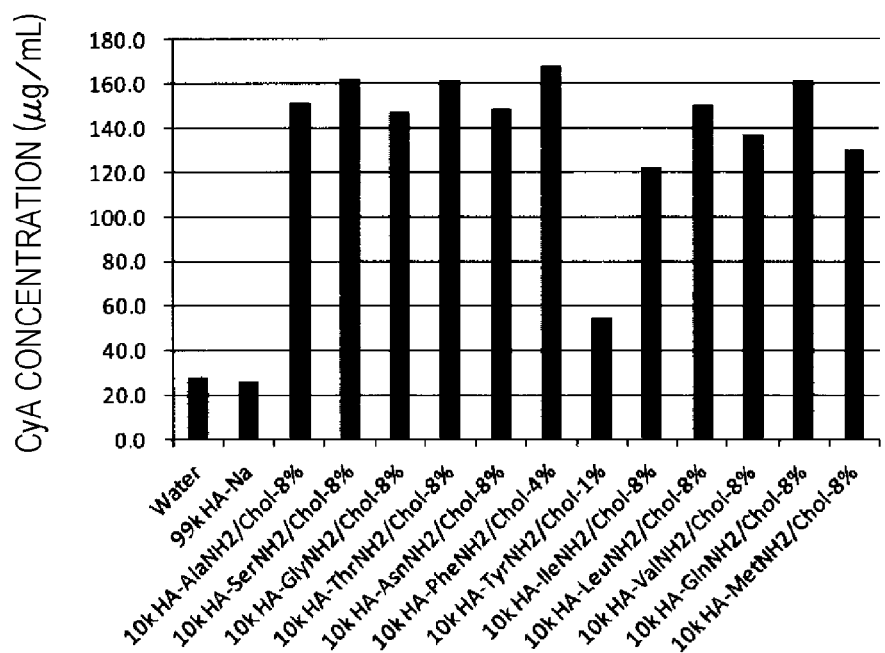
Figures 2, 4, 6:
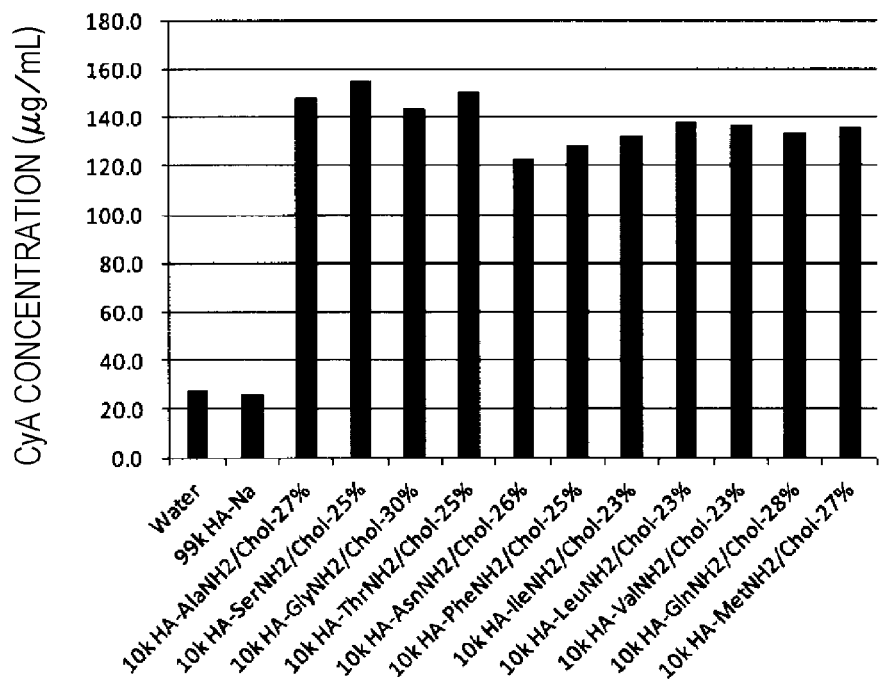
Figures 1, 7:
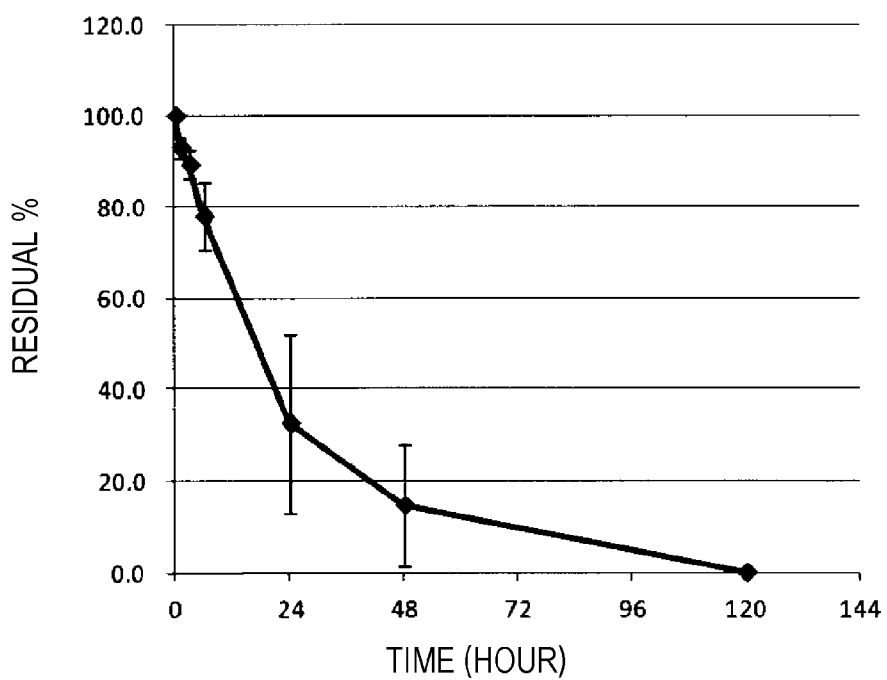
Figures 2, 7:
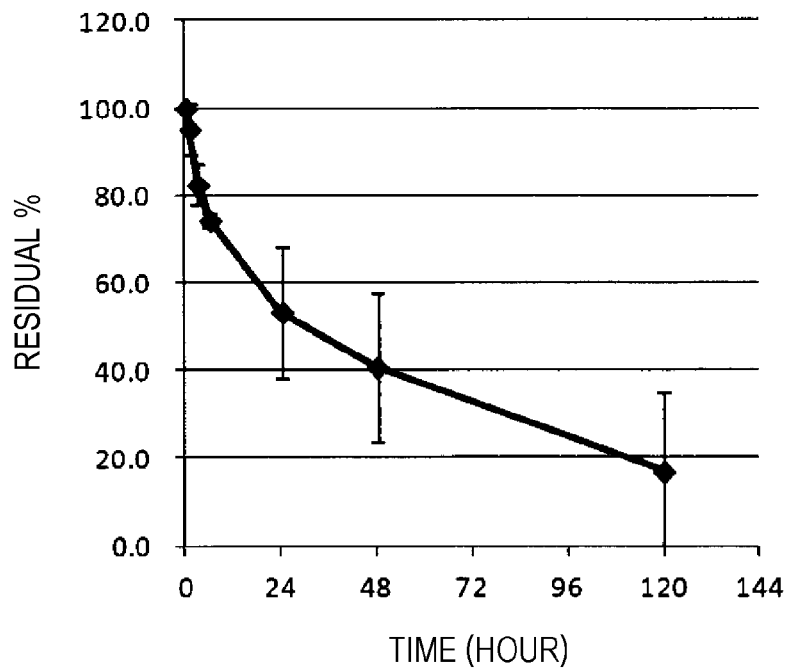
Figures 1, 8:
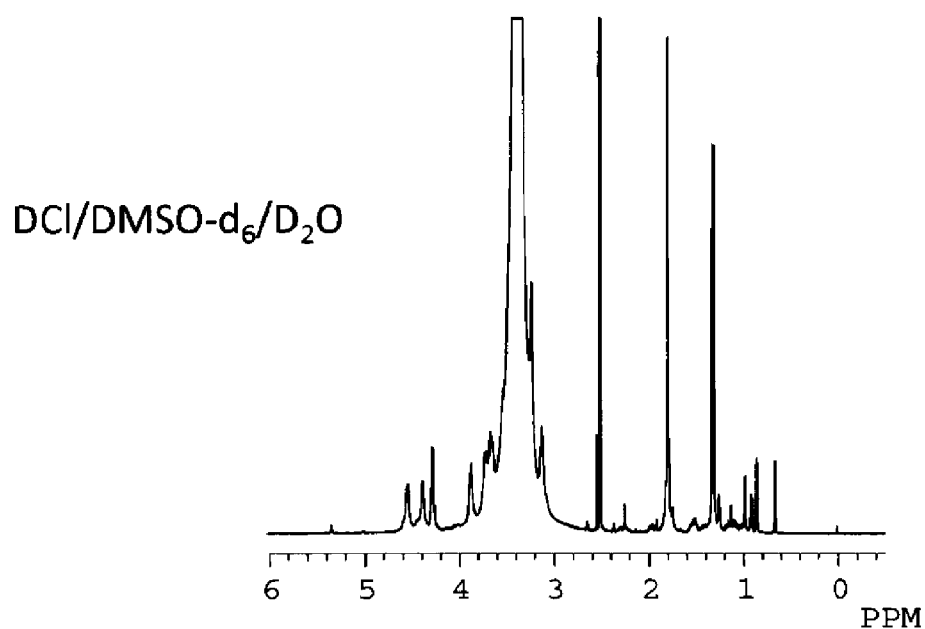
Figures 2, 8:
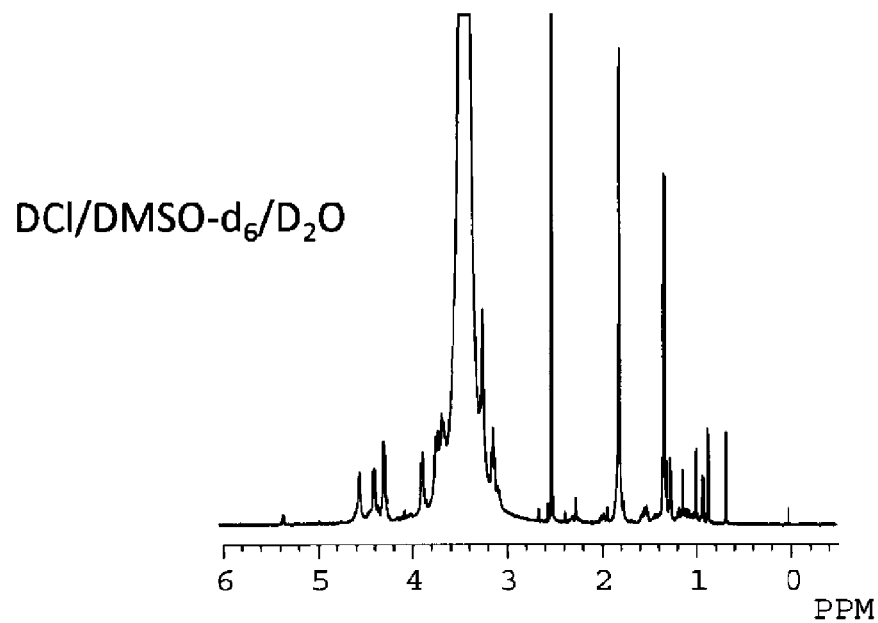
Figures 3, 8:
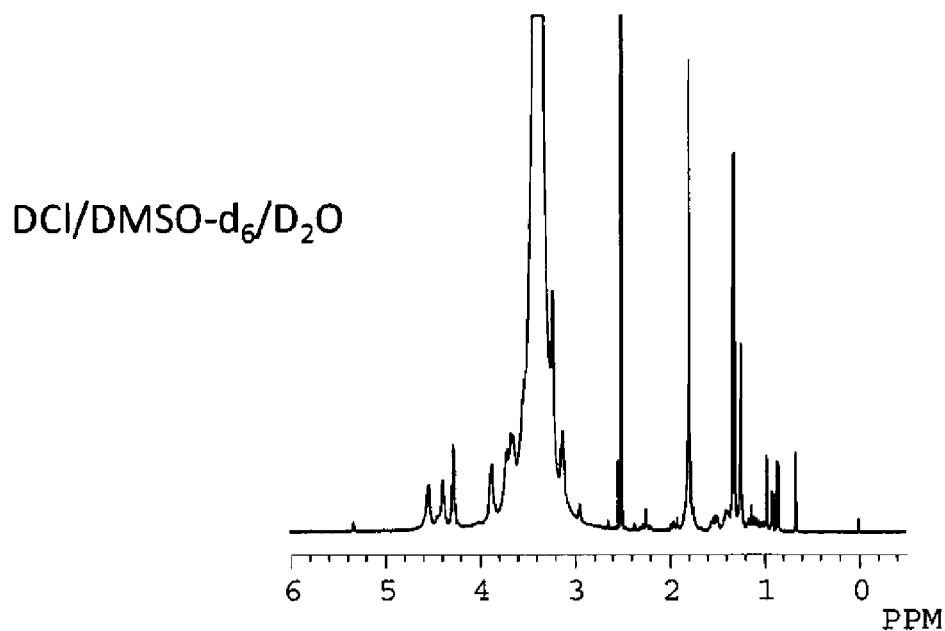
Figures 4, 8:
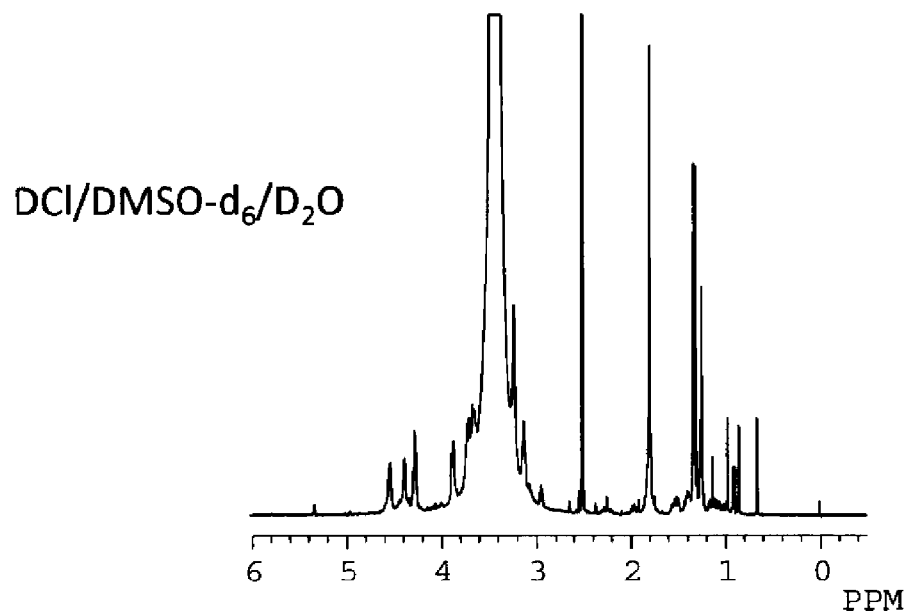
Figures 5, 8:
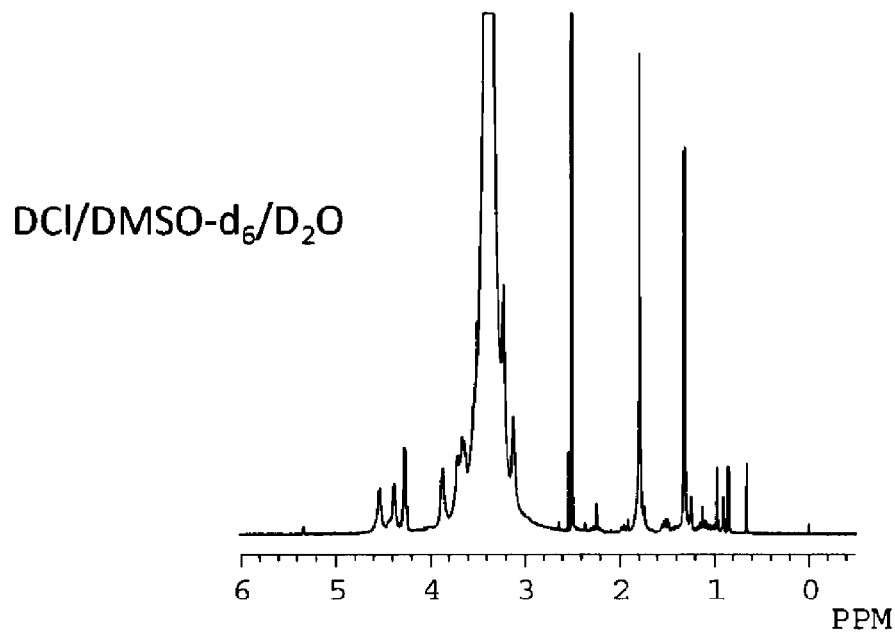
Figures 6, 8:
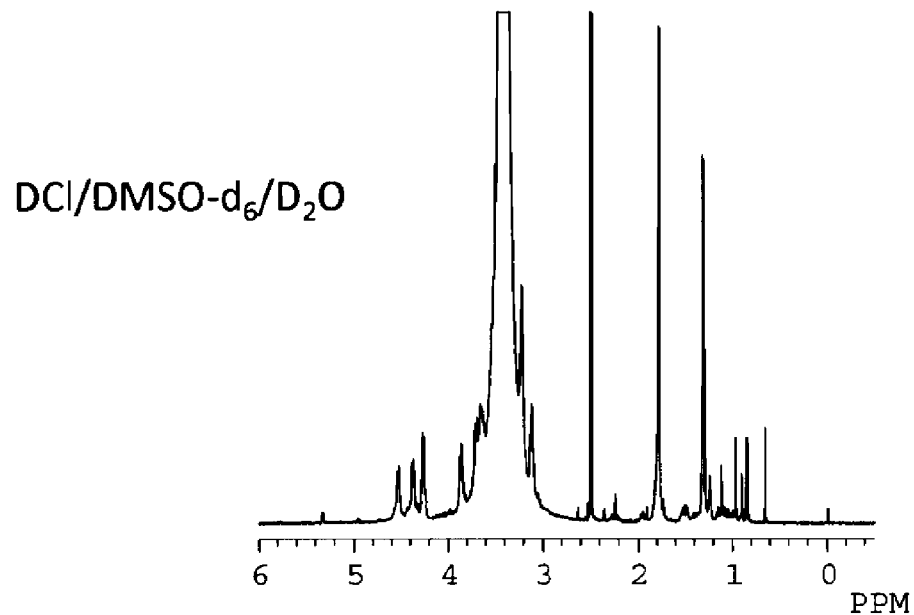
Figure 9:
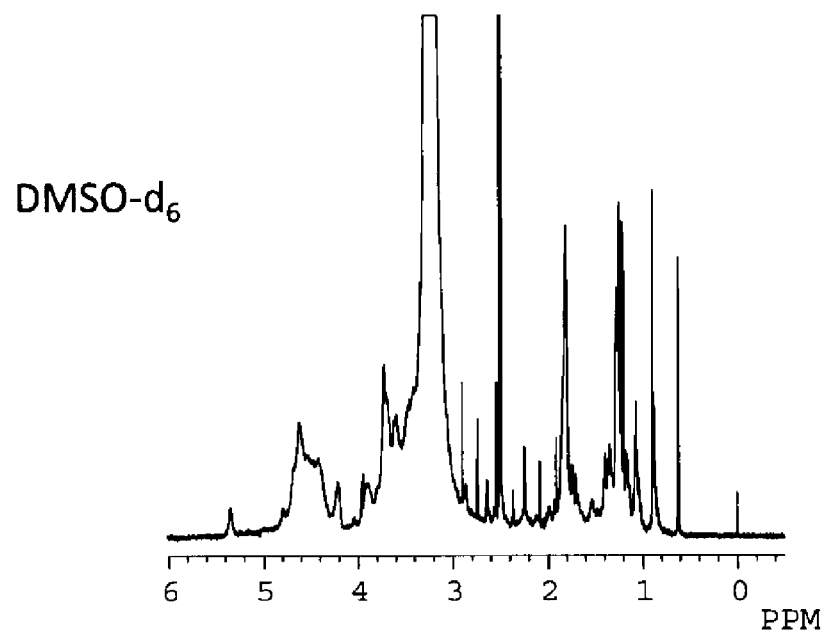

FIG. 4-1-10 is a graph illustrating changes of plasma concentrations of 10 k HA-Tyr-Chol-7%/FL (Table 15: comparative sample 4-3) and 10 k HA-Chol-15%/FL (Table 9: comparative sample 2-7) (Example 4-2).

FIG. 4-2-1 illustrates a size exclusion chromatography analysis of 99 k HA-Gln-Chol-6%/FL (Table 15: sample 4-1) and a liver sample of a mouse having received the sample, which indicates metabolism of the administered sample in the murine liver (Example 4-3).

FIG. 4-2-2 illustrates a size exclusion chromatography analysis of 99 k HA-Met-Chol-6%/FL (Table 15: sample 4-2) and a liver sample of a mouse having received the sample, which indicates metabolism of the administered sample in the murine liver (Example 4-3).

FIG. 4-2-3 illustrates a size exclusion chromatography analysis of 99 k HA-AlaNH$_2$/Chol-6%/FL (Table 15: sample 4-3) and a liver sample of a mouse having received the sample, which indicates metabolism of the administered sample in the murine liver (Example 4-3).

FIG. 4-2-4 illustrates a size exclusion chromatography analysis of 99 k HA-AsnNH$_2$/Chol-6%/FL (Table 15: sample 4-4) and a liver sample of a mouse having received the sample, which indicates metabolism of the administered sample in the murine liver (Example 4-3).

FIG. 4-2-5 illustrates a size exclusion chromatography analysis of 99 k HA-IleNH$_2$/Chol-6%/FL (Table 15: sample 4-5) and a liver sample of a mouse having received the sample, which indicates metabolism of the administered sample in the murine liver (Example 4-3).

FIG. 4-2-6 illustrates a size exclusion chromatography analysis of 99 k HA-GlnNH$_2$/Chol-6%/FL (Table 15: sample 4-6) and a liver sample of a mouse having received the sample, which indicates metabolism of the administered sample in the murine liver (Example 4-3).

FIG. 4-2-7 illustrates a size exclusion chromatography analysis of 99 k HA-MetNH$_2$/Chol-6%/FL (Table 15: sample 4-7) and a liver sample of a mouse having received the sample, which indicates metabolism of the administered sample in the murine liver (Example 4-3).

FIG. 4-2-8 illustrates a size exclusion chromatography analysis of 99 k HA-Glu-Chol-6%/FL (Table 15: comparative sample 4-1) and a liver sample of a mouse having received the sample, which indicates metabolism of the administered sample in the murine liver (Example 4-3).

FIG. 4-2-9 illustrates a size exclusion chromatography analysis of 99 k HA-Trp-Chol-6%/FL (Table 15: comparative sample 4-2) and a liver sample of a mouse having received the sample, which indicates metabolism of the administered sample in the murine liver (Example 4-3).

FIG. 4-2-10 illustrates a size exclusion chromatography analysis of 10 k HA-Tyr-Chol-7%/FL (Table 15: comparative sample 4-3) and a liver sample of a mouse having received the sample, which indicates metabolism of the administered sample in the murine liver (Example 4-3).

FIG. 5-1 illustrates an example of NMR spectra of HA-TyrNH$_2$/Chol/FL prepared in Example 5-1 (introduction ratio of cholesteryl group: 6%).

FIG. 5-2 illustrates an example of NMR spectra of HA-TrpNH$_2$/Chol/FL prepared in Example 5-2 (introduction ratio of cholesteryl group: 6%).

FIG. 5-3 illustrates an example of NMR spectra of HA-PheNH$_2$/Chol/FL prepared in Example 5-3 (introduction ratio of cholesteryl group: 6%).

FIG. 6-1-1 is a graph illustrating encapsulation of paclitaxel, a poorly soluble drug, to a hyaluronic acid derivative of the present invention (formation a complex of the hyaluronic acid derivative of the present invention and paclitaxel) in Example 6-1, in which the ordinate indicates the paclitaxel concentration (solubility) in the supernatant which is improved by the presence of hyaluronic acid derivative of the present invention. The higher value on the ordinate indicates the more encapsulation.

FIG. 6-1-2 is a graph illustrating encapsulation of paclitaxel, a poorly soluble drug to a hyaluronic acid derivative of the present invention (formation a complex of the hyaluronic acid derivative of the present invention and paclitaxel) in Example 6-1, in which the ordinate indicates the paclitaxel concentration (solubility) in the supernatant which is improved by the presence of hyaluronic acid derivative of the present invention. The higher value on the ordinate indicates the more encapsulation.

FIG. 6-1-3 is a graph illustrating encapsulation of paclitaxel, a poorly soluble drug to a hyaluronic acid derivative of the present invention (formation a complex of the hyaluronic acid derivative of the present invention and paclitaxel) in Example 6-1, in which the ordinate indicates the paclitaxel concentration (solubility) in the supernatant which is improved by the presence of hyaluronic acid derivative of the present invention. The higher value on the ordinate indicates the more encapsulation.

FIG. 6-1-4 is a graph illustrating encapsulation of paclitaxel, a poorly soluble drug to a hyaluronic acid derivative of the present invention (formation a complex of the hyaluronic acid derivative of the present invention and paclitaxel) in Example 6-1, in which the ordinate indicates the paclitaxel concentration (solubility) in the supernatant which is improved by the presence of hyaluronic acid derivative of the present invention. The higher value on the ordinate indicates the more encapsulation.

FIG. 6-2-1 is a graph illustrating encapsulation of cyclosporine, a poorly soluble drug, to a hyaluronic acid derivative of the present invention (formation a complex of the hyaluronic acid derivative of the present invention and paclitaxel) in Example 6-2, in which the ordinate indicates the cyclosporine concentration (solubility) in the supernatant which is improved by the presence of hyaluronic acid derivative of the present invention. The higher value on the ordinate indicates the more encapsulation.

FIG. 6-2-2 is a graph illustrating encapsulation of cyclosporine, a poorly soluble drug to a hyaluronic acid derivative of the present invention (formation a complex of the hyaluronic acid derivative of the present invention and paclitaxel) in Example 6-2, in which the ordinate indicates the cyclosporine concentration (solubility) in the supernatant which is improved by the presence of hyaluronic acid derivative of the present invention. The higher value on the ordinate indicates the more encapsulation.

FIG. 6-2-3 is a graph illustrating encapsulation of cyclosporine, a poorly soluble drug to a hyaluronic acid derivative of the present invention (formation a complex of the hyaluronic acid derivative of the present invention and paclitaxel) in Example 6-2, in which the ordinate indicates the cyclosporine concentration (solubility) in the supernatant which is improved by the presence of hyaluronic acid derivative of the present invention. The higher value on the ordinate indicates the more encapsulation.

FIG. 6-2-4 is a graph illustrating encapsulation of cyclosporine, a poorly soluble drug to a hyaluronic acid derivative of the present invention (formation a complex of the hyaluronic acid derivative of the present invention and paclitaxel) in Example 6-2, in which the ordinate indicates the cyclosporine concentration (solubility) in the supernatant which is improved by the presence of hyaluronic acid derivative of the present invention. The higher value on the ordinate indicates the more encapsulation.

FIG. 7-1 is a graph illustrating release of paclitaxel from HA-Ala-Chol-41% in Example 7-1, in which the abscissa and ordinate represent time (hour) and the amount of paclitaxel encapsulated in HA-Ala-Chol-41% without being released (in a complex with HA-Ala-Chol-41%), respectively.

FIG. 7-2 is a graph illustrating release of cyclosporine from HA-Ala-Chol-41% in Example 7-2, in which the abscissa and ordinate represent time (hour) and the amount of cyclosporine encapsulated in HA-Ala-Chol-41% without being released (in a complex with HA-Ala-Chol-41%), respectively.

FIG. 8-1 illustrates an example of NMR spectra of HA-Ala-$C_2$-Chol prepared in Example 8 (introduction ratio of cholesteryl group: 6%).

FIG. 8-2 illustrates an example of NMR spectra of HA-Ala-$C_2$-Chol prepared in Example 8 (introduction ratio of cholesteryl group: 7%).

FIG. 8-3 illustrates an example of NMR spectra of HA-Ala-$C_{12}$-Chol prepared in Example 8 (introduction ratio of cholesteryl group: 7%).

FIG. 8-4 illustrates an example of NMR spectra of HA-Ala-$C_{12}$-Chol prepared in Example 8 (introduction ratio of cholesteryl group: 7%).

FIG. 8-5 illustrates an example of NMR spectra of HA-Ala-$EO_2$-Chol prepared in Example 8 (introduction ratio of cholesteryl group: 5%).

FIG. 8-6 illustrates an example of NMR spectra of HA-Ala-$EO_2$-Chol prepared in Example 8 (introduction ratio of cholesteryl group: 6%).

FIG. 9 illustrates an example of NMR spectra of HA-Ala-CA prepared in Example 9-2 (introduction ratio of cholanoyl group: 13%).

DESCRIPTION OF EMBODIMENTS

Hyaluronic acid derivatives of the present invention are hyaluronic acid derivatives containing one or more disaccharide units (also, repeating units) represented by formula (I).

In one embodiment of the present invention, a hyaluronic acid derivative is substantially composed of repeating units represented by (a) the above formula (I), (b) the above formulas (I) and (II), (c) the above formulas (I) and (IIb), or (d) the above formulas (I) and (II) and (IIb). The hyaluronic acid derivative contains disaccharide repeating units of D-glucuronic acid and N-acetylglucosamine, of which, for example, 80% or more, preferably 90% or more, and more preferably 95% or more are repeating units represented by formula (I), (II), or (IIb). In one embodiment of the present invention, a hyaluronic acid derivative is exclusively composed of repeating units represented by (a) the above formula (I), (b) the above formulas (I) and (II), (c) the above formulas (I) and (IIb), or (d) the above formulas (I) and (II) and (IIb).

The percentage of a particular disaccharide unit to the disaccharide repeating units in a hyaluronic acid derivative of the present invention indicates the percentage of the particular disaccharide unit to all the disaccharide units contained in a certain amount of the hyaluronic acid derivative of the present invention, which is a polysaccharide having disaccharide units as its repeating units.

In formula (I) representing disaccharide units contained in hyaluronic acid derivatives of the present invention, $R^1$, $R^2$, $R^3$, and $R^4$ are preferably all hydrogen atoms. $R^5$ is preferably a hydrogen atom or $C_{1-6}$ alkylcarbonyl, more preferably a hydrogen atom or acetyl, and even more preferably acetyl. In formulas (II) and (IIb) representing disaccharide units contained in hyaluronic acid derivatives of the present invention, $R^{1a}$, $R^{2a}$, $R^{3a}$, and $R^{4a}$ and $R^{1b}$, $R^{2b}$, $R^{3b}$, and $R^{4b}$ are preferably all hydrogen atoms. $R^{5a}$ and $R^{5b}$ are preferably a hydrogen atom or $C_{1-6}$ alkylcarbonyl, more preferably a hydrogen atom or acetyl, and even more preferably both acetyl.

Specific examples of $R^a$ in formula (I) include a hydrogen atom, methyl, hydroxymethyl, 1-hydroxyethyl, carbamoylmethyl, carboxymethyl, 1-methylpropyl, 2-methylpropyl, isopropyl, 2-carboxyethyl, 2-methylthioethyl, 2-carbamoylethyl, phenylmethyl, (4-hydroxyphenyl)methyl and indol-3-ylmethyl.

If the group —$CHR^a$— has an asymmetric center, it includes respective optical active forms and mixtures thereof. When referred to as $H_2N$—$CHR^a$—COOH (amino acid), it preferably represents the L-form (natural form).

In formula (I), R, $R^7$, $R^8$, and $R^9$ are, for example, independently a hydrogen atom or methyl, but preferably all hydrogen atoms.

For example, the group —CHR$^a$—COOH is included as an embodiment of the group —CHR$^a$—CO—X$^1$ in formula (I). Specific examples of this group include the following groups.

[Chemical Formula 5]

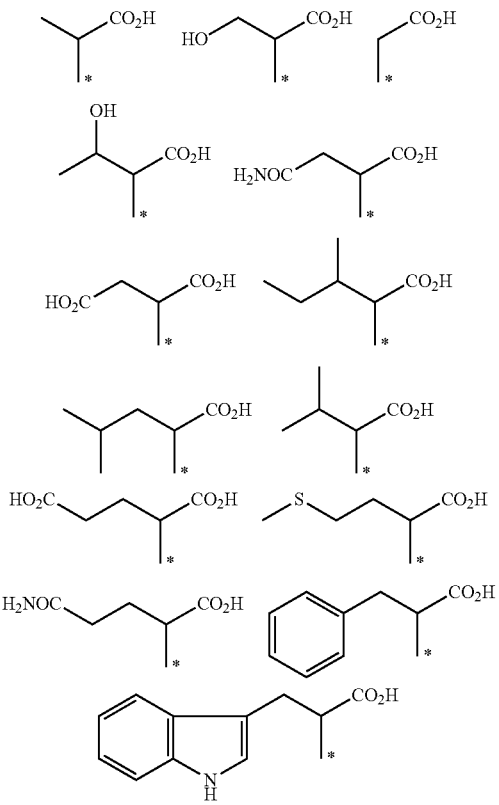

* represents the position attached to —NR$^6$— (hereinafter the same).

Preferable examples of the group —CHR$^a$—COOH include the following groups.

[Chemical Formula 6]

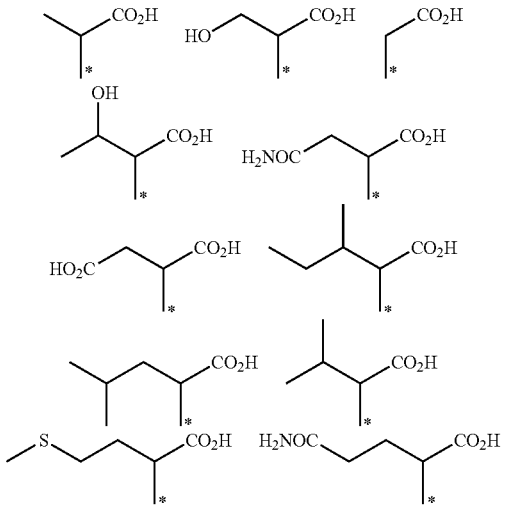

Preferable examples of the group —CHR$^a$—COOH include the following groups.

[Chemical Formula 7]

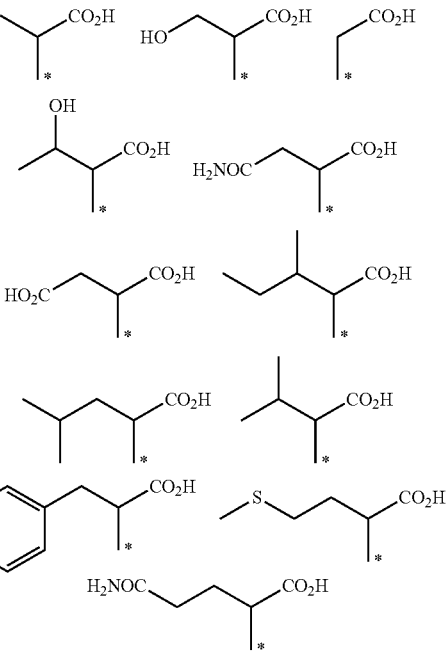

Preferable examples of the group —CHR$^a$—COOH include the following groups.

[Chemical Formula 8]

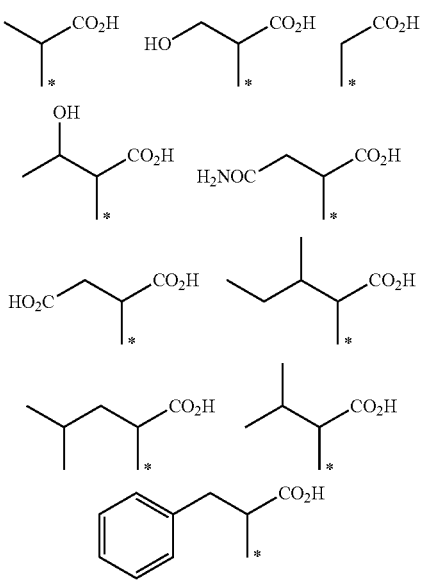

Preferable examples of the group —CHR$^a$—COOH include the following groups.

[Chemical Formula 9]

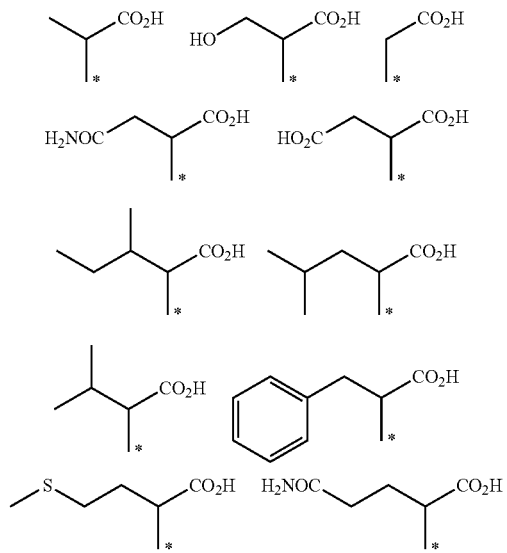

Preferable examples of the group —CHR$^a$—COOH include the following groups.

[Chemical Formula 10]

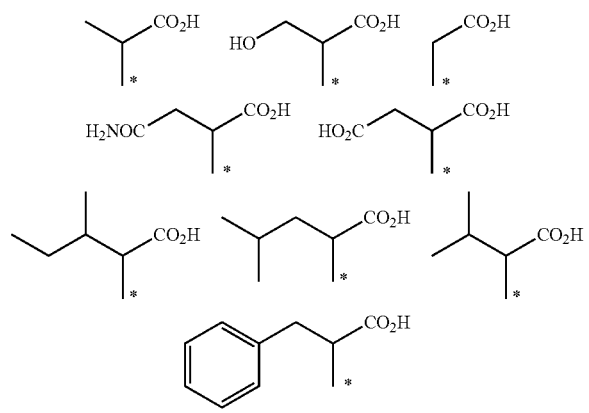

Any of the group —CHR$^a$—COOH shown above may be, all or in part, converted into the group —CHR$^a$—CONH—Z$^1$—Z$^2$. Examples of the group —Z$^1$—Z$^2$ are as described later.

Other forms of the group —CHR$^a$—CO—X$^1$ in formula (I) includes the group —CHR$^a$—CONH$_2$. Specific examples of this group include the following groups.

[Chemical Formula 11]

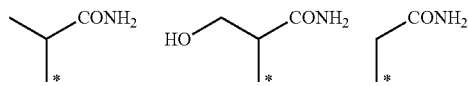

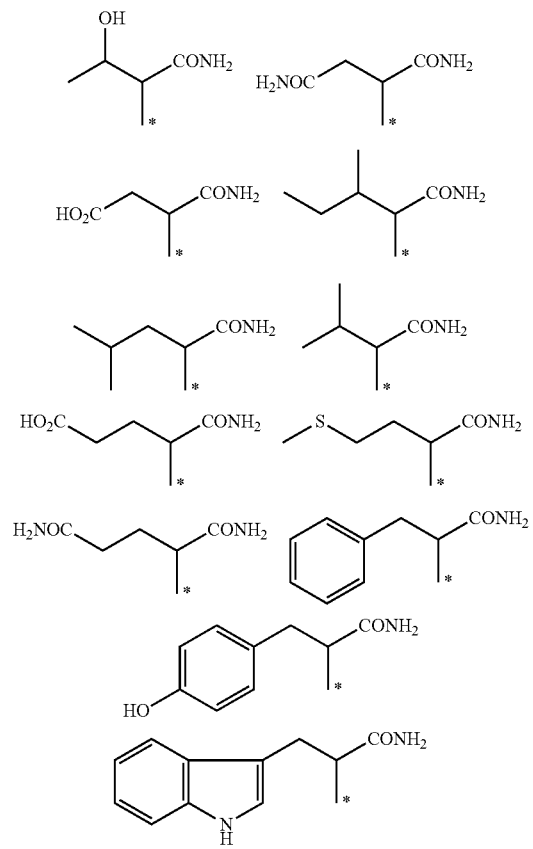

Preferable examples of group —CHR$^a$—CONH$_2$ include the following group.

[Chemical Formula 12]

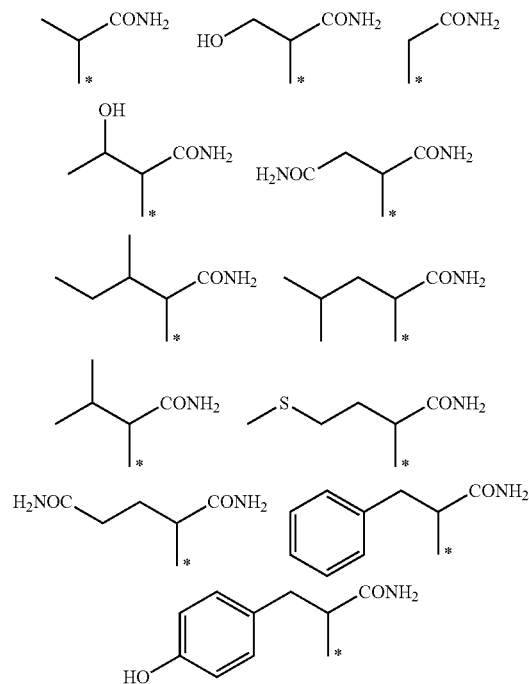

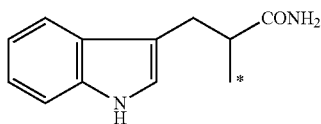

Preferable examples of the group —CHR$^a$—CONH$_2$ include the following groups.

[Chemical Formula 13]

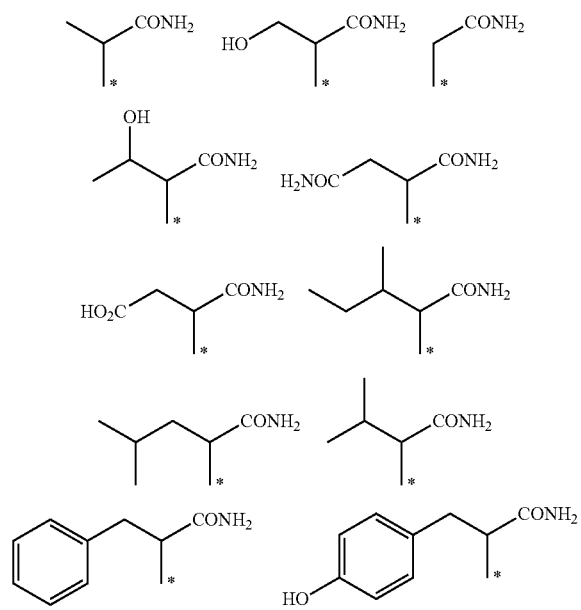

Preferable examples of the group —CHR$^a$—CONH$_2$ include the following groups.

[Chemical Formula 14]

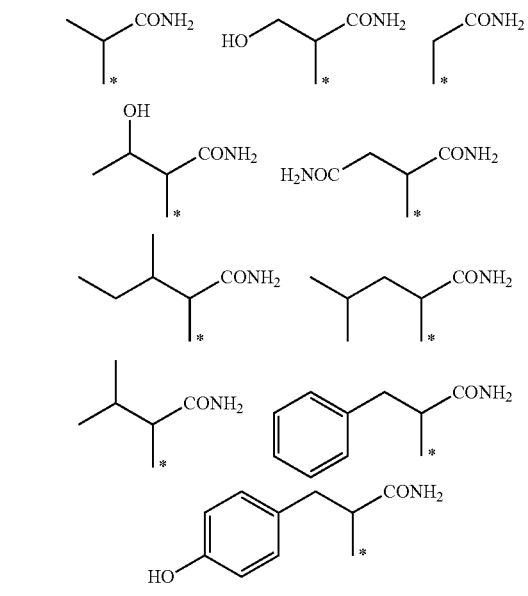

Preferable examples of the group —CHR$^a$—CONH$_2$ include the following groups.

[Chemical Formula 15]

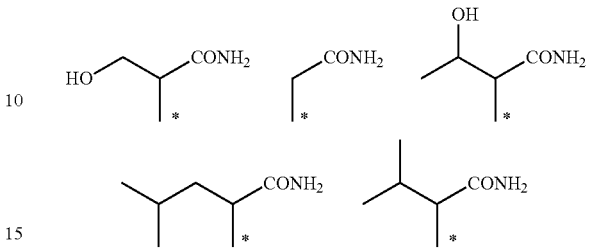

Also, these groups are preferable groups in that they have properties of both biodegradability and retention in the blood.

In terms of the properties of both biodegradability and retention in the blood, preferable examples of the group —CHR$^a$—CONH$_2$ include the following groups.

[Chemical Formula 16]

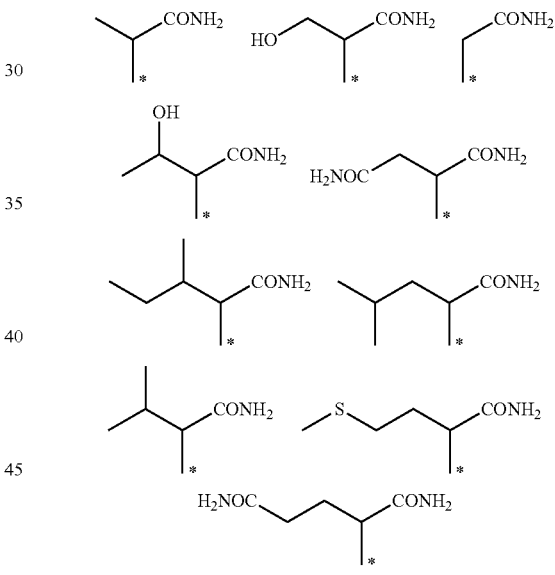

In terms of the properties of both biodegradability and retention in the blood, more preferable examples of the group —CHR$^a$—CONH$_2$ include the following groups.

[Chemical Formula 17]

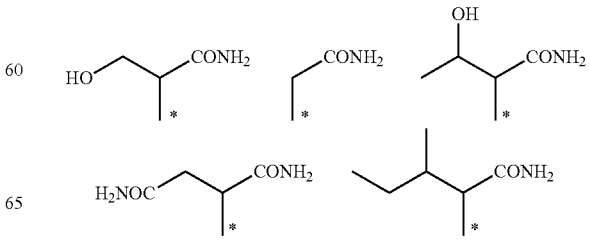

-continued

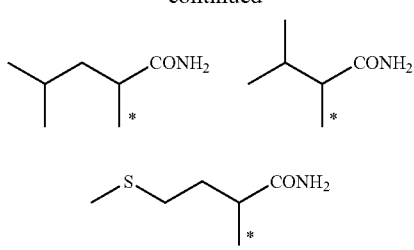

In terms of good dispersibility in pure water, preferable examples of the group —CHR$^a$—CONH$_2$ include the following groups.

[Chemical Formula 18]

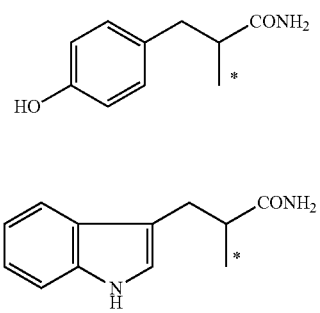

These two groups are preferable examples also in terms of matrix for injections for sustained subcutaneous administration.

In terms of matrix for injections for sustained subcutaneous administration, preferable examples of the group —CHR$^a$—CONH$_2$ include the following groups.

[Chemical Formula 19]

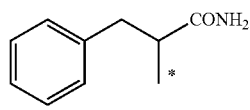

As R$^7$, a hydrogen atom and methyl are more preferable, and a hydrogen atom is even more preferable.

Carboxy defined in formula (I), (II), and (IIb) may be in a form of salt represented in the formula —COO$^-$Q$^+$. In the formula, Q$^+$ is not particularly limited as long as it is a counter cation forming salt with carboxy in water. When it is divalent or more, Q$^+$ forms salt with a plurality of carboxy depending on the valency. Example of the counter cation include metal ions such as lithium ion, sodium ion, rubidium ion, cesium ion, magnesium ion, and calcium ion; and ammonium ions represented by formula N$^+$R$^j$R$^k$R$^l$R$^m$, wherein R$^j$, R$^k$, R$^l$, and R$^m$ are each independently selected from a hydrogen atom and C$_{1-6}$ alkyl. Preferably examples include sodium ion, potassium ion, and tetraalkylammonium ions (for example, tetra-n-butylammonium ion). Preferably, R$^j$, R$^k$, R$^l$, and R$^m$ are all the same group selected from C$_{1-6}$ alkyl, and preferably n-butyl.

Other forms of the group —CHR$^a$—CO—X$^1$ in formula (I) include the group —CHR$^a$—CONH—Z$^1$—Z$^2$. Specific examples of this group include the following groups.

[Chemical Formula 20]

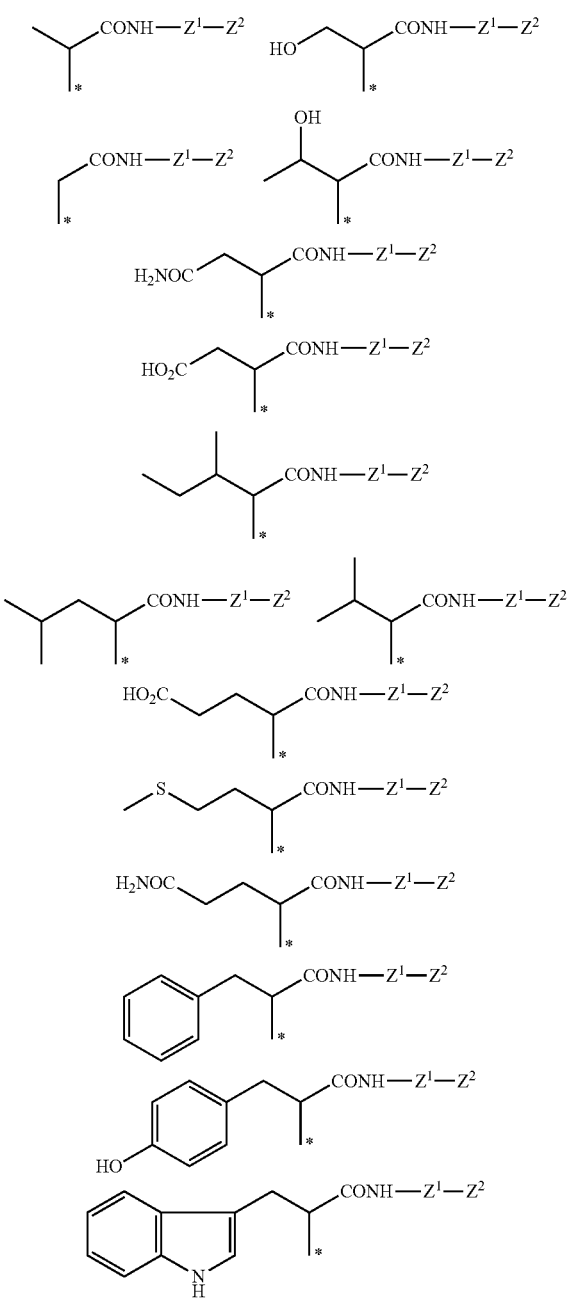

Other specific examples of the group include the following groups.

[Chemical Formula 21]

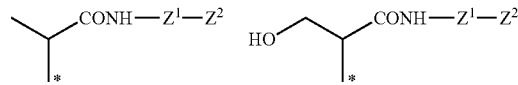

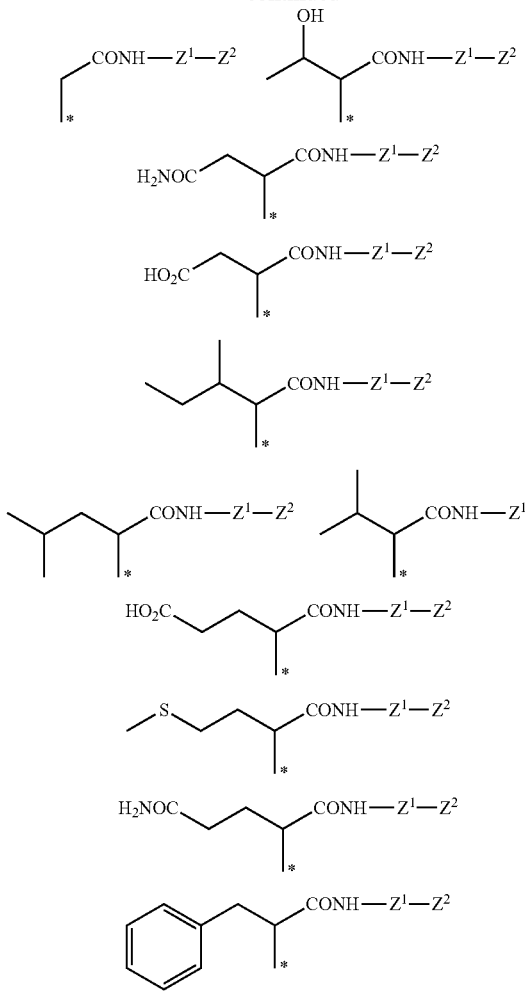
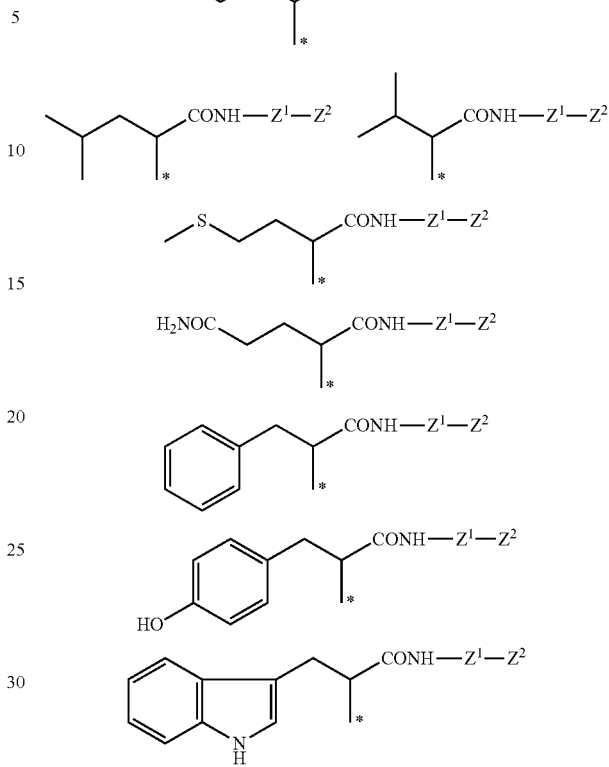
Preferable examples of the group —CHR$^a$—CONH—Z$^1$—Z$^2$ include the following groups.
[Chemical Formula 23]
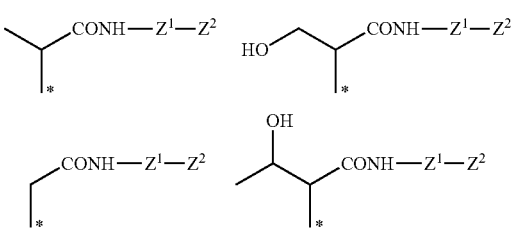
Preferable examples of the group —CHR$^a$—CONH—Z$^1$—Z$^2$ include the following groups.
[Chemical Formula 22]
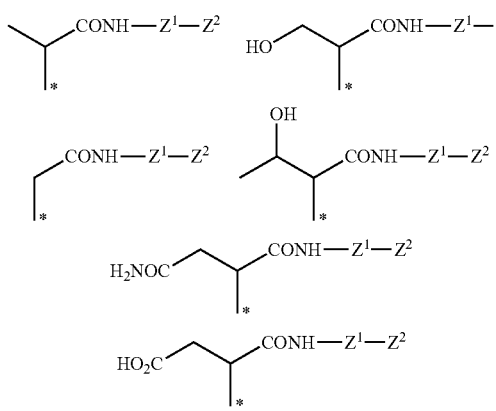
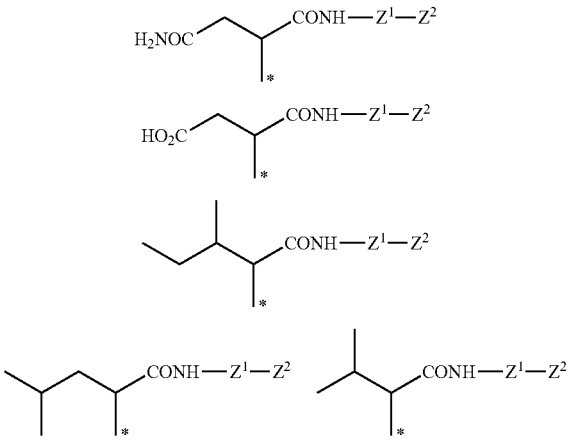

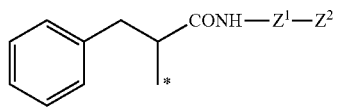

Preferable examples of the group —CHR$^a$—CONH—Z$^1$—Z$^2$ include the following groups.

[Chemical Formula 24]

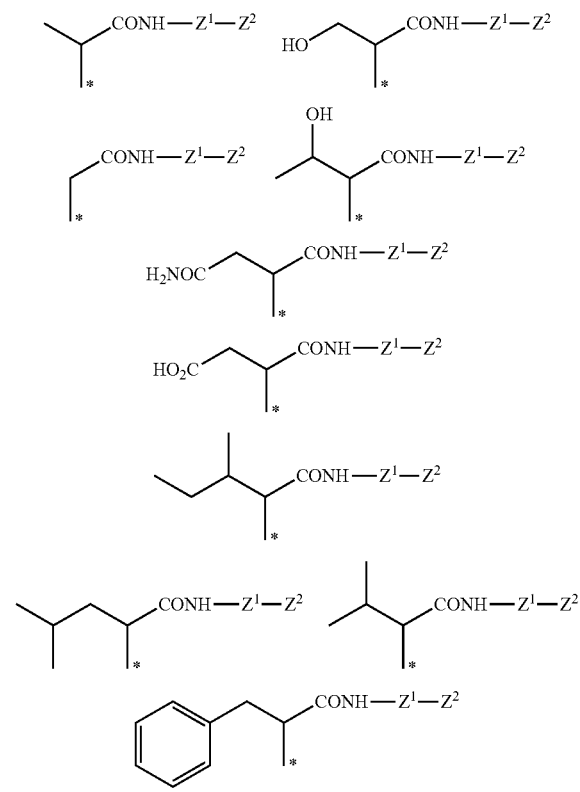

In terms of the properties of both biodegradability and retention in the blood, preferable examples of the group —CHR$^a$—CONH—Z$^1$—Z$^2$ include the following groups.

[Chemical Formula 25]

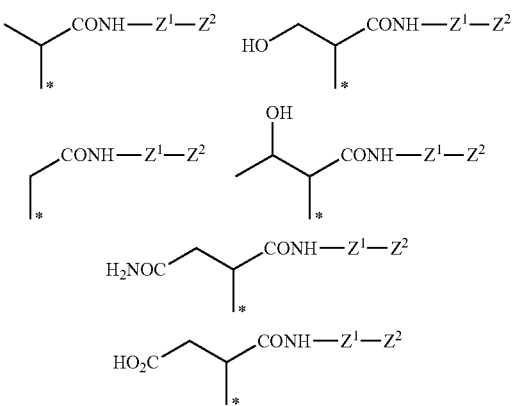

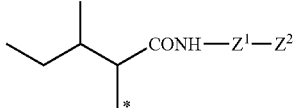

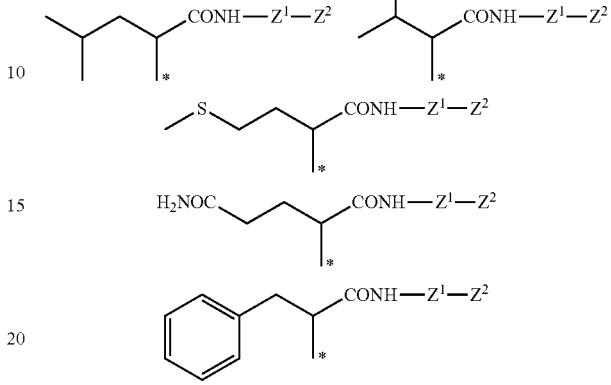

Examples of the group —Z$^1$—Z$^2$ include the group —(C$_{2-10}$ alkylene)-NH—COO—Z$^3$, as well as the group —(C$_{2-12}$ alkylene)-NH—COO—Z$^3$. Examples of C$_{2-12}$ alkylene preferably include —(CH$_2$)$_2$—, —(CH$_2$)$_6$—, —(CH$_2$)$_8$—, —(CH$_2$)$_{10}$— and —(CH$_2$)$_{12}$—, and more preferably, —(CH$_2$)$_2$— and —(CH$_2$)$_6$—. Examples of the group —Z$^1$—Z$^2$ include the group —(CH$_2$CH$_2$O)$_m$—CH$_2$CH$_2$—NH—Z$^3$. In the formula, m is preferably 1 to 20, more preferably 1 to 10, and more preferably 1 to 3. Specific examples of preferable m include 2. Examples of the group —Z$^1$—Z$^2$ preferably include the group -(hexane-1,6-diyl)-NH—COO—Z$^3$, the group -(ethane-1,2-diyl)-NH—COO—Z$^3$ and the group —(CH$_2$CH$_2$O)$_2$—CH$_2$CH$_2$—NH—Z$^3$; more preferably, the group -(hexane-1,6-diyl)-NH—COO-cholesteryl, the group -(ethane-1,2-diyl)-NH—COO-cholesteryl, and the group —(CH$_2$CH$_2$O)$_2$—CH$_2$CH$_2$—NH-cholanoyl; and more preferably, the group -(hexane-1,6-diyl)-NH—COO-cholesteryl. Examples of Z$^1$, Z$^2$, and the group —Z$^1$—Z$^2$ include those corresponding to Y, X$^1$, and the group —Y—X$^1$ described in International Publication No. 2010/053140. Examples of the group —CO—NR$^c$—Z$^3$ and the group —O—CO—NR$^c$—Z$^3$ include the respective groups where R$^e$ is a hydrogen atom.

Preferable hyaluronic acid derivatives of the present invention are hyaluronic acid derivatives containing repeating units represented by formula (II). In a more preferable embodiment, X$^2$ in formula (II) and X$^1$ in formula (I) are the same. In one aspect of the present invention, a hyaluronic acid derivative containing a repeating unit represented by formula (I) where X$^1$ is —NR$^9$—Z$^1$—Z$^2$, a repeating unit represented by formula (II) and a repeating unit represented by formula (IIb) is provided.

The term "steryl group" used herein refers to a group having a steroid frame, without particularly limitation. Specific examples of steroid include cholesterol, Dehydrocholesterol, coprostenol, coprosterol, cholestanol, campestanol, ergostanol, stigmastanol, coprostanol, stigmasterol, sitosterol, lanosterol, ergosterol, simiarenol, bile acids (cholanic acid, lithocholic acid, hyodeoxycholic acid, chenodeoxycholic acid, ursodeoxycholic acid, deoxycholic acid, apocholic acid, cholic acid, dehydrocholic acid, glycocholic acid, taurocholic acid), testosterone, estradiol, progesterone, cortisol, cortisone, aldosterone, corticosterone, and deoxycorticosterone. Examples of the steryl group include cholesteryl, stigmasteryl, lanosteryl, ergosteryl, cholanoyl, and choloyl groups. Preferred examples include cholesteryl groups (in particular, the cholest-5-en-3β-yl group represented by the following formula) and cholanoyl groups (in particular, the 5β-cholan-24-oil group represented by the following formula).

[Chemical Formula 26]

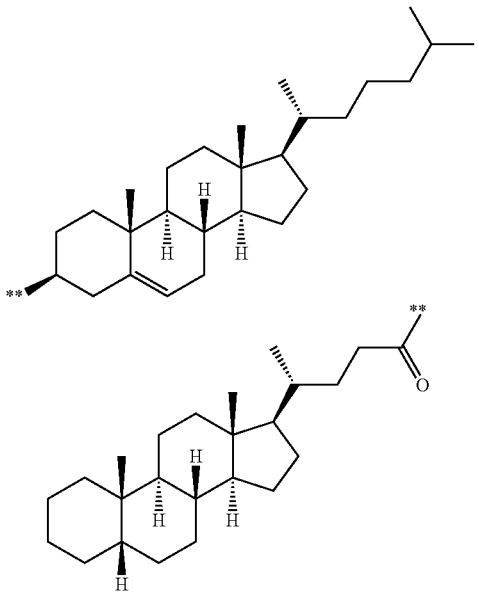

where ** represents the position attached to the neighboring group.

The term "$C_{1-20}$ alkyl" used herein refers to a linear or branched alkyl group having 1 to 20 carbon atoms. For example, the term includes "$C_{1-4}$ alkyl" such as methyl, ethyl, n-propyl, i-propyl, n-butyl, s-butyl, i-butyl, t-butyl, as well as, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethyl butyl and 2-ethylbutyl. $C_{1-20}$ alkyl includes "$C_{1-12}$ alkyl" having 1 to 12 carbon atoms and "$C_{1-6}$ alkyl" having 1 to 6 carbon atoms.

The term "$C_{1-6}$ alkyl" used herein refers to a linear or branched alkyl group having 1 to 6 carbon atoms. For example, the term includes "$C_{1-4}$ alkyl" such as methyl, ethyl, n-propyl, i-propyl, n-butyl, s-butyl, i-butyl, and t-butyl.

The term "$C_{1-6}$ alkoxy" used herein refers to linear or branched alkyl having 1 to 6 carbon atoms. For example, the term includes "$C_{1-4}$ alkoxy" such as methoxy, ethoxy, n-propoxy, i-propoxy, n-butoxy, s-butoxy, i-butoxy, and t-butoxy.

The term "$C_{1-6}$ alkylcarbonyl" used herein refers to an alkylcarbonyl group in which alkyl part is $C_{1-6}$ alkyl described above. For example, the term includes "$C_{1-4}$ alkylcarbonyl" such as acetyl, propionyl, n-propylcarbonyl, i-propylcarbonyl, n-butylcarbonyl, s-butylcarbonyl, i-butylcarbonyl, and t-butylcarbonyl.

The term "$C_{1-6}$ alkoxy" used herein refers to alkyloxy group, in which alkyl part is $C_{1-6}$ alkyl described above. For example, the term includes methoxy ($H_3C$—O—), ethoxy, n-propoxy, i-propoxy, n-butoxy, s-butoxy, i-butoxy, and t-butoxy.

The term "$C_{1-6}$ alkylthio" used herein refers to an alkylthio group in which alkyl part is $C_{1-6}$ alkyl described above. For example, the term includes methylthio ($H_3C$—S—), ethylthio, n-propylthio, i-propylthio, n-butylthio, s-butylthio, i-butylthio, and t-butylthio, but it is preferably methylthio.

The term "amino $C_{2-20}$ alkyl" used herein refers to linear or branched alkyl having 2 to 20 carbon atoms, which has amino as a substituent. For example, amino may be located on a carbon atom at an end of the alkyl. Amino $C_{2-20}$ alkyl includes "amino $C_{2-12}$ alkyl" having 2 to 12 carbon atoms.

The term "hydroxy $C_{2-20}$ alkyl" used herein refers to a linear or branched alkyl group having 2 to 20 carbon atoms, which has hydroxy as a substituent. For example, hydroxy may be located on a carbon atom at an end of the alkyl. Hydroxy $C_{2-20}$ alkyl includes "hydroxy $C_{2-12}$ alkyl" having 2 to 12 carbon atoms.

The term "$C_{2-30}$ alkylene" used herein refers to a linear or branched, saturated divalent hydrocarbon group having 2 to 30 carbon atoms. For example, the term includes ethylene and propylene, as well as $C_{2-20}$ alkylene, $C_{2-8}$ alkylene, the group —$(CH_2)_n$—, where n is 2 to 30, preferably 2 to 20, and more preferably 2 to 15.

The term "$C_{1-5}$ alkylene" used herein refers to a linear or branched, saturated divalent hydrocarbon group having 1 to 5 carbon atoms. For example, the term includes ethylene (ethane-1,2-diyl, ethane-1,1-diyl), propylene (propane-1,1-diyl, propane-1,2-diyl, propane-1,3-diyl), butane-1,4-diyl and penetane-1,5-diyl.

The term "$C_{2-10}$ alkylene" used herein refers to a linear or branched, saturated divalent hydrocarbon group having 2 to 10 carbon atoms. For example, the term includes ethylene (ethane-1,2-diyl, ethane-1,1-diyl), propylene (propane-1,1-diyl, propane-1,2-diyl, propane-1,3-diyl), butane-1,4-diyl, penetane-1,5-diyl, hexane-1,6-diyl, heptane-1,7-diyl, and octane-1,8-diyl. "$C_{2-10}$ alkylene" includes "$C_{2-6}$ alkylene" having 2 to 6 carbon atoms and "$C_{2-8}$ alkylene" having 2 to 8 carbon atoms.

The term "$C_{2-8}$ alkylene" used herein refers to a linear or branched, saturated divalent hydrocarbon group having 2 to 8 carbon atoms. For example, the term includes ethylene (ethane-1,2-diyl, ethane-1,1-diyl), propylene (propane-1,1-diyl, propane-1,2-diyl, propane-1,3-diyl), butane-1,4-diyl, penetane-1,5-diyl, hexane-1,6-diyl, heptane-1,7-diyl, and octane-1,8-diyl.

The term "$C_{2-8}$ alkenylene" used herein refers to a linear or branched, divalent hydrocarbon group having 2 to 8 carbon atoms, which contains one or more double bonds. For example, the term includes —CH=CH—, —C($CH_3$)=CH—, 2-butene-1,4-diyl, hepta-2,4-diene-1,6-diyl and octa-2,4,6-triene-1,8-diyl. In case of geometrical isomerism, the term includes the both isomers and mixtures thereof.

"Aryl" used herein refers to an aromatic carbocyclic group, for example, an aromatic carbocyclic group having 6 to 14 carbon atoms. Examples of aryl include phenyl and naphthyl (1-naphthyl and 2-naphthyl). Examples of aryl substituted with one or more hydroxy include 4-hydroxyphenyl.

"Heteroaryl" used herein refers to an aromatic ring group containing one or more heteroatoms selected from a nitrogen atom, an oxygen atom, and a sulfur atom among the atoms constituting the ring, which may be partially saturated. The ring may be a monocyclic ring or bicyclic heteroaryl condensed with a benzene ring or a monocyclic heteroaryl ring. The ring may be constituted of, for example, 4 to 15, preferably 5 to 14, more preferably 6 to 10 atoms. Examples of heteroaryl include, for example, furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyrimidyl, pyridazinyl, pyrazinyl, triazinyl, benzofuranyl, benzothienyl, benzothiadiazolyl, benzothiazolyl, benzoxazolyl, benzoxadiazolyl, benzimidazolyl, indolyl, isoindolyl, indazolyl, quinolyl, isoquinolyl, cinnolinyl, quinazolinyl, quinoxalinyl, benzodioxolyl, indolizinyl, and imidazopyridyl; and indol-2-yl is preferred.

The hyaluronic acid derivatives of the present invention can be used as a drug carrier, and the drug carrier is biodegradable. "Biodegradable" means that the drug carrier detected in the liver turns into lower molecular weight molecules within 15 days after intravenous administration to rat and/or human. Having turned "into lower molecular weight molecules" can be determined by measuring the size of the drug carrier in the liver by size exclusion column chromatography (see Example 2-3 in this specification). A drug carrier is determined to be biodegradable if the peak top of the drug carrier recovered from the liver is shifted to the lower molecular weight side (i.e. retention time in the column chromatogram become longer) compared with the peak top of the drug carrier before the administration. Biodegradable drug carriers are excreted from the body in urine, feces, or the like. Thus, the change of the drug carrier into lower molecular weight molecules may be detected in urine. However, urinary excretion of the hyaluronic acid derivatives of the present invention having a hydrophobic group may be suppressed due to their hydrophobicity. The detection of the change into lower molecular weight molecules in the liver, which is the main metabolic organ of hyaluronic acid, is therefore more preferable for the direct determination of biodegradability of drug carriers despite of the troublesomeness and the limitation in the number of detection.

According to further aspect of the present invention, a hyaluronic acid derivative defined herein in which a percentage of the disaccharide unit having the group —$NR^9$—$Z^1$—$Z^2$ (hereinafter referred to as hydrophobic group) represented by formula (I) and/or (II) to disaccharide repeating units present in the derivative (introduction ratio of the hydrophobic group) is 3 to 50% is provided.

This introduction ratio of the hydrophobic group is calculated by the following formulas:

[Formula 1]

$$\text{(Introduction ratio of hydrophobic group)} = \frac{\text{(Number of disaccharide repeating units into which hydrophobic group is introduced)}}{\text{(Number of existing disaccharide repeating units)}} \times 100$$

The "disaccharide repeating units present in the derivative" include the repeating units represented by formulas (I) and (II) and the repeating unit represented by the formula (IIb). The introduction ratio can be controlled by reaction conditions, for example, ratio of reagents and can be determined, for example, by NMR analysis.

The introduction ratio of the hydrophobic group is 3 to 50%, preferably 5 to 40%, more preferably 5 to 35%, more preferably 5 to 25%, more preferably 5 to 20%, and more preferably 5 to 10%.

In one embodiment of the present invention, the hyaluronic acid derivative in which $X^1$ is —$NR^9$—$Z^1$—$Z^2$ in formula (I), as illustrated in Example 1-4 described below, is provided. The percentage of the disaccharide unit of formula (I) to the disaccharide repeating units present in the hyaluronic acid derivative of the present invention is, for example, 70% or more, preferably 75% or more, more preferably 90% or more. The upper limit may be 100% or less, so as to have properties of both biodegradability and retention in the blood. The range of the percentage is, for example, 70 to 100% preferably 75 to 100%, more preferably 90 to 100%. The hyaluronic acid derivative may further contain a repeating unit represented by formula (II).

In one embodiment of the present invention, a hyaluronic acid derivative which does not contain the repeating unit represented by formula (I) where $X^1$ is —$NR^9$—$Z^1$—$Z^2$, as illustrated in Example 1-5 described below, is provided. In this case, a sum of percentages of the repeating unit represented by (I) and the repeating unit represented by formula (II) in the existing disaccharide repeating units is 70 to 100%, preferably 80 to 100%, and more preferably 90 to 100%.

The percentage of the repeating unit represented by formula (II) in the existing disaccharide repeating units is preferably 3 to 50%, more preferably 5 to 40%, more preferably 5 to 35%, more preferably 5 to 25%, more preferably 5 to 20%, and more preferably 5 to 10%. The percentage of the repeating unit represented by (I) in the existing disaccharide repeating units is preferably 20 to 97%, more preferably 30 to 95%, more preferably 35 to 95%, more preferably 45 to 95%, more preferably 50 to 95%, and more preferably 60 to 95%.

If the percentage of the repeating unit represented by formula (II) is 5 to 10%, in the existing disaccharide repeating units, the percentage of the repeating unit represented by (I) is preferably 60 to 95%, more preferably 70 to 95%, and more preferably 75 to 95%.

If the percentage of the repeating unit represented by formula (II) in the existing disaccharide repeating units is 20 to 40% and preferably 20 to 35%, the percentage of the repeating unit represented by (I) is preferably 30 to 80%, more preferably 45 to 80%, and more preferably 60 to 80%.

If the percentage of the repeating unit represented by formula (II) in the existing disaccharide repeating units is 10 to 20%, the percentage of the repeating unit represented by formula (I) is preferably 50 to 90%, more preferably 60 to 90%, and more preferably 70 to 90%.

Hyaluronic acid or a salt thereof can be used as a starting material for producing hyaluronic acid derivatives according to the present invention. Examples of the salt of hyaluronic acid include alkali metal salts such as sodium salts, potassium salts, and lithium salts, and particularly preferable salts are sodium salts frequently used as pharmaceutical products. HA or pharmaceutically acceptable salts thereof can be produced by known methods, such as by methods including extraction of those derived from living organisms such as from cockscombs and porcine subcutaneous tissue or by fermentation. They are also commercially available (for example, from DENKI KAGAKU KOGYO KABUSHIKI KAISHA, Shiseido Co., Ltd., SEIKAGAKU CORPORATION, R&D Systems, Inc., etc.).

The weight-average molecular weight of hyaluronic acid (including a salt thereof) exclusively composed of the disaccharide unit represented by formula (IIb) used as a starting material is preferably 1 kDa to 2000 kDa, more preferably 3 kDa to 1500 kDa, and more preferably 5 kDa to 1000 kDa; more preferably 10 kDa to 500 kDa, more preferably 10 kDa to 200 kDa, more preferably 45 kDa to 200 kDa, and more preferably 50 kDa to 99 kDa. To have a smaller particle size, a lower viscosity, or a higher solubility, the weight-average molecular weight is preferably 1 kDa to 100 kDa, more preferably 2 kDa to 70 kDa, more preferably 3 kDa to 50 kDa, and more preferably 5 kDa to 30 kDa. To have a higher viscosity or an increased retention under the skin or in the articular cavity, the weight-average molecular weight is preferably 45 kDa to 2000 kDa, more preferably 50 kDa to 2000 kDa, more preferably 100 kDa to 1000 kDa, and more preferably 200 kDa to 1000 kDa. In terms of matrix for injections for sustained subcutaneous administration, the weight-average molecular weight is preferably 5 kDa to 200 kDa. Specific examples of the weight-average molecular weight include, for example, 5 kDa, 10 kDa, 50 kDa, 99 kDa, 230 kDa, and 1058 kDa. "kDa" is an abbreviation for "kilodalton".

The weight-average molecular weight of the hyaluronic acid (including a salt thereof) exclusively composed of the disaccharide unit represented by formula (IIb) refers to the weight-average molecular weight of the hyaluronic acid, where $R^{1b}$, $R^{2b}$, $R^{3b}$, and $R^{4b}$ are all hydrogen atoms, $R^{5b}$ is acetyl, and $X^b$ is —O⁻Na⁺ in formula (IIb), while having the structure of the main chain of the hyaluronic acid derivative according to the present invention. Accordingly, an embodiment in which, for example, all or a part of disaccharide units in the hyaluronic acid used actually as a starting material is a disaccharide unit, where $X^b$ is —O⁻ (tetra-n-butyl ammonium ion), and the weight-average molecular weight calculated as described above is 45 kDa to 200 kDa, is a preferable embodiment of the present invention.

The molecular weight of hyaluronic acid (including a salt thereof) is calculated as a number average molecular weight or a weight-average molecular weight, since it is difficult to obtain hyaluronic acid as a single molecular species. In the present invention, the molecular weight is calculated as a weight-average molecular weight. The weight-average molecular weight can be measured by any of various known methods such as those measuring light scattering, osmotic pressure, or viscosity, as described in, for example, Seiichi Nakahama et al. "Essential Polymer Science" (KODAN-SHA LTD., ISBN 4-06-153310-X). The viscosity average molecular weight used herein can be measured by a method generally used in the art to which the present invention belongs, for example, by using the Ubbelohde viscometer. Accordingly, molecular weights of hyaluronic acid (including a salt thereof) used as a starting material and the hyaluronic acid derivatives according to the present invention are calculated as a weight-average molecular weight. When a commercially available hyaluronic acid (including a salt thereof) whose molecular weight is specifically stated is used, the specifically stated value may be used as the molecular weight of the hyaluronic acid.

The hyaluronic acid derivative according to the present invention is not particularly limited in terms of molecular weight, but hyaluronic acid having a high viscosity and a high molecular weight is preferable if a function of providing controlled release based on delayed diffusion upon local administration is expected and hyaluronic acid having a low viscosity and a low molecular weight is preferable for a smooth administration if the final dosage form is a solution.

The hyaluronic acid derivative of the present invention containing a disaccharide unit represented by formula (I) can be produced by converting the carboxy in the glucuronic acid moiety into amide, for example, by converting the starting material hyaluronic acid (including a salt thereof or the like), preferably hyaluronic acid exclusively composed of the disaccharide unit represented by formula (IIb) into a tetraalkylammonium salt (for example, a tetrabutylammonium (TBA) salt) by ion exchange; reacting the hyaluronic acid salt with a compound represented by the formula $HNR^6$—$CHR^a$—$COOR^z$, where $R^z$ is an ester-forming group for protecting carboxy and $R^6$ and the $R^a$ are as defined herein above, or the formula $HNR^6$—$CHR^a$—$CONR^7R^8$, where $R^7$ and $R^8$ are as defined herein above, in the presence of a suitable condensation agent in a solvent; and removing a protecting group (deprotection), if present (step 1). The ester-forming group is not particular limited as long as it is a group generally used for protection of carboxy. Examples of the ester-forming group include $C_{1-6}$ alkyl, benzyl, $C_{1-6}$ alkoxy $C_{1-6}$ alkyl and benzyloxy $C_{1-6}$ alkyl.

The groups —$NR^6$—$CHR^a$—$COOR^z$ and —$NR^6$—$CHR^a$—$CONR^7R^8$ in formula (I) may be the same or different in each of a plurality of disaccharide units present. For example, compounds represented by different formulas $HNR^6$—$CHR^a$—$COOR^z$ and/or $HNR^6$—$CHR^a$—$CONR^7R^8$ can be used to carry out the above reaction.

Condensation agents that can be used in the reaction described above include, but are not particularly limited, for example, 4-(4,6-dimethoxy-1,3,5-triazine)-4-methylmorpholinium (DMT-MM), N,N'-carbonyldiimidazole (CDI), N,N'-dicyclohexylcarbodiimide (DCC), N-ethoxycarbonyl-2-ethoxy-1,2-dihydroquinoline (EEDQ), 2-benzotriazole-1,1,3,3-tetramethyluronium tetrafluoroborate (TBTU), 3,4-dihydro-3-hydroxy-4-oxo-1,2,3-benzotriazine (HODhbt), benzotriazole-1-oxy-trispyrrolidino-phosphonium hexafluorophosphate (PyBOP), benzotriazol-1-yl-oxy-tris(dimethylamino)phosphonium hexafluorophosphate (BOP), 1-ethyl-3-(3-dimethylaminopropyl)carbodiimide (EDC), or N-hydroxysuccinimide (NHS) can be used.

Without particular limitation, DMT-MM is preferable in that the reaction is highly efficient in a mixed solvent of water and an organic solvent. In addition, use of DMT-MM as a condensation agent allows highly selective formation of amide bond between amino and carboxy while suppressing formation of ester bond in the system with a large number of hydroxy. Use of the condensation agent prevents, for example, the reaction between solvent alcohol and carboxy in the hyaluronic acid moiety and intramolecular or intermolecular bonding between hydroxy and carboxy collocated on the hyaluronic acid moiety to form undesired crosslinking.

Examples of the solvent used in the reaction described above include water, dimethyl sulfoxide (DMSO), dimethylformamide (DMF), dimethylacetamide (DMAc), 1,3-dimethyl-2-imidazolidinone (DMI), sulfolane (SF), N-methylpyrrolidone (NMP), dioxane (for example, 1,4-dioxane), methanol, ethanol, propanol, butanol, acetonitrile, tetrahydrofuran, dichloromethane, chloroform, hexane, diethyl ether, ethyl acetate and mixed solvents thereof. In terms of the solubility of starting materials, modified products and products and reactivity of condensation agents, DMSO alone or water/DMSO mixed solvent is preferably used. Depending on a kind of amino-carboxylic acid that is the modified product, it may be used for a reaction as a methanol or dioxane solution.

Examples of the compound represented by the formula $HNR^6$—$CHR^a$—$COOR^z$ include, for example, alanine ester, serine ester, glycine ester, threonine ester, asparagine ester, aspartic acid diester, valine ester, leucine ester, isoleucine ester, glutamic acid diester, methionine ester, glutamine ester, phenylalanine ester, tyrosine ester and tryptophan ester. The esters above are, for example, $C_{1-6}$ alkyl esters, aryl esters, $C_{1-6}$ alkoxy $C_{1-6}$ alkyl esters, aryl $C_{1-6}$ alkyl esters, and preferably methyl esters, ethyl esters, benzyl esters, etc.

Examples of compounds represented by the formula $HNR^6$—$CHR^a$—$CONR^7R^8$ include alaninamide, serinamide, glycinamide, threoninamide, asparaginamide, aspartic acid diamide, valinamide, leucinamide, isoleucinamide, glutaminic acid diamide, methioninamide, glutaminamide, phenylalaninamide, tyrosinamide and tryptophanamide.

The hydrophobic group can be introduced by converting the carboxy in glucuronic acid or the group —$NR^6$—$CHR^a$—COOH in formula (I) into amide (step 2). Exemplary methods include a method including converting a starting material hyaluronic acid or derivative thereof into a tetraalkyl ammonium salt (for example, tetrabutyl ammonium (TBA) salt) and reacting the hyaluronic acid salt with an amine modified with a hydrophobic group represented by the formula $HNR^9$—$Z^1$—$Z^2$, where $R^9$, $Z^1$, and $Z^2$ are as defined above, in the presence of a suitable condensation agent in solvent.

Condensation agents that can be used in the reaction described above include, but are not particularly limited, 4-(4,6-dimethoxy-1,3,5-triazine)-4-methylmorpholinium (DMT-MM), N,N'-carbonyldiimidazole (CDI), N,N'-dicyclohexylcarbodiimide (DCC), N-ethoxycarbonyl-2-ethoxy-1,2-dihydroquinoline (EEDQ), 2-benzotriazole-1,1,3,3-tetramethyluronium tetrafluoroborate (TBTU), 3,4-dihydro-3-hydroxy-4-oxo-1,2,3-benzotriazine (HODhbt), benzotriazole-1-oxy-trispyrrolidino-phosphonium hexafluorophosphate (PyBOP), benzotriazol-1-yl-oxy-tris(dimethylamino)phosphonium hexafluorophosphate (BOP) or 1-ethyl-3-(3-dimethylaminopropyl)carbodiimide (EDC) or N-hydroxysuccinimide (NHS).

Examples of the solvent used in the reaction of introducing the hydrophobic group include water, DMSO, methanol, ethanol, propanol, butanol, acetonitrile, DMF, THF, dichloromethane, chloroform, hexane, diethyl ether, ethyl acetate and mixed solvents thereof.

Alternatively, the hydrophobic group can be introduced by converting the carboxy in glucuronic acid or the carboxy in the group —$NR^6$—$CHR^a$—COOH in formula (I) into tetraalkyl ammonium salt (for example, tetrabutyl ammonium (TBA) salt), reacting the hyaluronic acid salt with a spacer moiety in the presence of a suitable condensation agent in solvent (in this step, protection and deprotection may be conducted, if necessary), converting the carboxy (—COOH), and then reacting it with a suitable reagent. Exemplary combinations of a group converted from carboxy and a reaction reagent are shown below.

—$CONR^9$—$Z^1$—$NR^bH$+Hal-$Z^3$,
—$CONR^9$—$Z^1$—$NR^bH$+Hal-$COOZ^3$,
—$CONR^9$—$Z^1$—$NR^bH$+HOCO—$Z^3$,
—$CONR^9$—$Z^1$—$NR^bH$+Hal-CO—$Z^3$,
—$CONR^9$—$Z^1$—COOH+HO—$Z^3$,
—$CONR^9$—$Z^1$—OH+Hal-COO—$Z^3$,
—$CONR^9$—$Z^1$—COOH+$NR^c$—$Z^3$,
—$CONR^9$—$Z^1$—OCO-Hal+$NR^c$—$Z^3$,
—$CONR^9$—$Z^1$—OCOOH+HO—$Z^3$,
—$CONR^9$—$Z^1$—OCOOH+Hal-$Z^3$,
—$CONR^9$—$Z^1$—OCO-Hal+HO—$Z^3$,
—$CONR^9$—$Z^1$—SH+Hal-$Z^3$,
—$CONR^9$—$Z^1$—Hal+HS—$Z^3$,
—$CONR^9$—$Z^1$—CO—$Y^a$-Hal+HS—$Z^3$,
—$CONR^9$—$Z^1$—CO—$Y^a$—SH+Hal-$Z^3$,
—$CONR^9$—$Z^1$—O—CO—CH=$CH_2$+HS—$Z^3$,
—$CONR^9$—$Z^1$—$NR^b$—CO—C($CH_3$)=$CH_2$+HS—$Z^3$,
—$CONR^9$—$Z^1$—SH+HS—R,
where $R^9$, $Z^1$, $R^b$, $R^c$, and $Z^3$ are as defined hereinabove, and Hal represents a halogen atom selected from a fluorine atom, a chlorine atom, a bromine atom and an iodine atom.

Examples of the reaction mode include dehydrohalogenation reactions, condensation reactions, dehydration reactions, nucleophilic addition reactions such as Michael addition, oxidative disulfide-forming reaction, which are well-known reactions, and can be appropriately selected and carried out in preferable reaction conditions by a person skilled in the art. If a converted product or reaction product has carboxy, it can be converted into N-hydroxy succinic acid imide (hereinafter also referred to as "NHS") ester to be reacted.

Exemplary methods also include a method including reacting 2-aminoethyl-2-pyridyldisulfide with the carboxy in glucuronic acid or the carboxy in the group —$NR^6$—$CHR^a$—COOH in formula (I) to prepare a hyaluronic acid derivative modified with a spacer having a mercapto modified with a leaving group at the terminal, and reacting this with thiocholesterol by a nucleophilic substitution reaction to form a disulfide bond.

Exemplary methods also include a method including preparing a compound modified with a part of a spacer on the carboxy in glucuronic acid or the carboxy in the group —$NR^6$—$CHR^a$—COOH in formula (I) and a compound modified with a part of the spacer on a steryl group and reacting these compounds. While some of specific examples are listed above, exemplary methods further include, if Y contains —S—S—, a method including preparing a hyaluronic acid derivative modified with a spacer having mercapto at the terminal on the carboxy in glucuronic acid or the carboxy in the group —$NR^6$—$CHR^a$—COOH in formula (I) and a steryl group modified with a spacer having mercapto at the terminal and reacting them oxidatively to form disulfide bond. In this method, one mercapto may be reacted with 2-mercaptopyridine to form disulfide, and then it may be substituted with the other mercapto.

The order of step 1 and step 2 is not relevant. For example, a starting material hyaluronic acid (including a salt thereof), preferably hyaluronic acid exclusively composed of the disaccharide unit represented by formula (IIb), may be converted into a tetraalkyl ammonium salt (for example, tetrabutyl ammonium (TBA) salt), the hyaluronic acid salt may be reacted with an amine modified with a hydrophobic group represented by $HNR^9$—$Z^1$—$Z^2$, where $R^9$, $Z^1$, and $Z^2$ are as defined herein above, in the presence of a suitable condensation agent in solvent, and then the reaction product may be reacted with a compound represented by the formula $HNR^6$—$CHR^a$—$COOR^z$, where $R^z$ is an ester-forming group to protect carboxy and $R^6$ and $R^a$ are as defined herein above, or the formula $HNR^6$—$CHR^a$—$CONR^7R^8$, where $R^7$ and $R^8$ are as defined herein above, in the presence of a suitable condensation agent in solvent.

In one embodiment of the present invention, a hyaluronic acid derivative is obtained by reacting a hyaluronic acid derivative containing a repeating unit represented by formula (IIb) and a repeating unit represented by formula (Ia):

[Chemical Formula 27]

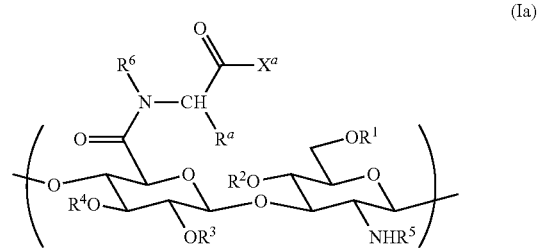

(Ia)

[where Xa is selected from hydroxy, —O⁻Q⁺, $C_{1-6}$ alkoxy and —NR⁷R⁸, and R1, R2, R3, R4, R5, R⁶, R⁷, R⁸, Q⁺, and $R^a$ are as defined herein above] with a compound represented by the following formula HNR⁹—Z¹—Z² [where R⁹, Z¹, and Z² are as defined herein above].

The reaction is carried out by condensing carboxy (including a salt thereof) and amino to convert carboxy into amide and a method similar to step 2 can be used.

The present invention may contain a repeating unit represented by the following formula (III). Accordingly in one embodiment of the present invention, presented is a hyaluronic acid derivative containing one or more disaccharide units represented by (a) formula (I) and formula (III), (b) formula (I) and formula (II) and formula (III), (c) formula (I) and formula (IIb) and formula (III), or (d) formula (I) and formula (II) and formula (IIb) and formula (III).

The disaccharide unit represented by formula (III):

[Chemical Formula 28]

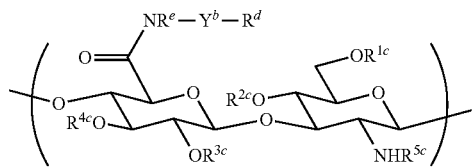

(III)

[where $R^{1c}$, $R^{2c}$, $R^{3c}$, and $R^{4c}$ are independently selected from a hydrogen atom, $C_{1-6}$ alkyl, formyl, and $C_{1-6}$ alkylcarbonyl;

$R^{5c}$ is a hydrogen atom, formyl, or $C_{1-6}$ alkylcarbonyl;

$R^e$ is a hydrogen atom or $C_{1-6}$ alkyl;

$R^d$ is a hydrogen atom, $C_{1-6}$ alkyl, —CO—C(R¹⁰)=CH₂ or —CO-G⁴-X^c;

R¹⁰ is a hydrogen atom or methyl;

G⁴ is selected from phenylene, $C_{3-8}$ cycloalkylene, or -G⁵-($C_{1-10}$ alkylene)-G⁶-, where into the $C_{1-10}$ alkylene moiety 1-3 phenylene or $C_{3-8}$ cycloalkylene may be inserted;

G⁵ and G⁶ are each independently selected from direct binding, phenylene or $C_{3-8}$ cycloalkylene;

$X^c$ is mercapto, a halogen atom or a group represented by the formula:

[Chemical Formula 29]

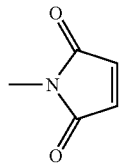

$Y^b$ is —CH₂—(CHR¹⁵)$_{1-2}$—CH₂—NH—, —CH₂—(CHR¹⁶)$_{p-2}$—CH₂—O—, —(CH₂)$_j$—S—, or —(CH₂)$_a$—(Y¹—(CH₂)$_b$)$_c$-G-;

l, p, and j are integers each independently selected from 2 to 10, R¹⁵ and R¹⁶ are each independently a hydrogen atom or hydroxy;

a is an integer selected from 2 to 10;
b is an integer each independently selected from 2 to 10;
c is an integer selected from 1 to 200;
Y¹ is an oxygen atom or —NR″—;
G is an oxygen atom, a sulfur atom or —NH—;

R″ is a hydrogen atom, $C_{1-6}$ alkyl, —CO—(CH₂)$_d$—R°, —(CH₂)$_e$—R^p or —(CH₂)$_f$—(Y²—(CH₂)$_g$)$_h$—R^q;

g is an integer each independently selected from 2 to 10;

d, e, f, and h are integers each independently selected from 2 to 10;

R°, R^p, and R^q are each independently a hydrogen atom, hydroxy, carboxy, or —NHR^r;

Y² is an oxygen atom or —NH—;

R^r is a hydrogen atom, formyl, or $C_{1-6}$ alkylcarbonyl.]

Exemplary methods for producing a hyaluronic acid derivative according to the present invention containing a disaccharide unit represented by formula (III) include, for example, a method including reacting the tetrabutyl ammonium salt of the hyaluronic acid described above with the hyaluronic acid salt and a compound represented by the formula HNR^e—Y^b—R^w, where R^w is a hydrogen atom, $C_{1-6}$ alkyl, —CO—C(R¹⁰)=CH₂, —CO-G⁴-X^c, a protecting group for hydroxy, a protecting group for amino or a protecting group for mercapto, and R^e, Y^b, R¹⁰, G⁴, and X^c are as defined herein above, in the presence of a suitable condensation agent in solvent, and, if a protecting group is present, removing the protecting group (deprotection). In the above reaction, a condensation agent and a solvent defined herein above can be used.

Specific examples of —CO-G⁴-X^c include groups represented by the following formulas:

[Chemical Formula 30]

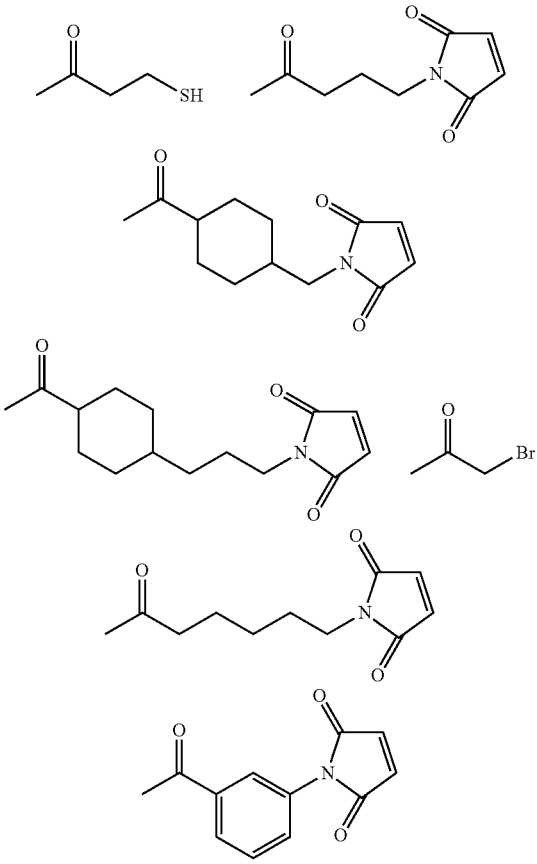

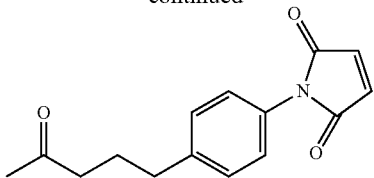

Specific examples of a protecting group used in the reaction described above are described in, for example, T. W. Greene, P. G. M. Wuts, Protective Groups in Organic Synthesis, Third Edition, John Wiley & Sons, Inc., New York, 1999.

Examples of the protecting group for hydroxy include $C_{1-6}$ alkylcarbonyl, arylcarbonyl, heteroarylcarbonyl, $C_{1-6}$ alkoxycarbonyl, $C_{1-6}$ alkoxy $C_{1-6}$ alkyl, $C_{1-6}$ alkylaminocarbonyl, di($C_{1-6}$ alkyl)aminocarbonyl, aryl $C_{1-6}$ alkyl, heteroaryl $C_{1-6}$ alkyl, aryl $C_{1-6}$ alkylaminocarbonyl, $C_{1-6}$ alkyl, $C_{1-6}$ alkylsulfonyl, ((amino $C_{1-6}$ alkyl)carbonyloxy) $C_{1-6}$ alkyl, unsaturated heterocycle carbonyloxy $C_{1-6}$ alkyl, aryldi($C_{1-6}$ alkyl)silyl, and tri($C_{1-6}$ alkyl)silyl. Preferable examples of the protecting group for hydroxy include acetyl.

Examples of the protecting group for —NH— or amino include $C_{1-6}$ alkylcarbonyl, aryl $C_{1-6}$ alkylcarbonyl, arylcarbonyl, heteroarylcarbonyl, $C_{1-6}$ alkoxycarbonyl, $C_{1-6}$ alkylaminocarbonyl, di($C_{1-6}$ alkyl)aminocarbonyl, aryl $C_{1-6}$ alkyl, heteroaryl $C_{1-6}$ alkyl, and (aryl $C_{1-6}$ alkyl)aminocarbonyl. Preferable examples of the protecting group for amino include acetyl, t-butoxycarbonyl, and 9-fluorenylmethoxycarbonyl. By protection, amino may form a saturated or unsaturated heterocyclic group such as a phthalic acid imide, a succinic acid imide, a glutaric acid imide, and 1-pyrrolyl.

Examples of the protecting group for mercapto include, for example, $C_{1-6}$ alkylthio such as ethylthio and t-butylthio, substituted phenylthio such as 2-nitrophenylthio and 2-carboxy phenylthio, and heteroarylthio such as 2-pyridylthio. A preferable example is 2-pyridylthio.

Examples of the group represented by —$NR^e$—$Y^b$—$R^d$ in formula (III) above include groups represented by formulas:
—NH—$CH_2$—$(CHR^{15})_{1-2}$—$CH_2$—$NH_2$;
—NH—$CH_2$—$CH_2$—$(Y^1$—$CH_2$—$CH_2)_c$—$NH_2$;
—NH—$CH_2$—$(CHR^6)_{p-2}$—$CH_2$—OH;
—NH—$CH_2$—$CH_2$—$(Y^1$—$CH_2$—$CH_2)_c$—OH;
—NH—$(CH_2)_j$—SH;
—NH—$CH_2$—$CH_2$—$(Y^1$—$CH_2$—$CH_2)_c$—SH;
—NH—$(CH_2)_p$—O—CO—C($R^{10}$)=$CH_2$;
—NH—$(CH_2)_1$—NHCO—C($R^{10}$)=$CH_2$;
—NH—$CH_2$—$(CHR^{15})_{1-2}$—$CH_2$—NH—CO—$CH_2$—SH;
—NH—$CH_2$—$CH_2$—$(Y^1$—$CH_2$—$CH_2)_c$—NH—CO—$(CH_2)_u$—SH;
—NH—$(CH_2)_p$—O—CO—$CH_2$—$CH_2$—SH;
—NH—$(CH_2)_1$—NHCO—$(CH_2)_u$—SH;
—NH—$CH_2$—$CH_2$—$(Y^1$—$CH_2$—$CH_2)_c$—O—CO—$CH_2$—$CH_2$—SH;
—NH—$CH_2$—$CH_2$—$(Y^1$—$CH_2$—$CH_2)_c$—NHCO—$CH_2$—$CH_2$—SH;
—NH—$CH_2$—$(CHR^{15})_{1-2}$—$CH_2$—NH—CO—$CH_2$—Br;
—NH—$CH_2$—$CH_2$—$(Y^1$—$CH_2$—$CH_2)_c$—NH—CO—$CH_2$—I;
—NH—$CH_2$—$CH_2$—$(Y^1$—$CH_2$—$CH_2)_c$—NHCO—C($R^1$)=$CH_2$; or
—NH—$CH_2$—$CH_2$—$(Y^1$—$CH_2$—$CH_2)_c$—O—CO—C($R^{10}$)=$CH_2$

[where $R^{10}$, $R^{15}$, $R^{16}$, $Y^1$, c, j, l, and p are as defined herein, and u is an integer of 1 to 3.]

The numbers of $CHR^{15}$ and $CHR^{16}$, where $R^{15}$ and $R^{16}$ are hydroxy, contained in the hyaluronic acid derivative molecule are each 0 to 8, preferably 0 to 3, more preferably 0 to 1. By controlling the numbers of $CHR^{15}$ and $CHR^{16}$, where $R^{15}$ and $R^{16}$ are hydroxy, the solubility in water of the hyaluronic acid derivative according to the present invention can be controlled. If all $R^{15}$s are hydrogen atoms, preferably l is 2 to 6, and specific examples include 2 and 6. If one of the $R^{15}$s is hydroxy, specific examples of l include 3. If $Y^1$ is an oxygen atom, specific examples of c include 2. If $Y^1$ is —NH—, specific examples of c include 1 to 3. Specific examples of l and p include 3.

Specific examples of —$(CH_2)_a$—$(Y^1$—$(CH_2)_b)_c$-G- include, for example, —$(CH_2)_2$—(O—CH—$CH_2)_c$—O—, —$(CH_2)_2$—(O—$CH_2$—$CH_2)_c$—NH—, —$(CH_2)_3$—(O—$CH_2$—$CH_2$—$CH_2)_c$—O—, —$(CH_2)_3$—(O—$CH_2$—$CH_2$—$CH_2)_c$—NH—, —$(CH_2)_2$—$NR''$—$(CH_2)_2$—O—, —$(CH_2)_2$—$NR''$—$(CH_2)_2$—NH—, —$(CH_2)_3$—$NR''$—$(CH_2)_4$—O—, —$(CH_2)_3$—$NR''$—$(CH_2)_4$—NH—, —$(CH_2)_6$—$NR''$—$(CH_2)_6$—O—, —$(CH_2)_6$—$NR''$—$(CH_2)_6$—NH—, —$(CH_2)_3$—$NR''$—$(CH_2)_2$—$NR''$—$(CH_2)_3$—O—, —$(CH_2)_3$—$NR''$—$(CH_2)_2$—$NR''$—$(CH_2)_3$—NH—, —$(CH_2)_3$—$NR^6$—$(CH_2)_4$—$NR''$—$(CH_2)_3$—O—, —$(CH_2)_3$—$NR''$—$(CH_2)_4$—$NR''$—$(CH_2)_3$—NH-(a spermine type), —$(CH_2)_2$—$NR''$—$(CH_2)^2$—$NR''$—$(CH_2)_2$—$NR''$—$(CH_2)_2$—O—, —$(CH_2)_2$—$NR''$—$(CH_2)_2$—$NR''$—$(CH_2)_2$—$NR''$ —$(CH_2)_2$—NH—, —$(CH_2)_2$—$NR''$—$(CH_2)_2$—$NR''$—$(CH_2)_2$—$NR''$—$(CH_2)_2$—$NR''$—$(CH_2)_2$—O—, and —$(CH_2)_2$—$NR''$—$(CH_2)_2$—$NR''$—$(CH_2)_2$—$NR''$ —$(CH_2)_2$—$NR''$—$(CH_2)_2$—NH—. Preferably $R''$s are all hydrogen atoms.

Specific examples of $R^d$ that binds to these —$(CH_2)_a$—$(Y^1$—$(CH_2)_b)_c$-G- include, for example, a hydrogen atom, —CO—CH=$CH_2$, —CO—C($CH_3$)=$CH_2$, —CO—$CH_2$—Cl, —CO—$CH_2$—Br, —CO—$CH_2$—I, —CO—$CH_2$—SH, and —CO—$CH_2$—$CH_2$—SH.

Specific examples of the group represented by —$NR^e$—$Y^b$—$R^d$ include —NH—$(CH_2)_3$—N(—$(CH_2)_4$—NH—$(CH_2)_3$—$NHCOCH_3$)—$(CH_2)_2$—SH, —NH—$(CH_2)_2$—N(—$(CH_2)_3$—NH—$(CH_2)_4$—$NHCOCH_3$)—$(CH_2)_3$—SH, and —NH—$(CH_2)_5$—N(—$(CH_2)_3$—NH—$(CH_2)_2$—$NHCOCH_3$)—$(CH_2)_2$—SH.

Furthermore, specific examples of the group represented by —$NR^e$—$Y^b$—$R^d$ include the following groups: —NH—$(CH_2)_{p1}$—O—CO—CH($R^{17}$)—$CH_2$—S—$CH_2$—CH(OH)—CH(OH)—$CH_2$—SH;
—NH—$(CH_2)_{p1}$—NH—C(=NH)—$(CH_2)_3$—SH;
—NH—$(CH_2)_{p1}$—NH—CO—CH($R^{17}$)—$CH_2$—S—$CH_2$—CH(OH)—CH(OH)—$CH_2$—SH;
—NH—$(CH_2)_{p1}$—NH—CO—CH($NH_2$)—$CH_2$—SH;
—NH—$(CH_2)_{p1}$—NH—CO—CH($NH_2$)—$(CH_2)_2$—SH;
—NH—NH—CO—$(CH_2)_4$—CO—NH—NH—C(=NH)—$(CH_2)_3$—SH;
—NH—$(CH_2$—$CH_2$—O)$_q$—$CH_2$—$CH_2$—O—CO—CH($R^{17}$)—$CH_2$—S—$CH_2$—CH(OH)—CH(OH)—$CH_2$—SH;
—NH—$(CH_2$—$CH_2$—O)$_q$$CH_2$—$CH_2$—NH—C(=NH)—$(CH_2)_3$—SH;
—NH—$(CH_2$—$CH_2$—O)$_q$—$CH_2$—$CH_2$—NH—CO—CH($R^{17}$)—$CH_2$—S—$CH_2$—CH(OH)—CH(OH)—$CH_2$—SH;
—NH—$(CH_2$—$CH_2$—O)$_q$—$CH_2$—$CH_2$—NH—CO—CH($NH_2$)—$CH_2$—SH;

—NH—(CH$_2$—CH$_2$—O)$_q$—CH$_2$—CH$_2$—NH—CO—CH(NH$_2$)—(CH$_2$)$_2$—SH;
—NH—CH(CO$_2$H)—(CH$_2$)—SH;
—NH—CH(CO$_2$H)—(CH$_2$)$_2$—SH; and
—NH—CH(CO$_2$H)—(CH$_2$)$_2$—CONH—CH(CONH—CH$_2$—CO$_2$H)—CH$_2$—SH
[where R$^{17}$ is a hydrogen atom or C$_{1-6}$ alkyl, p1 represents an integer of 2 to 10, and q represents an integer of 1 to 200.]

The percentage of the repeating unit represented by formula (III) in the existing disaccharide repeating units is, for example, 0.1 to 99.5%, and preferably 1 to 30%.

Exemplary methods for producing the hyaluronic acid derivative according to the present invention containing the disaccharide unit represented by formula (III) include a method (step 3a) including reacting the carboxy (—COOH) of the glucuronic acid moiety of the hyaluronic acid with a diamine represented by the formula H$_2$N—CH$_2$—(CHR$^{15}$)$_{1-2}$—CH$_2$—NH$_2$ to convert it into an amide represented by the formula —CONH—CH$_2$—(CHR$^{15}$)$_{1-2}$—CH$_2$—NH$_2$, and further modifying the terminal amino to convert it into an amide represented by the group —CONH—CH$_2$—(CHR$^{15}$)$_{1-2}$—CH$_2$—NHR$^d$.

Specific examples of the diamine described above include, for example, H$_2$N—(CH$_2$)$_2$—NH$_2$, H$_2$N—(CH$_2$)$_3$—NH$_2$, H$_2$N—(CH$_2$)$_4$—NH$_2$, H$_2$N—(CH$_2$)$_5$—NH$_2$, H$_2$N—(CH$_2$)$_6$—NH$_2$, H$_2$N—(CH$_2$)$_7$—NH$_2$, H$_2$N—(CH$_2$)$_8$—NH$_2$, H$_2$N—(CH$_2$)$_9$—NH$_2$, H$_2$N—(CH$_2$)$_{10}$—NH$_2$, H$_2$N—CH$_2$—CHOH—CH$_2$—NH$_2$, H$_2$N—CH$_2$—CHOH—(CH$_2$)$_2$—NH$_2$, H$_2$N—CH$_2$—(CHOH)$_2$—CH$_2$—NH$_2$, H$_2$N—CH$_2$—CHOH—(CH$_2$)$_3$—NH$_2$, H$_2$N—(CH$_2$)$_2$—CHOH—(CH$_2$)$_2$—NH$_2$, H$_2$N—CH$_2$—(CHOH)$_2$—(CH$_2$)$_2$—NH$_2$, H$_2$N—(CH$_2$—CHOH)$_2$—CH$_2$—NH$_2$, H$_2$N—CH$_2$—(CHOH)$_3$—CH$_2$—NH$_2$, H$_2$N—CH$_2$—CHOH—(CH$_2$)$_4$—NH$_2$, H$_2$N—(CH$_2$)$_2$—CHOH—(CH$_2$)$_3$—NH$_2$, H$_2$N—CH$_2$—(CHOH)$_2$—(CH$_2$)$_3$—NH$_2$, H$_2$N—CH$_2$—CHOH—CH$_2$—CHOH—(CH$_2$)$_2$—NH$_2$, H$_2$N—CH$_2$—CHOH—(CH$_2$)$_2$—CHOH—CH$_2$—NH$_2$, H$_2$N—(CH$_2$)$_2$—(CHOH)$_2$—(CH$_2$)$_2$—NH$_2$, H$_2$N—CH$_2$—(CHOH)$_3$—(CH$_2$)$_2$—NH$_2$, H$_2$N—CH$_2$—(CHOH)$_2$—CH$_2$—CHOH—CH$_2$—NH$_2$, H$_2$N—(CH$_2$)$_2$—CHOH—(CH$_2$)$_4$—NH$_2$, H$_2$N—(CH$_2$)$_3$—CHOH—(CH$_2$)$_4$—NH$_2$, H$_2$N—(CH$_2$)$_2$—CHOH—(CH$_2$)$_6$—NH$_2$ and H$_2$N—(CH$_2$)$_5$—CHOH—(CH$_2$)$_4$—NH$_2$.

Exemplary methods for producing the hyaluronic acid derivative according to the present invention containing the disaccharide unit represented by formula (III) include a method (step 3b) including reacting the carboxy (—COOH) in the glucuronic acid moiety of the hyaluronic acid with a hydroxyamine represented by the formula H$_2$N—CH$_2$—(CHR$^{16}$)$_{p-2}$—CH$_2$—OH to convert it into an amide represented by the formula —CONH—CH$_2$—(CHR$^{16}$)$_{p-2}$—CH$_2$—OH, and further modifying the terminal hydroxy to convert it into the group —CONH—CH$_2$—(CHR$^{16}$)$_2$—CH$_2$—OR$^d$. Combined steps 3a and 3b are designated as step 3.

Specific examples of the hydroxyamine described above include, for example, H$_2$N—(CH$_2$)$_2$—OH, H$_2$N—(CH$_2$)$_3$—OH, H$_2$N—(CH$_2$)$_4$—OH, H$_2$N—(CH$_2$)$_5$—OH, H$_2$N—(CH$_2$)$_6$—OH, H$_2$N—(CH$_2$)$_7$—OH, H$_2$N—(CH$_2$)$_8$—OH, H$_2$N—(CH$_2$)$_9$—OH, H$_2$N—(CH$_2$)$_{10}$—OH, H$_2$N—CH$_2$—CHOH—CH$_2$—OH, H$_2$N—CH$_2$—CHOH—(CH$_2$)$_2$—OH, H$_2$N—CH$_2$—(CHOH)$_2$—CH$_2$—OH, H$_2$N—CH$_2$—CHOH—(CH$_2$)$_3$—OH, H$_2$N—(CH$_2$)$_2$—CHOH—(CH$_2$)$_2$—OH, H$_2$N—CH$_2$—(CHOH)$_2$—(CH$_2$)$_2$—OH, H$_2$N—(CH$_2$—CHOH)$_2$—CH$_2$—OH, H$_2$N—CH$_2$—(CHOH)$_3$—CH$_2$—OH, H$_2$N—CH$_2$—CHOH—(CH$_2$)$_4$—OH, H$_2$N—(CH$_2$)$_2$—CHOH—(CH$_2$)$_3$—OH, H$_2$N—CH$_2$—(CHOH)$_2$—(CH$_2$)$_3$—OH, H$_2$N—CH$_2$—CHOH—CH$_2$—CHOH—(CH$_2$)$_2$—OH, H$_2$N—CH$_2$—CHOH—(CH$_2$)$_2$—CHOH—CH$_2$—OH, H$_2$N—(CH$_2$)$_2$—(CHOH)$_2$—(CH$_2$)$_2$—OH, H$_2$N—CH$_2$—(CHOH)$_3$—(CH$_2$)$_2$—OH, H$_2$N—CH$_2$—(CHOH)$_2$—CH$_2$—CHOH—CH$_2$—OH, H$_2$N—(CH$_2$)$_2$—CHOH—(CH$_2$)$_4$—OH, H$_2$N—(CH$_2$)$_3$—CHOH—(CH$_2$)$_4$—OH, H$_2$N—(CH$_2$)$_2$—CHOH—(CH$_2$)$_6$—OH, and H$_2$N—(CH$_2$)$_5$—CHOH—(CH$_2$)$_4$—OH.

These compounds are commercially available from, for example, Sigma-Aldrich Co. LLC. They may be synthesized according to or in reference to a method described in reference.

Groups —NR$^e$—Y$^b$—R$^d$ in formula (III) present in a plurality of disaccharide units may be the same or different. For example, a compound represented by a different formula HNR$^e$—Y$^b$—R$^d$ can be used to carry out the above reaction.

If X$^1$ in formula (I) is hydroxy, —O$^-$Q$^+$ or C$_{1-6}$ alkoxy, the group —NR$^e$—Y$^b$—R$^d$ may be not only present at the indicated position in a disaccharide unit represented by formula (III), a part or all of the group may substitute X$^1$ in formula (I) with X$^1$ being —NR$^e$—Y$^b$—R$^d$.

The order of step 1, step 2 and step 3 is not relevant. Preferable orders include the order of step 1, step 2, and step 3, the order of step 2, step 1 and step 3 and the order of step 1, step 3 and step 2.

Hyaluronic acid derivatives containing a reactive carbon-carbon double bond in the disaccharide unit represented by formula (III) can be subjected to a crosslinking reaction with a crosslinker (for example, dithiothreitol: DTT, butanedithiol, polyethyleneglycoldithiol) having 2 or more mercapto groups. The hyaluronic acid derivative containing mercapto in the disaccharide unit represented by formula (III) can be subjected to a crosslinking reaction by disulfide formation with a crosslinker (for example, dithiothreitol: DTT, butanedithiol, polyethylene glycoldithiol) having 2 or more mercapto groups or a crosslinking reaction using a crosslinker (for example, divinylsulfone) containing 2 or more reactive carbon-carbon double bonds. The hyaluronic acid derivative according to the present invention can be turned into gel by crosslinking.

Other examples of the crosslinking reaction include crosslinkage by a condensation reaction of a hyaluronic acid derivative modified by amino with a crosslinker (for example, bis[sulfosuccinimidyl] suberate (BS$_3$), ethyleneglycol-bis[sulfosuccinimidyl] succinate (Sulfo-EGS), dimethyladipimidate hydrochloride (DMA), or the like) having succinimidyl esters or other imide esters at the both ends of C$_{2-20}$ alkylene; crosslinkage of a hyaluronic acid derivative modified by amino with a crosslinker (for example, glutaraldehyde) having formyl at the both ends of C$_{2-20}$ alkylene; crosslinkage by oxidative reaction under oxidative conditions (for example, in the presence of sodium tetrathionate (STT)) for hyaluronic acid derivatives modified with mercapto; crosslinkage by Michael addition reaction of a hyaluronic acid derivative modified with mercapto and a crosslinker (for example, 1,4-bis-maleimidebutane (BMB), ethylene dimethacrylate (EDMA)) having unsaturated bonds of, for example, maleimide (MAL) or methacryloyl at the both ends of C$_{2-20}$ alkylene; crosslinkage by radical polymerization of a hyaluronic acid derivative modified with an unsaturated bond of such as alkloyl and the methacryloyl and various polymerization initiators (for example, potassium peroxodisulfate (KPS)/N,N,N',N'-tetramethylethylenediamine (TEMED), Irgacure 2959); and crosslinkage with a condensation agent (for example, N,N'-carbonyldiimidazole (CDI), N,N'-dicyclohexylcarbodiimide (DCC), N-ethoxycarbonyl-2-ethoxy-1,2-dihydroquinoline (EEDQ), 4-(4,6-dimethoxy-1,3,5-triazine)-4-methylmorpholinium chloride (DMT-MM), 2-benzotriazole-1,1,3,3-tetramethyluronium tetrafluoroborate (TBTU), 3,4-dihydro-3-hydroxy-4-oxo-1,2,3-benzotriazine (HODhbt), benzotriazole-1-oxy-tri(pyrrolidino)phosphonium hexafluorophosphate (PyBOP), benzotriazol-1-yl-oxy-tri(dimethylamino) phosphonium hexafluorophosphate (BOP), 1-ethyl-3-(3-dimethylaminopropyl)carbodiimide (EDC), or N-hydroxysuccinimide (NHS)) in the presence of a diamine compound (for example, EDA, 2,2'-(ethylenedioxy)bis(ethylenediamine)). The crosslinkage described above may be intramolecular crosslinkage in a hyaluronic acid derivative or intermolecular crosslinkage between plural hyaluronic acid derivatives.

Conditions for the step of gelation of the hyaluronic acid derivative according to the present invention by chemical crosslinking may be appropriately selected. Conditions for crosslinking include a method of crosslinking, the polymer concentration, the crosslinker concentration, solvent, solvent pH, the salt concentration, temperature, and time.

In the step of gelation of the hyaluronic acid derivative according to the present invention, the crosslink density of produced gel can be increased by, for example, increasing the polymer concentration in the chemical crosslinking and introduction ratio of crosslinkable groups among reaction conditions of the crosslinkage.

When a crosslinker having crosslinkable groups at the both terminals are added to the hyaluronic acid derivative according to the present invention in the step of gelation of the hyaluronic acid derivative, the crosslinker is preferably added to the hyaluronic acid derivative at a ratio of the crosslinker to the hyaluronic acid derivative, where the ratio (for example, molar ratio) is such that the groups may rapidly participate in crosslinking reaction without excess or deficiency. For example, preferably the molar ratio of SH group:MA group=3:1 to 1:3, and particularly preferably 2:1 to 1:2, when the polymer containing methacryloyl (MA group) is crosslinked by Michael addition reaction with DTT.

The solvent in the step of gelation of the hyaluronic acid derivative according to the present invention is preferably a solvent that can sufficiently dissolve polymers and crosslinkers, and without particular limitation, water, dimethylsulfoxide (DMSO), dimethylacetamide (DMAc), dimethylformamide (DMF), N-methylpyrrolidone (NMP) and mixed solvents of those selected from thereof are preferably used. In addition, an organic solvent that is miscible to these solvents can be mixed and used. The organic solvent that is miscible is not particularly limited, but its examples include, for example, methanol, ethanol, propanol, isopropanol, butanol, acetone, and acetonitrile.

The chemical crosslink structure that gel of the hyaluronic acid derivative according to the present invention has may contain a structure to disintegrate in the body. For example, without particular limitation, groups having an ester bond and methacryloyl may be used as a group to be subjected to a crosslinking reaction. In addition, a compound having an ester bond such as Sulfo-EGS or EDMA, or a compound having a peptide spacer digestible with an enzyme in the living body may be used as a crosslinker. In addition, a gel crosslinked by disulfide bonds formed by oxidation of mercapto is disintegrated in the living body by a disulfide exchange reaction and a reduction reaction. Because the hyaluronic acid derivative according to the present invention has a degradable chemical crosslink structure, the degradation rate of gel of the hyaluronic acid derivative can be controlled in the living body and therefore the release rate of the drug can be controlled.

The hyaluronic acid derivative according to the present invention forms nano-particles in an aqueous solution, and can therefore be formed into nanosize fine gel particles by crosslinking under a diluted condition, and such gel particles can be used as a controlled release carrier in blood or a targeting carrier. The diluted condition refers to 10 mg/mL or less, preferably 5 mg/mL or less, and more preferably 1 mg/mL or less. Alternatively, by crosslinking under a high density condition, the hyaluronic acid derivative can be formed into bulk gel in which fine particles are crosslinked. This is useful as a carrier for subcutaneous controlled release. A high density condition refers to 5 mg/mL or more, preferably 20 mg/mL or more, and more preferably 40 mg/mL.

The step of gelation of the hyaluronic acid derivative according to the present invention may be carried out in bulk, or in discontinuous phase such as in emulsion or in dispersed droplets. For example, to carry out the step in a W/O emulsion, a water phase in which a polymer or crosslinker is dissolved may be emulsified in a water-immiscible solvent and a gelation reaction may be carried out. Examples of the water-immiscible solvent include, without particular limitation, hexane, chloroform, dichloromethane, ethyl acetate, medium chain triglyceride (MCT), liquid paraffin, and bean oil. A surfactant to stabilize the emulsification may be added. In addition, the step may be carried out in a solvent that can be displaced (desolvation), for example, in supercritical carbon dioxide or in PEG. In this case, a gel with a higher crosslink density can be obtained by emulsifying and/or dispersing a water or organic solvent phase in which a polymer, a crosslinker, or the like is dissolved in a solvent listed above since the polymer is concentrated in association with desolvation (solvent diffusion).

In the step of gelation of the hyaluronic acid derivative according to the present invention and after that, the operation of stopping crosslinking and the operation of deactivating or washing a remaining crosslinking functional group can be carried out. Crosslinking functional groups which have not involved in the reaction, groups which are bound to only one end of a crosslinker, remaining crosslinkers, and the like are preferably removed in terms of safety, stability during the preservation, and elimination of side reactions with an encapsulated drug. For example, without particular limitation, if unreacted crosslinkers are remained, they may be eliminated by washing with excessive water. In addition, if methacryloyl substituted onto a polymer remains, for example, excessive mercaptoethanol may be added to deactivate the methacryloyl, and then the surplus mercaptoethanol may be removed by washing with excess water. Additionally, if mercapto remains, for example, surplus 3-maleimidepropionic acid and/or iodoacetic acid is added to deactivated mercapto, and then the surplus 3-maleimidepropionic acid and/or iodoacetic acid may be removed by washing with excess water.

A crushing step may be carried out after the step of gelation of the hyaluronic acid derivative according to the present invention. A method for crushing includes crushing with a pestle and mortar and crushing with a mill, but crushing with a mill is preferable. Examples of the mill crushing equipment include rotary disc crushing equipment such as a centrifuge-type crusher (NISSEI Corporation) and an impact mill (Dalton Co., Ltd.), screen mill crushing equipment such as an atomizer (Tokyo Atomizer M.F.G.

Co., Ltd.), a sample mill (Tokyo Atomizer M.F.G. Co., Ltd.), a bantam mill (Tokyo Atomizer M.F.G. Co., Ltd.) and an SK mill (Tokken Inc.), jet crushing equipment such as a laboratory super micro jet mill (A-O jet mil, Seishin Enterprise Co., Ltd.), and a linrex mill (Liquid Gas Co., Ltd.) that can crush at the very-low temperature, but an SK mill and a linrex mill are preferable.

A drying step may be carried out after the step of gelation of the hyaluronic acid derivative according to the present invention. Exemplary methods for drying include, for example, ventilation drying, drying in a thermostat, vacuum drying, and hot air circulating drying. The blowing velocity, drying time, temperature, and pressure are selected as appropriate as long as gel of the present invention does not decompose or denature.

A pharmaceutical composition can be prepared by encapsulating a drug in gel of the hyaluronic acid derivative according to the present invention. In one aspect of the present invention, a hyaluronic acid derivative containing one or more disaccharide units represented by (a) formula (I) and formula (III), (b) formula (I) and formula (II) and formula (III), (c) formula (I) and formula (IIb) and formula (III), or (d) formula (I) and formula (II) and formula (IIb) and formula (III) can be crosslinked using a crosslinker, turned into gel, and used as a carrier for encapsulating a drug (a low molecular weight compound, a protein, a peptide, or a nucleic acid). Exemplary methods for encapsulating a drug include a method of adding a drug solution to the hyaluronic acid derivative gel crosslinked beforehand. In the method, the drug is first absorbed by diffusion into the swelled gel, and the absorbed drug is encapsulated by being kept in physical crosslinked domains by the hydrophobic interaction of the hyaluronic acid derivative gel. Conditions including, but are not particularly limited to, solvent, salt concentration, pH, temperature, time, and addition of denaturant may be selected as appropriate such that the drug is encapsulated stably in a high yield. For example, a swelling degree and density of hyaluronic acid derivative gel change and the ionization state of the drug and the like also change depending on salt concentration and pH at the time of the drug encapsulation, therefore suitable conditions should be chosen in a combination thereof as appropriate. Due to electrostatic repulsion between carboxy groups of the hyaluronic acid derivative, conducting the drug encapsulation at a low salt concentration results in a decreased gel density, which enables encapsulation of an increased amount or a higher molecular weight of drug. After drug encapsulation, raising salt concentration weakens electrostatic repulsion, increases gel density, and reducing the size of the gel mesh less than the size of the drug, which makes possible to keep the drug tightly and delay the release. At the time, the salt concentration may be a physiological salt concentration.

Exemplary methods for encapsulating a drug also include a method including forming a complex of the drug and the hyaluronic acid derivative according to the present invention and crosslinking to turn the hyaluronic acid derivative into gel. Conditions including, but are not particularly limited to, ratio of solvents for complex formation, salt concentration, pH, temperature, time, addition of denaturant, concentration of the above hydrophilic polysaccharide derivative (HP), drug concentration, ratio of HP and the drug, may be selected as appropriate such that the drug is complexed with nanogel stably in a high yield. Free drugs not complexed may be separated and removed by dialysis, size exclusion chromatography (SEC) or the like. For crosslinking, it is preferable to use crosslinking conditions in which the encapsulated drug does not denature.

The drug encapsulated in gel of the hyaluronic acid derivative according to the present invention is released by simple diffusion of the drug in the gel, degradation of the gel of the hyaluronic acid derivative, and replacement of the drug with a biogenic component. If the drug is released by diffusion of the drug, the release rate can be controlled by the crosslink density of the gel and quantity and hydrophobicity of the crosslink domain. Examples of the degradation of gel include degradation of the chemical crosslink domain and degradation of the backbone of the hyaluronic acid derivative. These degradation causes decrease in crosslink density (increase in swelling ratio). Decrease in crosslink density increases the diffusion rate of drug in the gel, and cleavage of bond also promotes the release. Drug-release rate can be therefore controlled by controlling the degradability of chemical crosslink domain, the degradability of polymer backbone, and the degradability of spacer.

The replacement with a biogenic component refers to drug release, for example, by administration of a gel to a living body, subcutaneously or in blood, permeation of a substance such as a plasma protein such as albumin or a lipid present in the living body into the gel, and replacement of an encapsulated drug with the substance. The gel of the hyaluronic acid derivative according to the present invention can suppress the replacement of drug with a biogenic component associated with permeation of the component not only by physical crosslinking between hydrophobic groups, but also by the chemical crosslinking described above. Rates of permeation of biogenic components can be controlled by the crosslink density of the gel and electric charges in the gel. When a drug is to be encapsulated by adding a drug solution after the formation of gel by crosslinking described above, encapsulating conditions can be selected as appropriate so as to facilitate absorption of the drug into gel during the encapsulation, and to suppress the permeation of biogenic components in the living body. For example, without limitation, if a protein is encapsulated, the electrostatic repulsion between the hyaluronic acid derivative and the drug can be suppressed by carrying out the encapsulating step in the vicinity of its isoelectric point. Also, by carrying out the encapsulating step at pH equal to or lower than pKa (approximately 4.0) of carboxylic acid derived from the glucuronic acid in the hyaluronic acid, the negative charge that the gel has can be weakened. This suppresses electrostatic repulsion between the gel and proteins charged with a negative charge on the condition, and makes it possible to improve the encapsulating efficiency. In addition, carrying out the encapsulating step, for example, at the salt concentration lower than those in the living body makes gel swollen at a swelling rate higher than that in the living body and facilitates the encapsulating.

Furthermore, a hyaluronic acid derivative modified with both a hydrophobic group and a crosslinking functional group of the present invention can be turned into gel by chemical crosslinking in the coexistence of a hydrophilic polysaccharide derivative having a hydrophobic group. Specifically, by mixing and crosslinking a hyaluronic acid derivative modified with both a hydrophobic group and a functional group having an unsaturated bond according to the present invention and a hydrophilic polysaccharide derivative having a hydrophobic group, a hyaluronic acid derivative gel in which the hydrophilic polysaccharide derivative having a hydrophobic group is physically encapsulated can be prepared.

The hydrophilic polysaccharide derivative having a hydrophobic group is a hydrophilic polysaccharide that can be obtained by introducing a hydrophobic group into a hydrophilic polysaccharide or a derivative thereof at least one or more molecule per one polysaccharide molecule. The hydrophilic polysaccharide is not particularly limited, but is preferably pullulan, amylopectin, amylose, dextran, mannan, levan, inulin, chitin, chitosan, hyaluronic acid, or dextrin. These polysaccharides having various average molecular weights can be obtained commercially or according to a method described in literature. Particularly preferable hydrophilic polysaccharides are pullulan, hyaluronic acid, and dextrin. Preferably, the dextrin is Cluster dextrin (registered trademark). Cluster dextrin (registered trademark) can be commercially obtained from Ezaki Glico Co., Ltd. and used. The hydrophobic group is not particularly limited, but is preferably a group such as a $C_{8-50}$ hydrocarbon group, a steryl group, a polylactic acid (PLA) group, a polylactic acid-glycolic acid copolymer (PLGA) group, or a group containing such a group. A particularly preferable group is a group containing a cholesteryl group, a linear or branched $C_{8-30}$ alkyl or a group containing such a group. The hydrophobic group may be introduced via a spacer.

Examples of the hydrophilic polysaccharide derivative having a hydrophobic group include the hyaluronic acid derivative according to the present invention. Accordingly, fine particles composed of the hyaluronic acid derivative according to the present invention may be encapsulated in a suitable gel.

The hydrophilic polysaccharide derivative having a hydrophobic group can be prepared by known methods. A hydrophilic polysaccharide derivative (hereinafter also referred to as "cholesterol pullulan" and "CHP") in which N-[6-(cholesteryloxycarbonylamino)hexyl]carbamoyl as a hydrophobic group is introduced into hydroxy in pullulan as hydrophilic polysaccharide is commercially available (for example, from NOF Corporation). The hydrophilic polysaccharide derivative having a hydrophobic group forms fine particles (nanogel) having nanosize (1 to 1000 nm) gel structure by spontaneous association of several molecules by hydrophobic interaction in an aqueous solution, and is therefore capable of form a complex with a hydrophobic drug, or a protein or a peptide having an efficacy.

The molecular weight of the hydrophilic polysaccharide derivative having a hydrophobic group used in the present invention is not particularly limited, but is preferably 1 kDa to 1000 kDa, and more preferably 10 kDa to 300 kDa. The above hydrophilic polysaccharide derivative may also be a pharmaceutically acceptable salt.

Furthermore, for example, hydroxy contained in the hyaluronic acid derivative according to the present invention and the hydrophilic polysaccharide derivative having a hydrophobic group is also available as a crosslinkable group. Accordingly, hydroxy in the hyaluronic acid derivative according to the present invention and the hydrophilic polysaccharide derivative having a hydrophobic group can be crosslinked by a particular crosslinker, for example, divinylsulfone (DVS), carbodiimide, or a crosslinker having glycidyl ether at the both ends of $C_{2-20}$ alkylene.

When carboxy groups of a hyaluronic acid are substituted with plural kinds of substituents, these substituents may be introduced concomitantly or sequentially.

According to a further aspect of the present invention, a hyaluronic acid derivative defined herein characterized in that the hyaluronic acid derivative forms fine particles by association in water is provided. The hyaluronic acid derivative have a property of forming nanoscale fine particles by spontaneous association in water due to, without limitation, hydrophobic interaction of the introduced group —$NR^9$—$Z^1$—$Z^2$. To construct a desired drug delivery system, nanoparticles formed of the hyaluronic acid derivative according to the present invention are one of the very potent means, and they can be used as a capsule for delivering a protein, a peptide, or a low molecular weight compound that is an active ingredient to the target site while maintaining them in a hydrophobic domain formed inside. A drug can be also delivered to the target site by conjugation of the drug.

Nanoscale fine particles can be administered systemically, and particularly intravenously, and can be used as carriers for controlled drug release in blood, by which encapsulated (complexed) drugs are released in the blood in a controlled manner, or for targeting, by which drugs are delivered selectively to target organs and cells. When used as carriers for targeting, targeting elements can be added for targeting to each organs and cells. Examples of the targeting element include target tissue specific peptides, antibodies, antibody fragments, aptamers, RGD peptides for cancer cells, folic acid, anisamide, transferrin, galactose for the liver, and tocopherol. To improve drug retention in the blood, hyaluronic acid derivatives may be further crosslinked chemically.

Molecules smaller than a certain size are known to excreted by the kidney. For example, polyethylene glycol (PEG), which is a linear polymer as hyaluronic acid, is having a molecular weight of 40 kDa or less is reported to be excreted by the kidney (Europian Journal of Cancer. Vol. 31, p. 766-770, 1995). Therefore, hyaluronic acids and hyaluronic acid derivatives having a molecular weight in the same order may be immediately eliminated from the blood. However, HA derivatives modified with a hydrophobic group of the present invention can form complexes by association and can be therefore used as carriers for controlled drug release in blood and for targeting even if the HA derivatives have molecular weights smaller than those of PEGs that are excreted by the kidney.

Fine particles of a hyaluronic acid derivative are formed by self-association in an aqueous solution, and can be therefore formed by dissolving the solid hyaluronic acid derivative in water or an aqueous salt solution. Alternatively, fine particles can be formed by dissolving a hyaluronic acid derivative in another solvent (for example, DMSO), and then replacing the solvent with water or an aqueous salt solution. Sonication can be performed to form similar sizes of fine particles.

Increasing the introduction ratio of the hydrophobic group into the hyaluronic acid derivative reduces the solubility into water. To form fine particles that can be dispersed in an aqueous solution, the hyaluronic acid derivative which have been prepared so that the hydrophobic group introduced by covalent bond is 80% or less, and preferably 60% or less is preferably used.

Since hyaluronic acid has carboxy, which is a dissociation group, increasing the ionic strength in the system reduces its solubility. Accordingly, by controlling the introduction ratio, a hyaluronic acid derivative that is dissolved at low salt concentrations or in salt-free conditions and aggregate or precipitate in physiological salt concentrations can be prepared. This can be used as a matrix for a subcutaneous controlled release formulation. Hyaluronic acid derivatives modified with a hydrophobic group in such a degree that stable fine particles are formed at physiological salt concentrations can be used as drug carriers for systemic administrations.

Particle sizes of fine particles to be formed are not particularly limited, but are preferably 200 µm or less, and more preferably 100 µm or less to allow passage through needles without clogging when administered by injection.

For intravenous administration, particle sizes are preferably 500 nm or less, and more preferably 200 nm or less to avoid occlusion of peripheral blood vessels. In addition, to avoid uptake by the reticuloendothelial system and improve retention in the blood, particle sizes are preferably 100 nm or less, and more preferably 50 nm or less.

The hyaluronic acid derivative according to the present invention can be used as a drug carrier in a pharmaceutical formulation, and a pharmaceutical composition containing the hyaluronic acid derivative of the present invention and a drug can be provided. Since the hyaluronic acid derivative according to the present invention can spontaneously form a complex with drug in an aqueous solution without special operations, it is possible to easily form a carrier-drug complex and hold a drug by mixing the hyaluronic acid derivative and the drug in an aqueous solution, and incubating the solution. The driving force of the complex formation is mainly hydrophobic interaction of the hydrophobic group of the hyaluronic acid derivative and the drug, but if the drug is basic, electrostatic interaction with carboxylic acid in the hyaluronic acid derivative may contribute. At salt concentrations in a living body, electrostatic interaction is weaker, and hydrophobic interaction is stronger, therefore, complexes are considered to be formed mainly by hydrophobic interaction.

If $Z^1$ is alkylene in formulas (I) and (II) above, as the longer the carbon chain of the alkylene, the higher the hydrophobicity of the group is, and the firmer fine particles can be formed by the higher hydrophobic interaction. In addition, the longer alkylene produces the larger intermolecular entanglement and the higher viscosity. Sizes of fine particles can be also controlled by changing the length of alkylene.

If the linker (spacer) moiety in a hydrophobic group is ester or carbonate (for example, $X^1$ or $X^2$ contains —COO—$Z^3$ or —O—COO—$Z^3$), ester or carbonate is degraded in the living body and the hydrophobicity of the hyaluronic acid derivative is decreased. This increases the biodegradability and is preferable in terms of safety. In addition, tumor tissue is known to have decreased pH around the tissue. By having such a spacer, the assembly of the hyaluronic acid derivative according to the present invention that holds a drug of interest can disintegrate around the tumor to release the drug around the tumor.

Particularly, if the linker is a linker having β thiocarboxylate ester structure such as —O—CO—$CH_2$—$CH_2$—S—, degradation is promoted by a slight decrease in pH (at pH 6 or so). Therefore, it responds to pH change sharper than usual ester. If it is intended to deliver a drug into cells, such a linker responds to pH decrease in endosomes, and is capable of releasing the drug only after cellular uptake of the drug.

If a linker (spacer) moiety has a disulfide bond (for example, $X^1$ or $X^2$ contains —S—S—$Z^3$), the linker decomposes under reducing conditions and the assembly of the hyaluronic acid derivative according to the present invention disintegrates due to the decrease in hydrophobicity of the hyaluronic acid derivative. Since cytoplasm is known to be a reducing environment, by encapsulating a drug in a hyaluronic acid derivative containing this linker and administering it, it is possible to release the drug only in cytoplasm but not in the blood.

Conditions during the carrier-drug complex formation, such as solvent, salt concentration, pH, temperature, time, and addition of denaturant, can be changed as appropriate dependent on the drug to be used. For example, depending on the salt concentration and pH during encapsulation of the drug, the hyaluronic acid derivative changes in density and the drug is also varied in the ionization state. Examples of the denaturants to be used include urea, guanidine hydrochloride, and sodium dodecylsulfate. If a denaturant is added, the surplus denaturant can be removed by washing with excessive water after the complex formation.

For example, without limitation, if a complex of the hyaluronic acid derivative according to the present invention and a protein is formed, quantity of the protein contained in the complex can be increased by carrying out the complex formation in the vicinity of the isoelectric point, since this can suppress electrostatic repulsion of the hyaluronic acid derivative and the protein. In addition, by carrying out the complex formation step in conditions at pH equal to or lower than pKa (approximately 4.0) of carboxy in the glucuronic acid moiety, quantity of the protein contained in the complex can be increased since the negative charge that the hyaluronic acid derivative has can be weakened and electrostatic repulsion can be suppressed, if the protein is electricity charged with a negative charge in the conditions. Furthermore, by carrying out the complex formation step, for example, at a salt concentration lower than those in the living body, quantity of the protein contained in the complex can be increased since the density of fine particles of the hyaluronic acid derivative formed in the aqueous solution decreases. In addition, by increasing the salt concentration in such a state, the density of the fine particles can be increased and the protein can be encapsulated firmly.

The complex formation of the hyaluronic acid derivative and the protein can be influenced by the molecular weight of the protein. Generally, as the lower molecular weight the protein has, the higher the speed of transfer of the protein into the fine particles of the hyaluronic acid derivative is. In addition, the density of fine particles depending on the introduction ratio of the hydrophobic group can affect the speed of the complex formation with the protein and the quantity of the protein contained in the complex.

The drug release from the complex of the hyaluronic acid derivative and the drug in the living body is promoted by replacement of the drug with components in the living body, in addition to the diffusion of the drug from the complex. The controlled release of the drug can be controlled by increasing or decreasing the density of the fine particles to control this diffusion and replacement.

The living body contains biogenic components such as plasma proteins and lipids. When a complex of a hyaluronic acid derivative and a drug administered to the living body such as subcutaneously or in the blood, the drug may be released by replacement of the drug in the complex with these components in the living body. Albumin is expected to be a major biogenic protein that causes such a replacement. By lowering the introduction ratio of the hydrophobic group in the hyaluronic acid derivative according to the present invention, negative charges of carboxy in the glucuronic acid moiety can be increased, and replacement with albumin (pI=4.6), which has a negative charge, can be suppressed.

Exemplary methods for using the hyaluronic acid derivative according to the present invention as a drug carrier include a method of allowing the derivative to spontaneously form a complex with a drug in an aqueous solution described above, as well as a method of making a conjugate in which the drug is coupled with the hyaluronic acid derivative according to the present invention. Accordingly, in another aspect of the present invention, a hyaluronic acid derivative-drug conjugate in which one or more of the drugs described above are coupled to a hyaluronic acid derivative containing a disaccharide unit represented by formula (I) is provided. In one embodiment of this aspect, as the hyaluronic acid derivative, a hyaluronic acid derivative containing one or more disaccharide units represented by (a) formula (I) and formula (III), (b) formula (I) and formula (II) and formula (III), (c) formula (I) and formula (IIb) and formula (III), or (d) formula (I) and formula (II) and formula (IIb) and formula (III) can be used. For example, by coupling hydroxy, amino, mercapto, a halogen atom (such as bromo and iodo), or reactive carbon-carbon double bond (such as methacryloyl and acryloyl) contained in the group —$NR^e$—$Y^b$—$R^d$ in formula (III) and the drug, the hyaluronic acid derivative-drug conjugate described above can be prepared.

In addition, between the group —$NR^e$—$Y^b$—$R^d$ and the drug, a spacer represented by formula -$G^1$-$G^2$-$G^3$-J-* [where * represents the binding site with the drug, $G^1$ is selected from a direct bond, —C(=O)—, —$NR^5$—, and —S—, $G^2$ is selected from —$(CH_2)_i$— and —$(CH_2)_{qa}$—(O—$CH_2$—$CH_2)_k$—, $G^3$ is selected from a direct bond, —C(=O)—$NR^t$—$(CH_2)_r$—, and —$NR^u$—C(=O)—$(CH_2)_{ma}$—, J represents a group represented by the following formula,

[Chemical Formula 31]

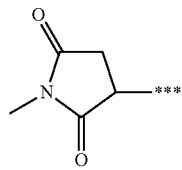

$R^s$, $R^t$, and $R^u$ are independently selected from a hydrogen atom and $C_{1-6}$ alkyl, i is an integer selected from 1 to 10, qa is an integer selected from 2 to 10, k is an integer selected from 1 to 100, r and ma are integers independently selected from 1 to 10] may be further inserted.

Specific examples of formula -$G^1$-$G^2$-$G^3$-J-*** include, for example, the following formulas:

[Chemical Formula 32]

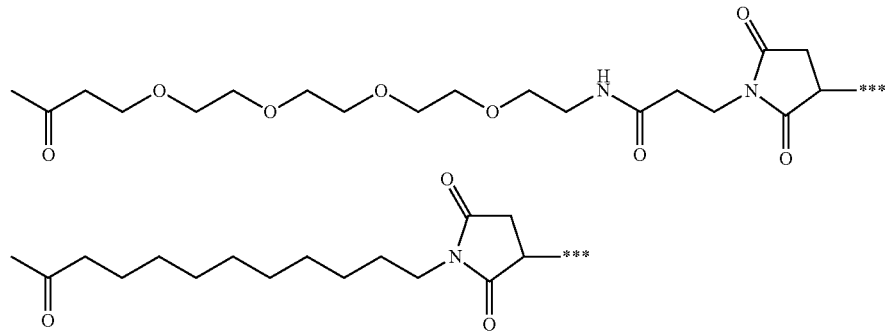

The hydroxy groups at the 4-position of the glucuronic acid and the 1-position of the acetylglucosamine present the ends of the backbone of the hyaluronic acid derivative according to the present invention may be converted into another group, and examples of such a group include $C_{1-6}$ alkoxy, formyloxy, and $C_{1-6}$ alkylcarbonyloxy.

To prepare a conjugate of the hyaluronic acid derivative according to the present invention and a drug, a method used in the preparation of a conjugate of a known polymer and a drug can be used and, for example, the following reactions can be used:

a reaction of carboxy of the glucuronic acid moiety of the hyaluronic acid derivative with amino, hydroxy, iodo, or bromo in a drug or amino, hydroxy, bromo, or iodo introduced into a drug;

a reaction of hydroxy at the 6-position of the N-acetylglucosamine moiety of the hyaluronic acid derivative with carboxy in a drug or carboxy introduced into a drug;

a reaction of amino introduced into the hyaluronic acid derivative with carboxy in a drug or carboxy introduced into a drug;

a reaction of amino introduced into the hyaluronic acid derivative with a drug converted into a group such as isothiocyanate, isocyanate, acylazide, NHS ester, and epoxide by modification;

a reaction of amino in a drug or amino introduced into a drug with the hyaluronic acid derivative converted into a group such as isothiocyanate, isocyanate, acylazide, carbonyl, NHS ester, and epoxide by modification;

Schiff base formation and reductive amination of amino in the hyaluronic acid derivative and a drug (such as aldehyde and ketone) having carbonyl or a drug into which carbonyl is introduced;

Schiff base formation and reductive amination of amino in a drug or amino introduced into a drug and the hyaluronic acid derivative into which carbonyl is introduced by modification;

a reaction of mercapto introduced into the hyaluronic acid derivative with a drug which is a compound having an unsaturated bond (such as maleimide, acrylate ester, acrylamide, methacrylate ester, methacrylamide, an allyl compound, and vinylsulfone), a halide (such as chloroacetat- ester, bromoacetate ester, iodoacetate ester, chloroacetamide, bromoacetamide, and iodoacetamide), or thiol or a drug converted into such a compound by modification; and a reaction of mercapto introduced into a drug with the hyaluronic acid derivative converted into a compound which has an unsaturated bond (maleimide, acrylate ester, acrylamide, methacrylate ester, methacrylamide, an allyl compound, vinylsulfone), a halide (chloroacetate ester, bromoacetate ester, iodoacetate ester, chloroacetamide, bromoacetamide, iodoacetamide) or thiol by modification.

In addition, a linker (spacer) containing the ester or carbonate used to introduce a hydrophobic group into an HA derivative and described above, β thioester, disulfide, or a peptide that is cleaved at a specific site can be used as a linker for the conjugation with a drug. These linkers are cleaved at a target site to release the drug, as described above.

Reagents used for modification of the hyaluronic acid derivative or the drug for preparation of the conjugate is not particularly limited, as long as they cause no undesired reaction in the preparation of the conjugate. The compounds are those that are available as a reagent or that can be synthesized in reference to a method known to the public through publication.

Specifically, by synthesizing the hyaluronic acid derivative according to the present invention and reacting the derivative with a drug having amino or a drug into which amino is introduced using a condensation agent such as DMT-MM, a conjugate can be prepared by amide linkage. In this reaction, the drug may be added with, for example, cholesteryl 6-aminohexylcarbamate hydrochloride to introduce a hydrophobic group at the same time. In addition, such compound may be added after or before the drug. In addition, the drug may be reacted after synthesis and purification of the hyaluronic acid derivative according to the present invention or a hydrophobic group derivative may be introduced after synthesis and purification of the hyaluronic acid derivative into which the drug is introduced.

In addition, a drug may be conjugated to a hyaluronic acid derivative via an ester bond by synthesizing hyaluronic acid derivative according to the present invention, and reacting a drug having hydroxy or a drug into which hydroxy is introduced using a condensation agent such as DMT-MM, 1,3-dichlorohexyl carbodiimide (DCC). In this reaction, the drug may be added with, for example, cholesteryl 6-aminohexylcarbamate hydrochloride to introduce a hydrophobic group at the same time. In addition, such compound may be added after or before the drug. However, it is desirable to conjugate the drug after the introduction of the hydrophobic group to avoid hydrolysis of the ester. The above method can be carried out in reference to a report (Bioconjugate Vol. 19, 1319-1325, 2008) that paclitaxel was introduced into HA by ester.

In addition, a drug can be conjugated by synthesizing the hyaluronic acid derivative according to the present invention, reacting a drug which is a bromide or an iodide or a drug converted into a bromide or an iodide by modification, and converting carboxy in the glucuronic acid moiety into ester. It is desirable to conjugate the drug after the introduction of a hydrophobic group to avoid hydrolysis of the ester.

A drug may be conjugated to a hyaluronic acid derivative via an ester bond by synthesizing the hyaluronic acid derivative according to the present invention, converting a drug having carboxy or a drug into which carboxy is introduced into NHS ester, and reacting the carboxy with hydroxy at the 6-position of the N-acetylglucosamine moiety. In this reaction, the drug may be added after introducing a hydrophobic group into HA by, for example, cholesteryl 6-aminohexylcarbamate hydrochloride, or the drug may be added before the introduction. In addition, the drug may be reacted after synthesis and purification of the hyaluronic acid derivative according to the present invention or a hydrophobic group derivative may be introduced after synthesis and purification of the hyaluronic acid derivative into which a drug is introduced. To avoid hydrolysis of the ester bond, it is desirable to conjugate the drug after the introduction of a hydrophobic group derivative. The above method can be carried out in reference to a report (International Publication No. 2009/074678) that camptothecin was introduced into HA by ester bond.

In one embodiment, amino can be introduced by dehydration reaction of carboxy of the glucuronic acid moiety and diamine such as ethylenediamine after synthesis of the hyaluronic acid derivative according to the present invention. Furthermore, a hyaluronic acid derivative into which iodoacetyl was introduced can be synthesized by reacting N-succinimidyl iodoacetate (PIERCE) or N-succinimidyl [4-iodoacetyl] aminobenzoate (PIERCE) with amino. A drug having mercapto can be conjugated to this hyaluronic acid derivative. This method is particularly effective for high molecular weight drugs, such as protein, peptide, and nucleic acid, which have many reactive groups such as amino, since the conjugation can be mercapto selectively. In this reaction, the introduction of the drug may be before or after the introduction of a hydrophobic group derivative into HA.

The hyaluronic acid derivative according to the present invention in which $X^1$ is —NH$_2$—COO—R is synthesized and a part of carboxy groups in the glucuronic acid moiety is reacted with 2-aminoethyl 2-pyridyl disulfide hydrochloride. To this hyaluronic acid derivative, a drug having mercapto and a drug into which mercapto is introduced can be introduced by disulfide bond exchange reaction, i.e. a substitution reaction.

In this reaction, the length of a linker between the drug and the hyaluronic acid derivative can be adjusted to keep the bioactivity of the conjugate effective. In addition, a peptide linker cut with an enzyme at a specific site in the living body can be introduced. For example, this can be done in reference to a report (International Publication No. 2005/095464) that methotrexate was introduced into HA via a linker containing a peptide and a report (International Publication No. 2002/090209) that doxorubicin was introduced via a linker containing HPMA (N-(2-hydroxypropyl)methacrylamide) and a peptide, or the like.

In addition, there are many reports on ADC (Antibody Drug Conjugate) in which a low molecular weight compound is conjugated to an antibody (International Publication No. 2009/026274; Expert Opinion. Vol. 15, p. 1087-1103, 2005; Bioconjugate Chem. Vol. 19, p. 1960-1963, 2008; Bioconjugate Chem. in press, Bernhard Stump et al., Antibody-Drug Conjugates: Linking Cytotoxic Payloads to Monoclonal Antibodies) and a conjugate of a hyaluronic acid derivative and a low molecular weight compound can be prepared in reference to these.

A pharmaceutical composition containing one or more drugs and the hyaluronic acid derivative according to the present invention and a conjugate in which one or more drugs are coupled with the hyaluronic acid derivative according to the present invention may be in the form of nanoparticles, microparticles, solution, emulsion, suspension, gel, micelle, implant, powder, or film. Powder can be produced by crushing a solid obtained by lyophilization or spray drying or produced from a material obtained by drying precipitate.

Pharmaceutical compositions and conjugates of the present invention may be administered via oral, parenteral, intranasal, intravaginal, intraocular, subcutaneous, intravenous, intramuscular, intradermal, Intraperitoneal, intraarticular, intracerebral, or intraoral routes.

The pharmaceutical compositions and the conjugates of the present invention particularly for controlled release in local is preferably 200 μm or less, and more preferably 100 μm or less to pass thorough needles without clogging.

The pharmaceutical compositions and the conjugates of the present invention particularly for targeting to a hyaluronic acid receptor including CD44 are preferably 5 µm or less in size.

The pharmaceutical compositions and the conjugates of the present invention particularly for extended retention in the blood and accumulation to tumor tissue or inflammatory tissue is preferably 500 nm or less, and more preferably, 200 nm or less in size. In addition, it is preferably 100 nm or less to avoid uptake into the reticuloendothelial system and improve retention in the blood.

The pharmaceutical compositions and the conjugates of the present invention for a non-aggression administration of those having an adhesion property to mucous membrane is preferably 200 µm or less in size. In terms of adhesion to mucous membrane, introduction ratio of a hydrophobic group in the hyaluronic acid derivative to be used is preferably low.

Drugs forming a complex with the hyaluronic acid derivative according to the present invention are not particularly limited as long as it can be held. In addition, drugs to be coupled with the hyaluronic acid derivative according to the present invention are not particularly limited, as long as a conjugate can be prepared. Examples of the drugs include protein and/or peptide, polysaccharide, nuclear acid, low molecular weight compounds, and preferable examples include protein and/or peptide.

Examples of the low molecular weight compounds include, for example, anticancer agents (such as, for example, alkylating agents, antimetabolites, alkaloids such as paclitaxel), immunosuppressive drugs such as cyclosporine, antiinflammatory agents (such as steroid and non-steroid antiinflammatory agents), antirheumatic agents, and antibiotics (such as beta-lactam antibiotics, aminoglycoside derivative antibiotics, macrolide derivative antibiotics, tetracycline antibiotics, new quinolone antibiotics, and sulfa drugs).

Examples of the proteins and the peptides include, for example, erythropoietin (EPO), granulocyte-colony stimulating factor (G-CSF), Interferon-α, β, γ, (INF-α, β, γ), thrombopoietin (TPO), ciliary neurotrophic factor (CNTF), tumor necrosis factor (TNF), tumor necrosis factor binding protein (TNFbp), interleukin-10 (IL-10), FMS-like tyrosine kinase (Flt-3), growth hormone (GH), insulin, insulin-like growth factor-1 (IGF-1), platelet-derived growth factor (PDGF), interleukin-1 receptor antagonist (IL-1ra), brain-derived neurotrophic factor (BDNF), keratinocyte growth factor (KGF), stem cell factor (SCF), megakaryocyte growth and development factor (MGDF), osteoprotegerin (OPG), leptin, parathormone (PTH), basic fibroblast growth factor (b-FGF), bone morphogenetic protein (BMP), atrial natriuretic peptide (ANP), brain natriuretic peptide (BNP), C-type natriuretic peptide (CNP), glucagon-like peptide-1 (GLP-1), antibody, diagram body, mini-body, and antibody fragments.

Examples of the nuclear acids include, for example, DNA, RNA, antisense, decoy, ribozyme, small interfering RNA, and RNA aptamer.

The hyaluronic acid derivative according to the present invention in which a drug is encapsulated or the hyaluronic acid derivative-drug conjugate according to the present invention can be administered in a pharmaceutical composition containing one or more pharmaceutically acceptable diluents, wetting agents, emulsifiers, dispersants, adjuvants, preservatives, buffers, binders, and/or stabilizers in any suitable form depending on the intended route of administration. The route of administration may be a parenteral route or an oral route.

According to the present invention, a prolonged controlled release of drugs such as proteins, peptides, nucleic acids, and low molecular weight compounds, which was not possible with a conventional controlled release preparation, and/or safe controlled release formulations and pharmaceutical compositions having an appropriate biodegradability can be provided.

EXAMPLES

Specific preferable embodiments of the present invention will be described as Examples below.

HA unit described below refers to N-acetylglucosamine-glucuronic acid repeating unit (1 unit) in hyaluronic acid. The measurement of $^1$H-NMR spectra was conducted by using JNM-ECA500 (JEOL Ltd.). Dialysis was conducted using a dialysis membrane made of regenerated cellulose (Spectra Pore 4: molecular weight cutoff: 12 k~14 kDa, when using hyaluronic acid sodium salt having molecular weights of 50 kDa and 99 kDa as a starting material; Spectra Pore 7: molecular weight cutoff: 1 kDa or 2 kDa, when using hyaluronic acid sodium salt of a molecular weight of 10 kDa as a starting material).

Example 1

Synthesis of Hyaluronic Acid Derivative

Example 1-1

Preparation of Cholesteryl 6-Amino Hexyl Carbamate Hydrochloride

Triethylamine (TEA, 1.05 mL) was added to a solution of cholesteryl chloroformate (3.37 g, 7.5 µmmol) in anhydrous dichloromethane (20 mL) under argon atmosphere and the mixture was stirred. 6-(t-Butoxycarbonyl)amino-1-aminohexane (1.12 mL, 5 µmmol) was added dropwise on ice, the mixture was stirred on ice for 30 minutes, and then warmed to room temperature. The mixture was stirred overnight. The reaction mixture was washed with ultrapure water and saturated brine and dried over anhydrous magnesium sulfate. The solvent was then distilled off under reduced pressure. The resultant residue was purified by silica gel column chromatography (eluent: ethyl acetate:n-hexane=1: 4). The fractions containing the target were combined and the solvent was distilled off under reduced pressure. The resulting residue was dissolved in ethyl acetate (40 mL), and a solution of 4 N hydrochloric acid/ethyl acetate (40 mL) was added. The mixture was stirred at room temperature overnight and the resultant precipitate was collected by centrifugation. The obtained solid was washed with ethyl acetate 4 times, and then dried under reduced pressure to obtain cholesteryl 6-aminohexylcarbamate (Chol-C$_6$) hydrochloride (1.2 g). The $^1$H-NMR spectrum (EtOH-d$_6$) of the product was shown in FIG. 1-1.

Example 1-2

Tetrabutyl Ammonium (TBA) Salt Formation of Cationic Exchange Resin

DOWEX (registered trademark) 50WX-8-400 (Sigma-Aldrich) was suspended in ultrapure water and the resin was washed 3 times or so with ultrapure water by decantation. A 40% by weight aqueous solution of tetrabutyl ammonium hydroxide (TBA-OH; Sigma-Aldrich) was added to the resin at approximately 1.5 mol equivalents per cationic exchange capacity and the mixture was stirred for 30 minutes. Surplus TBA-OH solution was removed by decantation, then washing was repeated with excessive ultrapure water, and finally filtering the solution with a 0.45 µm filter to obtain TBA salt of the cationic exchange resin.

Example 1-3

Preparation of TBA salts of HA

Hyaluronic acid sodium salts (HA-Na, Shiseido Co., Ltd.) having molecular weights of 10 kDa, 50 kDa, and 99 kDa were each dissolved in ultrapure water in a concentration of 15 mg/mL. Suspensions of the TBA salt of cationic exchange resin prepared in Example 1-2 were added at 5 µmol equivalents per mol of HA unit (unit molecular weight 401.3) in terms of ion exchange capacity of the resin. After stirring for 15 minutes, the suspensions were filtered with a 0.45 µm filter. The filtrate was freeze-dried to obtain TBA salts of hyaluronic acid (HA-TBA) as white solid.

As a representative example, $^1$H-NMR spectrum of the product produced from the starting material 99 kDa HA-Na in D$_2$O as a solvent is shown in FIG. 1-2. Based on the integrated value of signals (—COCH$_3$, 2.0 ppm; 3H) derived from acetyl in glucosamine in HA and the integrated value of signals (N(CH$_2$CH$_2$CH$_2$CH$_3$)$_4$, 1.4, 1.7 ppm; 16H) derived from four ethylene groups in TBA, the quantity ratios of TBA to HA units were calculated. The unit average molecular weights of HA-TBAs were calculated from these ratios. For example, the unit average molecular weight of HA-TBA produced from the starting material 99 kDa HA-Na was 752.6.

Example 1-4

Synthesis of a Fluorescent Labeled HA Derivative Modified with L-Alanine (Ala) and Cholesteryl 6-Aminohexylcarbamate (HA-Ala-Chol/FL)

Solutions (5 mg/mL) of HA-TBA synthesized from the starting materials HA-Na (10 kDa, 50 kDa, 99 kDa) in Example 1-3 in anhydrous DMSO were prepared. Subsequently, L-alanine ethyl ester hydrochloride (Aldrich) was added at 5 mol equivalents per HA unit. 4-(4,6-Dimethoxy-1,3,5-triazin-2-yl)-4-methylmorpholinium chloride (DMT-MM) was then added at 6 mol equivalents per HA unit. The mixtures were stirred at room temperature overnight. The reaction solutions were dialyzed against an aqueous solution of 0.3 M NaCl and with ultrapure water in this order. To the resultant dialysates were added 2 N NaOH to pH 12.5 or more and the mixtures were stirred for 1 hour to hydrolyze the ethyl ester to deprotect the carboxy. The mixtures were subsequently neutralized with 2 N HCl, further dialyzed, and then freeze-dried to obtain HA-Ala as white solid. A representative example of $^1$H-NMR spectrum of HA-Ala (the product produced from the starting material 99 kDa HA) measured in the conditions same as those described in Example 1-3 is shown in FIG. 1-3. Based on the integrated value of peak derived from acetyl (—COCH$_3$, 2.0 ppm; 3H) in glucosamine and the integrated value of peak derived from methyl (—CH$_3$, 1.4 ppm; 3H) in alanine, introduction ratio of alanine (introduction ratio of Ala) in HA units was calculated according to the expression shown below (Table 1).

[Formula 2]

Introduction ratio of Ala (%) =

$$\frac{\text{Integrated value derived from methyl in alanine}}{\text{Integrated value of acetyl derived from } HA} \times 100$$

A suspension of the TBA salt of the cationic exchange resin prepared in Example 1-2 was added to aqueous solutions of HA-Ala at about 5 mol equivalents. After stirring for 15 minutes, the suspensions were filtered with a 0.45 µm filter. The filtrates were freeze-dried to obtain TBA salts of HA-Ala (HA-Ala-TBA) as white solid. Based on the $^1$H-NMR spectra of HA-Ala-TBA, measured in the conditions same as those described in Example 1-3, the quantity ratios of TBA to HA unit were calculated by the method same as the description of Example 1-3 and based on the integrated value of peak derived from acetyl in glucosamine and the integrated value of peak derived from methyl (—Si(CH$_3$)$_3$, 0.0 ppm; 9H) in sodium 3-(trimethylsilyl)propionate-d$_4$ (TSP-d$_4$) used as an internal standard, HA unit contents per weight were quantified.

Solutions (10 mg/mL) of HA-Ala-TBA in anhydrous DMSO were prepared. Subsequently, Chol-C$_6$ hydrochloride prepared in Example 1-1 was added to respective solutions at the ratios to HA-Ala-TBA unit shown in Table 1 below. DMT-MM was then added to HA-Ala-TBA at the ration shown in Table 1 below. 5-Aminomethylfluoresceine (FL) hydrochloride (Invitrogen) hydrochloride and DMT-MM were added at 0.04 mol equivalents and 0.07 mol equivalents per HA-Ala-TBA unit, respectively. The mixture was stirred at room temperature overnight. The reaction solution was dialyzed against a solution of 0.3 M ammonium acetate/DMSO, an aqueous solution of 0.15 M NaCl, and ultrapure water in this order. The resultant dialysates were freeze-dried to obtain the target products (HA-Ala-Chol/FL) as yellow solid.

A representative example of $^1$H-NMR spectrum (the product that is produced from the starting material 99 kDa HA-Na and has a introduction ratio of a cholesteryl group of 7%) in a mixed solution of 0.02 N DCl DMSO-d$_6$/D$_2$O (2 N DCl D$_2$O:DMSO-d$_6$=1:99) as a measurement solvent is shown in FIG. 1-4. Based on the integrated value of peak derived from acetyl (COCH$_3$, 1.6 to 2.0 ppm; 3H) in glucosamine and the integrated value of peak derived from methyl (CH$_3$, 0.7 ppm; 3H) in the cholesteryl group, the introduction ratio of the cholesteryl group in HA units was calculated according to the expression below (Table 1). Since peaks around 1.6 to 2.0 ppm including peaks derived from acetyl in glucosamine are overlaps with peaks (5H) derived from the cholesteryl group, values obtained by subtracting 5/3 of the integrated value of peak (0.7 ppm) derived from methyl in the cholesteryl group from the integrated value of peaks around 1.6 to 2.0 ppm (i.e. integrated value (1.6 to 2.0 ppm)−integrated value (0.7 ppm)×5/3) were used as integrated values of acetyl derived from HA to calculate the introduction ratio.

[Formula 3]

Introduction ratio of cholesteryl group % =

$$\frac{\text{Integrated value of methyl derived from cholesteryl group (0.7 ppm)}}{\text{Integrated value of acetyl derived from } HA} \times 100$$
(1.6 to 2.0 ppm, value after correction)

TABLE 1

Amount of reagent used in preparation of HA-Ala-Chol/FL and introduction ratio

| Abbreviation | Molecular weight | Introduction ratio of Ala (unit %) | Mol ratio of Chol-C$_6$ hydrochloride and DMT-MM added (HA unit/Chol-C$_6$/DMT-MM) | Introduction ratio of Chol (unit %) |
|---|---|---|---|---|
| 99k HA-Ala-Chol-7%/FL | 99k | 101 | 100/8/12 | 7 |
| 99k HA-Ala-Chol-24%/FL | 99k | 101 | 100/27/41 | 24 |
| 99k HA-Ala-Chol-30%/FL | 99k | 101 | 100/35/53 | 30 |
| 50k HA-Ala-Chol-6%/FL | 50k | 101 | 100/7/11 | 6 |
| 50k HA-Ala-Chol-22%/FL | 50k | 101 | 100/24/36 | 22 |
| 50k HA-Ala-Chol-26%/FL | 50k | 101 | 100/32/48 | 26 |
| 10k HA-Ala-Chol-16%/FL | 10k | 101 | 100/16/24 | 16 |

In this Example, examples of the group with which amino in Chol-C$_6$ hydrochloride can react include both carboxy in the glucuronic acid moiety of hyaluronic acid and carboxy in Ala. If a hydrophobic group can be introduced to two reactive groups like this, an abbreviation with a hyphen such as "-Chol" is used to designate the target.

Example 1-5

Synthesis of Fluorescent Labeled HA Derivative Modified with L-Threoninamide (ThrNH$_2$) and Cholesteryl 6-Aminohexylcarbamate (HA-ThrNH$_2$/Chol/FL)

Solutions (10 mg/mL) of HA-TBA synthesized from the starting material HA-Na (99 kDa) in Example 1-3 in anhydrous DMSO were prepared. Subsequently, Chol-C$_6$ hydrochloride prepared in Example 1-1 was added to respective solutions at the ratios to HA units shown in Table 2 below. DMT-MM was then added at the ratios to HA units shown in Table 2 below, 5-Aminomethylfluoresceine (FL) hydrochloride (Invitrogen) hydrochloride and DMT-MM were added at 0.04 mol equivalents and 0.07 mol equivalents per HA unit, respectively. The mixture was stirred at room temperature for 7 hours. Subsequently, L-threoninamide hydrochloride (WATANABE CHEMICAL INDUSTRIES, LTD.) was added at 3 mol equivalents per HA unit. DMT-MM was then added at 5 mol equivalents per HA unit. The mixture was stirred at room temperature overnight. The reaction solution was dialyzed against a solution of 0.3 M ammonium acetate/DMSO, an aqueous solution of 0.15 M NaCl, and ultrapure water in this order. The resultant dialysates were freeze-dried to obtain the target products (HA-ThrNH$_2$/Chol/FL) as yellow solid.

A representative example of $^1$H-NMR spectrum (the product that is produced from the starting material 99 kDa HA-Na and has an introduction ratio of a cholesteryl group of 6%) in a mixed solution of 0.02 N DCl DMSO-d$_6$/D$_2$O (2 N DCl D$_2$O:DMSO-d$_6$=1:99) as a measurement solvent is shown in FIG. 1-5. Based on the integrated value of peaks derived from acetyl (COCH$_3$, 1.6 to 2.0 ppm; 3H) in glucosamine and the integrated value of peak derived from methyl (CH$_3$, 0.7 ppm; 3H) in the cholesteryl group, the introduction ratio of cholesteryl group in HA units was calculated according to the expression below (Table 2). Since peaks around 1.6 to 2.0 ppm including peaks derived from acetyl in glucosamine are overlaps with peaks (5H) derived from the cholesteryl group, values obtained by subtracting 5/3 of the integrated value of peak (0.7 ppm) derived from methyl in the cholesteryl group from the integrated value of peaks around 1.6 to 2.0 ppm (i.e. integrated value (1.6 to 2.0 ppm)–integrated value (0.7 ppm)×5/3) were used as integrated values of acetyl derived from HA to calculate the introduction ratio.

[Formula 4]

Introduction ratio of cholesteryl group % =

$$\frac{\text{Integrated value of methyl derived from cholesteryl group (0.7 ppm)}}{\text{Integrated value of acetyl derived from } HA} \times 100$$
(1.6 to 2.0 ppm, value after correction)

Based on the integrated value of peak derived from acetyl in glucosamine and the integrated value of peak derived from methyl (—CH$_3$, 1.2 ppm; 3H) in threoninamide, the introduction ratio of threoninamide in HA units was calculated

[Formula 5]

Introduction ratio of threoninamide (%) =

$$\frac{\text{Integrated value of methyl derived from threoninamide}}{\text{Integrated value of acetyl derived from } HA} \times 100$$

TABLE 2

Amount of reagent used in preparation of HA-ThrNH$_2$/Chol/FL and introduction ratio

| Abbreviation | Molecular weight | Introduction ratio of ThrNH$_2$ (unit %) | Mol ratio of Chol-C$_6$ hydrochloride and DMT-MM added (HA unit/Chol-C$_6$/DMT-MM) | Introduction ratio of Chol (unit %) | Sum of introduction ratio of ThrNH$_2$ and Chol |
|---|---|---|---|---|---|
| 99k HA-ThrNH$_2$/Chol-6%/FL | 99k | 83 | 100/6/6 | 6 | 89 |
| 99k HA-ThrNH$_2$/Chol-24%/FL | 99k | 73 | 100/24/24 | 24 | 97 |
| 99k HA-ThrNH$_2$/Chol-31%/FL | 99k | 70 | 100/32/32 | 31 | 101 |

In this Example, amino in Chol-C$_6$ hydrochloride reacts only with carboxy in the glucuronic acid moiety of hyaluronic acid and no hydrophobic group is further introduced into the introduced ThrNH$_2$. If a hydrophobic group can be introduced to only the carboxy in the glucuronic acid moiety of hyaluronic acid like this, an abbreviation with a slash such as "/Chol" is used to designate the target.

Example 1-6

Synthesis of Fluorescent Labeled HA Derivative Modified with L-Serine (Ser) and Cholesteryl 6-Aminohexylcarbamate (HA-Ser-Chol/FL)

HA-Ser was obtained as white solid in a method similar to that of Example 1-4 except that ethyl L-serinate hydrochloride (Aldrich) was used instead of ethyl L-alaninate hydrochloride. In addition, a part of the dialysate (HA-Ser-OEt) before deprotecting carboxy was collected and freeze-dried as a sample for calculation of introduction ratio. $^1$H-NMR spectrum of the sample for the calculation of introduction ratio as measured in the conditions same as those described in Example 1-3 is shown in FIG. 1-6. Based on the integrated value of peak derived from acetyl (—COCH$_3$, 1.9 ppm; 3H) in glucosamine and the integrated value of peak derived from methyl (—CH$_3$, 1.2 ppm; 3H) in ethyl ester of serine, the introduction ratio of serine in HA units was calculated similarly to Example 1-4 (Table 3). In addition, $^1$H-NMR spectrum of the deprotected sample as measured in the conditions same as those described in Example 1-3 is shown in FIG. 1-7. A TBA salt of HA-Ser (HA-Ser-TBA) was obtained as white solid in the conditions same as those described in Example 1-4. Then, it was reacted with Chol-C$_6$ hydrochloride and FL in a method similar to that of Example 1-4 to obtain the target (HA-Ser-Chol/FL) as yellow solid. $^1$H-NMR spectrum measured in the conditions same as those described in Example 1-4 is shown in FIG. 1-8. The introduction ratio of cholesteryl group was calculated in the method described in Example 1-4 (Table 3).

Example 1-7

Synthesis of Fluorescent Labeled HA Derivative Modified with L-Glycine (Gly) and Cholesteryl 6-Aminohexylcarbamate (HA-Gly-Chol/FL)

HA-Gly was obtained as white solid in a method similar to that of Example 1-4 except that ethyl glycinate hydrochloride (Wako Pure Chemical Industries, Ltd.) was used instead of ethyl L-alaninate hydrochloride. In addition, a part of the dialysate (HA-Gly-OEt) before deprotecting carboxy was collected and freeze-dried as a sample for calculation of introduction ratio. $^1$H-NMR spectrum of the sample for the calculation of introduction ratio as measured in the conditions same as those described in Example 1-3 is shown in FIG. 1-9. Based on the integrated value of peak derived from acetyl (—COCH$_3$, 2.0 ppm; 3H) in glucosamine and the integrated value of peak derived from methyl (—CH$_3$, 1.3 ppm, 3H) in ethyl ester of glycine, the introduction ratio of glycine in HA units was calculated similarly to Example 1-4 (Table 3). In addition, $^1$H-NMR spectrum of the deprotected sample as measured in the conditions same as those described in Example 1-3 is shown in FIG. 1-10. A TBA salt of HA-Gly (HA-Gly-TBA) was obtained as white solid in the conditions same as those described in Example 1-4. Then, it was reacted with Chol-C$_6$ hydrochloride and FL in a method similar to that of Example 1-4 to obtain the target (HA-Gly-Chol/FL) as yellow solid. $^1$H-NMR spectrum measured in the conditions same as those described in Example 1-4 is shown in FIG. 1-11. The introduction ratio of cholesteryl group was calculated in the method described in Example 1-4 (Table 3).

Example 1-8

Synthesis of Fluorescent Labeled HA Derivative Modified with L-Threonine (Thr) and Cholesteryl 6-Aminohexylcarbamate (HA-Thr-Chol/FL)

HA-Thr was obtained as white solid in a method similar to that of Example 1-4 except that methyl L-threoninate hydrochloride (Bachem) was used instead of ethyl L-alaninate hydrochloride. $^1$H-NMR spectrum measured in the conditions same as those described in Example 1-3 is shown in FIG. 1-12. Based on the integrated value of peak derived from acetyl (—COCH$_3$, 2.0 ppm; 3H) in glucosamine and the integrated value of peak derived from methyl (—CH$_3$, 1.2 ppm; 3H) in threonine, the introduction ratio of threonine in HA units was calculated similarly to Example 1-4 (Table 3). A TBA salt of HA-Thr (HA-Thr-TBA) was obtained as white solid in the conditions same as those described in Example 1-4. Then, it was reacted with Chol-C$_6$ hydrochloride and FL in a method similar to that of Example 1-4 to obtain the target (HA-Thr-Chol/FL) as yellow solid.

$^1$H-NMR spectrum measured in the conditions same as those described in Example 1-4 is shown in FIG. 1-13. The introduction ratio of cholesteryl group was calculated in the method described in Example 1-4 (Table 3).

Example 1-9

Synthesis of Fluorescent Labeled HA Derivative Modified with L-Asparagine (Asn) and Cholesteryl 6-Aminohexylcarbamate (HA-Asn-Chol/FL)

HA-Asn was obtained as white solid in a method similar to that of Example 1-4 except that methyl L-asparaginate hydrochloride (Bachem) was used instead of ethyl L-alaninate hydrochloride. $^1$H-NMR spectrum measured in the conditions same as those described in Example 1-3 is shown in FIG. 1-14. Based on the integrated value of peak derived from acetyl (—COCH$_3$, 2.0 ppm; 3H) in glucosamine and the integrated value of peaks derived from methylene (—CH$_2$CONH$_2$, 2.7, 2.8 ppm; 2H) in asparagine, the introduction ratio of asparagine in HA units was calculated similarly to Example 1-4 (Table 3). A TBA salt of HA-Asn (HA-Asn-TBA) was obtained as white solid in the conditions same as those described in Example 1-4. Then, it was reacted with Chol-C$_6$ hydrochloride and FL in a method similar to that of Example 1-4 to obtain the target (HA-Asn-Chol/FL) as yellow solid. $^1$H-NMR spectrum measured in the conditions same as those described in Example 1-4 is shown in FIG. 1-15. The introduction ratio of cholesteryl group was calculated in the method described in Example 1-4 (Table 3).

Example 1-10

Synthesis of Fluorescent Labeled HA Derivative Modified with L-Aspartic Acid (Asp) and Cholesteryl 6-Aminohexylcarbamate (HA-Asp-Chol/FL)

HA-Asp was obtained as white solid in a method similar to that of Example 1-4 except that diethyl L-aspartate hydrochloride (WATANABE CHEMICAL INDUSTRIES, LTD.) was used instead of ethyl L-alaninate hydrochloride. $^1$H-NMR spectrum measured in the conditions same as those described in Example 1-3 is shown in FIG. 1-16. Based on the integrated value of peak derived from acetyl (—COCH$_3$, 2.0 ppm; 3H) in glucosamine and the integrated value of peaks derived from methylene (—CH$_2$COOH$_2$, 2.7, 2.8 ppm; 2H) in aspartic acid, the introduction ratio of aspartic acid in HA units was calculated similarly to Example 1-4 (Table 3). A TBA salt of HA-Asp (HA-Asp-TBA) was obtained as white solid in the conditions same as those described in Example 1-4. Then, it was reacted with Chol-C$_6$ hydrochloride and FL in a method similar to that of Example 1-4 to obtain the target (HA-Asp-Chol/FL) as yellow solid. $^1$H-NMR spectrum measured in the conditions same as those described in Example 1-4 is shown in FIG. 1-17. The introduction ratio of cholesteryl group was calculated in the method described in Example 1-4 (Table 3).

Example 1-11

Synthesis of Fluorescent Labeled HA Derivative Modified with L-Isoleucine (Ile) and Cholesteryl 6-Aminohexylcarbamate (HA-Ile-Chol/FL)

HA-Ile was obtained as white solid in a method similar to that of Example 1-4 except that methyl L-isoleucinate hydrochloride (WATANABE CHEMICAL INDUSTRIES, LTD.) was used instead of ethyl L-alaninate hydrochloride. $^1$H-NMR spectrum measured in the conditions same as those described in Example 1-3 is shown in FIG. 1-18. Based on the integrated value of peak derived from acetyl (—COCH$_3$, 2.0 ppm; 3H) in glucosamine and the integrated value of peak derived from two methyl (—CH(CH$_3$)CH$_2$CH$_3$, 0.9 ppm; 6H) in isoleucine, the introduction ratio of isoleucine in HA units was calculated similarly to Example 1-4 (Table 3). Since the peak of hydrogen at the 3-position of isoleucine (—CH(CH$_3$)CH$_2$CH$_3$, 1.9 ppm; 1H) overlaps with peaks derived from acetyl in glucosamine, the value obtained by subtracting ⅙ of the integrated value of the peak at 0.9 ppm from the integrated value of peaks at 1.8 to 2.2 ppm was used as peaks derived from acetyl in glucosamine to calculate the introduction ratio. A TBA salt of HA-Ile (HA-Ile-TBA) was obtained as white solid in the conditions same as those described in Example 1-4. Then, it was reacted with Chol-C$_6$ hydrochloride and FL in a method similar to that of Example 1-4 to obtain the target (HA-Ile-Chol/FL) as yellow solid. $^1$H-NMR spectrum measured in the conditions same as those described in Example 1-4 is shown in FIG. 1-19. The introduction ratio of cholesteryl group was calculated in the method described in Example 1-4 (Table 3).

Example 1-12

Synthesis of Fluorescent Labeled HA Derivative Modified with L-Leucine (Leu) and Cholesteryl 6-Aminohexylcarbamate (HA-Leu-Chol/FL)

HA-Leu was obtained as white solid in a method similar to that of Example 1-4 except that ethyl L-leucinate hydrochloride (Tokyo Chemical Industry Co., Ltd.) was used instead of ethyl L-alaninate hydrochloride. $^1$H-NMR spectrum measured in the conditions same as those described in Example 1-3 is shown in FIG. 1-20. Based on the integrated value of peak derived from acetyl (—COCH$_3$, 2.0 ppm; 3H) in glucosamine and the integrated value of peak derived from two methyl (—CH(CH$_3$)$_2$, 0.9 ppm; 6H) in leucine, the introduction ratio of leucine in HA units was calculated similarly to Example 1-4 (Table 3). A TBA salt of HA-Leu (HA-Leu-TBA) was obtained as white solid in the conditions same as those described in Example 1-4. Then, it was reacted with Chol-C$_6$ hydrochloride and FL in a method similar to that of Example 1-4 to obtain the target (HA-Leu-Chol/FL) as yellow solid. $^1$H-NMR spectrum measured in the conditions same as those described in Example 1-4 is shown in FIG. 1-21. The introduction ratio of cholesteryl group was calculated in the method described in Example 1-4 (Table 3).

Example 1-13

Synthesis of Fluorescent Labeled HA Derivative Modified with L-Valine (Val) and Cholesteryl 6-Aminohexylcarbamate (HA-Val-Chol/FL)

HA-Val was obtained as white solid in a method similar to that of Example 1-4 except that ethyl L-valinate hydrochloride (WATANABE CHEMICAL INDUSTRIES, LTD.) was used instead of ethyl L-alaninate hydrochloride. $^1$H-NMR spectrum measured in the conditions same as those described in Example 1-3 is shown in FIG. 1-22. Based on the integrated value of peak derived from acetyl (—COCH$_3$, 2.0 ppm, 3H) in glucosamine and the integrated value of peak derived from two methyl (—CH(CH$_3$)$_2$, 0.9 ppm; 6H)

in valine, the introduction ratio of valine in HA units was calculated similarly to Example 1-4 (Table 3). Since the peak of hydrogen at the 3-position of valine (—CH(CH$_3$)$_2$, 2.1 ppm; 1H) overlaps with peaks derived from acetyl in glucosamine, the value obtained by subtracting ⅙ of the integrated value of the peak at 0.9 ppm from the integrated value of peaks at 1.8 to 2.2 ppm was used as peaks derived from acetyl in glucosamine to calculate the introduction ratio. A TBA salt of HA-Val (HA-Val-TBA) was obtained as white solid in the conditions same as those described in Example 1-4. Then, it was reacted with Chol-C$_6$ hydrochloride and FL in a method similar to that of Example 1-4 to obtain the target (HA-Val-Chol/FL) as yellow solid. $^1$H-NMR spectrum measured in the conditions same as those described in Example 1-4 is shown in FIG. 1-23. The introduction ratio of cholesteryl group was calculated in the method described in Example 1-4 (Table 3).

Example 1-14

Synthesis of Fluorescent Labeled HA Derivative Modified with L-Phenylalanine (Phe) and Cholesteryl 6-Aminohexylcarbamate (HA-Phe-Chol/FL)

HA-Phe was obtained as white solid in a method similar to that of Example 1-4 except that ethyl L-phenylalaninate hydrochloride (Aldrich) was used instead of ethyl L-alaninate hydrochloride. $^1$H-NMR spectrum measured in the conditions same as those described in Example 1-3 is shown in FIG. 1-24. Based on the integrated value of peak derived from acetyl (—COCH$_3$, 2.0 ppm; 3H) in glucosamine and the integrated value of peaks derived from phenyl (—C$_6$H$_5$, 7.2 to 7.4 ppm; 5H) in phenylalanine, the introduction ratio of phenylalanine in HA units was calculated similarly to Example 1-4 (Table 3). A TBA salt of HA-Phe (HA-Phe-TBA) was obtained as white solid in the conditions same as those described in Example 1-4. Then, it was reacted with Chol-C$_6$ hydrochloride and FL in a method similar to that of Example 1-4 to obtain the target (HA-Phe-Chol/FL) as yellow solid. $^1$H-NMR spectrum measured in the conditions same as those described in Example 1-4 is shown in FIG. 1-25. The introduction ratio of cholesteryl group was calculated in the method described in Example 1-4 (Table 3).

TABLE 3

Amount of reagent used in preparation of HA-AA/Chol/FL and introduction ratio

| Abbreviation | Molecular weight | Species and introduction ratio of AA (unit %) | Mol ratio of Chol-C$_6$ hydrochloride and DMT-MM added (HA unit/Chol-C$_6$/DMT-MM) | Introduction ratio of Chol (unit %) |
|---|---|---|---|---|
| 99k HA-Ser-Chol-6%/FL | 99k | Ser 96 | 100/7/11 | 6 |
| 99k HA-Gly-Chol-6%/FL | 99k | Gly 80 | 100/10/15 | 6 |
| 99k HA-Thr-Chol-6%/FL | 99k | Thr 103 | 100/7/11 | 6 |
| 99k HA-Asn-Chol-6%/FL | 99k | Asn 85 | 100/10/15 | 7 |
| 99k HA-Asp-Chol-6%/FL | 99k | Asp 102 | 100/7/11 | 6 |
| 99k HA-Ile-Chol-6%/FL | 99k | Ile 106 | 100/7/11 | 6 |
| 99k HA-Leu-Chol-6%/FL | 99k | Leu 100 | 100/7/11 | 6 |
| 99k HA-Val-Chol-6%/FL | 99k | Val 106 | 100/7/11 | 6 |
| 99k HA-Phe-Chol-6%/FL | 99k | Phe 99 | 100/7/11 | 6 |

Example 1-15

Synthesis of Fluorescent Labeled HA Derivative Modified with L-Serinamide (SerNH$_2$) and Cholesteryl 6-Aminohexylcarbamate (HA-SerNH$_2$/Chol/FL)

HA-SerNH$_2$-Chol/FL was obtained as yellow solid in a method similar to that of Example 1-5 except that L-serinamide hydrochloride (WATANABE CHEMICAL INDUSTRIES, LTD.) was used instead of L-threoninamide hydrochloride. $^1$H-NMR spectrum measured in the conditions same as those described in Example 1-5 is shown in FIG. 1-26. The introduction ratio of cholesteryl group in HA units was calculated in the same method as that described in Example 1-5 (Table 4). In addition, $^1$H-NMR spectrum of the product as measured in the same conditions as those described in Example 1-3 is shown in FIG. 1-27. Based on the integrated value of peak derived from acetyl (—COCH$_3$, 2.0 ppm; 3H) in glucosamine and the integrated value of peak derived from methylene (—CH$_2$—, 3.9 ppm; 2H) in serinamide, the introduction ratio of serinamide in HA units was calculated similarly to Example 1-5 (Table 4). Since the peak derived from methylene in serinamide overlaps with peaks (4H) of the 2 to 5-positions of glucuronate and peaks (6H) of the 2 to 6-positions of glucosamine, the value obtained by subtracting 10/3 of the integrated value of the peak at 2.0 ppm from the integrated value of peaks at 3.2 to 4.2 ppm was used as peaks derived from methylene in serinamide to calculate the introduction ratio.

Example 1-16

Synthesis of Fluorescent Labeled HA Derivative Modified with L-Glycinamide (GlyNH$_2$) and Cholesteryl 6-Aminohexylcarbamate (HA-GlyNH$_2$/Chol/FL)

HA-GlyNH$_2$-Chol/FL was obtained as yellow solid in a method similar to that of Example 1-5 except that glycinamide hydrochloride (WATANABE CHEMICAL INDUSTRIES, LTD.) was used instead of L-threoninamide hydrochloride.

$^1$H-NMR spectrum measured in the conditions same as those described in Example 1-5 is shown in FIG. 1-28. The introduction ratio of cholesteryl group in HA units was calculated in the same method as that described in Example 1-5 (Table 4). In addition, $^1$H-NMR spectrum of the product as measured in the same conditions as those described in Example 1-3 is shown in FIG. 1-29. Based on the integrated value of peak derived from acetyl (—COCH$_3$, 2.0 ppm; 3H) in glucosamine and the integrated value of peak derived from methylene (—CH$_2$—; 2H) in glycinamide, the introduction ratio of glycinamide in HA units was calculated similarly to Example 1-5 (Table 4). Since the peak derived from methylene in glycinamide overlaps with peaks (4H) of the 2 to 5-positions of glucuronate and peaks (6H) of the 2 to 6-positions of glucosamine, the integrated value of the peak derived from methylene in glycinamide was calculated in a method similar to Example 1-15.

Example 1-17

Synthesis of Fluorescent Labeled HA Derivative Modified with L-Leucinamide (LeuNH$_2$) and Cholesteryl 6-Aminohexylcarbamate (HA-LeuNH$_2$/Chol/FL)

HA-LeuNH$_2$-Chol/FL was obtained as yellow solid in a method similar to that of Example 1-5 except that L-leucinamide hydrochloride (Tokyo Chemical Industry Co., Ltd.) was used instead of L-threoninamide hydrochloride.

$^1$H-NMR spectrum measured in the conditions same as those described in Example 1-5 is shown in FIG. 1-30. The introduction ratio of cholesteryl group in HA units was calculated in the same method as that described in Example 1-5 (Table 4). Based on the integrated value of peak derived from acetyl (—COCH$_3$, 1.9 ppm; 3H) in glucosamine and the integrated value of peak derived from two methyl (—CH(CH$_3$)$_2$, 0.9 ppm; 6H) in leucinamide, the introduction ratio of leucinamide in HA units was calculated similarly to Example 1-5 (Table 4).

Example 1-18

Synthesis of Fluorescent Labeled HA Derivative Modified with L-Valinamide (ValNH$_2$) and Cholesteryl 6-Aminohexylcarbamate (HA-ValNH$_2$/Chol/FL)

A HA-ValNH$_2$-Chol/FL was obtained as yellow solid in a method similar to that of Example 1-5 except that L-valinamide hydrochloride (Tokyo Chemical Industry Co., Ltd.) was used instead of L-threoninamide hydrochloride.

$^1$H-NMR spectrum measured in the conditions same as those described in Example 1-5 is shown in FIG. 1-31. The introduction ratio of cholesteryl group in HA units was calculated in the same method as that described in Example 1-5 (Table 4). Based on the integrated value of peak derived from acetyl (—COCH$_3$, 1.9 ppm; 3H) in glucosamine and the integrated value of peak derived from two methyl (—CH(CH$_3$)$_2$, 1.0 ppm; 6H) in valinamide, the introduction ratio of valinamide in HA units was calculated similarly to Example 1-5 (Table 4).

TABLE 4

Amount of reagent used in preparation of HA-AANH$_2$/Chol/FL and introduction ratio

| Abbreviation | Molecular weight | Species and introduction ratio of AANH$_2$ (unit %) | Mol ratio of Chol-C$_6$ hydrochloride and DMT-MM added (HA unit/Chol-C$_6$/DMT-MM) | Introduction ratio of Chol (unit %) | Sum of introduction ratio of AANH$_2$ and Chol |
|---|---|---|---|---|---|
| 99k HA-SerNH$_2$-Chol-6%/FL | 99k | SerNH$_2$ 90 | 100/7/7 | 6 | 96 |
| 99k HA-GlyNH$_2$-Chol-6%/FL | 99k | GlyNH$_2$ 90 | 100/7/7 | 6 | 96 |
| 99k HA-LeuNH$_2$-Chol-6%/FL | 99k | LeuNH$_2$ 99 | 100/7/7 | 6 | 105 |
| 99k HA-ValNH$_2$-Chol-6%/FL | 99k | ValNH$_2$ 97 | 100/7/7 | 6 | 103 |

Example 1-19

Synthesis of Fluorescent Labeled HA Derivative Modified with L-Alanine (Ala) and Cholesteryl 6-Aminohexylcarbamate (HA-Ala/Chol/FL)

HA-Ala-Chol/FL was obtained as yellow solid in a method similar to that of Example 1-5 except that ethyl L-alanine hydrochloride (Aldrich) was used instead of L-threoninamide hydrochloride and dialysate was once removed during dialysis against ultrapure water to deprotect carboxy with 2 N NaOH. $^1$H-NMR spectrum measured in the conditions same as those described in Example 1-5 is shown in FIG. 1-32. The introduction ratio of cholesteryl group in HA units was calculated in the same method as that described in Example 1-5 (Table 5). Based on the integrated value of peak derived from acetyl (—COCH$_3$, 1.9 ppm; 3H) in glucosamine and the integrated value of peak derived from methyl (—CH$_3$, 1.3 ppm; 3H) in alanine, the introduction ratio of alanine in HA units was calculated similarly to Example 1-4 (Table 5). Since the peak derived from methyl in alanine overlaps with peaks (0.8 to 1.6 ppm, 41H) derived from cholesteryl 6-aminohexylcarbamate, the value obtained by subtracting 41/3 of the integrated value of the peak at 0.7 ppm from the integrated value of peaks at 0.8 to 1.6 ppm was used as peaks derived from methyl in alanine to calculate the introduction ratio.

Example 1-20

Synthesis of Fluorescent Labeled HA Derivative Modified with L-Serine (Ser) and Cholesteryl 6-Aminohexylcarbamate (HA-Ser/Chol/FL)

HA-Ser/Chol/FL was obtained as yellow solid in a method similar to that of Example 1-5 except that ethyl L-serinate hydrochloride (Aldrich) was used instead of L-threoninamide hydrochloride and dialysate was once removed during dialysis against ultrapure water to deprotect carboxy with 2 N NaOH. In addition, a part of the dialysate (HA-Ser-OEt/Chol/FL) before deprotecting carboxy was collected and freeze-dried as a sample for calculation of introduction ratio. $^1$H-NMR spectrum of the sample for the calculation of introduction ratio as measured in the conditions same as those described in Example 1-3 is shown in FIG. 1-33. Based on the integrated value of peak derived from acetyl (—COCH$_3$, 2.3 ppm; 3H) in glucosamine and the integrated value of peak derived from methyl (—CH$_3$, 1.6 ppm; 3H) in ethyl ester of serine, the introduction ratio of serine in HA units was calculated similarly to Example 1-6 (Table 5). In addition, $^1$H-NMR spectrum of the deprotected sample as measured in the conditions same as those described in Example 1-5 is shown in FIG. 1-34. The introduction ratio of cholesteryl group was calculated in the method described in Example 1-5 (Table 5).

TABLE 5

Amount of reagent used in preparation of HA-AA/Chol/FL and introduction ratio

| Abbreviation | Molecular weight | Species and introduction ratio of AA (unit %) | Mol ratio of Chol-C$_6$ hydrochloride and DMT-MM added (HA unit/Chol-C$_6$/DMT-MM) | Introduction ratio of Chol (unit %) | Sum of introduction ratio of AA and Chol |
|---|---|---|---|---|---|
| 99k HA-Ala-Chol-6%/FL | 99k | Ala 90 | 100/7/7 | 6 | 96 |
| 99k HA-Ser-Chol-6%/FL | 99k | Ser 97 | 100/7/7 | 6 | 103 |

Example 1-21

Synthesis of Hyaluronic Acid Derivative with No Fluorescent Label

HA-Ala-Chol, HA-ThrNH$_2$/Chol, HA-SerNH$_2$/Chol, and HA-ValNH$_2$/Chol were obtained as white solid respectively in the methods described in Example 1-4 (Ala), Example 1-5 (ThrNH$_2$), Example 1-15 (SerNH$_2$), and Example 1-18 (ValNH$_2$) except that 5-aminomethylfluoresceine was not added. The introduction ratio of cholesteryl group and the introduction ratio of amino acid and amino acid amide were calculated in the methods same as those described in the corresponding Examples (Table 6).

TABLE 6

Amount of reagent used in preparation of hyaluronic acid derivatives and introduction ratio

| Abbreviation | Molecular weight | Species and introduction ratio of AA(NH$_2$) (unit %) | Mol ratio of Chol-C$_6$ hydrochloride and DMT-MM added (HA unit/Chol-C$_6$/DMT-MM) | Introduction ratio of Chol (unit %) |
|---|---|---|---|---|
| 99k HA-Ala-Chol-3% | 99k | Ala 101 | 100/4/6 | 3 |
| 99k HA-Ala-Chol-6% | 99k | Ala 101 | 100/8/12 | 6 |
| 99k HA-Ala-Chol-14% | 99k | Ala 101 | 100/16/24 | 14 |
| 99k HA-Ala-Chol-26% | 99k | Ala 101 | 100/32/48 | 26 |

TABLE 6-continued

Amount of reagent used in preparation of hyaluronic acid derivatives and introduction ratio

| Abbreviation | Molecular weight | Species and introduction ratio of AA(NH$_2$) (unit %) | Mol ratio of Chol-C$_6$ hydrochloride and DMT-MM added (HA unit/Chol-C$_6$/DMT-MM) | Introduction ratio of Chol (unit %) |
|---|---|---|---|---|
| 99k HA-Ala-Chol-39% | 99k | Ala 101 | 100/48/72 | 39 |
| 10k HA-Ala-Chol-3% | 10k | Ala 104 | 100/4/6 | 3 |
| 10k HA-Ala-Chol-7% | 10k | Ala 104 | 100/8/12 | 7 |
| 10k HA-Ala-Chol-15% | 10k | Ala 104 | 100/16/24 | 15 |
| 10k HA-Ala-Chol-27% | 10k | Ala 104 | 100/32/48 | 27 |
| 10k HA-Ala-Chol-41% | 10k | Ala 104 | 100/48/72 | 41 |
| 99k HA-ThrNH$_2$-Chol-7% | 99k | ThrNH$_2$ 95 | 100/8/8 | 7 |
| 99k HA-ThrNH$_2$-Chol-15% | 99k | ThrNH$_2$ 98 | 100/16/16 | 15 |
| 10k HA-ThrNH$_2$-Chol-8% | 10k | ThrNH$_2$ 100 | 100/8/8 | 8 |
| 10k HA-ThrNH$_2$-Chol-15% | 10k | ThrNH$_2$ 96 | 100/16/16 | 15 |
| 99k HA-SerNH$_2$-Chol-7% | 99k | SerNH$_2$ 91 | 100/8/8 | 7 |
| 99k HA-SerNH$_2$-Chol-15% | 99k | SerNH$_2$ 85 | 100/16/16 | 15 |
| 10k HA-SerNH$_2$-Chol-8% | 10k | SerNH$_2$ 87 | 100/8/8 | 8 |
| 10k HA-SerNH$_2$-Chol-16% | 10k | SerNH$_2$ 85 | 100/16/16 | 16 |
| 99k HA-ValNH$_2$-Chol-6% | 99k | ValNH$_2$ 97 | 100/8/8 | 6 |
| 99k HA-ValNH$_2$-Chol-13% | 99k | ValNH$_2$ 84 | 100/16/16 | 13 |
| 10k HA-ValNH$_2$-Chol-7% | 10k | ValNH$_2$ 93 | 100/8/8 | 7 |
| 10k HA-ValNH$_2$-Chol-14% | 10k | ValNH$_2$ 85 | 100/16/16 | 14 |

Comparative Example 1-1

Synthesis of Fluorescent Labeled HA Derivative Modified with Cholesteryl 6-Aminohexylcarbamate (HA-Chol/FL)

Solutions (10 mg/mL) of HA-TBA synthesized from the starting material HA-Na (10 k, 50 k, 99 kDa) and prepared in Example 1-3 in anhydrous DMSO were prepared. Subsequently, Chol-C$_6$ hydrochloride prepared in Example 1-1 was added to respective solutions at the ratios to HA units shown in Table 7 below. DMT-MM was then added at the ratios to HA units shown in Table 7 below and 5-Aminomethylfluoresceine (FL) hydrochloride (Invitrogen) hydrochloride and DMT-MM were added at 0.04 mol equivalents and 0.07 mol equivalents per HA unit, respectively. The reaction solution was dialyzed against a solution of 0.3 M ammonium acetate/DMSO, an aqueous solution of 0.15 M NaCl, and ultrapure water in this order. The resultant dialysates were freeze-dried to obtain the target products (HA-Chol/FL) as yellow solid.

A representative example of $^1$H-NMR spectrum (the product that is produced from the starting material 99 kDa HA-Na and has an introduction ratio of a cholesteryl group of 6%) in a mixed solution of 0.02 N DCl DMSO-d$_6$/D$_2$O (2 N DCl D$_2$O:DMSO-d$_6$=1:99) as a measurement solvent is shown in FIG. 1-35. The introduction ratio of cholesteryl group in HA units was calculated in the method described in Example 1-4 (Table 7).

TABLE 7

Amount of reagent used in preparation of HA-Chol/FL and introduction ratio

| Abbreviation | Molecular weight | Mol ratio of Chol-C$_6$ hydrochloride and DMT-MM added (HA unit/Chol-C$_6$/DMT-MM) | Introduction ratio of Chol (unit %) |
|---|---|---|---|
| 10k HA-Chol-15%/FL | 10k | 100/17.6/16 | 15 |
| 50k HA-Chol-6%/FL | 50k | 100/6/6 | 6 |
| 50k HA-Chol-20%/FL | 50k | 100/26.4/24 | 20 |
| 50k HA-Chol-27%/FL | 50k | 100/35.2/32 | 27 |
| 99k HA-Chol-6%/FL | 99k | 100/6/6 | 6 |
| 99k HA-Chol-24%/FL | 99k | 100/24/24 | 24 |
| 99k HA-Chol-25%/FL | 99k | 100/35.2/32 | 25 |

Comparative Example 1-2

Synthesis of Fluorescent Labeled HA Derivative Modified with EDOBEA (HA-EDOBEA-Ac/FL)

Solutions (5 mg/mL) of HA-TBA synthesized from the starting material HA-Na (99 kDa) in Example 1-3 in anhydrous DMSO were prepared. Subsequently, EDOBEA and BOP were added in this order at an equivalent ratio of HA unit/BOP (Wako Pure Chemical Industries, Ltd.)/2,2'-(ethylenedioxy)bis(ethylamine) (EDOBEA, Sigma-Aldrich)=1/2.5/50 (mol/mol/mol) and the mixture was stirred at room temperature overnight. The reaction solution was dialyzed against an aqueous solution of 0.3 M NaCl and with ultrapure water in this order, and then freeze-dried to obtain HA-EDOBEA having a high introduction ratio.

$^1$H-NMR spectrum of HA-EDOBEA having a high introduction ratio measured in the conditions same as those described in Example 1-3 is shown in FIG. 1-36. In this measurement, NaOD was added to 0.0046 N to make the solution alkaline. Based on the integrated value of peak derived from acetyl (—COCH$_3$, 2.0 ppm; 3H) in glucosamine and the integrated value of peak derived from methylene (—CH$_2$NH$_2$, 2.8 ppm; 2H) in the EDOBEA terminal, the introduction ratio of EDOBEA in HA units was calculated similarly to Example 1-4 to be 82%.

The obtained HA-EDOBEA having a high introduction ratio was dissolved in ultrapure water at 10 mg/mL, and then was 2 times diluted with 100 mM phosphate buffer (pH 7.4) to prepare a 5 mg/mL solution. A solution of NHS-fluoresceine in DMSO was added to this solution at 0.04 mol equivalents per HA unit and the mixture was stirred at room temperature for 1 hour. The terminal amino of excess EDOBEA was acetylated by adding acetic anhydride (Wako Pure Chemical Industries, Ltd.) at 40 mol equivalents per HA unit and further stirring for 1 hour. The reaction solution was dialyzed in dark with an aqueous solution of 0.3 M NaCl and with ultrapure water in this order, and then freeze-dried to obtain HA-EDOBEA-Ac/FL as yellow solid. $^1$H-NMR spectrum of the product as measured in the same conditions as those described in Example 1-3 is shown in FIG. 1-37.

Comparative Example 1-3

Synthesis of Fluorescent Labeled HA Derivative Modified with L-Tyrosine (Tyr) and Cholesteryl 6-Aminohexylcarbamate (HA-Tyr-Chol/FL)

HA-Tyr was obtained as white solid in a method similar to that of Example 1-4 except that ethyl L-tyrosinate hydrochloride (Wako Pure Chemical Industries, Ltd.) was used instead of ethyl L-alaninate hydrochloride. $^1$H-NMR spectrum measured in the conditions same as those described in Example 1-3 is shown in FIG. 1-38. Based on the integrated value of peak derived from acetyl (—COCH$_3$, 2.0 ppm; 3H) in glucosamine and the integrated value of peaks derived from hydroxyphenyl (—C$_6$H$_4$OH, 6.8, 7.2 ppm; 4H) in tyrosine, the introduction ratio of tyrosine in HA units was calculated similar to Example 1-4 (Table 8). A TBA salt of HA-Tyr (HA-Tyr-TBA) was obtained as white solid in the conditions same as those described in Example 1-4. Then, it was reacted with Chol-C$_6$ hydrochloride and FL in a method similar to that of Example 1-4 to obtain the target (HA-Tyr-Chol/FL) as yellow solid. $^1$H-NMR spectrum measured in the conditions same as those described in Example 1-4 is shown in FIG. 1-39. The introduction ratio of cholesteryl group was calculated in the method described in Example 1-4 (Table 8).

TABLE 8

Amount of reagent used in preparation of HA-Tyr-Chol/FL and introduction ratio

| Abbreviation | Molecular weight | Introduction ratio of Tyr (unit %) | Mol ratio of Chol-C$_6$ hydrochloride and DMT-MM added (HA unit/Chol-C$_6$/DMT-MM) | Introduction ratio of Chol (unit %) |
|---|---|---|---|---|
| 99k HA-Tyr-Chol-6%/FL | 99k | 105 | 100/7/11 | 6 |

Example 2

Confirmation of Retention in the Blood and Biodegradability In Vivo

Example 2-1

Collection of Biological Sample from Rat Given HA Derivative

Single doses of 10 mg/kg of compounds obtained in Examples 1-4 to 1-20 and Comparative Examples 1-1 and 1-3 were intravenously administered to rats. The Jugular vein blood was collected at 5 minutes, 2, 7, 24, 48, 72, 168, 240, and 336 hours after the administration using syringes treated with sodium heparin and the plasma was obtained by centrifugation. Some blood samples in Comparative Examples were collected also at 96 hours after the administration. These plasma samples were cryopreserved at −20° C. or less until the measurement. In addition, the urine was collected using metabolic cages at 0 to 24 hours, 24 to 48 hours, 48 to 72 hours, 72 to 96 hours, 168 to 192 hours, 240 to 264 hours, and 336 to 360 hours after the administration and cryopreserved at −20° C. or less until the measurement. Furthermore, the liver was extracted 15 days after the administration and cryopreserved at −20° C. or less until the measurement. Single doses of 20 mg/kg of the compound obtained in Comparative Example 1-2 was intravenously administered to rats followed by urine collection and the liver extraction.

Example 2-2

Analysis of Plasma of Rat Given HA Derivatives

The plasma samples were thawed and 2 times diluted with HP-β-CD (100 mM)/tris buffer (500 mM, pH 9.0), incubated at 37° C. for 1 hour, and then measured for the concentrations of fluorescent labeled HA derivatives with a 96-well plate reader (ARVO; quantification limit: 0.4 μg/mL). Changes in the plasma concentrations of the fluorescent labeled HA derivatives are shown in FIG. 2-1-1 to FIG. 2-1-26. In addition, a pharmacokinetic parameter (extrapolation of area under the curve of plasma concentration-time (AUC∞)) was analyzed by WinNonlin Ver.6.1 (Pharsight). The values are shown in Table 9. In addition, ratios of AUC∞ to the comparative samples into which cholesterol was introduced at the same level, calculated by the following expression were shown in Table 10.

$$\text{Ratio of } AUC\infty = \frac{AUC\infty \text{ of sample}}{AUC\infty \text{ of corresponding comparative sample}} \quad \text{[Formula 6]}$$

TABLE 9

Pharmacokinetic parameter of fluorescent labeled HA derivatives

| Sample | Fluorescent labeled HA derivative | AUC∞ (µg · hr/mL) |
|---|---|---|
| Sample 2-1 | 99k HA-Ala-Chol-7%/FL | 2460.8 |
| Sample 2-2 | 99k HA-Ala-Chol-24%/FL | 775.6 |
| Sample 2-3 | 99k HA-Ala-Chol-30%/FL | 1557.3 |
| Sample 2-4 | 50k HA-Ala-Chol-6%/FL | 2226.0 |
| Sample 2-5 | 50k HA-Ala-Chol-22%/FL | 594.3 |
| Sample 2-6 | 50k HA-Ala-Chol-26%/FL | 1393.4 |
| Sample 2-7 | 10k HA-Ala-Chol-16%/FL | 1873.0 |
| Sample 2-8 | 99k HA-ThrNH$_2$/Chol-6%/FL | 2819.3 |
| Sample 2-9 | 99k HA-ThrNH$_2$/Chol-24%/FL | 2268.9 |
| Sample 2-10 | 99k HA-ThrNH$_2$/Chol-31%/FL | 3714.0 |
| Sample 2-11 | 99k HA-Ser-Chol-6%/FL | 2853.5 |
| Sample 2-12 | 99k HA-Gly-Chol-6%/FL | 2798.6 |
| Sample 2-13 | 99k HA-Thr-Chol-6%/FL | 1381.3 |
| Sample 2-14 | 99k HA-Asn-Chol-7%/FL | 2978.0 |
| Sample 2-15 | 99k HA-Asp-Chol-6%/FL | 2903.2 |
| Sample 2-16 | 99k HA-Ile-Chol-6%/FL | 2185.0 |
| Sample 2-17 | 99k HA-Leu-Chol-6%/FL | 1834.5 |
| Sample 2-18 | 99k HA-Val-Chol-6%/FL | 1814.7 |
| Sample 2-19 | 99k HA-Phe-Chol-6%/FL | 2879.6 |
| Sample 2-20 | 99k HA-ValNH$_2$/Chol-6%/FL | 2935.3 |
| Sample 2-21 | 99k HA-SerNH$_2$/Chol-6%/FL | 2218.2 |
| Sample 2-22 | 99k HA-LeuNH$_2$/Chol-6%/FL | 2345.1 |
| Sample 2-23 | 99k HA-GlyNH$_2$/Chol-6%/FL | 2011.3 |
| Sample 2-24 | 99k HA-Ala/Chol-6%/FL | 2073.6 |
| Sample 2-25 | 99k HA-Ser/Chol-6%/FL | 1709.5 |
| Comparative Sample 2-1 | 99k HA-Chol-6%/FL | 546.9 |
| Comparative Sample 2-2 | 99k HA-Chol-24%/FL | 161.3 |
| Comparative Sample 2-3 | 99k HA-Chol-25%/FL | 361.4 |
| Comparative Sample 2-4 | 50k HA-Chol-6%/FL | 533.1 |
| Comparative Sample 2-5 | 50k HA-Chol-20%/FL | 199.5 |
| Comparative Sample 2-6 | 50k HA-Chol-27%/FL | 308.1 |
| Comparative Sample 2-7 | 10k HA-Chol-15%/FL | 1696.4 |
| Comparative Sample 2-8 | 99k HA-Tyr-Chol-6%/FL | 403.6 |

TABLE 10

Ratio of AUC∞

| Sample | Fluorescent labeled HA derivative | Comparative sample compared | Ratio to comparative sample |
|---|---|---|---|
| Sample 2-1 | 99k HA-Ala-Chol-7%/FL | Comparative sample 2-1 | 4.5 |
| Sample 2-2 | 99k HA-Ala-Chol-24%/FL | Comparative sample 2-2 | 4.8 |
| Sample 2-3 | 99k HA-Ala-Chol-30%/FL | Comparative sample 2-3 | 4.3 |
| Sample 2-4 | 50k HA-Ala-Chol-6%/FL | Comparative sample 2-4 | 4.2 |
| Sample 2-5 | 50k HA-Ala-Chol-22%/FL | Comparative sample 2-5 | 3.0 |
| Sample 2-6 | 50k HA-Ala-Chol-26%/FL | Comparative sample 2-6 | 4.5 |
| Sample 2-7 | 10k HA-Ala-Chol-16%/FL | Comparative sample 2-7 | 1.1 |
| Sample 2-8 | 99k HA-ThrNH$_2$/Chol-6%/FL | Comparative sample 2-1 | 5.2 |
| Sample 2-9 | 99k HA-ThrNH$_2$/Chol-24%/FL | Comparative sample 2-2 | 14.1 |
| Sample 2-10 | 99k HA-ThrNH$_2$/Chol-31%/FL | Comparative sample 2-3 | 10.3 |
| Sample 2-11 | 99k HA-Ser-Chol-6%/FL | Comparative sample 2-1 | 5.2 |
| Sample 2-12 | 99k HA-Gly-Chol-6%/FL | Comparative sample 2-1 | 5.1 |
| Sample 2-13 | 99k HA-Thr-Chol-6%/FL | Comparative sample 2-1 | 2.5 |
| Sample 2-14 | 99k HA-Asn-Chol-6%/FL | Comparative sample 2-1 | 5.4 |
| Sample 2-15 | 99k HA-Asp-Chol-6%/FL | Comparative sample 2-1 | 5.3 |
| Sample 2-16 | 99k HA-Ile-Chol-6%/FL | Comparative sample 2-1 | 4.0 |
| Sample 2-17 | 99k HA-Leu-Chol-6%/FL | Comparative sample 2-1 | 3.4 |
| Sample 2-18 | 99k HA-Val-Chol-6%/FL | Comparative sample 2-1 | 3.3 |
| Sample 2-19 | 99k HA-Phe-Chol-6%/FL | Comparative sample 2-1 | 5.3 |
| Sample 2-20 | 99k HA-ValNH$_2$/Chol-6%/FL | Comparative sample 2-1 | 5.4 |
| Sample 2-21 | 99k HA-SerNH$_2$/Chol-6%/FL | Comparative sample 2-1 | 4.1 |
| Sample 2-22 | 99k HA-LeuNH$_2$/Chol-6%/FL | Comparative sample 2-1 | 4.3 |
| Sample 2-23 | 99k HA-GlyNH$_2$/Chol-6%/FL | Comparative sample 2-1 | 3.7 |
| Sample 2-24 | 99k HA-Ala/Chol-6%/FL | Comparative sample 2-1 | 3.8 |
| Sample 2-25 | 99k HA-Ser/Chol-6%/FL | Comparative sample 2-1 | 3.1 |
| Comparative sample 2-8 | 99k HA-Tyr-Chol-6%/FL | Comparative sample 2-1 | 0.7 |

The HA derivatives (samples 2-1 to 2-25) in which an amino acid or amino acid amide and a cholesteryl group are introduced into carboxy were revealed to maintain plasma concentrations better than HA derivatives (comparative samples 2-1 to 2-7) in which only a cholesteryl group is introduced into carboxy.

Example 2-3

Analysis of Liver of Rat Having Received HA Derivative

To approximately 1 g of liver sample was added tris buffer (10 mM, pH 9.0) and the sample was homogenized using beads. A solution of 4 mg/mL pronase was added and the mixture was incubated at 37° C. overnight. After centrifugation, the sample was 2 times diluted with HP-β-CD (100 mM)/tris buffer (500 mM, pH 9.0), further incubated at 37° C. for 1 hour, and then filtered. The sample was analyzed by size exclusion chromatography in the following conditions. In addition, the liver from a rat without any sample administration was treated similarly and the mixtures of that and samples before administration were similarly analyzed as a standard.

Conditions of Analysis by Size Exclusion Chromatography
Analysis column: TSKgel G5000 PWXL (Tosoh Corporation)
Column temperature: 25° C.
Mobile phase: HP-β-CD (10 mM)/tris buffer (500 mM, pH 9.0)
Flow rate: 0.5 mL/min
Detection: Ex 494 nm/Em 515 nm
Injection volume: 50 μL The results are shown in FIG. 2-2-1 to FIG. 2-2-27. The chromatograms were normalized with the respective highest peaks. While the HA derivative of Comparative Example 1-2 (HA-EDOBEA-Ac/FL, FIG. 2-2-26) was not found to be turned into lower molecular weight molecules in the liver, all administered compounds of the HA derivatives of the Examples were detected to be turned into lower molecular weight molecules. This indicates that the HA derivatives of the present invention have a biodegradability. After degradation, they are considered to be excreted in urine or feces out of the body.

Example 2-4

Analysis of Urine from Rat Having Received HA Derivative

Urine samples were filtered through a 0.22 μm filter and was 2 times diluted with HP-β-CD (100 mM)/tris buffer (500 mM, pH 9.0). After incubating at 37° C. for 1 hour, filtered, and analyzed by size exclusion chromatography in the conditions described in Example 2-3. In addition, a urine sample from a rat without any sample administration was treated similarly and the mixtures of that and samples before administration were similarly analyzed as a standard.

The results are shown in FIG. 2-3-1 to FIG. 2-3-27. In the figures, chromatograms at the time points in the same scale are shown to the left and those normalized with the highest peaks are shown to the right. Urine samples collected at 0 to 24 hours, 24 to 48 hours, 48 to 72 hours, 72 to 96 hours, 168 to 192 hours, 240 to 264 hours, and 336 to 360 hours after administration are respectively designated as 0-1d, 1-2d, 2-3d, 3-4d, 7-8d, 10-11d and 14-15d, and respective standards as STD in the figures.

While the administered compound of the HA derivative of Comparative Example 1-2 (HA-EDOBEA-Ac/FL) was not found to be turned into lower molecular weight molecules in urine, some of the administered compounds of the HA derivatives of the Examples were detected to be turned into lower molecular weight molecules in urine. This indicates that the biodegradability of the HA derivatives of the present invention can be evaluated easily by examining urine.

Example 3

Synthesis of Hyaluronic Acid Derivative

Example 3-1

Synthesis of Fluorescent Labeled HA Derivative Modified with L-Glutamine (Gln) and Cholesteryl 6-Aminohexylcarbamate (HA-Gln-Chol/FL)

HA-Gln was obtained as white solid in a method similar to that of Example 1-4 except that methyl L-glutaminate hydrochloride (Wako Pure Chemical Industries, Ltd.) was used instead of ethyl L-alaninate hydrochloride. $^1$H-NMR spectrum as measured in the same conditions as those described in Example 1-3 is shown in FIG. 3-1. Based on the integrated value of peak derived from acetyl (—COCH$_3$, 2.0 ppm; 3H) in glucosamine and the integrated value of peaks derived from methylene (—CH$_2$CH$_2$CONH$_2$, 2.3, 2.4 ppm; 2H) in glutamine, the introduction ratio of glutamine in HA units was calculated similarly to Example 1-4 (Table 11). Since the peak derived from acetyl in glucosamine overlaps with the peak of another methylene (—CH$_2$CH$_2$CONH$_2$, 2.1 ppm; 2H) in glutamine, the value obtained by subtracting the integrated value of peaks at 2.3 ppm and 2.4 ppm from the integrated value of peaks at 1.8 to 2.2 ppm was used as peaks derived from acetyl in glucosamine to calculate the introduction ratio. A TBA salt of HA-Gln (HA-Gln-TBA) was obtained as white solid in the conditions same as those described in Example 1-4. Then, it was reacted with Chol-C$_6$ hydrochloride and FL in a method similar to that of Example 1-4 to obtain the target (HA-Gln-Chol/FL) as yellow solid. $^1$H-NMR spectrum measured in the conditions same as those described in Example 1-4 is shown in FIG. 3-2. The introduction ratio of cholesteryl group was calculated in the method described in Example 1-4 (Table 11).

Example 3-2

Synthesis of Fluorescent Labeled HA Derivative Modified with L-Methionine (Met) and Cholesteryl 6-Aminohexylcarbamate (HA-Met-Chol/FL)

HA-Met was obtained as white solid in a method similar to that of Example 1-4 except that ethyl L-methioninate hydrochloride (WATANABE CHEMICAL INDUSTRIES, LTD.) was used instead of ethyl L-alaninate hydrochloride. $^1$H-NMR spectrum as measured in the same conditions as those described in Example 1-3 is shown in FIG. 3-3. Based on the integrated value of peak derived from acetyl (—COCH$_3$, 2.0 ppm; 3H) in glucosamine and the integrated value of peak derived from methylene (—CH$_2$SCH$_3$, 2.6 ppm; 2H) in methionine, the introduction ratio of methionine in HA units was calculated similarly to Example 1-4 (Table 11). Since the peak derived from acetyl in glucosamine overlaps with the peak derived from another methylene and methyl (—CH$_2$CH$_2$SCH$_3$, 2.1 ppm; 5H) in methionine, the value obtained by subtracting 5/2 of the integrated value of the peak at 2.6 ppm from the integrated value of peaks at 1.8 to 2.2 ppm was used as peak derived from acetyl in glucosamine to calculate the introduction ratio.

A TBA salt of HA-Met (HA-Met-TBA) was obtained as white solid in the conditions same as those described in Example 1-4. Then, it was reacted with Chol-C$_6$ hydrochloride and FL in a method similar to that of Example 1-4 to obtain the target (HA-Met-Chol/FL) as yellow solid. $^1$H-NMR spectrum measured in the conditions same as those described in Example 1-4. is shown in FIG. 3-4. The introduction ratio of cholesteryl group was calculated in the method described in Example 1-4 (Table 11).

[Table 11]

TABLE 11

Amount of reagent used in preparation of HA-AA-Chol/FL and introduction ratio

| Abbreviation | Molecular weight | Species and introduction ratio of AA (unit %) | Mol ratio of Chol-$C_6$ hydrochloride and DMT-MM added (HA unit/Chol-$C_6$/DMT-MM) | Introduction ratio of Chol (unit %) |
|---|---|---|---|---|
| 99k HA-Gln-Chol-6%/FL | 99k | Gln 80 | 100/7/11 | 6 |
| 99k HA-Met-Chol-6%/FL | 99k | Met 99 | 100/7/11 | 6 |

Example 3-3

Synthesis of Fluorescent Labeled HA Derivative Modified with L-Alaninamide (AlaNH$_2$) and Cholesteryl 6-Aminohexylcarbamate (HA-AlaNH$_2$/Chol/FL)

HA-AlaNH$_2$-Chol/FL was obtained as yellow solid in a method similar to that of Example 1-5 except that L-alaninamide hydrochloride (Tokyo Chemical Industry Co., Ltd.) was used instead of L-threoninamide hydrochloride. $^1$H-NMR spectrum of the product as measured in the conditions same as those described in Example 1-5 is shown in FIG. 3-5. The introduction ratio of cholesteryl group in HA units was calculated in the same method as that described in Example 1-5 (Table 12). Based on the integrated value of peak derived from acetyl (—COCH$_3$, 1.8 ppm; 3H) in glucosamine and the integrated value of peak derived from methyl (—CH$_3$—, 1.3 ppm; 3H) in alaninamide, the introduction ratio of alaninamide in HA units was calculated similarly to Example 1-5 (Table 12). Since the peak derived from methyl in alaninamide overlaps with the peaks (41H) derived from cholesteryl, the value obtained by subtracting 41/3 of the integrated value of the peak at 0.7 ppm from the integrated value of peaks at 0.8 to 1.6 ppm was used as peak derived from methyl in alaninamide to calculate the introduction ratio.

Example 3-4

Synthesis of Fluorescent Labeled HA Derivative Modified with L-Asparaginamide (AsnNH$_2$) and Cholesteryl 6-Aminohexylcarbamate (HA-AsnNH$_2$/Chol/FL)

HA-AsnNH$_2$-Chol/FL was obtained as yellow solid in a method similar to that of Example 1-5 except that L-asparaginamide hydrochloride (KOKUSAN CHEMICAL Co., Ltd.) was used instead of L-threoninamide hydrochloride. $^1$H-NMR spectrum of the product as measured in the conditions same as those described in Example 1-5 is shown in FIG. 3-6. The introduction ratio of cholesteryl group in HA units was calculated in the same method as that described in Example 1-5 (Table 12). In addition, $^1$H-NMR spectrum of the product as measured in the same conditions as those described in Example 1-3 is shown in FIG. 3-7. Based on the integrated value of peak derived from acetyl (—COCH$_3$, 2.0 ppm; 3H) in glucosamine and the integrated value of peaks derived from methylene (—CH$_2$CONH$_2$, 2.7, 2.8 ppm; 2H) in asparaginamide, the introduction ratio of serinamide in HA units was calculated similarly to Example 1-4 (Table 12).

Example 3-5

Synthesis of Fluorescent Labeled HA Derivative Modified with L-Isoleucinamide (IleNH$_2$) and Cholesteryl 6-Aminohexylcarbamate (HA-IleNH$_2$/Chol/FL)

HA-IleNH$_2$-Chol/FL was obtained as yellow solid in a method similar to that of Example 1-5 except that L-isoleucinamide hydrochloride (Tokyo Chemical Industry Co., Ltd.) was used instead of L-threoninamide hydrochloride. $^1$H-NMR spectrum of the product as measured in the conditions same as those described in Example 1-5 is shown in FIG. 3-8. The introduction ratio of cholesteryl group in HA units was calculated in the same method as that described in Example 1-5 (Table 12). Based on the integrated value of peak derived from acetyl (—COCH$_3$, 1.8 ppm; 3H) in glucosamine and the integrated value of peak derived from methylene and two methyl (—CH(CH$_3$)CH$_2$CH$_3$, 0.9 ppm; 8H) in isoleucinamide, the introduction ratio of isoleucinamide in HA units was calculated similarly to Example 1-4 (Table 3). Since the peak derived from methyl of isoleucinamide overlaps with the peaks (41H) derived from cholesteryl, the value obtained by subtracting 41/3 of the integrated value of the peak at 0.7 ppm from the integrated value of peaks at 0.8 to 1.6 ppm was used as peak derived from methylene in isoleucinamide to calculate the introduction ratio. Since the peak derived from acetyl in glucosamine overlaps with the peak of hydrogen at 3-position of isoleucine (—CH(CH$_3$)CH$_2$CH$_3$, 1.9 ppm; 1H), the value obtained by subtracting ⅛ of the integrated value of peaks at 0.8 to 1.6 ppm from the integrated value of peaks at 1.8 to 2.2 ppm was used as peak derived from acetyl in glucosamine to calculate the introduction ratio.

Example 3-6

Synthesis of Fluorescent Labeled HA Derivative Modified with L-Glutaminamide (GlnNH$_2$) and Cholesteryl 6-Aminohexylcarbamate (HA-GlnNH$_2$/Chol/FL)

HA-GlnNH$_2$-Chol/FL was obtained as yellow solid in a method similar to that of Example 1-5 except that L-glutaminamide hydrochloride (WATANABE CHEMICAL INDUSTRIES, LTD.) was used instead of L-threoninamide hydrochloride. $^1$H-NMR spectrum measured in the conditions same as those described in Example 1-5 is shown in FIG. 3-9. The introduction ratio of cholesteryl group in HA units was calculated in the same method as that described in Example 1-5 (Table 12). Based on the integrated value of peak derived from acetyl (—COCH$_3$, 1.8 ppm; 3H) in glucosamine and the integrated value of peak derived from methylene (—C$\underline{H}_2$CH$_2$CONH$_2$, 2.1 ppm; 2H) in glutaminamide, the introduction ratio of serinamide in HA units was calculated similarly to Example 1-4 (Table 12). Since the peak derived from methyl of glutaminamide overlaps with the peak (2H) derived from cholesteryl, the value obtained by subtracting ⅔ of the integrated value at the peak of 0.7 ppm was used as peak derived from methylene in glutaminamide to calculate the introduction ratio. Since the peak glucosamine and the integrated value of peak derived from methyl (—SCH$_3$, 2.1 ppm; 3H) in methioninamide, the introduction ratio of methioninamide in HA units was calculated similarly to Example 1-4 (Table 12). Since the peak derived from acetyl in glucosamine overlaps with the peak derived from methylene (—CH$_2$SCH$_3$, 1.9 ppm; 2H) in methioninamide, the value obtained by subtracting ⅔ of the integrated value of the peak at 2.1 ppm from the integrated value of peaks at 1.8 to 2.0 ppm was used as peak derived from acetyl in glucosamine to calculate the introduction ratio.

TABLE 12

Amount of reagent used in preparation of HA-AANH$_2$/Chol/FL and introduction ratio

| Abbreviation | Molecular weight | Species and introduction ratio of AANH$_2$ (unit %) | Mol ratio of Chol-C$_6$ hydrochloride and DMT-MM added (HA unit/Chol-C$_6$/DMT-MM) | Introduction ratio of Chol (unit %) | Sum of introduction ratio of AANH$_2$ and Chol |
|---|---|---|---|---|---|
| 99k HA-AlaNH$_2$/Chol-6%/FL | 99k | AlaNH$_2$ 96 | 100/7/7 | 6 | 102 |
| 99k HA-AsnNH$_2$/Chol-6%/FL | 99k | AsnNH$_2$ 85 | 100/7/7 | 6 | 91 |
| 99k HA-IleNH$_2$/Chol-6%/FL | 99k | IleNH$_2$ 93 | 100/7/7 | 6 | 99 |
| 10k HA-IleNH$_2$/Chol-7%/FL | 10k | IleNH$_2$ 93 | 100/7/7 | 7 | 100 |
| 99k HA-GlnNH$_2$/Chol-6%/FL | 99k | GlnNH$_2$ 85 | 100/7/7 | 6 | 91 |
| 99k HA-MetNH$_2$/Chol-6%/FL | 99k | MetNH$_2$ 66 | 100/7/7 | 6 | 72 |
| 10k HA-MetNH$_2$/Chol-7%/FL | 10k | MetNH$_2$ 73 | 100/7/7 | 7 | 80 | derived from acetyl in glucosamine overlaps with the peak derived from methylene (—CH$_2$C$\underline{H}_2$CONH$_2$, 1.9 ppm; 2H) in glutaminamide, the value obtained by subtracting 2/2 of the integrated value of the peak at 2.1 ppm from the integrated value of peaks at 1.8 to 2.0 ppm was used as peak derived from acetyl in glucosamine to calculate the introduction ratio.

Example 3-7

Synthesis of Fluorescent Labeled HA Derivative Modified with L-Methioninamide (MetNH$_2$) and Cholesteryl 6-Aminohexylcarbamate (HA-MetNH$_2$/Chol/FL)

HA-MetNH$_2$-Chol/FL was obtained as yellow solid in a method similar to that of Example 1-5 except that L-methioninamide hydrochloride (WATANABE CHEMICAL INDUSTRIES, LTD.) was used instead of L-threoninamide hydrochloride. $^1$H-NMR spectrum measured in the conditions same as those described in Example 1-5 is shown in FIG. 3-10. The introduction ratio of cholesteryl group in HA units was calculated in the same method as that described in Example 1-5 (Table 12). Based on the integrated value of peak derived from acetyl (—COCH$_3$, 1.8 ppm; 3H) in Comparative Example 3-1

Synthesis of Fluorescent Labeled HA Derivative Modified with L-Glutamic Acid (Glu) and Cholesteryl 6-Aminohexylcarbamate (HA-Glu-Chol/FL)

HA-Glu was obtained as white solid in a method similar to that of Example 1-4 except that diethyl L-glutamate hydrochloride (WATANABE CHEMICAL INDUSTRIES, LTD.) was used instead of ethyl L-alaninate hydrochloride. $^1$H-NMR spectrum as measured in the same conditions as those described in Example 1-3 is shown in FIG. 3-11. Based on the integrated value of peak derived from acetyl (—COCH$_3$, 2.0 ppm; 3H) in glucosamine and the integrated value of peak derived from methylene (—CH$_2$C$\underline{H}_2$COOH, 2.4 ppm; 2H) in glutamic acid, the introduction ratio of glutamic acid in HA units was calculated similarly to Example 1-4 (Table 13). Since the peak derived from acetyl of glucosamine overlaps with the peak another methylene (—C$\underline{H}_2$CH$_2$COOH, 2.1 ppm; 2H) derived from glutamic acid, the value obtained by subtracting the integrated value of the peak at 2.4 ppm from the integrated value of peaks at 1.8 to 2.2 ppm was used as peak derived from acetyl in glucosamine to calculate the introduction ratio. A TBA salt of HA-Glu (HA-Glu-TBA) was obtained as white solid in the conditions same as those described in Example 1-4. Then, it was reacted with Chol-C$_6$ hydrochloride and FL in a method similar to that of Example 1-4 to obtain the target (HA-Glu-Chol/FL) as yellow solid. $^1$H-NMR spectrum measured in the conditions same as those described in Example 1-4 is shown in FIG. 3-12. The introduction ratio of cholesteryl group was calculated in the method described in Example 1-4 (Table 13).

Comparative Example 3-2

Synthesis of Fluorescent Labeled HA Derivative Modified with L-Tryptophan (Trp) and Cholesteryl 6-Aminohexylcarbamate (HA-Trp-Chol/FL)

HA-Trp was obtained as white solid in a method similar to that of Example 1-4 except that ethyl L-tryptophanate hydrochloride (WATANABE CHEMICAL INDUSTRIES, LTD.) was used instead of ethyl L-alaninate hydrochloride. $^1$H-NMR spectrum as measured in the same conditions as those described in Example 1-3 is shown in FIG. 3-13. Based on the integrated value of peak derived from acetyl (—COCH$_3$, 2.0 ppm; 3H) in glucosamine and the integrated value of peak derived from indole ring (—C$_8$H$_6$N, 7.8 ppm; 1H) in tryptophan, the introduction ratio of tryptophan in HA unit was calculated similarly to Example 1-4 (Table 13). A TBA salt of HA-Trp (HA-Trp-TBA) was obtained as white solid in the conditions same as those described in Example 1-4. Then, it was reacted with Chol-C$_6$ hydrochloride and FL in a method similar to that of Example 1-4 to obtain the target (HA-Trp-Chol/FL) as yellow solid. $^1$H-NMR spectrum measured in the conditions same as those described in Example 1-4 is shown in FIG. 3-14. The introduction ratio of cholesteryl group was calculated in the method described in Example 1-4 (Table 13).

Comparative Example 3-3

Synthesis of Fluorescent Labeled HA Derivative Modified with L-Tyrosine (Tyr) and Cholesteryl 6-Aminohexylcarbamate (HA-Tyr-Chol/FL)

10 k HA-Tyr-Chol/FL was obtained as yellow solid in a method similar to that of Comparative Example 1-3 except that HA-TBA produced from the starting material 10 kDa HA-Na was used. The introduction ratio of tyrosine and a cholesteryl group was calculated by a method similar to that of Comparative Example 1-3 (Table 13).

TABLE 13

Amount of reagent used in preparation of HA-AA-Chol/FL and introduction ratio

| Abbreviation | Molecular weight | Species and introduction ratio of AA (unit %) | Mol ratio of Chol-C$_6$ hydrochloride and DMT-MM added (HA unit/Chol-C$_6$/DMT-MM) | Introduction ratio of Chol (unit %) |
|---|---|---|---|---|
| 99k HA-Glu-Chol-6%/FL | 99k | Glu 100 | 100/7/11 | 6 |
| 99k HA-Trp-Chol-6%/FL | 99k | Trp 101 | 100/7/11 | 6 |
| 10k HA-Tyr-Chol-7%/FL | 10k | Tyr 103 | 100/7/11 | 7 |

Example 3-8

Synthesis of Hyaluronic Acid Derivative Having No Fluorescent Label

Hyaluronic acid derivatives were obtained as white solid in methods described in Example 1-4 to Example 1-18 and Example 3-1 to Example 3-7 and Comparative Example 3-1 to Comparative Example 3-3 except that 5-aminomethylfluoresceine was not added and HA-Na having a different molecular weight was used as a start material. The introduction ratio of cholesteryl group and the introduction ratio of amino acid and amino acid amide were calculated in methods same as those described in the corresponding Examples (Table 14-1, Table 14-2). The 5 kDa hyaluronic acid used as a starting material was from R&D Systems, Inc. and the other hyaluronic acids used as starting materials were from Shiseido Co. Ltd.

TABLE 14-1

Amount of reagent used in preparation of hyaluronic acid derivative and introduction ratio

| Abbreviation | Molecular weight | Species and introduction ratio of AA(NH$_2$) (unit %) | Mol ratio of Chol-C$_6$ hydrochloride and DMT-MM added (HA unit/Chol-C$_6$/DMT-MM) | Introduction ratio of Chol (unit %) |
|---|---|---|---|---|
| 10k HA-Ala-Chol-30% | 10k | Ala 102 | 100/32/48 | 30 |
| 5k HA-Ala-Chol-13% | 5k | Ala 108 | 100/14/21 | 13 |
| 230k HA-Ala-Chol-5% | 230k | Ala 103 | 100/7/11 | 5 |
| 230k HA-Ala-Chol-23% | 230k | Ala 103 | 100/32/48 | 23 |
| 1058k HA-Ala-Chol-5% | 1058k | Ala 104 | 100/7/11 | 5 |
| 1058k HA-Ala-Chol-21% | 1058k | Ala 104 | 100/32/48 | 21 |
| 10k HA-Ser-Chol-28% | 10k | Ser 99 | 100/32/48 | 28 |
| 10k HA-Gly-Chol-32% | 10k | Gly 95 | 100/32/48 | 32 |

TABLE 14-1-continued

Amount of reagent used in preparation of hyaluronic acid derivative and introduction ratio

| Abbreviation | Molecular weight | Species and introduction ratio of AA(NH$_2$) (unit %) | Mol ratio of Chol-C$_6$ hydrochloride and DMT-MM added (HA unit/Chol-C$_6$/DMT-MM) | Introduction ratio of Chol (unit %) |
|---|---|---|---|---|
| 10k HA-Thr-Chol-32% | 10k | Thr 104 | 100/32/48 | 32 |
| 10k HA-Asn-Chol-20% | 10k | Asn 91 | 100/32/48 | 20 |
| 10k HA-Asp-Chol-32% | 10k | Asp 95 | 100/32/48 | 32 |
| 10k HA-Phe-Chol-31% | 10k | Phe 103 | 100/32/48 | 31 |
| 10k HA-Tyr-Chol-32% | 10k | Tyr 103 | 100/32/48 | 32 |
| 10k HA-Ile-Chol-28% | 10k | Ile 101 | 100/32/48 | 28 |
| 10k HA-Leu-Chol-31% | 10k | Leu 88 | 100/32/48 | 31 |
| 10k HA-Val-Chol-32% | 10k | Val 103 | 100/32/48 | 32 |
| 10k HA-Trp-Chol-24% | 10k | Trp 107 | 100/32/48 | 24 |
| 10k HA-Gln-Chol-32% | 10k | Gln 81 | 100/32/48 | 32 |
| 10k HA-Glu-Chol-32% | 10k | Glu 103 | 100/32/48 | 32 |

TABLE 14-2

Amount of reagent used in preparation of hyaluronic acid derivative and introduction ratio

| Abbreviation | Molecular weight | Species and introduction ratio of AA(NH$_2$) (unit %) | Mol ratio of Chol-C$_6$ hydrochloride and DMT-MM added (HA unit/Chol-C$_6$/DMT-MM) | Introduction ratio of Chol (unit %) |
|---|---|---|---|---|
| 10k HA-AlaNH$_2$/Chol-27% | 10k | AlaNH$_2$ 75 | 100/32/32 | 27 |
| 10k HA-SerNH$_2$/Chol-25% | 10k | SerNH$_2$ 68 | 100/32/32 | 25 |
| 10k HA-GlyNH$_2$/Chol-30% | 10k | GlyNH$_2$ 65 | 100/32/32 | 29 |
| 10k HA-ThrNH$_2$/Chol-25% | 10k | ThrNH$_2$ 79 | 100/32/32 | 25 |
| 10k HA-AsnNH$_2$/Chol-26% | 10k | AsnNH$_2$ 66 | 100/32/32 | 26 |
| 10k HA-IleNH$_2$/Chol-23% | 10k | IleNH$_2$ 77 | 100/32/32 | 23 |
| 10k HA-LeuNH$_2$/Chol-23% | 10k | LeuNH$_2$ 76 | 100/32/32 | 23 |
| 10k HA-ValNH$_2$/Chol-23% | 10k | ValNH$_2$ 80 | 100/32/32 | 23 |
| 10k HA-GlnNH$_2$/Chol-28% | 10k | GlnNH$_2$ 70 | 100/32/32 | 28 |
| 10k HA-MetNH$_2$/Chol-27% | 10k | MetNH$_2$ 58 | 100/32/32 | 27 |
| 10k HA-AlaNH$_2$/Chol-8% | 10k | AlaNH$_2$ 97 | 100/8/10 | 8 |
| 10k HA-SerNH$_2$/Chol-8% | 10k | SerNH$_2$ 85 | 100/8/10 | 8 |
| 10k HA-GlyNH$_2$/Chol-8% | 10k | GlyNH$_2$ 86 | 100/8/10 | 8 |
| 10k HA-ThrNH$_2$/Chol-8% | 10k | ThrNH$_2$ 97 | 100/8/10 | 8 |
| 10k HA-AsnNH$_2$/Chol-8% | 10k | AsnNH$_2$ 90 | 100/8/10 | 8 |
| 10k HA-IleNH$_2$/Chol-8% | 10k | IleNH$_2$ 91 | 100/8/10 | 8 |

TABLE 14-2-continued

Amount of reagent used in preparation of hyaluronic acid derivative and introduction ratio

| Abbreviation | Molecular weight | Species and introduction ratio of AA(NH$_2$) (unit %) | Mol ratio of Chol-C$_6$ hydrochloride and DMT-MM added (HA unit/Chol-C$_6$/DMT-MM) | Introduction ratio of Chol (unit %) |
|---|---|---|---|---|
| 10k HA-LeuNH$_2$/Chol-8% | 10k | LeuNH$_2$ 92 | 100/8/10 | 8 |
| 10k HA-ValNH$_2$/Chol-8% | 10k | ValNH$_2$ 95 | 100/8/10 | 8 |
| 10k HA-GlnNH$_2$/Chol-8% | 10k | GlnNH$_2$ 87 | 100/8/10 | 8 |
| 10k HA-MetNH$_2$/Chol-8% | 10k | MetNH$_2$ 83 | 100/8/10 | 8 |

Example 4

Confirmation of In Vivo Retention in Blood and Biodegradability

Example 4-1

Collection of Biological Sample from Rat Having Received HA Derivative

The compounds obtained in Examples 3-1 to 3-7 and Comparative Examples 3-1 to 3-3 were intravenously administered to rats in a single dose of 10 mg/kg. The Jugular vein blood was collected at 5 minutes, 2, 7, 24, 48, 72, and 168 hours after the administration using syringes treated with sodium heparin and the plasma was obtained by centrifugation. Some blood samples in Comparative Examples were collected also at 96 hours after the administration. These plasma samples were cryopreserved at −20° C. or less until the measurement. The liver was extracted 7 days after the administration and cryopreserved at −20° C. or less until the measurement.

Example 4-2

Analysis of Plasma from Rat Having Received HA Derivative

The plasma samples were thawed and 2 times diluted with HP-β-CD (100 mM)/tris buffer (500 mM, pH 9.0), incubated at 37° C. for 1 hour, and then measured for the concentrations of fluorescent labeled HA derivatives with a 96-well plate reader (ARVO; quantification limit: 0.4 μg/mL).

Changes in the plasma concentrations of the fluorescent labeled HA derivatives are shown in FIG. 4-1-1 to FIG. 4-1-10. In addition, a pharmacokinetic parameter (extrapolation of area under the curve of plasma concentration-time (AUC∞)) was analyzed by WinNonlin Ver.6.1 (Pharsight). The values are shown in Table 15. In addition, ratios of AUC∞ to the comparative samples into which cholesterol was introduced at the same level, as calculated by the following expression, were shown in Table 16.

[Formula 7]
$$\text{Ratio of } AUC\infty = \frac{AUC\infty \text{ of sample}}{AUC\infty \text{ of corresponding comparative sample}}$$

TABLE 15

Pharmacokinetic parameter of fluorescent labeled HA derivative

| Sample | Fluorescent labeled HA derivative | AUC∞ (μg · hr/mL) |
|---|---|---|
| Sample 4-1 | 99k HA-Gln-Chol-6%/FL | 2083.1 |
| Sample 4-2 | 99k HA-Met-Chol-6%/FL | 2774.9 |
| Sample 4-3 | 99k HA-AlaNH$_2$/Chol-6%/FL | 1446.8 |
| Sample 4-4 | 99k HA-AsnNH$_2$/Chol-6%/FL | 1800.2 |
| Sample 4-5 | 99k HA-IleNH$_2$/Chol-6%/FL | 1263.8 |
| Sample 4-6 | 99k HA-GlnNH$_2$/Chol-6%/FL | 1094.1 |
| Sample 4-7 | 99k HA-MetNH$_2$/Chol-6%/FL | 1555.5 |
| Comparative sample 4-1 | 99k HA-Glu-Chol-6%/FL | 546.8 |
| Comparative sample 4-2 | 99k HA-Trp-Chol-6%/FL | 284.3 |
| Comparative sample 4-3 | 10k HA-Tyr-Chol-7%/FL | 654.7 |

TABLE 16

Ratio of AUC∞

| Sample | Fluorescent labeled HA derivative | Comparative sample compared | Ratio to comparative sample |
|---|---|---|---|
| Sample 4-1 | 99k HA-Gln-Chol-6%/FL | Comparative sample 2-1 | 3.8 |
| Sample 4-2 | 99k HA-Met-Chol-6%/FL | Comparative sample 2-1 | 5.1 |
| Sample 4-3 | 99k HA-AlaNH$_2$/Chol-6%/FL | Comparative sample 2-1 | 2.6 |
| Sample 4-4 | 99k HA-AsnNH$_2$/Chol-6%/FL | Comparative sample 2-1 | 3.3 |
| Sample 4-5 | 99k HA-IleNH$_2$/Chol-6%/FL | Comparative sample 2-1 | 2.3 |
| Sample 4-6 | 99k HA-GlnNH$_2$/Chol-6%/FL | Comparative sample 2-1 | 2.0 |
| Sample 4-7 | 99k HA-MetNH$_2$/Chol-6%/FL | Comparative sample 2-1 | 2.8 |
| Comparative sample 4-1 | 99k HA-Glu-Chol-6%/FL | Comparative sample 2-1 | 1.0 |

TABLE 16-continued

| | | | Ratio of AUC∞ |
|---|---|---|---|
| Sample | Fluorescent labeled HA derivative | Comparative sample compared | Ratio to comparative sample |
| Comparative sample 4-2 | 99k HA-Trp-Chol-6%/FL | Comparative sample 2-1 | 0.5 |
| Comparative sample 4-3 | 10k HA-Tyr-Chol-7%/FL | Comparative sample 2-7 | 0.4 |

The HA derivatives (samples 4-1 to 4-7) in which an amino acid or amino acid amide and a cholesteryl group are introduced into carboxy were revealed to maintain plasma concentrations better than the HA derivative (comparative sample 2-1) in which only a cholesteryl group is introduced into carboxy. 10 k HA-Tyr-Chol-7%/FL (comparative sample 4-3) as well as 99 k HA-Tyr-Chol-6%/FL (comparative sample 2-8) had decreased retention in the blood in comparison with the HA derivative in which only a cholesteryl group is introduced into carboxy. On the other hand, 99 k HA-Ala-Chol-7%/FL (sample 2-1) and 10 k HA-Ala-Chol-16%/FL (sample 2-7) both maintained plasma concentrations in equal to or better than the HA derivative in which only a cholesteryl group is introduced into carboxy. This suggests that difference in the retention in the blood of HA derivatives dependent on the difference of the amino acid introduced into carboxy is not influenced by (not dependent on) the molecular weight of the starting material hyaluronic acid.

Example 4-3

Analysis of Liver from Rat Having Received HA Derivative

To approximately 1 g of liver sample was added tris buffer (10 mM, pH 9.0) and the sample was homogenized using beads. A solution of 4 mg/mL pronase was added and the mixture was incubated at 37° C. overnight. After centrifugation, the sample was 2 times diluted with HP-β-CD (100 mM)/tris buffer (500 mM, pH 9.0), further incubated at 37° C. for 1 hour, then filtered, and analyzed by size exclusion chromatography in the conditions described below. In addition, the liver from a rat without any sample administration was treated similarly and the mixtures of that and samples before administration were similarly analyzed as a standard.

Conditions of Analysis by Size Exclusion Chromatography

Analysis column: TSKgel G5000PWXL (Tosoh Corporation)
Column temperature: 25° C.
Mobile phase: HP-β-CD (10 mM)/tris buffer (50 mM, pH 9.0)
Flow rate: 0.5 mL/min
Detection: Ex 494 nm/Em 515 nm
Injection volume: 50 µL
The results are shown in FIG. 4-2-1 to FIG. 4-2-10.
The chromatograms were normalized with the respective highest peaks. While the HA derivative of Comparative Example 1-2 (HA-EDOBEA-Ac/FL, FIG. 2-2-26) was not found to be turned into lower molecular weight molecules in the liver, all administered compounds of the HA derivatives of the Examples were detected to be turned into lower molecular weight molecules. Based on these, it is considered that the HA derivatives of the present invention have a biodegradability and are excreted in urine or feces out of the body after degradation in the body.

Example 5

Controlled Release Formulation Having Precipitation Property Responsive to Salt Concentration Example 5-1

Synthesis of Fluorescent Labeled HA Derivative Modified with L-Tyrosinamide (TyrNH$_2$) and Cholesteryl 6-Aminohexylcarbamate (HA-TyrNH$_2$/Chol/FL)

HA-TyrNH$_2$-Chol/FL was obtained as a yellow solution in a method similar to that of Example 1-5 except that L-tyrosinamide hydrochloride (WATANABE CHEMICAL INDUSTRIES, LTD.) was used instead of L-threoninamide hydrochloride. $^1$H-NMR spectrum of the product obtained by measuring a freeze-dried product in the conditions same as those described in Example 1-5 is shown in FIG. 5-1. The introduction ratio of cholesteryl group in HA units was calculated in the same method as that described in Example 1-5 (Table 17). Based on the integrated value of peak derived from acetyl (—COCH$_3$, 1.8 ppm; 3H) in glucosamine and the integrated value of peaks derived from hydroxyphenyl (—C$_6$H$_4$OH, 6.8, 7.2 ppm; 4H) in tyrosine, the introduction ratio of tyrosinamide in HA units was calculated similarly to Example 1-4 (Table 17).

Example 5-2

Synthesis of Fluorescent Labeled HA Derivative Modified with L-Tryptophanamide (TrpNH$_2$) and Cholesteryl 6-Aminohexylcarbamate (HA-TrpNH$_2$/Chol/FL)

HA-TrpNH$_2$-Chol/FL was obtained as a yellow solution in a method similar to that of Example 1-5 except that L-tryptophanamide hydrochloride (WATANABE CHEMICAL INDUSTRIES, LTD.) was used instead of L-threoninamide hydrochloride. $^1$H-NMR spectrum of the product obtained by measuring a freeze-dried product in the conditions same as those described in Example 1-5 is shown in FIG. 5-2. The introduction ratio of cholesteryl group in HA units was calculated in the same method as that described in Example 1-5 (Table 17). Based on the integrated value of peak derived from acetyl (—COCH$_3$, 1.8 ppm; 3H) in glucosamine and the integrated value of peak derived from the indole ring (—C$_8$H$_6$N, 7.6 ppm; 1H) in tryptophanamide, the introduction ratio of tryptophanamide in HA units was calculated similarly to Example 1-4 (Table 17).

Example 5-3

Synthesis of Fluorescent Labeled HA Derivative Modified with L-Phenylalaninamide (PheNH$_2$) and Cholesteryl 6-Aminohexylcarbamate (HA-PheNH$_2$/Chol/FL)

HA-PheNH$_2$-Chol/FL was obtained as a yellow solution in a method similar to that of Example 1-5 except that L-phenylalaninamide hydrochloride (WATANABE CHEMICAL INDUSTRIES, LTD.) was used instead of L-threoninamide hydrochloride. $^1$H-NMR spectrum of the product obtained by measuring a freeze-dried product in the conditions same as those described in Example 1-5 is shown in FIG. 5-3. The introduction ratio of cholesteryl group in HA units was calculated in the same method as that described in Example 1-5 (Table 17). Based on the integrated value of peak derived from acetyl (—COCH$_3$, 1.8 ppm; 3H) in glucosamine and the integrated value of peaks derived from phenyl (—C$_6$H$_5$, 7.2 to 7.4 ppm; 5H) in phenylalanine, the introduction ratio of phenylalaninamide in HA units was calculated similarly to Example 1-4 (Table 17)

TABLE 17

Amount of reagent used in preparation of HA-AANH$_2$/Chol/FL and introduction ratio

| Abbreviation | Molecular weight | Species and introduction ratio of AANH$_2$ (unit %) | Mol ratio of Chol-C$_6$ hydrochloride and DMT-MM added (HA unit/Chol-C$_6$/DMT-MM) | Introduction ratio of Chol (unit %) | Sum of introduction ratio of AANH$_2$ and Chol |
|---|---|---|---|---|---|
| 99k HA-TyrNH$_2$/Chol-6%/FL | 99k | TyrNH$_2$ 85 | 100/7/7 | 6 | 91 |
| 10k HA-TyrNH$_2$/Chol-5%/FL | 10k | TyrNH$_2$ 82 | 100/5/5 | 5 | 87 |
| 99k HA-TrpNH$_2$/Chol-6%/FL | 99k | TrpNH$_2$ 83 | 100/7/7 | 6 | 89 |
| 99k HA-PheNH$_2$/Chol-6%/FL | 99k | PheNH$_2$ 85 | 100/7/7 | 6 | 91 |
| 10k HA-PheNH$_2$/Chol-5%/FL | 10k | PheNH$_2$ 83 | 100/5/5 | 5 | 88 |

Comparative Example 5-1

Synthesis of HA Derivative (HA-TyrNH$_2$) Modified with L-Tyrosinamide (TyrNH$_2$)

A solution of HA-TBA (99 kDa) synthesized from the starting material HA-Na in Example 1-3 in anhydrous DMSO was prepared. Subsequently, L-tyrosinamide hydrochloride (WATANABE CHEMICAL INDUSTRIES, LTD.) was added at 5 mole equivalents per HA unit. 4-(4,6-Dimethoxy-1,3,5-triazin-2-yl)-4-methylmorpholinium chloride (DMT-MM) was then added at 3 mole equivalents per HA unit. The mixture was stirred at room temperature overnight. The reaction solution was dialyzed against an aqueous solution of 0.15 M NaCl and with ultrapure water in this order. Precipitation occurred during dialysis and the target was not obtained as an aqueous solution.

Comparative Example 5-2

Synthesis of e HA Derivative (HA-TrpNH$_2$) Modified with L-Tryptophanamide (TrpNH$_2$)

The synthesis was carried out in a method similar to that of Comparative Example 5-1 except that L-tryptophanamide hydrochloride (WATANABE CHEMICAL INDUSTRIES, LTD.) was used instead of L-tyrosinamide hydrochloride. Precipitation occurred during dialysis and the target was not obtained as an aqueous solution.

Comparative Example 5-3

Synthesis of HA Derivative (HA-PheNH$_2$) Modified with L-Phenylalaninamide (PheNH$_2$)

The synthesis was carried out in a method similar to that of Comparative Example 5-1 except that L-phenylalaninamide hydrochloride (WATANABE CHEMICAL INDUSTRIES, LTD.) was used instead of L-tyrosinamide hydrochloride. HA-PheNH$_2$ was obtained as white solid.

Example 5-4)

The dissolution properties of the HA derivatives synthesized in Example 5-1, Example 5-2, Comparative Example 5-1, and Comparative Example 5-2 after dialysis against water are shown in Table 18.

TABLE 18

Dissolution property of HA derivative to water

| Sample | HA derivative | Dissolution property |
|---|---|---|
| Sample 5-1 | 99k HA-TyrNH$_2$/Chol-6%/FL | Dissolved |
| Sample 5-2 | 99k HA-TrpNH$_2$/Chol-6%/FL | Dissolved |
| Comparative sample 5-1 | 99k HA-TyrNH$_2$ | Not dissolved |
| Comparative sample 5-2 | 99k HA-TrpNH$_2$ | Not dissolved |

It was found that sample 5-1 and sample 5-2, in which a steryl group was introduced, are more dispersed in water than comparative sample 5-1 and comparative sample 5-2, in which no steryl group is introduced, in spite of the hydrophobicity that the steryl group has.

Example 5-5

Evaluation of Precipitation Property Dependent on Salt Concentration

To aqueous (ultrapure water) solutions of HA derivatives (99 k HA-TyrNH$_2$/Chol-6%/FL, 99 k HA-TrpNH$_2$/Chol-6%/FL, 99 k HA-PheNH$_2$/Chol-6%/FL, 99 k HA-AlaNH$_2$/Chol-6%/FL) obtained in Example 5-1, Example 5-2, Example 5-3, and Example 3-3 was added a concentrated buffer solution so that the final composition of the buffer solutions be 10 mM PB and 150 mM NaCl and the concentration of the HA derivatives be 4.5 mg/mL. The solutions were incubated at 37° C. for 20 minutes and centrifuged at 2000 G for 1 minute. The supernatants were measured for fluorescence intensity with a 96-well plate reader (ARVO). The concentrations of fluorescent labeled HA derivatives were calculated using a standard to calculate the percentages of residual to the initial amounts used (Table 19) 99 k HA-Chol-6%/FL (comparative sample 5-3) obtained in Comparative Example 1-1 was subjected to similar operations. The results of comparative samples 5-1 and 5-2 are the results described in WO2010/053140.

TABLE 19

Amount of residual of HA derivative in condition at 150 mM NaCl

| Sample | Fluorescent labeled HA derivative | Amount of residual at 150 mM NaCl |
| --- | --- | --- |
| Sample 5-1 | 99k HA-TyrNH$_2$/Chol-6%/FL | 1.4% |
| Sample 5-2 | 99k HA-TrpNH$_2$/Chol-6%/FL | 3.9% |
| Sample 5-3 | 99k HA-PheNH$_2$/Chol-6%/FL | 1% or less |
| Sample 5-4 | 99k HA-AlaNH$_2$/Chol-6%/FL | 98.9% |
| Comparative sample 5-1 | 50k HA-Chol-6%/FL | 99.6% |
| Comparative sample 5-2 | 50k HA-Chol-7%/FL | 22.6% |
| Comparative sample 5-3 | 99k HA-Chol-6%/FL | 98.4% |

WO2010/053140 discloses that 50 k HA-Chol-6%/FL (comparative sample 5-1) is dissolved both in low salt concentration conditions (ultrapure water) and at a physiological salt concentration (150 mM NaCl). It was also shown by this experiment that 99 k HA-Chol-6%/FL (comparative sample 5-3) also shows similar behavior. Meanwhile, it was confirmed that 99 k HA-PheNH$_2$/Chol-6%/FL (sample 5-3) shows salt concentration-dependent behavior in which it is dissolved in conditions at low salt concentrations (ultrapure water) and precipitated at a physiological salt concentration (150 mM NaCl). This result suggests possible use of a HA derivative of the present invention as a carrier in formulations that precipitate under the skin after administration, by preparation of low salt concentration solutions made isotonic with sugar or the like. In addition, the precipitation performance (amount of residual: 1% or less) was significantly higher than values previously reported on HA derivatives (comparative sample 5-2: 50 k HA-Chol-7%/FL: 22.6%).

99 k HA-TyrNH$_2$/Chol-6%/FL (sample 5-1) and 99 k HA-TrpNH$_2$/Chol-6%/FL (sample 5-2) also show salt concentration-dependent precipitation behavior similarly to 99 k HA-TrpNH$_2$/Chol-6%/FL (sample 5-3) and were shown to be useful in formulations having a salt concentration-dependent precipitation property.

Example 5-6

Evaluation of Precipitation Property Under Skin in Rat

Compounds obtained from fluorescent labeled HA derivatives (99 k HA-TyrNH$_2$/Chol-6%/FL, 99 k HA-TrpNH$_2$/Chol-6%/FL, and 99 k HA-PheNH$_2$/Chol-6%/FL) obtained in Example 5-1, Example 5-2, and Example 5-3 were subcutaneously administered to rats at a single dose (sucrose solution) of 10 mg/kg. The sites of administration were checked 7 days after the administration. It was confirmed that the fluorescent labeled HA derivatives were precipitated and remained.

Example 5-7

Synthesis of Hyaluronic Acid Derivative Having No Fluorescent Label

Hyaluronic acid derivatives were obtained as white solid in methods described in Example 5-1 to Example 5-3 except that 5-aminomethylfluoresceine was not added and HA-Na having a different molecular weight was used as a starting material. The introduction ratio of cholesteryl group and the introduction ratio of amino acid and amino acid amide were calculated in methods same as those described in the corresponding Examples (Table 20).

TABLE 20

Amount of reagent used in preparation of hyaluronic acid derivative and introduction ratio

| Abbreviation | Molecular weight | Species and introduction ratio of AA(NH$_2$) (unit %) | Mol ratio of Chol-C$_6$ hydrochloride and DMT-MM added (HA unit/Chol-C$_6$/DMT-MM) | Introduction ratio of Chol (unit %) |
| --- | --- | --- | --- | --- |
| 10k HA-PheNH$_2$/Chol-25% | 10k | PheNH$_2$ 68 | 100/32/32 | 25 |
| 10k HA-TyrNH$_2$/Chol-15% | 10k | TyrNH$_2$ 79 | 100/32/32 | 15 |

TABLE 20-continued

Amount of reagent used in preparation of hyaluronic acid derivative and introduction ratio

| Abbreviation | Molecular weight | Species and introduction ratio of AA(NH$_2$) (unit %) | Mol ratio of Chol-C$_6$ hydrochloride and DMT-MM added (HA unit/Chol-C$_6$/DMT-MM) | Introduction ratio of Chol (unit %) |
|---|---|---|---|---|
| 10k HA-PheNH$_2$/Chol-4% | 10k | PheNH$_2$ 98 | 100/8/10 | 4 |
| 10k HA-TyrNH$_2$/Chol-1% | 10k | TyrNH$_2$ 100 | 100/8/10 | 1 |

Example 6

Evaluation of Drug-Encapsulating Capacity

Example 6-1

Encapsulation of Paclitaxel (PTX)

To the aqueous (ultrapure water) solutions of the HA derivatives obtained in Example 1-4 and Example 1-21 and Example 3-8 and Example 5-7 was added Paclitaxel (10 mg/ml, solution in methanol) so that the final paclitaxel concentration be 100 μg/mL and the concentration of the HA derivatives be 1.0 mg/mL. The mixtures were left to stand at 4° C. overnight and then centrifuged at 4700 G for 10 minutes. To 100 μL aliquots of the supernatants were added 100 μL of 50% acetonitrile and 50 μL of 100 mM HP-β-CD and the mixtures were analyzed by reversed phase chromatography in the following conditions.

Conditions of Analysis by Reversed Phase Chromatography
Analysis column: PLRP-S 1,000 Å (Agilent), Column temperature: 40° C.
Mobile phase A: 0.1% TFA aqueous solution, Mobile phase B: 0.1% TFA acetonitrile solution
Gradient: B 5%→B 95% (3.4 minutes)
Flow rate: 2 mL/min
Detection: UV 254 nm
Injection volume: 30 μL The paclitaxel concentrations in the supernatants calculated using a standard are shown in FIG. 6-1-1 to FIG. 6-1-4. While the solubility of paclitaxel in the absence of HA derivatives is 0.6 μg/mL, improvement of the solubility of paclitaxel was confirmed significantly in the presence of HA derivatives. This suggests that poorly soluble low molecular weight compounds such as paclitaxel are encapsulated in HA derivatives.

Example 6-2

Encapsulation of Cyclosporine (Cyclosporin A: CyA)

To the aqueous (ultrapure water) solutions of the HA derivatives obtained in Example 1-4 and Example 1-21 and Example 3-8 and Example 5-7 was added cyclosporine (10 mg/ml, solution in methanol) so that the final cyclosporine concentration be 300 μg/mL and the concentration of HA derivatives be 1.0 mg/mL. The mixtures were left to stand at 4° C. overnight and then centrifuged at 4700 G for 30 minutes. To 100 μL aliquots of the supernatants were added 100 μL of 50% acetonitrile and 50 μL of 100 mM HP-β-CD and the mixtures were analyzed by reversed phase chromatography in the conditions described in Example 6-1. The detection was done at UV 210 nm. The cyclosporine concentrations in the supernatants calculated using a standard are shown in FIG. 6-2-1 to FIG. 6-2-4. While the solubility of cyclosporine in the absence of HA derivatives is 28 μg/mL, improvement of the solubility of cyclosporine was confirmed significantly in the presence of HA derivatives. This suggests that poorly soluble peptides such as cyclosporine are encapsulated in HA derivatives.

Example 7

In Vitro Release Test

Example 7-1

Paclitaxel Release Test

To an aqueous (ultrapure water) solution of 10 k HA-Ala-Chol-41% obtained in Example 1-21 was added Paclitaxel (10 mg/ml, solution in methanol) so that the final paclitaxel concentration be 100 μg/mL and the concentration of the HA derivatives be 1.0 mg/mL. The mixture was left to stand at 4° C. overnight. Free paclitaxel was removed at 4° C. with a dialysis membrane (3,000 MWCO). The resultant HA derivative/paclitaxel complexes were put in a dialysis membrane (3,000 MWCO) and incubated at 37° C. with PBS. The concentration of paclitaxel in dialysis membrane was quantified over time by reversed phase chromatography analysis to confirm the release. The amounts of paclitaxel retained in dialysis membrane are shown in FIG. 7-1. This result indicates that HA derivatives can be used as controlled release carriers.

Example 7-2

Cyclosporine Release Test

The test was carried out in a method described in Example 7-1 except that cyclosporine A was used instead of paclitaxel to confirm the release of cyclosporine. The amounts of cyclosporine retained in dialysis membrane are shown in FIG. 7-2. This result shows that HA derivatives can be used as controlled release carriers.

Example 8

Synthesis of HA-AA-Chol Having Different Linker

HA-AA-Chols (Table 21) having different linkers were obtained as solid in a method similar to that of Example 1-4 except that cholesteryl 2-aminoethylcarbamate (Chol-C2), cholesteryl 12-dodecylaminohexylcarbamate (Chol-C12), or cholesteryl 8-amino-3,6-dioxaoctylcarbamate (Chol-EO2) was used instead of cholesteryl 6-aminohexylcarbamate (Chol-C$_6$). Cholesteryl 2-aminoethylcarbamate, cholesteryl 12-dodecylaminohexylcarbamate, and cholesteryl 8-amino-3,6-dioxaoctylcarbamate were synthesized in the methods described in WO2010/053140. $^1$H-NMR spectra of the products measured in the conditions same as those described in Example 1-5 are shown in FIG. 8-1 to 8-6. The introduction ratio of cholesteryl group in HA units was calculated in the same method as that described in Example 1-5 (Table 21).

TABLE 21

Linker in preparation of hyaluronic acid derivative and introduction ratio

| Abbreviation | Molecular weight | Species and introduction ratio of AA(NH$_2$) (unit %) | Type of linker | Introduction ratio of Chol (unit %) |
|---|---|---|---|---|
| 99k HA-Ala-C$_2$-Chol-6% | 99k | Ala 91 | Chol-C$_2$ | 6 |
| 10k HA-Ala-C$_2$-Chol-7% | 10k | Ala 95 | Chol-C$_2$ | 7 |
| 99k HA-Ala-C$_{12}$-Chol-7% | 99k | Ala 91 | Chol-C$_{12}$ | 7 |
| 10k HA-Ala-C$_{12}$-Chol-7% | 10k | Ala 95 | Chol-C$_{12}$ | 7 |
| 99k HA-Ala-EO$_2$-Chol-5% | 99k | Ala 91 | Chol-EO$_2$ | 5 |
| 10k HA-Ala-EO$_2$-Chol-6% | 10k | Ala 95 | Chol-EO$_2$ | 6 |

Example 9

Synthesis of HA-Ala-Cholanic Acid (Example 9-1)
Synthesis of N-(2-aminoethyl) 5-cholanoamide Methyl 5β-cholanate (Steraloids, 100 μg) was dissolved in ethylenediamine (6 mL) and the solution was refluxed at 130° C. for 4 hours. After distilling off under reduced pressure, the residue was dissolved in dichloromethane and washed with ultrapure water. The solvent was distilled off under reduced pressure to obtain aminoethyl 5β-cholanoamide.

$^1$H-NMR (CDCl$_3$): δ=0.64 (3H, s, CH$_3$), 0.91 (3H, s, CH$_3$), 0.92 (3H, d, CH$_3$) 2.0-2.3 (2H, m, COCH$_2$), 2.8 (2H, m, CH$_2$CH$_2$NHCO), 3.3 (2H, m, CH$_2$CH$_2$NHCO), 5.9 (1H, br, NHCO).

Example 9-2

Synthesis of HA-Ala-Cholanic Acid

A solution (10 mg/mL) of HA-Ala-TBA synthesized in a method similar to that of Example 1-4 in anhydrous DMSO was prepared. Subsequently, to aliquots of the solution was added aminoethyl 5β-cholanoamide prepared in Example 9-1 at the ratios to HA-Ala-TBA units shown in Table 22 below. DMT-MM was then added to HA-Ala-TBA at the ratios shown in Table 22 below. The reaction solutions were dialyzed against a 1/1 mixed solution of methanol/water, an aqueous solution of 0.15 M NaCl, and ultrapure water in this order. The resultant dialysates were freeze-dried to obtain the target (HA-Ala-CA) as white solid.

A representative example of $^1$H-NMR spectra (the product that is produced from the starting material 99 kDa HA and have a cholanic acid introduction ratio of 13%) using DMSO-d$_6$ as a measurement solvent is shown in FIG. 9. Based on the integrated value of peak derived from acetyl (COCH$_3$, 1.6 to 2.0 ppm; 3H) in glucosamine and the integrated value of peak derived from methyl (CH$_3$, 0.6 ppm; 3H) in the cholesteryl group, the introduction ratio of cholanic acid in HA units was calculated according to the expression below (Table 22). Since peaks around 1.6 to 2.0 ppm including peak derived from acetyl in glucosamine overlap with peaks (7H) derived from the cholanic acid group, the value obtained by subtracting 7/3 of the integrated value of peak (0.6 ppm) derived from methyl in the cholanic acid group from the integrated value of peaks around 1.6 to 2.0 ppm (i.e. integrated value (1.6 to 2.0 ppm)−integrated value (0.7 ppm)×7/3) was used as the integrated value of acetyl derived from HA to calculate the introduction ratio.

[Exp. 8]

Introduction ratio of cholanic acid group % =

$$\frac{\text{Integrated value of methyl derived from cholanic acid (0.6 ppm)}}{\text{Integrated value of acetyl derived from } HA \text{ (1.6 to 2.0 ppm, value after correction)}} \times 100$$

TABLE 22

Amount of reagent used in preparation of HA-Ala-CA and introduction ratio

| Abbreviation | Molecular weight | Introduction ratio of Ala (unit %) | Mol ratio of CA-C$_2$ hydrochloride and DMT-MM added (HA unit/CA-C$_2$/DMT-MM) | Introduction ratio of CA (unit %) |
|---|---|---|---|---|
| 99k HA-Ala-CA-8% | 99k | 91 | 100/10/50 | 8 |
| 99k HA-Ala-CA-13% | 99k | 91 | 100/20/100 | 13 |

The invention claimed is:

1. A hyaluronic acid derivative, comprising a repeating unit represented by formula (I):

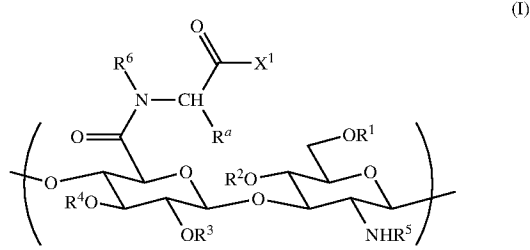

(I)

where $R^1$, $R^2$, $R^3$, and $R^4$ are independently selected from a hydrogen atom, $C_{1-6}$ alkyl, formyl, and $C_{1-6}$ alkylcarbonyl;

$R^5$ is a hydrogen atom, formyl, or $C_{1-6}$ alkylcarbonyl;

$X^1$ is hydroxy, $-O-Q^+$, $C_{1-6}$ alkoxy, $-NR^7R^8$, or $-NR^9-Z^1-Z^2$;

$Q^+$ represents a counter cation;

$R^6$, $R^7$, $R^8$, and $R^9$ are independently selected from a hydrogen atom and $C_{1-6}$ alkyl;

$R^a$ is a hydrogen atom, hydroxymethyl, 1-hydroxyethyl, carbamoylmethyl, carboxymethyl, 2-methylpropyl, isopropyl, 2-methylthioethyl, or phenylmethyl;

$Z^1$ is $C_{2-30}$ alkylene or $-(CH_2CH_2O)_m-CH_2CH_2-$, where into the alkylene 1 to 5 groups independently selected from $-O-$, $-NR^g-$, and $-S-S-$ may be inserted, and m is an integer selected from 1 to 100;

$Z^2$ is selected from groups represented by the following formulas:
$-NR^b-Z^3$,
$-NR^b-COO-Z^3$,
$-NR^b-CO-Z^3$,
$-NR^b-CO-NR^c-Z^3$,
$-COO-Z^3$,
$-CO-NR^c-Z^3$,
$-O-CO-NR^c-Z^3$,
$-O-COO-Z^3$,
$-S-Z^3$,
$-CO-Z^a-S-Z^3$,
$-O-CO-Z^b-S-Z^3$,
$-NR^b-CO-Z^b-S-Z^3$, and
$-S-S-Z^3$;

$R^b$ and $R^c$ are independently selected from a hydrogen atom, $C_{1-20}$ alkyl, amino $C_{2-20}$ alkyl, and hydroxy $C_{2-20}$ alkyl, where into the alkyl moieties of the groups 1 to 3 groups independently selected from $-O-$ and $-NR^f-$ may be inserted;

$R^f$ is independently selected from a hydrogen atom, $C_{1-12}$ alkyl, amino $C_{2-12}$ alkyl, and hydroxy $C_{2-12}$ alkyl, and into the alkyl moieties of the groups 1 to 2 groups independently selected from $-O-$ and $-NH-$ may be inserted;

$R^g$ is independently selected from a hydrogen atom, $C_{1-20}$ alkyl, amino $C_{2-20}$ alkyl, or hydroxy $C_{2-20}$ alkyl, and into the alkyl moieties of the groups 1 to 3 groups independently selected from $-O-$ and $-NH-$ may be inserted;

$Z^3$ is a steryl group;

$Z^a$ is $C_{1-5}$ alkylene; and $Z^b$ is $C_{2-8}$ alkylene or $C_{2-8}$ alkenylene, wherein if the hyaluronic acid derivative comprises no repeating units represented by formula (I) in which $X^1$ is $-NR^9-Z^1-Z^2$, then the hyaluronic acid derivative further comprises a repeating unit represented by formula (II):

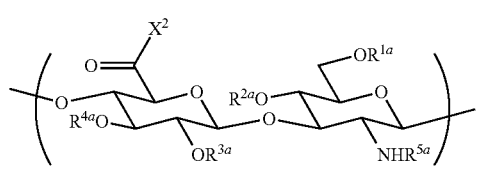

(II)

where $R^{1a}$, $R^{2a}$, $R^{3a}$, and $R^{4a}$ are independently selected from a hydrogen atom, $C_{1-6}$ alkyl, formyl, and $C_{1-6}$ alkylcarbonyl;

$R^{5a}$ is a hydrogen atom, formyl, or $C_{1-6}$ alkylcarbonyl; and $X^2$ is $-NR^9-Z^1-Z^2$, where $R^9$, $Z^1$, and $Z^2$ are as defined above.

2. The hyaluronic acid derivative according to claim 1, further comprising a repeating unit represented by formula (IIb):

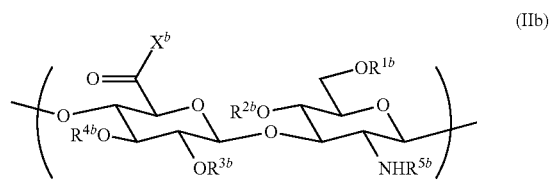

(IIb)

where $R^{1b}$, $R^{2b}$, $R^{3b}$, and $R^{4b}$ are each independently selected from a hydrogen atom, $C_{1-6}$ alkyl, formyl, and $C_{1-6}$ alkylcarbonyl;

$R^{5b}$ is selected from a hydrogen atom, formyl, and $C_{1-6}$ alkylcarbonyl; and $X^b$ is selected from hydroxy and $-O-Q^+$, where $Q^+$ represents a counter cation.

3. The hyaluronic acid derivative according to claim 1, wherein a percentage of the disaccharide unit comprising the group $-NR^9-Z^1-Z^2$ in existing disaccharide repeating units is 3 to 50%.

4. The hyaluronic acid derivative according to claim 1, wherein the hyaluronic acid derivative is produced by using hyaluronic acid exclusively consisting of the disaccharide unit represented by formula (IIb)

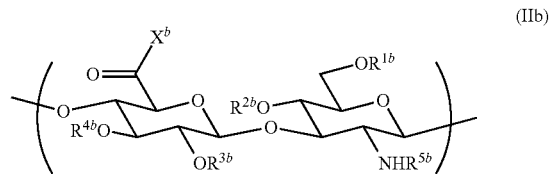

(IIb)

where $R^{1b}$, $R^{2b}$, $R^{3b}$ and $R^{4b}$ are all hydrogen atoms, $R^{5b}$ is acetyl, and $X^b$ is $-O-Na^+$ and has a weight-average molecular weight of 3 kilo Daltons to 1,500 kilo Daltons.

5. The hyaluronic acid derivative according to claim 1, wherein $Z^1$ is $C_{2-10}$ alkylene, $Z^2$ is $-NH-COO-Z^3$, and $Z^3$ is a cholesteryl group.

6. The hyaluronic acid derivative according to claim 2, wherein the hyaluronic acid derivative is obtained by reacting a hyaluronic acid derivative comprising a repeating unit represented by formula (IIb) and a repeating unit represented by formula (Ia),

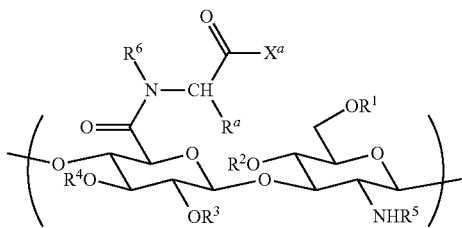

(Ia)

where $X^a$ is selected from hydroxy, $-O-Q^+$, $C_{1-6}$ alkoxy, and $-NR^7R^8$ and $R^1$, $R^2$, $R^3$, $R^4$, $R^5$, $R^6$, $R^7$, $R^8$, $Q^+$, and $R^a$ are as defined in claim 1, with a compound represented by formula below, $HNR^9-Z^1-Z^2$.

7. A pharmaceutical composition comprising the hyaluronic acid derivative according to claim 1 and a drug.

8. The pharmaceutical composition according to claim 7, wherein the drug is held by forming a complex with the hyaluronic acid derivative.

9. The hyaluronic acid derivative according to claim 1, wherein $X^1$ is $-NR^9-Z^1-Z^2$ in formula (I).

10. The hyaluronic acid derivative according to claim 1, wherein a percentage of the disaccharide unit represented by formula (I) in existing disaccharide repeating units is 70 to 100%.

11. The hyaluronic acid derivative according to claim 1, comprising no repeating units represented by formula (I) in which $X^1$ is $-NR^9-Z^1-Z^2$.

12. The hyaluronic acid derivative according to claim 1, wherein a sum of percentages of the repeating unit represented by formula (I) and the repeating unit represented by formula (II) in existing disaccharide repeating units is 70 to 100%.

* * * * *